United States Patent
Chakravarty et al.

(10) Patent No.: US 9,040,519 B2
(45) Date of Patent: May 26, 2015

(54) FUSED TETRACYCLIC PYRIDO [4,3-B] INDOLE AND PYRIDO [3,4-B] INDOLE DERIVATIVES AND METHODS OF USE

(75) Inventors: Sarvajit Chakravarty, Mountain View, CA (US); Barry Patrick Hart, Palo Alto, CA (US); Rajendra Parasmal Jain, Pune (IN)

(73) Assignee: Medivation Technologies, Inc., San Francisco, CA (US)

( * ) Notice: Subject to any disclaimer, the term of this patent is extended or adjusted under 35 U.S.C. 154(b) by 169 days.

(21) Appl. No.: 13/579,911

(22) PCT Filed: Feb. 18, 2011
(Under 37 CFR 1.47)

(86) PCT No.: PCT/US2011/025509
§ 371 (c)(1),
(2), (4) Date: Mar. 4, 2013

(87) PCT Pub. No.: WO2011/103485
PCT Pub. Date: Aug. 25, 2011

(65) Prior Publication Data
US 2013/0225558 A1   Aug. 29, 2013

Related U.S. Application Data

(60) Provisional application No. 61/305,880, filed on Feb. 18, 2010.

(51) Int. Cl.
| | | |
|---|---|---|
| C07D 471/14 | (2006.01) | |
| C07D 471/18 | (2006.01) | |
| C07D 471/16 | (2006.01) | |
| C07D 471/22 | (2006.01) | |
| C07D 498/16 | (2006.01) | |
| C07D 498/22 | (2006.01) | |
| C07D 471/20 | (2006.01) | |
| C07D 487/14 | (2006.01) | |
| C07D 498/14 | (2006.01) | |
| C07D 513/14 | (2006.01) | |

(52) U.S. Cl.
CPC ............ *C07D 471/14* (2013.01); *C07D 471/16* (2013.01); *C07D 471/22* (2013.01); *C07D 498/16* (2013.01); *C07D 498/22* (2013.01); *C07D 471/20* (2013.01); *C07D 487/14* (2013.01); *C07D 498/14* (2013.01); *C07D 513/14* (2013.01)

(58) Field of Classification Search
CPC .......................... C07D 471/14; C07D 471/18
USPC ................... 514/214.02, 250, 257, 281, 288;
540/477, 546, 579; 544/246, 247, 343;
546/43, 66
See application file for complete search history.

(56) References Cited

U.S. PATENT DOCUMENTS

| | | | |
|---|---|---|---|
| 3,299,078 | A | 1/1967 | Pachter |
| 5,223,625 | A | 6/1993 | Van Wijngaarden et al. |
| 5,620,973 | A | 4/1997 | Goto et al. |
| 6,187,785 | B1 | 2/2001 | Zefirov et al. |
| 6,548,493 | B1 | 4/2003 | Robichaud et al. |
| 7,071,206 | B2 | 7/2006 | Zefirov et al. |
| 8,338,408 | B2 | 12/2012 | Hung et al. |
| 8,338,447 | B2 | 12/2012 | Hung et al. |
| 8,362,277 | B2 | 1/2013 | Mcknight et al. |
| 8,541,437 | B2 | 9/2013 | Ivashchenko et al. |
| 8,546,381 | B2 | 10/2013 | Hung et al. |
| 8,569,287 | B2 | 10/2013 | Hung et al. |
| 8,604,074 | B2 | 12/2013 | Mcknight et al. |
| 8,735,440 | B2 | 5/2014 | Mcknight et al. |
| 8,741,919 | B2 | 6/2014 | Jain et al. |
| 8,791,132 | B2 | 7/2014 | Protter et al. |
| 8,815,843 | B2 | 8/2014 | Protter et al. |
| 8,859,561 | B2 | 10/2014 | Jain et al. |
| 8,877,797 | B2 | 11/2014 | Mcknight et al. |
| 8,906,925 | B2 | 12/2014 | Hung et al. |
| 8,907,097 | B2 | 12/2014 | Hung et al. |
| 8,927,571 | B2 | 1/2015 | Jain et al. |
| 2001/0020028 | A1 | 9/2001 | Zefirov et al. |
| 2002/0115682 | A1 | 8/2002 | Zefirov et al. |
| 2003/0225058 | A1 | 12/2003 | Frank et al. |
| 2004/0044022 | A1 | 3/2004 | Zefirov, Jr. et al. |
| 2004/0180875 | A1 | 9/2004 | Lee et al. |
| 2005/0054634 | A1 | 3/2005 | Busch et al. |

(Continued)

FOREIGN PATENT DOCUMENTS

| | | |
|---|---|---|
| EP | 0 725 068 A1 | 8/1996 |
| EP | 2 236 511 A2 | 10/2010 |

(Continued)

OTHER PUBLICATIONS

West, Anthony R., Solid State Chemistry and Its Applications, Wiley, New York, 1988, 358.*
Adham, N. et al. (Jun. 23, 1998). "Functional Characterization of the Recombinant Human 5-Hydroxytryptamine$_{7(a)}$ Receptor Isoform Coupled to Adenylate Cyclase Stimulation," *The Journal of Pharmacology and Experimental Therapeutics* 287(2):508-514.
Alekseyev, R. S. et al. (Jul. 2010). "γ-Carbolines and their Hydrogenated Derivatives. 2. Hydrogenated Derivatives of γ-Carbolines: Methods of Synthesis (Review)," *Chemistry of Heterocyclic Compounds* 46(7):777-821.
Bartolini, L. et al. (1996). "Aniracetam Restores Object Recognition Impaired by Age, Scopolamine, and Nucleus Basalis Lesions," *Pharmacology Biochemistry Behavior* 53(2):277-283.

(Continued)

*Primary Examiner* — Erich A Leeser
(74) *Attorney, Agent, or Firm* — Morrison & Foerster LLP

(57) ABSTRACT

This disclosure is directed to fused tetracyclic pyrido[4,3-b>] indole and pyrido[3,4-b]indole derivatives. Pharmaceutical compositions comprising the compounds are also provided, as are methods of using the compounds in a variety of therapeutic applications, including the treatment of a cognitive disorder, psychotic disorder, neurotransmitter-mediated disorder and/or a neuronal disorder.

16 Claims, No Drawings

(56) References Cited

U.S. PATENT DOCUMENTS

| | | |
|---|---|---|
| 2005/0282796 A1 | 12/2005 | Acker et al. |
| 2006/0140866 A1 | 6/2006 | Zefirov et al. |
| 2006/0178362 A1 | 8/2006 | Robichaud et al. |
| 2007/0015746 A1 | 1/2007 | Martin et al. |
| 2007/0117834 A1 | 5/2007 | Hung |
| 2007/0117835 A1 | 5/2007 | Hung |
| 2007/0179174 A1 | 8/2007 | Bachurin et al. |
| 2007/0225316 A1 | 9/2007 | Bachurin et al. |
| 2008/0234310 A1 | 9/2008 | Bachurin et al. |
| 2008/0261938 A1 | 10/2008 | Ercolani et al. |
| 2009/0221627 A1 | 9/2009 | Aksinenko et al. |
| 2010/0022580 A1 | 1/2010 | Hung et al. |
| 2010/0029706 A1 | 2/2010 | Miller et al. |
| 2010/0087471 A1 | 4/2010 | Schrimpf et al. |
| 2010/0099700 A1 | 4/2010 | Hung |
| 2010/0152108 A1 | 6/2010 | Hung et al. |
| 2010/0152225 A1 | 6/2010 | Hung |
| 2010/0178277 A1 | 7/2010 | Hung et al. |
| 2010/0216814 A1 | 8/2010 | Hung et al. |
| 2010/0249105 A1 | 9/2010 | Schrimpf et al. |
| 2010/0286188 A1 | 11/2010 | Bachurin et al. |
| 2011/0046368 A1 | 2/2011 | Ivashchenko et al. |
| 2011/0112132 A1 | 5/2011 | Bachurin et al. |
| 2011/0152308 A1 | 6/2011 | Shi |
| 2011/0237582 A1 | 9/2011 | Jain et al. |
| 2011/0245272 A1 | 10/2011 | Jain et al. |
| 2011/0269777 A1 | 11/2011 | Bachurin et al. |
| 2012/0022096 A1 | 1/2012 | Mcknight et al. |
| 2012/0101121 A1 | 4/2012 | Bachurin et al. |
| 2012/0136008 A1 | 5/2012 | Jain et al. |
| 2013/0040977 A1 | 2/2013 | Mcknight et al. |
| 2013/0053366 A1 | 2/2013 | Protter et al. |
| 2013/0053367 A1 | 2/2013 | Protter et al. |
| 2013/0079352 A1 | 3/2013 | Hung et al. |
| 2013/0123277 A1 | 5/2013 | Jain et al. |
| 2013/0131054 A1 | 5/2013 | Hung et al. |
| 2013/0131077 A1 | 5/2013 | Hung et al. |
| 2013/0137705 A1 | 5/2013 | Jain et al. |
| 2013/0172320 A1 | 7/2013 | Chakravarty et al. |
| 2013/0172366 A1 | 7/2013 | Jain et al. |
| 2013/0184269 A1 | 7/2013 | Hung et al. |
| 2013/0184303 A1 | 7/2013 | Jain et al. |
| 2013/0184304 A1 | 7/2013 | Jain et al. |
| 2013/0184306 A1 | 7/2013 | Hung et al. |
| 2013/0190293 A1 | 7/2013 | Chakravarty et al. |
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190322 A1 | 7/2013 | Hung et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1* | 8/2013 | Chakravarty et al. ...... 514/211.1 |
| 2013/0217675 A1 | 8/2013 | Chakravarty et al. |
| 2014/0024643 A1 | 1/2014 | Hung et al. |
| 2014/0088086 A1 | 3/2014 | Protter et al. |
| 2014/0088087 A1 | 3/2014 | Hung et al. |
| 2014/0155384 A1 | 6/2014 | Protter et al. |
| 2014/0194414 A1 | 7/2014 | Hung et al. |
| 2014/0206711 A1 | 7/2014 | Chakravarty et al. |
| 2014/0213577 A1 | 7/2014 | Hung et al. |
| 2014/0228353 A1 | 8/2014 | Protter et al. |
| 2014/0296209 A1 | 10/2014 | Protter et al. |
| 2014/0303144 A1 | 10/2014 | Protter et al. |
| 2015/0005322 A1 | 1/2015 | Jain et al. |
| 2015/0051218 A1 | 2/2015 | Hung et al. |

FOREIGN PATENT DOCUMENTS

| | | | | |
|---|---|---|---|---|
| JP | 05310738 | * | 4/1992 | ........ C07D 471/16 |
| JP | 05-310738 A | | 11/1993 | |
| WO | WO-2005/005951 A2 | | 6/2005 | |
| WO | WO-2005/005951 A3 | | 6/2005 | |
| WO | WO-2007/041697 A2 | | 4/2007 | |
| WO | WO-2007/041697 A3 | | 4/2007 | |
| WO | WO-2007/087425 A1 | | 8/2007 | |
| WO | WO-2008/036400 A2 | | 3/2008 | |
| WO | WO-2008/036400 A3 | | 3/2008 | |
| WO | WO-2008/036410 A2 | | 3/2008 | |
| WO | WO-2008/036410 A3 | | 3/2008 | |
| WO | WO-2008/051599 A2 | | 5/2008 | |
| WO | WO-2008/051599 A3 | | 5/2008 | |
| WO | WO-2008/060190 A2 | | 5/2008 | |
| WO | WO-2008/060190 A3 | | 5/2008 | |
| WO | WO-2008/069963 A1 | | 6/2008 | |
| WO | WO-2008/073231 A1 | | 6/2008 | |
| WO | WO-2008/115098 A2 | | 9/2008 | |
| WO | WO-2008/115098 A3 | | 9/2008 | |
| WO | WO-2008/115098 A3 | | 10/2008 | |
| WO | WO-2008/123796 A2 | | 10/2008 | |
| WO | WO-2008/123800 A2 | | 10/2008 | |
| WO | WO-2008/123800 A3 | | 10/2008 | |
| WO | WO-2008/147551 A1 | | 12/2008 | |
| WO | WO-2009/005771 A1 | | 1/2009 | |
| WO | WO-2009/017836 A1 | | 2/2009 | |
| WO | WO-2009/038161 A1 | | 3/2009 | |
| WO | WO-2009/038162 A1 | | 3/2009 | |
| WO | WO-2009/038163 A1 | | 3/2009 | |
| WO | WO-2009/038164 A1 | | 3/2009 | |
| WO | WO-2009/039420 A1 | | 3/2009 | |
| WO | WO-2009/039420 A9 | | 3/2009 | |
| WO | WO-2009/051503 A2 | | 4/2009 | |
| WO | WO-2009/051503 A3 | | 4/2009 | |
| WO | WO-2009/055828 A1 | | 4/2009 | |
| WO | WO-2009/082268 A2 | | 7/2009 | |
| WO | WO-2009/082268 A3 | | 7/2009 | |
| WO | WO-2009/094668 A1 | | 7/2009 | |
| WO | WO-2009/094668 A8 | | 7/2009 | |
| WO | WO-2009/094668 C1 | | 7/2009 | |
| WO | WO-2009/111540 A1 | | 9/2009 | |
| WO | WO-2009/120717 A2 | | 10/2009 | |
| WO | WO-2009/120717 A3 | | 10/2009 | |
| WO | WO-2009/120720 A1 | | 10/2009 | |
| WO | WO-2009/135091 A1 | | 11/2009 | |
| WO | WO-2010/036998 A2 | | 4/2010 | |
| WO | WO-2010/036998 A3 | | 4/2010 | |
| WO | WO-2010/051501 A1 | | 5/2010 | |
| WO | WO-2010/051503 A1 | | 5/2010 | |
| WO | WO-2010/081115 A1 | | 7/2010 | |
| WO | WO-2010/127177 A1 | | 11/2010 | |
| WO | WO-2011/008312 A2 | | 1/2011 | |
| WO | WO-2011/008312 A3 | | 1/2011 | |
| WO | WO-2011/014695 A1 | | 2/2011 | |
| WO | WO-2011/019417 A1 | | 2/2011 | |
| WO | WO-2011/038161 A1 | | 3/2011 | |
| WO | WO-2011/038162 A1 | | 3/2011 | |
| WO | WO-2011/038163 A1 | | 3/2011 | |
| WO | WO-2011/038164 A1 | | 3/2011 | |
| WO | WO-2011/103430 A1 | | 8/2011 | |
| WO | WO-2011/103433 A1 | | 8/2011 | |
| WO | WO-2011/103448 A1 | | 8/2011 | |
| WO | WO-2011/103460 A1 | | 8/2011 | |
| WO | WO-2011/103487 A1 | | 8/2011 | |
| WO | WO-2012/006419 A2 | | 1/2012 | |
| WO | WO-2012/006419 A3 | | 1/2012 | |
| WO | WO-2012/112961 A1 | | 8/2012 | |
| WO | WO-2012/112962 A1 | | 8/2012 | |
| WO | WO-2012/112963 A1 | | 8/2012 | |
| WO | WO-2012/112964 A2 | | 8/2012 | |
| WO | WO-2012/112964 A3 | | 8/2012 | |
| WO | WO-2012/112965 A1 | | 8/2012 | |
| WO | WO-2012/112966 A1 | | 8/2012 | |
| WO | WO-2012/154261 A1 | | 11/2012 | |
| WO | WO-2014/031125 A1 | | 2/2014 | |

(56) References Cited

FOREIGN PATENT DOCUMENTS

| WO | WO-2014/031165 A1 | 2/2014 |
|---|---|---|
| WO | WO-2014/031167 A1 | 2/2014 |
| WO | WO-2014/031170 A1 | 2/2014 |

OTHER PUBLICATIONS

Berge, S.M. et al. (Jan. 1977). "Pharmaceutical Salts," *J. Pharm. Sci.* 66(1):1-19.
Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.
Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.
Brown, C.M. et al. (1990). "$\alpha_2$-Adrenoceptor Subtypes and Imidazoline-Like Binding Sites in the Rat Brain," *Br. J. Pharmacol.* 99:803-809.
Bubber, P. et al. (May 2005, e-published Apr. 25, 2005). "Mitochondrial Abnormalities in Alzheimer Brain: Mechanistic Implications," *Ann Neurol.* 57(5):695-703.
De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.
Ennaceur, A. et al. (1988). "A New One-Trial Test for Neurobiological Studies of Memory in Rats. 1: Behavioral Data," *Behav. Brain. Res.* 31:47-59.
García-Sáinz, J.A. et al. (Jul. 31, 1992). "Species Heterogeneity of Hepatic $\alpha_1$-Adrenoceptors: $\alpha_{1A}$-, $\alpha_{1B}$- and $\alpha_{1C}$-Subtypes," *Biochemical and Biophysical Research Communications* 186(2):760-767.
Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$^{35}$S]GTP$\gamma$S Binding Assays," *Naunyn-Schmiedeberg's Archives of Pharmacology* 361:498-504.
Grandy, D.K. et al. (Dec. 1989). "Cloning of the cDNA and Gene for a Human D$_2$ Dopamine Receptor," *Proc. Natl. Acad. Sci. USA* 86:9762-9766.
Grossman, C.J. et al. (1993). "Development of a Radioligand Binding Assay for 5-HT$_4$ Receptors in Guinea-Pig and Rat Brain," *Br. J. Pharmacol.* 109:618-624.
Hardy, J. (1996). "New Insights Into the Genetics of Alzheimer's Disease," *Annals of Medicine* 28:255-258.
Hardy, J. (1997). "Amyloid, the Presenilins and Alzheimer's Disease," *Trends Neurosci.* 20(4):154-159.
Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.
Hoyer, D. et al. (1985). "Characterization of the 5-HT$_{1B}$ Recognition Site in Rat Brain: Binding Studies with (-)[$^{125}$I] Iodocyanopindolol," *European Journal of Pharmacology* 118:1-12.
International Search Report mailed on Jul. 28, 2011, for PCT Patent Application No. PCT/US2011/25509, filed on Feb. 18, 2011, 5 pages.
Ivachtchenko, A.V. et al. (2009, e-published May 3, 2009). "Synthesis and Biological Evaluation of Novel Gamma-Caronline Analogues of Dimebon as Potent 5-HT$_6$ Receptor Antagonists," *Bioorganic & Medicinal Chemistry Letters* 19(12):3183-3187.
Ivachtchenko, A.V. et al. (2010, e-published Oct. 31, 2009). "8-Sulfonyl-Substituted Tetrahydro-1H-Pyrido[4,3-b]Indoles as 5-HT$_6$ Receptor Antagonists," *European Journal of Medicinal Chemistry* 45(2):782-789.
Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.
Jerman, J.C. et al. (2001). "Pharmacological Characterisation of Human 5-HT$_2$ Receptor Subtypes," *European Journal of Pharmacology* 414:23-30.
Jongejan, A. et al. (Jul. 2005). "Linking Agonist Binding to Histamine H$_1$ Receptor Activation," *Nat. Chem. Biol.* 1(2):98-103.
Kenny, B.A. et al. (1995). "Characterization of an $\alpha_{1D}$-Adrenoceptor Mediating the Contractile Response of Rat Aorta to Noradrenaline," *British Journal of Pharmacology* 115:981-986.
Klabunde, T. et al. (2002). "Drug Design Strategies for Targeting G-Protein-Coupled Receptors," *ChemBiochem* 3(10):928-944.
Krueger, K. et al. (2005). "G Protein-Dependent Pharmacology of Histamine H$_3$ Receptor Ligands: Evidence for Heterogeneous Active State Receptor Conformations," *J Pharmacol Exp Ther* 314(1):271-281.
Martin, G.R. (1994). "Receptors for 5-Hydroxytryptamine: Current Perspectives on Classification and Nomenclature," *Neuropharmacology* 33(3/4):261-273.
May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.
Michel, A.D. et al. (1989). "Identification of a Single $\alpha_1$-Adrenoceptor Corresponding to the $\alpha_{1A}$-Subtype in Rat Submaxillary Gland," *Br. J. Pharmacol.* 98:883-889.
Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.
Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.
Monsma, F.J. Jr. et al. (1993). "Cloning and Expression of a Novel Serotonin Receptor with High Affinity for Tricyclic Psychotropic Drugs," *Molecular Pharmacology* 43:320-327.
Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.
Pfaffl, M.W. (2001). "A New Mathematical Model for Relative Quantification in Real-Time RT-PCR," *Nucleic Acids Res* 29(9):2002-2007.
Piercey, M.F. et al. (1988). "Dramatic Limbic and Cortical Effects Mediated by High Affinity PCP Receptors," *Life Sciences* 43(4):379-385.
Prichep, L.S. et al. (1994). "Quantitative EEG Correlates of Cognitive Deterioration in the Elderly," *Neurobiology of Aging* 15(1):85-90.
Reddy, P.H. et al. (2005, e-pub. Apr. 19, 2005). "Are Mitochondria Critical in the Pathogenesis of Alzheimer's Disease?" *Brain Res Rev.* 49(3):618-632.
Rees, S. et al. (Oct. 11, 1994). "Cloning and Characterisation of the Human 5-HT$_{5A}$ Serotonin Receptor," *FEBS Letters* 355:242-246.
Reisberg, B. et al. (Sep. 1982). "The Global Deterioration Scale for Assessment of Primary Degenerative Dementia," *Am. J. Psychiatry* 139(9):1136-1139.
Rostom et al. (2010, e-pub. Jan. 27, 2010). "Novel Fused Pyrrole Heterocyclic Ring Systems as Structure Analogs of LE 300: Synthesis and Pharmacological Evaluation as a Serotonin 5-HT$_{2A}$, Dopamine and Histamine H$_1$ Receptor Ligands," *Arch. Pharm. Chem. Life Sci.* 343(2):73-80.
Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.
Ruat, M. et al. (Mar. 1990). "Reversible and Irreversible Labeling and Autoradiographic Localization of the Cerebral Histamine H$_2$ Receptor Using [$^{125}$I]Iodinated Probes," *Proc. Natl. Acad. Sci. USA* 87(5):1658-1662.
Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

(56) References Cited

OTHER PUBLICATIONS

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vekrellis. K. et al. (2009). "Inducible Over-Expression of α-Synuclein in Human Neuronal Cells Leads to Caspase-Dependent Non-Apoptotic Death," *J Neurochem* 109:1348-1362.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Wolf, W.A. et al. (1997). "The Serotonin 5-HT$_{2C}$ Receptor Is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion of the International Searching Authority mailed on Jul. 28, 2011, for PCT Patent Application No. PCT/US2011/25509, filed on Feb. 18, 2011, 6 pages.

Wu, J. et al. (Oct. 21, 2008). "Evaluation of Dimebon in Cellular Model of Huntington's Diseases," *Molecular Neurodegeneration* 3:15: 11 pages.

Yanai, K. et al. (1994). "Binding Characteristics of a Histamine H$_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

U.S. Appl. No. 13/791,750, filed Mar. 8, 2013, by Hung et al.
U.S. Appl. No. 14/000,171, filed Aug. 16, 2013, by Protter et al.
U.S. Appl. No. 14/000,179, filed Aug. 16, 2013, by Chakravarty et al.
U.S. Appl. No. 14/000,184, filed Aug. 16, 2013, by Protter et al.
U.S. Appl. No. 14/000,197, filed Aug. 16, 2013, by Protter et al.
U.S. Appl. No. 14/048,656, filed Oct. 8, 2013, by Hung et al.

Lohr, J.B. et al. (Aug. 28, 1995). "Motor Asymmetry, a Neurobiologic Abnormality in the Major Psychoses," *Psychiatry Research* 57(3):279-282.

U.S. Appl. No. 14/485,238, filed Sep. 12, 2014, by Jain et al.

Bastable, J.W. et al. (Jan. 1, 1981). "Solvolytic Rearrangements of Azabicyclic Compounds," *J. Chem. Soc. Perkin.*| 1346-1351.

Burke, S.L. et al. (2011). "Effects of Chronic Sympatho-Inhibition on Renal Excretory Function in Renovascular Hypertension," *J. Hypertension* 29(5):945-952.

Carter, J.D. et al. (2009). "A Practical Guide to Rodent Islet Isolation and Assessment." *Biol. Proced. Online* 11(1): 3-31.

Chen, B. et al. (2011). "Sitagliptin Lowers Glucagon and Improves Glucose Tolerance in Prediabetic Obese SHROB Rats," *Exp. Biol. Med.* 236:309-414.

Cheng, Y. et al. (Sep. 15, 1973). "Relationship Between the Inhibition Constant ($K_f$) and the Concentration of Inhibitor Which Causes 50 Per Cent Inhibition ($I_{50}$) of an Enzymatic Reaction," *Biochem. Pharmacol.* 22(18):3099-3108.

Duprez, D.A. (2008). "Systolic Hypertension in the Elderly: Addressing an Unmet Need," *Am. J. Med.* 121 :179-184.

Franklin, S. S. et al. (2011). "The Significance of Low DBP in US Adults with Isolated Systolic Hypertension," *J. Hypertension* 29(6):1101-1108.

International Search Report mailed on Apr. 15, 2011 for PCT Patent Application No. PCT/US2011/025444, filed on Feb. 18, 2011, 3 pages.

International Search Report mailed on Apr. 22, 2011, for PCT Patent Application No. PCT/US2011/025475, filed on Feb. 18, 2011, 3 pages.

International Search Report mailed on Apr. 22, 2011 for PCT Patent Application No. PCT/US2011/025511, filed on Feb. 18, 2011, 3 pages.

International Search Report mailed on May 30, 2012, for PCT Application No. PCT/US12/25750, filed on Feb. 17, 2012, 3 pages.

International Search Report mailed on May 31, 2012, for PCT Application No. PCT/US2012/025754, filed on Feb. 17, 2012, 3 pages.

Ivashchenko, A.V. et al. (2009). "Synthesis of Substituted 1,2,3,4,5,6- Hexahydroazepine [4.3-b) Indoles," *Abstracts* 52(10):164.

Kebrle, F. et al. (1959). "A New Synthesis of γ-carbolines," *Helvetica Chimica Acta* 42:907918, Abstract only, 2 pages.

King, F.D. et al. (1993). "Substituted Benzamides With Conformationally Restricted Side Chains. 5. Azabicyclo[x.y.z] Derivatives as 5-HT4 Receptor Agonists and Gastric Motility Stimulants," *J. Med. Chem.* 36(6):683-689.

Kiseleva, B.B. et al. (1990). "New Opportunities of Search for Immunomodulators Among Compounds with Steroidal Structure," *Pharmacology and Toxicology: Moscow Medicine* 53(3): 8 pages. (with English Translation) 'I.

Kohen, R. et al. (1996). "Cloning, Characterization and Chromosomal Localization of a Human 5-HT$_6$Serotonin Receptor," *J. Neurochem.* 66(1):47-56.

Kost, A.N. et al. (1962). "Alkaloids and Alkaloid-Like Structures," *Zhurnal Obshchei Khimii* 32:2050-2056, Abstract only, 2 pages.

Kost, A.N. et al. (1970). "9-[2-(4-Pyridyl) Ethyl]-3,6-Dimethyl-1,2,3,4-Tetrandro-γ-Carboline," *U.S.S.R Otkrytiya, Izobret, Prom. Obraztsy, Tovarnye Znaki* 47(3):33, Abstract only, 2 pages.

Kuhn, C.M. et al. (1987). "Exaggerated Peripheral Responses to Catecholamines Contributes to Stress-Induced Hyperglycemia in the ob/ob Mouse," *Pharmacol. Biochem. Behav.* 26:491495.

Makaritsis, K.P. et al. (Jan. 1999). "Role of the$\alpha_{2B}$-Adrenergic Receptor in the Development of Salt-Induced Hypertension," *Hypertension* 33:14-17.

Meister, B. et al. (1994). Patterns of Messenger RNA Expression for Adrenergic Receptor Subtypes in the Rat Kidney, *J. Pharmacol. Exp. Therapeutics* 268(3):1606-1611.

Mewshaw, R.E. et al. (1993). "Synthesis and in Vitro Evaluation of 5,6,7,8,9,10-Hexahydro7,10-iminocyclohept[b]indoles: High-Affinity Ligands for the N,N-Di-o-tolylguanidine-Labeled σBinding Site," *J. Med. Chem.* 36(3):343-352.

Perrin, R.J. et al. (2003). Epitope Mapping and Specificity of the Anti-α-Synuclein Monoclonal Antibody Syn-1 in Mouse Brain and Cultured Cell Lines *Neurosci. Lett.* 349:133-135.

Pubchem Compound No. 10954584. (Oct. 26, 2006). Compound Summary and Structure located at <http://pubchem.ncbi.nlm.nih.gov/summary/summary.cgi?cid=10954584&loc=ec_rcs>, last visited Apr. 4, 2011, 3 pages.

Regard, J.B. et al. (Oct. 31, 2008). "Anatomical Profiling of G Protein-Coupled Receptor Expression," *Cell* 135:561-571.

Rosengren, A.H. et al. (Jan. 8, 2010). "Overexpression of Alpha2A-Adrenergic Receptors Contributes to Type 2 Diabetes," *Science* 327:217-220.

Saperstein, R. et al., (May 1990). "Effects of an α2-Adrenoceptor Antagonist on Glucose Tolerance in the Genetically Obese Mouse (C57BL/6J ob/ob)," *Metabolism* 39(5):445-451.

(56) References Cited

OTHER PUBLICATIONS

Talmud, P.J. et al. (2011). "Variants of *ADRA2A* are Associated with Fasting Glucose, Blood Pressure, Body Mass Index and Type 2 Diabetes Risk: Meta-Analysis of Four Prospective Studies," *Diabetologia* 54:1710-1719.

Velliquette, R.A. et al. (2003). "The Role of $1_1$-Imidazoline and α2-Adrenergic Receptors in the Modulation of Glucose Metabolism in the Spontaneously Hypertensive Obese Rat Model of Metabolic Syndrome X," *J. Pharmacol. Exp. Ther.* 306(2):646-657.

Wade, S.M. et al., (2001). "Inverse Agonist Activity at the $α_{2A}$-Adrenergic Receptor," *Mol. Pharmacol.* 59(3):532-542.

Written Opinion mailed on Apr. 15, 2011 for PCT Patent Application No. PCT/US2011/025444, filed on Feb. 18, 2011, 6 pages.
Written Opinion mailed on Apr. 22, 2011, for PCT Patent Application No. PCT/US2011/025475, filed on Feb. 18, 2011, 5 pages.
Written Opinion mailed on Apr. 22, 2011, for PCT Patent Application No. PCT/US2011/025511, filed on Feb. 18, 2011, 6 pages.
Written Opinion mailed on May 30, 2012, for PCT Application No. PCT/US12/25750, filed on Feb. 17, 2012, 5 pages.
Written Opinion mailed on May 31, 2012, for PCT Application No. PCT/US2012/025754, filed on Feb. 17, 2012, 4 pages.
U.S. Appl. No. 14/423,027, filed Feb. 20, 2015, by Protter et al.
U.S. Appl. No. 14/631,615, filed Feb. 25, 2015, by Hung et al.

\* cited by examiner

FUSED TETRACYCLIC PYRIDO [4,3-B] INDOLE AND PYRIDO [3,4-B] INDOLE DERIVATIVES AND METHODS OF USE

CROSS-REFERENCE TO RELATED APPLICATIONS

This application claims priority to U.S. Provisional Patent Application No. 61/305,880, filed Feb. 18, 2010, the disclosure of which is hereby incorporated herein by reference in its entirety.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barré syndrome, mild cognitive impairment, schizophrenia (such as cognitive impairment associated with schizophrenia (CIAS), positive symptoms, disorganized symptoms, and negative symptoms of schizophrenia), anxiety, multiple sclerosis, stroke, traumatic brain injury, spinal cord injury, diabetic neuropathy, fibromyalgia, bipolar disorders, psychosis, depression, attention-deficit disorder (ADD), attention-deficit hyperactivity disorder (ADHD) and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., histamine antagonists may find use as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121. Hydrogenated pyrido[4,3-b]indoles and uses thereof have been disclosed in PCT Patent Application Nos. PCT/US2008/081390, PCT/US2009/032065 and PCT/US2009/038142. Hydrogenated pyrido[3,4-b]indoles and uses thereof have been described in PCT/US2009/038138. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Hydrogenated pyrido[4,3-b]indoles and pyrido[3,4-b]indoles are described. Compositions and kits comprising the compounds are also provided, as are methods of using and making the compounds. The compounds provided herein may find use as new histamine receptor modulators, as well as modulators of other neurotransmitters. Compounds provided may also find use in treating neurodegenerative diseases. Compounds provided may also find use in treating diseases and/or conditions in which modulation of aminergic G protein-coupled receptors and/or neurite outgrowth may be implicated in therapy. Compounds disclosed herein may find use in the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

In one aspect, a compounds of the formula (VA) or a salt or solvate thereof is provided:

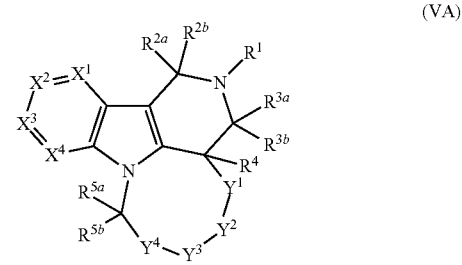

(VA)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—CH$_2$CH$_2$CH$_2$—) moiety or a butylene (—CH$_2$CH$_2$CH$_2$CH$_2$—) moiety, or R$^1$ and R$^4$ are taken together to form an ethylene (—CH$_2$CH$_2$—) moiety or a propylene (—CH$_2$CH$_2$CH$_2$—) moiety;

each R$^{2a}$ and R$^{2b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{2a}$ and R$^{2b}$ are taken together with the carbon to which they are attached to form a carbonyl moiety or a cycloalkyl moiety, or R$^{2a}$ and R$^1$ are taken together to form a propylene (—CH$_2$CH$_2$CH$_2$—) moiety or a butylene (—CH$_2$CH$_2$CH$_2$CH$_2$—) moiety, or R$^{2a}$ and R$^{3a}$ are taken together to form an ethylene (—CH$_2$—CH$_2$—) moiety or a propylene (—CH$_2$CH$_2$—CH$_2$—) moiety, or R$^{2a}$ and R$^4$ are taken together to form a methylene (—CH$_2$—) moiety or an ethylene (—CH$_2$CH$_2$—) moiety;

each R$^{3a}$ and R$^{3b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^{2a}$ are taken together to form an ethylene (—CH$_2$CH$_2$—) moiety or a propylene (—CH$_2$CH$_2$CH$_2$—) moiety, or R$^{3a}$ and R$^4$ are taken together to form a propylene (—CH$_2$CH$_2$CH$_2$—) moiety or a butylene (—CH$_2$CH$_2$CH$_2$CH$_2$—) moiety;

R$^4$ is H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^4$ and R$^1$ are taken together to form an ethylene (—CH$_2$CH$_2$—) moiety or a propylene (—CH$_2$CH$_2$CH$_2$—) moiety, or R$^4$ and R$^{2a}$ are taken together to form a methylene (—CH$_2$—) moiety or an ethylene (—CH$_2$CH$_2$—) moiety, or R$^4$ and R$^{3a}$ are taken together to form a propylene (—CH$_2$CH$_2$CH$_2$—) moiety or a butylene (—CH$_2$CH$_2$CH$_2$CH$_2$—) moiety, or R$^4$ and R$^{7a}$ are taken together to form a bond;

each R$^{5a}$ and R$^{5b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or R$^{5a}$ and R$^{5b}$ are taken together with the carbon to which they are attached to form a carbonyl moiety, or R$^{5a}$ and a vicinal R$^{7(a-h)}$, where applicable, are taken together to form a bond;

each X$^1$, X$^2$, X$^3$ and X$^4$ is independently N, CH or CR$^6$;

Y$^1$ is CR$^{7a}$R$^{7b}$, NR$^8$, O, S, S(O) or SO$_2$, provided that when Y$^1$ is NR$^8$, O, S, S(O) or SO$_2$, then Y$^2$ is CR$^{7c}$R$^{7d}$ or is taken together with Y$^3$ and Y$^4$ to form a bond, Y$^2$ is CR$^{7c}$R$^{7d}$, NR$^8$, O, S, S(O) or SO$_2$, or Y$^2$ is taken together with Y$^3$ and Y$^4$ to form a bond (rendering the Y$^1$-containing ring a five-membered ring), provided that when Y$^2$ is NR$^8$, O, S, S(O) or SO$_2$, then Y$^1$ is CR$^{7a}$R$^{7b}$ and Y$^3$ is CR$^{7e}$R$^{7f}$ or is taken together with Y$^4$ to form a bond;

Y$^3$ is CR$^{7e}$R$^{7f}$, NR$^8$, O, S, S(O) or SO$_2$, or Y$^3$ is taken together with Y$^4$ to form a bond (rendering the Y$^1$-containing ring a six-membered ring), provided that when Y$^3$ is NR$^8$, O, S, S(O) or SO$_2$, then Y$^2$ is CR$^{7c}$R$^{7d}$ and Y$^4$ is CR$^{7g}$R$^{7h}$ or a bond;

Y$^4$ is CR$^{7g}$R$^{7h}$, NR$^8$, O, S, S(O) or SO$_2$, or Y$^4$ is a bond (rendering the Y$^1$-containing ring a seven-membered ring), provided that when Y$^4$ is NR$^8$, O, S, S(O) or SO$_2$, then Y$^3$ is CR$^{7e}$R$^{7f}$;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{7a}$ and R$^{7b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or R$^{7a}$ and R$^{7b}$ are taken together with the carbon to which they are attached to form a carbonyl moiety, or R$^{7a}$ and R$^4$ are taken together to form a bond, or R$^{7a}$ and R$^{7c}$, where applicable, are taken together to form a bond, or R$^{7a}$ and a vicinal R$^{5a}$, where applicable, are taken together to form a bond;

each R$^{7c}$ and R$^{7d}$, where applicable, is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or R$^{7c}$ and R$^{7d}$ are taken together with the carbon to which they are attached to form a carbonyl moiety, or R$^{7c}$ and R$^{7a}$ are taken together to form a bond, or R$^{7c}$ and R$^{7e}$, where applicable, are taken together to form a bond, or R$^{7c}$ and a vicinal R$^{5a}$, where applicable, are taken together to form a bond;

each R$^{7e}$ and R$^{7f}$, where applicable, is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In some embodiments, the compound is of the formula (VA) or a salt or solvate thereof, provided that (1) at least one of $X^1$, $X^2$, $X^3$ and $X^4$ is CH or $CR^6$; and (2) when $Y^3$ is taken together with $Y^4$ to form a bond (rendering the $Y^1$-containing ring a six-membered ring), each $X^1$, $X^2$, $X^3$ and $X^4$ is CH, each $R^{2a}$, $R^{2b}$, $R^{3a}$, $R^{3b}$, $R^4$, $R^{5a}$ and $R^{5b}$ is H, $Y^1$ is $CR^{7a}R^{7b}$ where $R^{7a}$ and $R^{7b}$ are taken together with the carbon to which they are attached to form a carbonyl moiety and $Y^2$ is $CR^{7c}R^{7d}$ where $R^{7c}$ and $R^{7d}$ are each H, then $R^1$ is other than hydrogen.

In some embodiments, compounds of the formula (VA) have the structure (VA1):

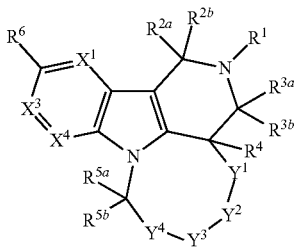

(VA1)

wherein $R^1$, $R^{2a}$, $R^{2b}$, $R^{3a}$, $R^{3b}$, $R^4$, $R^{5a}$, $R^{5b}$, $R^6$, $Y^1$, $Y^2$, $Y^3$, $Y^4$, $R^{7c}$, $R^{7d}$, $R^{7e}$, $R^{7f}$, $R^{7g}$, $R^{7h}$ and $R^8$, where applicable, are as defined for formula (VA);

each $X^1$, $X^3$ and $X^4$ is independently N or CH; and each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond.

In some embodiments, compounds of the formula (VA) have the structure (VA2):

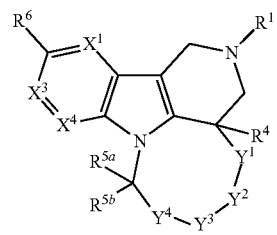

(VA2)

wherein $R^{5a}$, $R^{5b}$, $R^6$, $Y^1$, $R^{7c}$, $R^{7d}$, $R^{7e}$, $R^{7f}$, $R^{7g}$, $R^{7h}$ and $R^8$, where applicable, are as defined for formula (VA);

$R^1$ is H or substituted or unsubstituted $C_1$-$C_8$ alkyl;

$R^4$ is H, substituted or unsubstituted $C_1$-$C_8$ alkyl, or is taken together with $R^{7a}$ to form a bond;

each $X^1$, $X^3$ and $X^4$ is independently N or CH;

$Y^2$ is O or $CR^{7c}R^{7d}$, or $Y^2$ is taken together with $Y^3$ and $Y^4$ to form a bond (rendering the $Y^1$-containing ring a five-membered ring), provided that when $Y^2$ is O, then $Y^1$ is $CR^{7a}R^{7b}$ and $Y^3$ is $CR^{7e}R^{7f}$ or is taken together with $Y^4$ to form a bond;

$Y^3$ is O or $CR^{7e}R^{7f}$, or $Y^3$ is taken together with $Y^4$ to form a bond (rendering the $Y^1$-containing ring a six-membered ring), provided that when $Y^3$ is O, then $Y^2$ is $CR^{7c}R^{7d}$ and $Y^4$ is $CR^{7g}R^{7h}$ or a bond;

$Y^4$ is $CR^{7g}R^{7h}$, or $Y^4$ is a bond (rendering the $Y^1$-containing ring a seven-membered ring); and each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond.

In some embodiments, the compound is of the formula (VA2), where $R^4$ is H or methyl. In some embodiments, the compound is of the formula (VA2), where each $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is independently H, hydroxyl, substituted or unsubstituted $C_1$-$C_8$ alkyl, substituted or unsubstituted aryl, substituted or unsubstituted heteroaryl, substituted or unsubstituted heterocyclyl, substituted or unsubstituted aralkyl, or acylamino, or $R^{5a}$ and $R^{5b}$ are taken together with the carbon to which they are attached to form a carbonyl moiety, or $R^{5a}$ and a vicinal $R^{7(a-h)}$, where applicable, are taken together to form a bond. In some embodiments, the compound is of the formula (VA2), where at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is a group containing a cyclic moiety In some embodiments, the group containing a cyclic moiety is selected from the group consisting of substituted or unsubstituted aryl, substituted or unsubstituted heteroaryl, substituted or unsubstituted cycloalkyl, and substituted or unsubstituted heterocyclyl. In some embodiments, the group containing a cyclic moiety is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In some embodiments, the group containing a cyclic moiety is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another aspect, a compound of the formula (VB) or a salt or solvate thereof is provided:

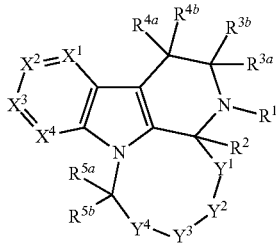

(VB)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2$—$CH_2$—) moiety or a propylene (—$CH_2CH_2$—$CH_2$—) moiety, or $R^{4a}$ and $R^2$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and a vicinal $R^{7(a-h)}$, where applicable, are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$ or is taken together with $Y^3$ and $Y^4$ to form a bond, $Y^2$ is $CR^{7c}R^{7d}$, $NR^8$, O, S, S(O) or $SO_2$, or $Y^2$ is taken together with $Y^3$ and $Y^4$ to form a bond (rendering the $Y^1$-containing ring a five-membered ring), provided that when $Y^2$ is $NR^8$, O, S, S(O) or $SO_2$, then $Y^1$ is $CR^{7a}R^{7b}$ and $Y^3$ is $CR^{7e}R^{7f}$ or is taken together with $Y^4$ to form a bond;

$Y^3$ is $CR^{7e}R^{7f}$, $NR^8$, O, S, S(O) or $SO_2$, or $Y^3$ is taken together with $Y^4$ to form a bond (rendering the $Y^1$-containing ring a six-membered ring), provided that when $Y^3$ is $NR^8$, O, S, S(O) or $SO_2$, then $Y^2$ is $CR^{7c}R^{7d}$ and $Y^4$ is $CR^{7g}R^{7h}$ or a bond;

$Y^4$ is $CR^{7g}R^{7h}$, $NR^8$, O, S, S(O) or $SO_2$, or $Y^4$ is a bond (rendering the $Y^1$-containing ring a seven-membered ring), provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^2$ are taken together to form a bond, or $R^{7a}$ and $R^{7c}$, where applicable, are taken together to form a bond, or $R^{7a}$ and a vicinal $R^{5a}$, where applicable, are taken together to form a bond;

each $R^{7c}$ and $R^{7d}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where applicable, are taken together to form a bond, or $R^{7c}$ and a vicinal $R^{5a}$, where applicable, are taken together to form a bond;

each $R^{7e}$ and $R^{7f}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In some embodiments, compounds of the formula (VB), and salts and solvates thereof, are embraced, provided that at least one of $X^1$, $X^2$, $X^3$ and $X^4$ is CH or $CR^6$ and provisions (A)-(D) apply:

(A) when $Y^2$ is taken together with $Y^3$ and $Y^4$ to form a bond (rendering the $Y^1$-containing ring a five-membered ring), provisions (1) and (2) apply:

(1) when each $X^1$, $X^2$, $X^3$ and $X^4$ is CH, each $R^2$, $R^{3a}$, $R^{3b}$, $R^{4a}$ and $R^{4b}$ is H, $R^{5a}$ and $R^{5b}$ are taken together with the carbon to which they are attached to form a carbonyl moiety, and $Y^1$ is $CR^{7a}R^{7b}$ where one of $R^{7a}$ and $R^{7b}$ is ethyl and the other is hydrogen, $R^1$ is other than benzyl; and (ii) when each $X^1$, $X^2$ and $X^4$ is CH, $X^3$ is $CR^6$ where $R^6$ is methoxy, CH, each $R^2$, $R^{3a}$, $R^{3b}$, $R^{4a}$, $R^{4b}$, $R^{5a}$ and $R^{5b}$ is H, and $Y^1$ is $CR^{7a}R^{7b}$ where each $R^{7a}$ and $R^{7b}$ is methyl, $R^1$ is other than hydrogen;

(B) when $Y^3$ is taken together with $Y^4$ to form a bond (rendering the $Y^1$-containing ring a six-membered ring), provisions (3) and (4) apply:

(3) when $Y^1$ is $CR^{7a}R^{7b}$ and is $Y^2$ is $CR^{7c}R^{7d}$, then at least one of $R^{5a}$, $R^{5b}$, $R^{7a}$, $R^{7b}$, $R^{7c}$ and $R^{7d}$ is a group containing a cyclic moiety; and (4) when $Y^1$ is $CR^{7a}R^{7b}$, $Y^2$ is $NR^8$, $R^{5a}$ and $R^{5b}$ are taken together with the carbon to which they are attached to form a carbonyl moiety, and each $R^2$, $R^{3a}$, $R^{3b}$, $R^{4a}$ and $R^{4b}$ is H, then at least one of $X^1$, $X^2$, $X^3$ and $X^4$ is N or $CR^6$;

(G) when $Y^4$ is a bond (rendering the $Y^1$-containing ring a seven-membered ring), then provisions (5)-(7) apply:

(5) when $Y^1$ is $CR^{7a}R^{7b}$, $Y^2$ is $CR^{7c}R^{7d}$, $Y^3$ is $CR^{7e}R^{7f}$, and each of $X^1$, $X^2$, $X^3$ and $X^4$ is CH, then at least one of $R^{5a}$, $R^{5b}$, $R^{7a}$, $R^{7b}$, $R^{7c}$, $R^{7d}$, $R^{7e}$ and $R^{7f}$ is a substituted or unsubstituted aryl, substituted or unsubstituted heteroaryl, substituted or unsubstituted cycloalkyl, substituted or unsubstituted heterocyclyl, substituted or unsubstituted aralkyl, or a substituted $C_1$-$C_8$ alkyl wherein the substituted $C_1$-$C_8$ alkyl is substituted with at least one substituted or unsubstituted heteroaryl;

(6) when $Y^1$ is $CR^{7a}R^{7b}$, $Y^2$ is $CR^{7c}R^{7d}$, $Y^3$ is $CR^{7e}R^{7f}$, each $R^2$, $R^{3a}$, $R^{3b}$, $R^{4a}$ and $R^{4b}$ is H, and at least one of $X^1$, $X^2$, $X^3$ and $X^4$ is N or $CR^6$, then at least one of $R^{5a}$, $R^{5b}$, $R^{7a}$, $R^{7b}$, $R^{7c}$, $R^{7d}$, $R^{7e}$ and $R^{7f}$ is a group containing a cyclic moiety; and (7) when $Y^1$ is $CR^{7a}R^{7b}$, $Y^2$ is $CR^{7c}R^{7d}$, $Y^3$ is $NR^8$, and each $R^2$, $R^{3a}$, $R^{3b}$, $R^{4a}$ and $R^{4b}$ is H, then at least one of $X^1$, $X^2$, $X^3$ and $X^4$ is N or $CR^6$, and $R^8$ is other than methyl; and (H) when $Y^1$ is $CR^{7a}R^{7b}$, $Y^2$ is $CR^{7c}R^{7d}$, $Y^3$ is $CR^{7e}R^{7f}$, $Y^4$ is $CR^{7g}R^{7h}$, and each $R^2$, $R^{3a}$, $R^{3b}$, $R^{4a}$ and $R^{4b}$ is H, then at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is hydroxyl, halo, cyano, substituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or is taken together with a vicinal $R^{7(a-h)}$, $R^{5a}$ or $R^2$ to form a bond.

In one aspect, compounds of the formula (IA) are provided:

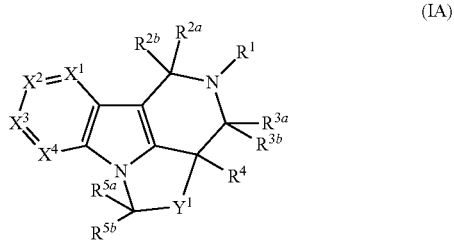

(IA)

or a salt or solvate thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2$ $CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7a}$ are taken together to form a bond;

each $X^1$, $X^2$, $X^3$ and $X^4$ is independently N, CH or $CR^6$;
$Y^1$ is $CR^{7a}R^{7b}$, $NR^8$, O, S, S(O) or $SO_2$;
each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{5a}$ are taken together to form a bond, or $R^{7a}$ and $R^4$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In another aspect, compounds of the formula (IB) are provided:

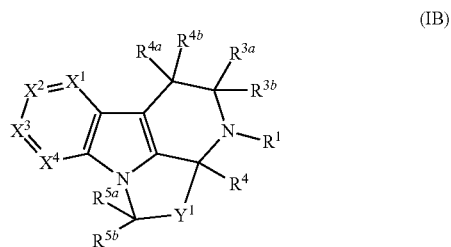

(IB)

or a salt or solvate thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2CH_2$—) moiety or a propylene (—$CH_2CH_2CH_2$—) moiety, or $R^{4a}$ and $R^2$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7a}$ are taken together to form a bond;

each $X^1$, $X^2$, $X^3$ and $X^4$ is independently N, CH or $CR^6$;
$Y^1$ is $CR^{7a}R^{7b}$, $NR^8$, O, S, S(O) or $SO_2$;
each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{5a}$ are taken together to form a bond, or $R^{7a}$ and $R^2$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IB), provided that the compound is other than cis-4-ethyl-2,3,3a,4-tetrahydro-3-(phenylmethyl)benzo[b]pyrido[2,3,4-gh]pyrrolizin-5(1H)-one and 1,2,3,3a,4,5-hexahydro-8-methoxy-4,4-dimethylbenzo[b]pyrido[2,3,4-gh]pyrrolizine.

In another variation, the compounds is of the formula (IB), provided that (i) when each $X^1$, $X^2$, $X^3$ and $X^4$ is CH, each $R^2$, $R^{3a}$, $R^{3b}$, $R^{4a}$ and $R^{4b}$ is H, $R^{5a}$ and $R^{5b}$ are taken together with the carbon to which they are attached to form a carbonyl moiety, and $Y^1$ is $CR^{7a}R^{7b}$ where one of $R^{7a}$ and $R^{7b}$ is ethyl and the other is hydrogen, $R^1$ is other than benzyl, and (ii) when each $X^1$, $X^2$ and $X^4$ is CH, $X^3$ is $CR^6$ where $R^6$ is methoxy, CH, each $R^2$, $R^{3a}$, $R^{3b}$, $R^{4a}$, $R^{4b}$, $R^{5a}$ and $R^{5b}$ is H, $Y^1$ is $CR^{7a}R^{7b}$ where each $R^{7a}$ and $R^{7b}$ is methyl, $R^1$ is other than hydrogen.

In another aspect, compounds of the formula (IIA) are provided:

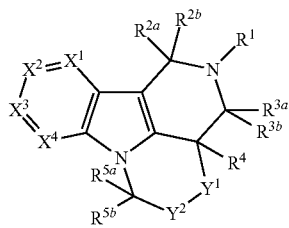

(IIA)

or a salt or solvate thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7c}$ are taken together to form a bond;

each $X^1$, $X^2$, $X^3$ and $X^4$ is independently N, CH or $CR^6$;
$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;
$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IIA), provided that the compound is other than 1,2,3,3a,5,6-hexahydro-4H-indolo[3,2,1-ij][1,6]naphthyridin-4-one.

In another variation, the compound is of the formula (IIA), provided that when each $X^1$, $X^2$, $X^3$ and $X^4$ is CH, each $R^{2a}$, $R^{2b}$, $R^{3a}$, $R^{3b}$, $R^4$, $R^{5a}$ and $R^{5b}$ is H, $Y^1$ is carbonyl and $Y^2$ is $CH_2$, $R^1$ is other than hydrogen.

In another aspect, compounds of the formula (IIB) are provided:

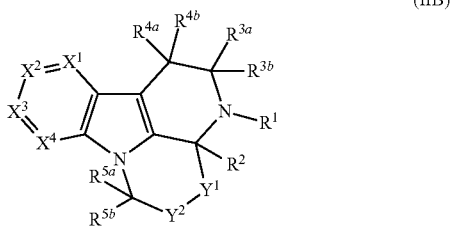

(IIB)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2$—$CH_2$—) moiety or a propylene (—$CH_2CH_2$—$CH_2$—) moiety, or $R^{4a}$ and $R^2$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7c}$ are taken together to form a bond;

each $X^1$, $X^2$, $X^3$ and $X^4$ is independently N, CH or $CR^6$;
$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;
$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$;
each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^2$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$ and $Y^2$ are as defined for formula (IIB), provided that at least one of $X^1$, $X^2$, $X^3$ and $X^4$ is N or $CR^6$.

In another variation, the compound is of the formula (IIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$ and $Y^2$ are as defined for formula (IIB), provided that at least one of $X^1$, $X^2$, $X^3$ and $X^4$ is N or $CR^6$, and when $Y^1$ is $CR^{7a}R^{7b}$ and $Y^2$ is $CR^{7c}R^{7d}$, at least one of $R^{5a}$, $R^{5b}$, $R^{7a}$, $R^{7b}$, $R^{7c}$ and $R^{7d}$ is a group containing a cyclic moiety. In one such variation, at least one of $R^{5a}$, $R^{5b}$, $R^{7a}$, $R^{7b}$, $R^{7c}$ and $R^{7d}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$ and $R^{7d}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ and $R^{7d}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another aspect, compounds of the formula (IIIA) are provided:

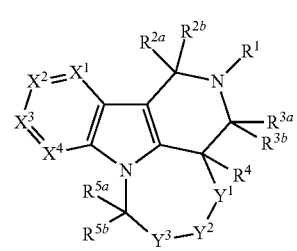

(IIIA)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7e}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In another aspect, compounds of the formula (IIIB) are provided:

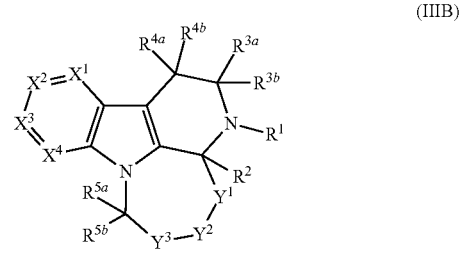

(IIIB)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—CH$_2$CH$_2$CH$_2$—) moiety, or R$^2$ and R$^{4a}$ are taken together to form a methylene (—CH$_2$—) moiety or an ethylene (—CH$_2$CH$_2$—) moiety, or R$^2$ and R$^{7a}$ are taken together to form a bond;

each R$^{3a}$ and R$^{3b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^2$ are taken together to form an ethylene (—CH$_2$CH$_2$—) moiety or a propylene (—CH$_2$CH$_2$CH$_2$—) moiety, or R$^{3a}$ and R$^{4a}$ are taken together to form a propylene (—CH$_2$CH$_2$CH$_2$—) moiety or a butylene (—CH$_2$CH$_2$CH$_2$CH$_2$—) moiety;

each R$^{4a}$ and R$^{4b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{4a}$ and R$^{4b}$ are taken together with the carbon to which they are attached to form a carbonyl moiety or a cycloalkyl moiety, or R$^{4a}$ and R$^1$ are taken together to form an ethylene (—CH$_2$—CH$_2$—) moiety or a propylene (—CH$_2$CH$_2$—CH$_2$—) moiety, or R$^{4a}$ and R$^2$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;

each R$^{5a}$ and R$^{5b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{5a}$ and R$^{5b}$ are taken together with the carbon to which they are attached to form a carbonyl moiety, or R$^{5a}$ and R$^{7e}$ are taken together to form a bond;

each X$^1$, X$^2$, X$^3$ and X$^4$ is independently N, CH or CR$^6$;

Y$^1$ is CR$^{7a}$R$^{7b}$, NR$^8$, O, S, S(O) or SO$_2$, provided that when Y$^1$ is NR$^8$, O, S, S(O) or SO$_2$, then Y$^2$ is CR$^{7c}$R$^{7d}$;

Y$^2$ is CR$^{7c}$R$^{7d}$, NR$^8$, O, S, S(O) or SO$_2$, provided that when Y$^2$ is NR$^8$, O, S, S(O) or SO$_2$, then Y$^1$ is CR$^{7a}$R$^{7b}$ and Y$^3$ is CR$^{7e}$R$^{7f}$;

Y$^3$ is CR$^{7e}$R$^{7f}$, NR$^8$, O, S, S(O) or SO$_2$, provided that when Y$^3$ is NR$^8$, O, S, S(O) or SO$_2$, then Y$^2$ is CR$^{7c}$R$^{7d}$;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{7a}$ and R$^{7b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7a}$ and R$^{7b}$ are taken together with the carbon to which they are attached to form a carbonyl moiety, or R$^{7a}$ and R$^{7c}$ are taken together to form a bond, or R$^{7a}$ and R$^2$ are taken together to form a bond;

each R$^{7c}$ and R$^{7d}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7c}$ and R$^{7d}$ are taken together with the carbon to which they are attached to form a carbonyl moiety, or R$^{7c}$ and R$^{7a}$ are taken together to form a bond, or R$^{7c}$ and R$^{7e}$ are taken together to form a bond;

each R$^{7e}$ and R$^{7f}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7e}$ and R$^{7f}$ are taken together with the carbon to which they are attached to form a carbonyl moiety, or R$^{7e}$ and R$^{7c}$ are taken together to form a bond, or R$^{7e}$ and R$^{5a}$ are taken together to form a bond; and each R$^8$ is independently H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IIIB), wherein R$^1$, R$^2$, R$^{3a}$, R$^{3b}$, R$^{4a}$, R$^{4b}$, R$^{5a}$, R$^{5b}$, X$^1$, X$^2$, X$^3$, X$^4$, Y$^1$, Y$^2$ and Y$^3$ are as defined for formula (IIB), provided that at least one of X$^1$, X$^2$, X$^3$ and X$^4$ is N or CR$^6$.

In another variation, the compound is of the formula (IIIB), wherein R$^1$, R$^2$, R$^{3a}$, R$^{3b}$, R$^{4a}$, R$^{4b}$, R$^{5a}$, R$^{5b}$, X$^1$, X$^2$, X$^3$, X$^4$, Y$^1$, Y$^2$ and Y$^3$ are as defined for formula (IIIB), provided that at least one of X$^1$, X$^2$, X$^3$ and X$^4$ is N or CR$^6$, and when Y$^1$ is CR$^{7a}$R$^{7b}$ and Y$^2$ is CR$^{7c}$R$^{7d}$, at least one of R$^{5a}$, R$^{5b}$, R$^{7a}$, R$^{7b}$, R$^{7c}$ and R$^{7d}$ is a group containing a cyclic moiety. In one such variation, at least one of R$^{5a}$, R$^{5b}$, R$^{7a}$, R$^{7b}$, R$^{7c}$ and R$^{7d}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$ and $R^{7d}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ and $R^{7d}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another variation, the compound is of the formula (IIIB), wherein $R^1$, $R^2$, $R^{3a}$ $R^{3b}$, $R^{4a}$, $R^{4b}$, $R^{5a}$, $R^{5b}$, $X^2$, $X^3$, $X^4$, $Y^1$, $Y^2$ and $Y^3$ are as defined for formula (IIIB), provided that at least one of $X^1$, $X^2$, $X^3$ and $X^4$ is N or $CR^6$, and when $Y^1$ is $CR^{7a}R^{7b}$, $Y^2$ is $CR^{7c}R^{7d}$ and $Y^3$ is $CR^{7e}R^{7f}$ at least one of $R^{5a}$, $R^{5b}$, $R^{7a}$, $R^{7b}$, $R^{7c}$, $R^{7d}$, $R^{7e}$ and $R^{7f}$ is a group containing a cyclic moiety. In one such variation, at least one of $R^{5a}$, $R^{5b}$, $R^{7a}$, $R^{7b}$, $R^{7c}$, $R^{7d}$, $R^{7e}$ and $R^{7f}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$, $R^{7d}$, $R^{7e}$ and $R^{7f}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$, $R^{7d}$, $R^{7e}$ and $R^{7f}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another aspect, compounds of the formula (IVA) are provided:

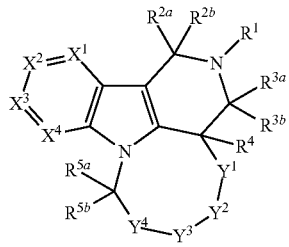

(IVA)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{1a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$ is $CR^{7g}R^{7h}$;

$Y^4$ is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$ are taken together to form a bond;

each $R^{7g}$ and $R^{7h}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In another aspect, compounds of the formula (IVB) are provided:

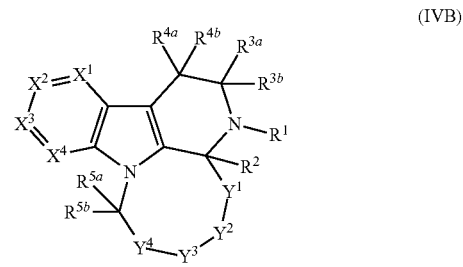

(IVB)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^2$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$—CH$_2$—) moiety or a propylene (—CH$_2$CH$_2$—CH$_2$—) moiety, or $R^{4a}$ and $R^2$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or SO$_2$, provided that when $Y^1$ is $NR^8$, O, S, S(O) or SO$_2$, then $Y^2$ is $CR^{7c}R^{7d}$;

$Y^2$ is $CR^{7c}R^{7d}$, $NR^8$, O, S, S(O) or SO$_2$, provided that when $Y^2$ is $NR^8$, O, S, S(O) or SO$_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or SO$_2$, provided that when $Y^3$ is $NR^8$, O, S, S(O) or SO$_2$, then $Y^2$ is $CR^{7c}R^{7d}$ and $Y^4$ is $CR^{7g}R^{7h}$;

$Y^4$ is $CR^{7g}R^{7h}$, $NR^8$, O, S, S(O) or SO$_2$, provided that when $Y^4$ is $NR^8$, O, S, S(O) or SO$_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7b}$ are taken together to form a bond, or $R^{7a}$ and $R^2$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$ are taken together to form a bond;

each $R^{7g}$ and $R^{7h}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IVB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1, Y^2, Y^3$ and $Y^4$ are as defined for formula (IVB), provided when $Y^1$ is $CR^{7a}R^{7b}$, $Y^2$ is $CR^{7c}R^{7d}$, $Y^3$ is $CR^{7e}R^{7f}$ and $Y^4$ is $CR^{7g}R^{7h}$ at least one of $R^{5a}, R^{5b}, R^{7a}, R^{7b}, R^{7c}, R^{7d}, R^{7e}, R^{7f}, R^{7g}$ and $R^{7h}$ is a group containing a cyclic moiety. In one such variation, at least one of $R^{5a}, R^{5b}, R^{7a}, R^{7b}, R^{7c}, R^{7d}, R^{7e}, R^{7f}, R^{7g}$ and $R^{7h}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}, R^{5b}, R^{7a}, R^{7b}, R^{7c}, R^{7d}, R^{7e}, R^{7f}, R^{7g}$ and $R^{7h}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}, R^{5b}, R^{7a}, R^{7b}, R^{7c}, R^{7d}, R^{7e}, R^{7f}, R^{7g}$ and $R^{7h}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another variation, the compound is of the formula (IVB), wherein $R^1, R^2, R^{3a}, R^{3b}, R^{4a}, R^{4b}, R^{5a}, R^{5b}, X^1, X^2, X^3, X^4, Y^1, Y^2, Y^3$ and $Y^4$ are as defined for formula (IVB), provided when $Y^1$ is $CR^{7a}R^{7b}$, $Y^2$ is $CR^{7c}R^{7d}$, $Y^3$ is $CR^{7e}R^{7f}$ and $Y^4$ is $CR^{7g}R^{7h}$ at least one of $X^1, X^2, X^3$ and $X^4$ is N or $CR^6$ and $R^{5a}$ and $R^{5b}$ are not taken together with the carbon to which they are attached to form a carbonyl moiety.

In another aspect, compounds of the formulae formula (J-1), (J-2), (J-3) and (J-4) are provided:

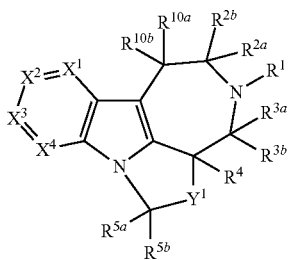
(J-1)

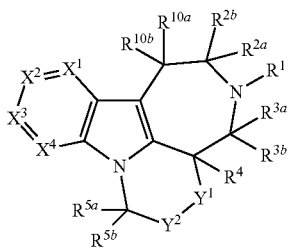
(J-2)

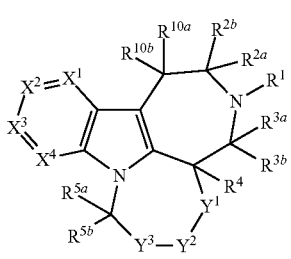
(J-3)

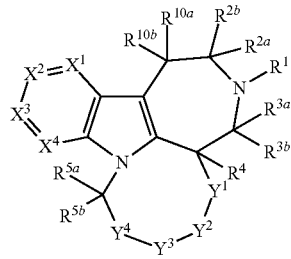
(J-4)

or a salt or solvate thereof, wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;
each $R^{2a}$ and $R^{2b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{2a}$ and $R^{2b}$ are taken together with the carbon to which they are attached to form a carbonyl moiety or a cycloalkyl moiety;
each $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{3a}$ and $R^{3b}$ are taken together with the carbon to which they are attached to form a carbonyl moiety or a cycloalkyl moiety;
$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;
each $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{10a}$ and $R^{10b}$ are taken together with the carbon to which they are attached to form a carbonyl moiety or a cycloalkyl moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or in formula (J-1) $R^{5a}$ and $R^{7a}$ are taken together to form a bond, or in formula (J-2) $R^{5a}$ and $R^{7c}$ are taken together to form a bond, or in formula (J-3) $R^{5a}$ and $R^{7e}$ are taken together to form a bond, or in formula (J-4) $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In another aspect, compounds of the formulae (K-1), (K-2), (K-3) and (K-4) are provided:

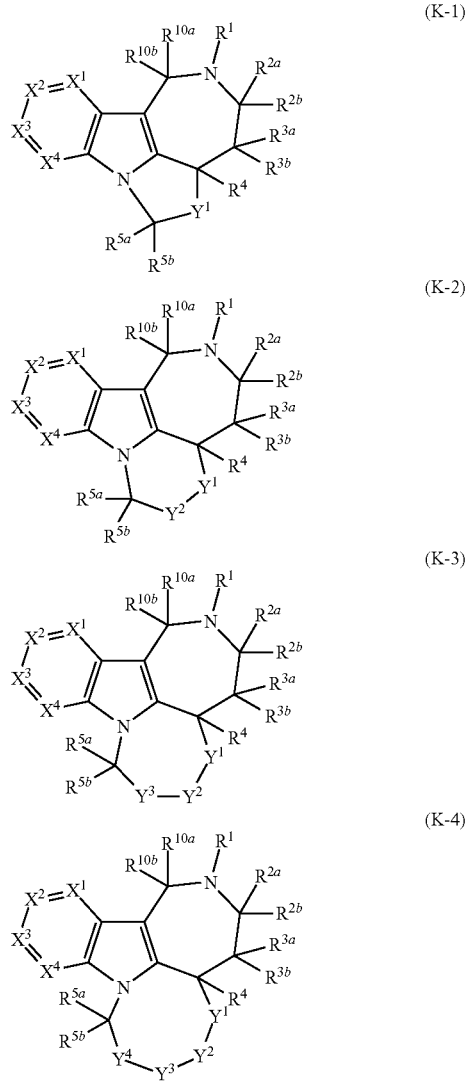

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{2a}$ and $R^{2b}$ are taken together with the carbon to which they are attached to form a carbonyl moiety or a cycloalkyl moiety;

each $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{3a}$ and $R^{3b}$ are taken together with the carbon to which they are attached to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;

each $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{10a}$ and $R^{10b}$ are taken together with the carbon to which they are attached to form a carbonyl moiety or a cycloalkyl moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or in formula (J-1) $R^{5a}$ and $R^{7a}$ are taken together to form a bond, or in formula (J-2) $R^{5a}$ and $R^{7c}$ are taken together to form a bond, or in formula (J-3) $R^{5a}$ and $R^{7e}$ are taken together to form a bond, or in formula (J-4) $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In another aspect, the invention provides a method of treating a cognitive disorder, psychotic disorder, neurotransmitter-mediated disorder or a neuronal disorder in an individual comprising administering to an individual in need thereof an effective amount of a compound of any formulae detailed herein, such as a compound of formulae (IA)-(VA), (IB)-(VB), (IA1)-(IA6), (IIA1)-(IIA6), (IIIA1)-(IIIA6), (IVA1)-(IVA6), (VA1), (VA2), (A1)-(A4), (B1)-(B2), (C1)-(C8), (D1)-(D4), (E1)-(E4), (F1)-(F7), (G1)-(G10), (H1)-(H2), (J-1)-(J-4), (J-1a)-(J-4-a), (K-1)-(K-4), or (K-1a)-(K-4-a).

The invention also includes all salts of compounds referred to herein, such as pharmaceutically acceptable salts. The invention also includes N-oxides of the tertiary amines where one or more tertiary amine moieties are present in the compounds described. The invention also includes any or all of the stereochemical forms, including any enantiomeric or diastereomeric forms and geometric isomers of the compounds described, or mixtures thereof. Unless stereochemistry is explicitly indicated in a chemical structure or name, the structure or name is intended to embrace all possible stereoisomers, including geometric isomers, of a compound depicted. Unless olefin geometry is explicitly indicated, substituted olefinic bonds may be present as cis or trans or (Z) or (E) isomeric forms, or as mixtures thereof. In addition, where a specific stereochemical form is depicted, it is understood that other stereochemical forms are also embraced by the invention. For example, where only a Z form of a compound is specifically listed, it is understood that the E form of the compound is also embraced. All forms of the compounds are also embraced by the invention, such as crystalline or non-crystalline forms of the compounds. Compositions comprising a compound of the invention are also intended, such as a composition of substantially pure compound, which in some embodiments is a specific stereochemical form, including a specific geometric isomer. Compositions comprising a mixture of compounds of the invention in any ratio are also embraced by the invention, including mixtures of two or more stereochemical forms of a compound of the invention in any ratio, such that racemic, non-racemic, enantio-enriched and scalemic mixtures of a compound are embraced, or mixtures thereof.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a cognitive disorder, psychotic disorder, neurotransmitter-mediated disorder or a neuronal disorder.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, schizophrenia, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least two of the following receptors are modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least three of the following receptors are modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, each of the following receptors is modulated: adrenergic receptor (e.g., $\alpha_{1D}$, $\alpha_{2A}$ and/or $\alpha_{2B}$), serotonin receptor (e.g., 5-$HT_{2A}$, 5-$HT_{2C}$, 5-$HT_6$ and/or 5-$HT_7$), dopamine receptor (e.g., $D_{2L}$) and histamine receptor (e.g., $H_1$, $H_2$ and/or $H_3$). In another variation, at least one of the following receptors is modulated: $\alpha_{1D}$, $\alpha_{2A}$, $\alpha_{1D}$, 5-$HT_{2A}$, 5-$HT_{2C}$, 5-$HT_6$, 5-$HT_7$, $D_{2L}$, $H_1$, $H_2$ and $H_3$. In another variation, at least one of the following receptors is modulated: $\alpha_{1D}$, $\alpha_{2A}$, $\alpha_{2B}$, 5-$HT_{2A}$, 5-$HT_{2C}$, 5-$HT_6$, 5-$HT_7$, $D_2$, $H_1$, $H_2$ and $H_3$. In another variation, at least two or three or four or five or six or seven or eight or nine or ten or eleven of the following receptors are modulated: $\alpha_{1D}$, $\alpha_{2A}$, $\alpha_{1D}$, 5-$HT_{2A}$, 5-$HT_{2C}$, 5-$HT_6$, 5-$HT_7$, $D_{2L}$, $H_1$, $H_2$ and $H_3$. In another variation, at least two or three or four or five or six or seven or eight or nine or ten or eleven of the following receptors are modulated: $\alpha_{1D}$, $\alpha_{2A}$, $\alpha_{2B}$, 5-$HT_{2A}$, 5-$HT_{2C}$, 5-$HT_6$, 5-$HT_7$, $D_2$, $H_1$, $H_2$ and $H_3$. In a particular variation, at least dopamine receptor $D_2$ is modulated. In still another variation, at least dopamine receptor $D_{2L}$ is modulated. In another particular variation, at least dopamine receptor $D_2$ and serotonin receptor 5-$HT_{2A}$ are modulated. In another particular variation, at least dopamine receptor $D_{2L}$ and serotonin receptor 5-$HT_{2A}$ are modulated. In a further particular variation, at least adrenergic receptors $\alpha_{1D}$, $\alpha_{2A}$, $\alpha_{2B}$ and serotonin receptor 5-$HT_6$ are modulated. In another particular variation, at least adrenergic receptors $\alpha_{1D}$, $\alpha_{2A}$, $\alpha_{2B}$, serotonin receptor 5-$HT_6$ and one or more of serotonin receptor 5-$HT_7$, 5-$HT_{2A}$, 5-$HT_{2C}$ and histamine receptor $H_1$ and $H_2$ are modulated. In a further particular variation, histamine receptor $H_1$ is modulated. In another variation, compounds of the invention exhibit any receptor modulation activity detailed herein and further stimulate neurite outgrowth and/or neurogenesis and/or enhance neurotrophic effects. In one variation, compounds detailed herein inhibit binding of a ligand to histamine receptor $H_1$ and/or $H_2$ by less than about 80% as determined by a suitable assay known in the art such as the assays described herein. In another variation, binding of a ligand to histamine receptor $H_1$ and/or $H_2$ is inhibited by less than about any of 75%, 70%, 65%, 60%, 55%, or 50% as determined by a suitable assay known in the art such as the assays described herein. In a further variation, compounds detailed herein: (a) inhibit binding of a ligand to histamine receptor $H_1$ and/or $H_2$ by less than about 80% (which can in different variations be less than about any of 75%, 70%, 65%, 60%, 55%, or 50%) as determined by a suitable assay known in the art such as the assays described herein and (b) inhibit binding of a ligand to dopamine receptor $D_{2L}$ by greater than about any of 80%, 85%, 90%, 95%, 100% or between about 85% and about 95% or between about 90% and about 100%, as determined in a suitable assay known in the art such as the assays described herein. In a further variation, compounds detailed herein: (a) inhibit binding of a ligand to histamine receptor $H_1$ and/or $H_2$ by less than about 80% (which can in different variations be less than about any of 75%, 70%, 65%, 60%, 55%, or 50%) as determined by a suitable assay known in the art such as the assays described herein and (b) inhibit binding of a ligand to a dopamine receptor $D_2$ by greater than about any of 80%, 85%, 90%, 95%, 100% or between about 85% and about 95% or between about 90% and about 100%, as determined in a suitable assay known in the art such as the assays described herein.

DETAILED DESCRIPTION OF THE INVENTION

Definitions

For use herein, unless clearly indicated otherwise, use of the terms "a", "an" and the like refers to one or more.

As used herein, reference to "about" a value or parameter herein includes (and describes) embodiments that are directed to that value or parameter per se. For example, description referring to "about X" includes description of "X".

As used herein, the term "aminergic G protein-coupled receptors" refers to a family of transmembrane proteins involved in cellular communication. Aminergic G protein coupled receptors are activated by biogenic amines and represent a subclass of the superfamily of G protein coupled receptors, which are structurally characterized by seven transmembrane helices. Aminergic G protein-coupled receptors include but are not limited to adrenergic receptors, serotonin receptors, dopamine receptors, histamine receptors and imidazoline receptors.

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an α1-adrenergic receptor (e.g., $\alpha_{1A}$, $\alpha_{1B}$ and/or $\alpha_{1D}$) and/or a α2-adrenergic receptor (e.g., $\alpha_{2A}$, $\alpha_{2B}$ and/or $\alpha_{2C}$) and/or reduces or eliminates or increases or enhances or mimics an activity of a $\alpha_1$-adrenergic receptor (e.g., $\alpha_{1A}$, $\alpha_{1B}$ and/or $\alpha_{1D}$) and/or a $\alpha_2$-adrenergic receptor (e.g., $\alpha_{2A}$, $\alpha_{2B}$ and/or $\alpha_{2C}$) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 ($D_1$) and/or a dopamine-2 ($D_2$) receptor or reduces or eliminates or increases or enhances or mimics an activity of a dopamine-1 ($D_1$) and/or a dopamine-2 ($D_2$) receptor in a reversible or irreversible manner. Dopamine $D_2$ receptors are divided into two categories, $D_{2L}$ and $D_{2S}$, which are formed from a single gene by differential splicing. $D_{2L}$ receptors have a longer intracellular domain than $D_{2S}$. In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a 5-$HT_{1A}$ and/or a 5-$HT_{1B}$ and/or a 5-$HT_{2A}$ and/or a 5-$HT_{2B}$ and/or a 5-$HT_{2C}$ and/or a 5-$HT_3$ and/or a 5-$HT_4$ and/or a 5-$HT_6$ and/or a 5-$HT_7$ receptor or reduces or eliminates or increases or enhances or mimics an activity of a 5-$HT_{1A}$ and/or a 5-$HT_{1B}$ and/or a 5-$HT_{2A}$ and/or a 5-$HT_{2B}$ and/or a 5-$HT_{2C}$ and/or a 5-$HT_3$ and/or a 5-$HT_4$ and/or a 5-$HT_6$ and/or a 5-$HT_7$ receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that binds to or inhibits binding of a ligand to a histamine receptor or reduces or eliminates or increases or enhances or mimics an activity of a histamine receptor. As such, a "histamine receptor modulator" encompasses both a histamine receptor antagonist and a histamine receptor agonist. In some embodiments, the histamine receptor modulator binds to or inhibits binding of a ligand to a histamine $H_1$ and/or $H_2$ and/or $H_3$ receptor or reduces or eliminates or increases or enhances or mimics an activity of a histamine $H_1$ and/or $H_2$ and/or $H_3$ receptor in a reversible or irreversible manner. In some embodiments, the histamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the histamine receptor modulator reduces an activity of a histamine receptor by at least about or about any of 10%, 20%, 30%, 40%, 50%, 60%, 70%, 80%, 90%, 95% or 100% as compared to the corresponding activity in the same subject prior to treatment with the histamine receptor modulator or compared to the corresponding activity in other subjects not receiving the histamine receptor modulator. In some embodiments, the histamine receptor modulator enhances an activity of a histamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the histamine receptor modulator or compared to the corresponding activity in other subjects not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to a human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining a beneficial or desired result, such as a clinical result. For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, a family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic, and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (A$\beta$), which is the cleavage product of beta amyloid precursor protein ($\beta$APP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. A$\beta$ appears to have a central role in the neuropathology of Alzheimer's disease. Familial forms of the disease have been linked to mutations in APP and the presenilin genes (Tanzi et al, Neurobiol. Dis. 3:159-168, 1996; Hardy, Ann. Med. 28:255-258, 1996). Diseased-linked mutations in these genes result in increased production of the 42-amino acid form of A$\beta$, the predominant form found in amyloid plaques. Mitochondrial dysfunction has also been reported to be an important component of Alzheimer's disease (Bubber et al, Mitochondrial abnormalities in Alzheimer brain: Mechanistic Implications, Ann. Neurol. 57(5):695-703, 2005; Wang et al, Insights into amyloid-$\beta$-induced mitochondrial dysfunction in Alzheimer disease, Free Radical Biology & Medicine 43:1569-1573, 2007; Swerdlow et al, Mitochondria in Alzheimer's disease, Int. Rev. Neurobiol. 53:341-385, 2002; and Reddy et al, Are mitochondria critical in the pathogenesis of Alzheimer's disease?, Brain Res Rev. 49(3):618-32, 2005). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntington protein; the mutated huntington protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" is used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg et al, Am. J. Psychiatry 139:1136-1139, 1982) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep et al, Neurobiol. Aging 15:85-90, 1994).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (e.g., battlefield injuries, including post-concussion syndrome, and the like), neurotoxic treatment (e.g., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (e.g., where a nerve or nerves have been torn or ripped) or spinal cord injury (e.g., damage to white matter or myelinated fiber tracts that carry sensation and motor signals to and from the brain). Spinal cord injury can occur from many causes, including physical trauma (e.g., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

"Cognitive impairment associated with schizophrenia" or "CIAS" includes neuropsychological deficits in attention, working memory, verbal learning, and problem solving. These deficits are believed to be linked to impairment in functional status (e.g., social behavior, work performance, and activities of daily living).

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein, attention-deficit hyperactivity disorder (ADHD) is the most common child neuropsychiatric condition present in school-aged children, affecting about 5-8% of this population. ADHD refers to a chronic disorder that initially manifests in childhood and is characterized by hyperactivity, impulsivity, and/or inattention. ADHD is characterized by persistent patterns of inattention and/or impulsivity-hyperactivity that are much more extreme than is observed in individuals at the same developmental level or stage. There is considerable evidence, from family and twin studies, that ADHD has a significant genetic component. This disorder is thought to be due to an interaction of environmental and genetic factors. ADHD includes all known types of ADHD. For example, *Diagnostic & Statistical Manual for Mental Disorders* (DSM-IV) identifies three subtypes of ADHD: (1) ADHD, Combined Type which is characterized by both inattention and hyperactivity-impulsivity symptoms; (2) ADHD, Predominantly Inattentive Type which is characterized by inattention but not hyperactivity-impulsivity symptoms; and (3) ADHD, Predominantly Hyperactive-Impulsive Type which is characterized by Hyperactivity-impulsivity but not inattention symptoms.

As used herein, attention-deficit disorder (ADD) refers to a disorder in processing neural stimuli that is characterized by distractibility and impulsivity that can result in inability to control behavior and can impair an individual's social, academic, or occupational function and development. ADD may be diagnosed by known methods, which may include observing behavior and diagnostic interview techniques.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and another compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, e.g., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, e.g., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. A pharmaceutically acceptable salt intends ionic interactions and not a covalent bond. As such, an N-oxide is not considered a salt. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al, Pharmaceutical Salts, J. Pharm. Sci. 66(1):1-19, 1977. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, isobutyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl").

Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—CH$_2$—), ethylene (—CH$_2$CH$_2$—), propylene (—CH$_2$CH$_2$CH$_2$—), butylene (—CH$_2$CH$_2$CH$_2$CH$_2$—) and the like.

"Alkenyl" refers to an unsaturated hydrocarbon group having at least one site of olefinic unsaturation (i.e., having at least one moiety of the formula C═C) and preferably having from 2 to 10 carbon atoms and more preferably 2 to 8 carbon atoms. Examples of alkenyl include but are not limited to —CH$_2$—CH═CH—CH$_3$ and —CH$_2$—CH$_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "C$_3$-C$_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula CC) and preferably having from 2 to 10 carbon atoms and more preferably 2 to 8 carbon atoms and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —C(O)$NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or $R_a$ and $R_b$ groups can be joined together with the nitrogen atom to form a heterocyclic or substituted heterocyclic ring.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, $R_a$ is H or alkyl.

"Aminosulfonyl" refers to the groups —$NRSO_2$-alkyl, —$NRSO_2$ substituted alkyl, —$NRSO_2$-alkenyl, —$NRSO_2$-substituted alkenyl, —$NRSO_2$-alkynyl, —$NRSO_2$-substituted alkynyl, —$NRSO_2$-cycloalkyl, —$NRSO_2$-substituted cycloalkyl, —$NRSO_2$-aryl, —$NRSO_2$-substituted aryl, —$NRSO_2$-heteroaryl, —$NRSO_2$-substituted heteroaryl, —$NRSO_2$-heterocyclic, and —$NRSO_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —$SO_2NH_2$, —$SO_2NR$-alkyl, —$SO_2NR$-substituted alkyl, —$SO_2NR$-alkenyl, —$SO_2NR$-substituted alkenyl, —$SO_2NR$-alkynyl, —$SO_2NR$-substituted alkynyl, —$SO_2NR$-aryl, —$SO_2NR$-substituted aryl, —$SO_2NR$-heteroaryl, —$SO_2NR$-substituted heteroaryl, —$SO_2NR$-heterocyclic, and —$SO_2NR$-substituted heterocyclic, where R is H or alkyl, or —$SO_2NR_2$, where the two R groups are taken together and with the nitrogen atom to which they are attached to form a heterocyclic or substituted heterocyclic ring.

"Sulfonyl" refers to the groups —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic.

"Aminocarbonylalkoxy" refers to the group —$NR_aC(O)OR_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Carbonylalkylenealkoxy" refers to the group —C(=O)—$(CH_2)_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Cyano" refers to the group —CN.

"Oxo" refers to the moiety =O.

"Nitro" refers to the group —$NO_2$.

"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

Compounds of the Invention

Compounds according to the invention are detailed herein, including in the Brief Summary of the Invention and elsewhere. The invention includes the use of all of the compounds described herein, including any and all stereoisomers, including geometric isomers (cis/trans or E/Z isomers), salts and solvates of the compounds described herein, as well as methods of making such compounds.

In one aspect, compounds of the formula (VA) are provided:

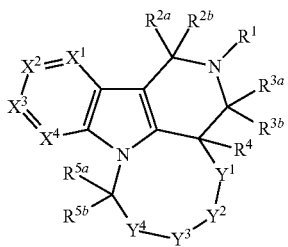

(VA)

or a salt or solvate thereof; wherein:

R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or R$^1$ and R$^{2a}$ are taken together to form a propylene (—CH$_2$CH$_2$CH$_2$—) moiety or a butylene (—CH$_2$CH$_2$CH$_2$CH$_2$—) moiety, or R$^1$ and R$^{3a}$ are taken together to form a propylene (—CH$_2$CH$_2$CH$_2$—) moiety or a butylene (—CH$_2$CH$_2$CH$_2$CH$_2$—) moiety, or R$^1$ and R$^4$ are taken together to form an ethylene (—CH$_2$CH$_2$—) moiety or a propylene (—CH$_2$CH$_2$CH$_2$—) moiety;

each R$^{2a}$ and R$^{2b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{2a}$ and R$^{2b}$ are taken together with the carbon to which they are attached to form a carbonyl moiety or a cycloalkyl moiety, or R$^{2a}$ and R$^1$ are taken together to form a propylene (—CH$_2$CH$_2$CH$_2$—) moiety or a butylene (—CH$_2$CH$_2$CH$_2$CH$_2$—) moiety, or R$^{2a}$ and R$^{3a}$ are taken together to form an ethylene (—CH$_2$—CH$_2$—) moiety or a propylene (—CH$_2$CH$_2$—CH$_2$—) moiety, or R$^{2a}$ and R$^4$ are taken together to form a methylene (—CH$_2$—) moiety or an ethylene (—CH$_2$CH$_2$—) moiety;

each R$^{3a}$ and R$^{3b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{3a}$ and R$^{3b}$ are taken together with the carbon to which they are attached to form a carbonyl moiety or a cycloalkyl moiety, or R$^{3a}$ and R$^1$ are taken together to form a propylene (—CH$_2$CH$_2$CH$_2$—) moiety or a butylene (—CH$_2$CH$_2$CH$_2$CH$_2$—) moiety, or R$^{3a}$ and R$^{2a}$ are taken together to form an ethylene (—CH$_2$CH$_2$—) moiety or a propylene (—CH$_2$CH$_2$CH$_2$—) moiety, or R$^{3a}$ and R$^4$ are taken together to form a propylene (—CH$_2$CH$_2$CH$_2$—) moiety or a butylene (—CH$_2$CH$_2$CH$_2$CH$_2$—) moiety;

R$^4$ is H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^4$ and R$^1$ are taken together to form an ethylene (—CH$_2$CH$_2$—) moiety or a propylene (—CH$_2$CH$_2$CH$_2$—) moiety, or R$^4$ and R$^{2a}$ are taken together to form a methylene (—CH$_2$—) moiety or an ethylene (—CH$_2$CH$_2$—) moiety, or R$^4$ and R$^{3a}$ are taken together to form a propylene (—CH$_2$CH$_2$CH$_2$—) moiety or a butylene (—CH$_2$CH$_2$CH$_2$CH$_2$—) moiety, or R$^4$ and R$^{7a}$ are taken together to form a bond;

each R$^{5a}$ and R$^{5b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or R$^{5a}$ and R$^{5b}$ are taken together with the carbon to which they are attached to form a carbonyl moiety, or R$^{5a}$ and a vicinal R$^{7(a-h)}$, where applicable, are taken together to form a bond;

each X$^1$, X$^2$, X$^3$ and X$^4$ is independently N, CH or CR$^6$;

Y$^1$ is CR$^{7a}$R$^{7b}$, NR$^8$, O, S, S(O) or SO$_2$, provided that when Y$^1$ is NR$^8$, O, S, S(O) or SO$_2$, then Y$^2$ is CR$^{7c}$R$^{7d}$ or is taken together with Y$^3$ and Y$^4$ to form a bond, Y$^2$ is CR$^{7c}$R$^{7d}$, NR$^8$, O, S, S(O) or SO$_2$, or Y$^2$ is taken together with Y$^3$ and Y$^4$ to form a bond (rendering the Y$^1$-containing ring a five-membered ring), provided that when $Y^2$ is $NR^8$, O, S, S(O) or $SO_2$, then $Y^1$ is $CR^{7a}R^{7b}$ and $Y^3$ is $CR^{7e}R^{7f}$ or is taken together with $Y^4$ to form a bond;

$Y^3$ is $CR^{7e}R^{7f}$, $NR^8$, O, S, S(O) or $SO_2$, or $Y^3$ is taken together with $Y^4$ to form a bond (rendering the $Y^1$-containing ring a six-membered ring), provided that when $Y^3$ is $NR^8$, O, S, S(O) or $SO_2$, then $Y^2$ is $CR^{7c}R^{7d}$ and $Y^4$ is $CR^{7g}R^{7h}$ or a bond;

$Y^4$ is $CR^{7g}R^{7h}$, $NR^8$, O, S, S(O) or $SO_2$, or $Y^4$ is a bond (rendering the $Y^1$-containing ring a seven-membered ring), provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond;

each $R^{7c}$ and $R^{7d}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where applicable, are taken together to form a bond, or $R^{7c}$ and a vicinal $R^{5a}$, where applicable, are taken together to form a bond;

each $R^{7e}$ and $R^{7f}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, compounds of the formula (VA), and salts and solvates thereof, are embraced, provided that (1) at least one of $X^1$, $X^2$, $X^3$ and $X^4$ is CH or $CR^6$; and (2) when $Y^3$ is taken together with $Y^4$ to form a bond (rendering the $Y^1$-containing ring a six-membered ring), each $X^1$, $X^2$, $X^3$ and $X^4$ is CH, each $R^{2a}$, $R^{2b}$, $R^{3a}$, $R^{3b}$, $R^4$, $R^{5a}$ and $R^{5b}$ is H, $Y^1$ is $CR^{7a}R^{7b}$ where $R^{7a}$ and $R^{7b}$ are taken together with the carbon to which they are attached to form a carbonyl moiety and $Y^2$ is $CR^{7c}R^{7d}$ where $R^{7c}$ and $R^{7d}$ are each H, then $R^1$ is other than hydrogen.

In one aspect, compounds of the formula (VB) are provided:

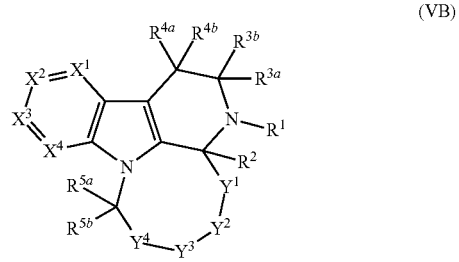

(VB)

or a salt or solvate thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2$—$CH_2$—) moiety or a propylene (—$CH_2CH_2$—$CH_2$—) moiety, or $R^{4a}$ and $R^2$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and a vicinal $R^{7(a-h)}$, where applicable, are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$ or is taken together with $Y^3$ and $Y^4$ to form a bond, $Y^2$ is $CR^{7c}R^{7d}$, $NR^8$, O, S, S(O) or $SO_2$, or $Y^2$ is taken together with $Y^3$ and $Y^4$ to form a bond (rendering the $Y^1$-containing ring a five-membered ring), provided that when $Y^2$ is $NR^8$, O, S, S(O) or $SO_2$, then $Y^1$ is $CR^{7a}R^{7b}$ and $Y^3$ is $CR^{7e}R^{7f}$ or is taken together with $Y^4$ to form a bond;

$Y^3$ is $CR^{7e}R^{7f}$, $NR^8$, O, S, S(O) or $SO_2$, or $Y^3$ is taken together with $Y^4$ to form a bond (rendering the $Y^1$-containing ring a six-membered ring), provided that when $Y^3$ is $NR^8$, O, S, S(O) or $SO_2$, then $Y^2$ is $CR^{7c}R^{7d}$ and $Y^4$ is $CR^{7g}R^{7h}$ or a bond;

$Y^4$ is $CR^{7g}R^{7h}$, $NR^8$, O, S, S(O) or $SO_2$, or $Y^4$ is a bond (rendering the $Y^1$-containing ring a seven-membered ring), provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^2$ are taken together to form a bond, or $R^{7a}$ and $R^{7c}$, where applicable, are taken together to form a bond, or $R^{7a}$ and a vicinal $R^{5a}$, where applicable, are taken together to form a bond;

each $R^{7c}$ and $R^{7d}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where applicable, are taken together to form a bond, or $R^{7c}$ and a vicinal $R^{5a}$, where applicable, are taken together to form a bond;

each $R^{7e}$ and $R^{7f}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, compounds of the formula (VB), and salts and solvates thereof, are embraced, provided that at least one of $X^1$, $X^2$, $X^3$ and $X^4$ is CH or $CR^6$ and provisions (A)-(D) apply:

(A) when $Y^2$ is taken together with $Y^3$ and $Y^4$ to form a bond (rendering the $Y^1$-containing ring a five-membered ring), provisions (1) and (2) apply:
  (1) when each $X^1$, $X^2$, $X^3$ and $X^4$ is CH, each $R^2$, $R^{3a}$, $R^{3b}$, $R^{4a}$ and $R^{4b}$ is H, $R^{5a}$ and $R^{5b}$ are taken together with the carbon to which they are attached to form a carbonyl moiety, and $Y^1$ is $CR^{7a}R^{7b}$ where one of $R^{7a}$ and $R^{7b}$ is ethyl and the other is hydrogen, $R^1$ is other than benzyl; and
  (ii) when each $X^1$, $X^2$ and $X^4$ is CH, $X^3$ is $CR^6$ where $R^6$ is methoxy, CH, each $R^2$, $R^{3a}$, $R^{3b}$, $R^{4a}$, $R^{4b}$, $R^{5a}$ and $R^{5b}$ is H, and $Y^1$ is $CR^{7a}R^{7b}$ where each $R^{7a}$ and $R^{7b}$ is methyl, $R^1$ is other than hydrogen;

(B) when $Y^3$ is taken together with $Y^4$ to form a bond (rendering the $Y^1$-containing ring a six-membered ring), provisions (3) and (4) apply:
  (3) when $Y^1$ is $CR^{7a}R^{7b}$ and is $Y^2$ is $CR^{7c}R^{7d}$, then at least one of $R^{5a}$, $R^{5b}$, $R^{7a}$, $R^{7b}$, $R^{7c}$ and $R^{7''}$ is a group containing a cyclic moiety; and
  (4) when $Y^1$ is $CR^{7a}R^{7b}$, $Y^2$ is $NR^8$, $R^{5a}$ and $R^{5b}$ are taken together with the carbon to which they are attached to form a carbonyl moiety, and each $R^2$, $R^{3a}$, $R^{3b}$, $R^{4a}$ and $R^{4b}$ is H, then at least one of $X^1$, $X^2$, $X^3$ and $X^4$ is N or $CR^6$;

(G) when $Y^4$ is a bond (rendering the $Y^1$-containing ring a seven-membered ring), then provisions (5)-(7) apply:
  (5) when $Y^1$ is $CR^{7a}R^{7b}$, $Y^2$ is $CR^{7c}R^{7d}$, $Y^3$ is $CR^{7e}R^{7f}$, and each of $X^1$, $X^2$, $X^3$ and $X^4$ is CH, then at least one of $R^{5a}$, $R^{5b}$, $R^{7a}$, $R^{7b}$, $R^{7c}$, $R^{7d}$, $R^{7e}$ and $R^{7f}$ is a substituted or unsubstituted aryl, substituted or unsubstituted heteroaryl, substituted or unsubstituted cycloalkyl, substituted or unsubstituted heterocyclyl, substituted or unsubstituted aralkyl, or a substituted $C_1$-$C_8$ alkyl wherein the substituted $C_1$-$C_8$ alkyl is substituted with at least one substituted or unsubstituted heteroaryl; $R^{3a}$, $R^{3b}$, $R^{4a}$
  (6) when $Y^1$ is $CR^{7a}R^{7b}$, $Y^2$ is $CR^{7c}R^{7d}$, $Y^3$ is $CR^{7e}R^{7f}$, each $R^2$, $R^{3a}$, $R^{3b}$, $R^{4a}$, and $R^{4b}$ is H, and at least one of $X^1$, $X^2$, $X^3$ and $X^4$ is N or $CR^6$, then at least one of $R^{5a}$, $R^{5b}$, $R^{7a}$, $R^{7b}$, $R^{7c}$, $R^{7d}$, $R^{7e}$ and $R^{7f}$ is a group containing a cyclic moiety; and
  (7) when $Y^1$ is $CR^{7a}R^{7b}$, $Y^2$ is $CR^{7c}R^{7d}$, $Y^3$ is $NR^8$, and each $R^2$, $R^{3a}$, $R^{3b}$, $R^{4a}$ and $R^{4b}$ is H, then at least one of $X^1$, $X^2$, $X^3$ and $X^4$ is N or $CR^6$, and $R^8$ is other than methyl; and (H) when $Y^1$ is $CR^{7a}R^{7b}$, $Y^2$ is $CR^{7c}R^{7d}$, $Y^3$ is $CR^{7e}R^{7f}$, $Y^4$ is $CR^{7g}R^{7h}$, and each $R^2$, $R^{3a}$, $R^{3b}$, $R^{4a}$ and $R^{4b}$ is H, then at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is hydroxyl, halo, cyano, substituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or is taken together with a vicinal $R^{7(a-h)}$, $R^{5a}$ or $R^2$ to form a bond.

In some embodiments, the compound is of the formula (VA) or (VB) wherein at least one of $X^1$, $X^2$, $X^3$ and $X^4$ is CH or $CR^6$, and at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is a substituted or unsubstituted aryl. In some embodiments, the substituted aryl is other than substituted phenyl. In some embodiments, the unsubstituted aryl is other than unsubstituted phenyl. Examples of aryl include, but are not limited to, phenyl, 1-naphthyl, 2-naphthyl, anthracenyl, phenanthracenyl, and the like. Examples of substituted aryl include, but are not limited to, fluorophenyl (e.g. 4-fluorophenyl), aminosulfonylphenyl, (e.g., 2-(aminosulfonyl)phenyl, 3-(aminosulfonyl)phenyl and 4-(aminosulfonyl)phenyl), methanesulfonylphenyl (e.g., 4-(methanesulfonyl)phenyl), pyridylphenyl (e.g., 4-(pyridine-4-yl)phenyl), and the like.

In some embodiments, the compound is of the formula (VA) or (VB) wherein at least one of $X^1$, $X^2$, $X^3$ and $X^4$ is CH or $CR^6$, and at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is a substituted or unsubstituted heteroaryl. Examples of unsubstituted heteroaryl include, but are not limited to, pyridyl (e.g., pyridin-2-yl, pyridin-3-yl and pyridine-4-yl), pyrimidyl (e.g., 5-pyrimidyl, 2-pyrimidyl, and 4-pyrimidyl), furanyl (e.g., furan-2-yl and furan-3-yl), thiophenyl (e.g., 2-thiophenyl and 3-thiophenyl), thiazolyl (e.g., 5-thiazolyl), pyrrolyl (e.g., pyrrol-2-yl and pyrrol-3-yl), and the like. Examples of substituted heteroaryl include, but are not limited to, methylpyridyl (e.g. 6-methylpyridin-3-yl, 2-methylpyridin-4-yl, 3-methylpyridin-4-yl), N-oxo-pyridyl, 2-methyl-1-oxo-pyridin-4-yl, 6-methyl-1-oxo-pyridin-3-yl, 2,6-dimethylpyridin-4-yl, pyridylpyridyl (e.g., 5-(pyridine-4-yl)pyridine-2-yl), 1-methylpyrrol-3-yl, 2-methlyfuran-3-yl, methylthiophenyl (e.g., 5-methylthiophen-2-yl, 3-methylthiophen-2-yl), pyridylthiophenyl (e.g., 4-(pyridine-4-yl)thiophen-3-yl), aminosulfonylthiophenyl, 2-aceylamido-5-thiazolyl, and the like.

In some embodiments, the compound is of the formula (VA) or (VB) wherein at least one of $X^1$, $X^2$, $X^3$ and $X^4$ is CH or $CR^6$, and at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is a substituted or unsubstituted aralkyl. In some embodiments, the aralkyl is a fused ring system where at least one cycloalkyl moiety is fused with at least one aryl moiety, and wherein the aralkyl group may be attached to the parent structure at either the aryl or the cycloalkyl residue. In some embodiments, the aralkyl group is an alkaryl such as a $C_1$-$C_3$ alkaryl (e.g., benzyl, 4-fluorobenzyl, 2-phenylethyl, and 2-phenyl-2-hydroxyethyl) and the like.

In some embodiments, the compound is of the formula (VA) or (VB) wherein at least one of $X^1$, $X^2$, $X^3$ and $X^4$ is CH or $CR^6$, and at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is a substituted $C_1$-$C_8$ alkyl wherein the substituted $C_1$-$C_8$ alkyl is substituted with at least one substituted or unsubstituted heteroaryl, such as pyridylalkyl (e.g., (pyridin-4-yl)methyl, (pyridin-4-yl)hydroxymethyl, (pyridin-3-yl)hydroxymethyl, 2-(6-methylpyridin-3-yl)ethyl, and 2-(6-methylpyridin-3-yl)-2-hydroxyethyl) and the like.

In some embodiments, the compound is of the formula (VA) or (VB) wherein at least one of $X^1$, $X^2$, $X^3$ and $X^4$ is CH or $CR^6$. In another variation, at least two of $X^1$, $X^2$, $X^3$ and $X^4$ is CH or $CR^6$. In another variation, at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In one variation, compounds of the formula (VA) have the structure (VA1):

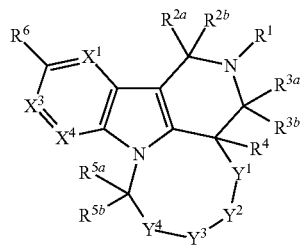

(VA1)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heteroaryl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene ($-CH_2CH_2CH_2-$) moiety or a butylene ($-CH_2CH_2CH_2CH_2-$) moiety, or $R^1$ and $R^{3a}$ are taken together to form a propylene ($-CH_2CH_2CH_2-$) moiety or a butylene ($-CH_2CH_2CH_2CH_2-$) moiety, or $R^1$ and $R^4$ are taken together to form an ethylene ($-CH_2CH_2-$) moiety or a propylene ($-CH_2CH_2CH_2-$) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene ($-CH_2CH_2CH_2-$) moiety or a butylene ($-CH_2CH_2CH_2CH_2-$) moiety, or $R^{2a}$ and $R^{3a}$ are taken together to form an ethylene ($-CH_2-CH_2-$) moiety or a propylene ($-CH_2CH_2-CH_2-$) moiety, or $R^{2a}$ and $R^4$ are taken together to form a methylene ($-CH_2-$) moiety or an ethylene ($-CH_2CH_2-$) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene ($-CH_2CH_2CH_2-$) moiety or a butylene ($-CH_2CH_2CH_2CH_2-$) moiety, or $R^{3a}$ and $R^{2a}$ are taken together to form an ethylene ($-CH_2CH_2-$) moiety or a propylene ($-CH_2CH_2CH_2-$) moiety, or $R^{3a}$ and $R^4$ are taken together to form a propylene ($-CH_2CH_2CH_2-$) moiety or a butylene ($-CH_2CH_2CH_2CH_2-$) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene ($-CH_2CH_2-$) moiety or a propylene ($-CH_2CH_2CH_2-$) moiety, or $R^4$ and $R^{2a}$ are taken together to form a methylene ($-CH_2-$) moiety or an ethylene ($-CH_2CH_2-$) moiety, or $R^4$ and $R^{3a}$ are taken together to form a propylene ($-CH_2CH_2CH_2-$) moiety or a butylene ($-CH_2CH_2CH_2CH_2-$) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, $-S(O)$-alkyl, $-S(O)$-aryl, $-S(O)$-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and a vicinal $R^{7(a-h)}$, where applicable, are taken together to form a bond;

each $X^1$, $X^3$ and $X^4$ is independently N or CH;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$ or is taken together with $Y^3$ and $Y^4$ to form a bond, $Y^2$ is $CR^{7c}R^{7d}$, $NR^8$, O, S, S(O) or $SO_2$, or $Y^2$ is taken together with $Y^3$ and $Y^4$ to form a bond (rendering the $Y^1$-containing ring a five-membered ring), provided that when $Y^2$ is $NR^8$, O, S, S(O) or $SO_2$, then $Y^1$ is $CR^{7a}R^{7b}$ and $Y^3$ is $CR^{7e}R^{7f}$ or is taken together with $Y^4$ to form a bond;

$Y^3$ is $CR^{7e}R^{7f}$, $NR^8$, O, S, S(O) or $SO_2$, or $Y^3$ is taken together with $Y^4$ to form a bond (rendering the $Y^1$-containing ring a six-membered ring), provided that when $Y^3$ is $NR^8$, O, S, S(O) or $SO_2$, then $Y^2$ is $CR^{7c}R^{7d}$ and $Y^4$ is $CR^{7g}R^{7h}$ or a bond;

$Y^4$ is $CR^{7g}R^{7h}$, $NR^8$, O, S, S(O) or $SO_2$, or $Y^4$ is a bond (rendering the $Y^1$-containing ring a seven-membered ring), provided that when $Y^4$ is $NR^8$, O, S, S(O) or $SO_2$, then $Y^3$ is $CR^{7e}R^{7f}$;

$R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond;

each $R^{7c}$ and $R^{7d}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where applicable, are taken together to form a bond, or $R^{7c}$ and a vicinal $R^{5a}$, where applicable, are taken together to form a bond;

each $R^{7e}$ and $R^{7f}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In another variation, compounds of the formula (VA) have the structure (VA2):

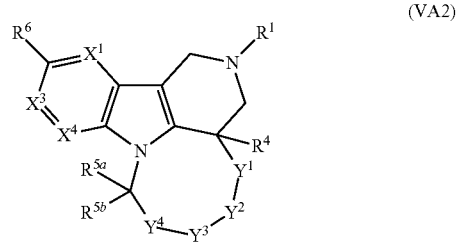

(VA2)

wherein:

$R^1$ is H or substituted or unsubstituted $C_1$-$C_8$ alkyl;

$R^4$ is H, substituted or unsubstituted $C_1$-$C_8$ alkyl, or is taken together with $R^{7a}$ to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and a vicinal $R^{7(a-h)}$, where applicable, are taken together to form a bond;

each $X^1$, $X^3$ and $X^4$ is independently N or CH;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$ or is taken together with $Y^3$ and $Y^4$ to form a bond, $Y^2$ is O or $CR^{7c}R^{7d}$, or $Y^2$ is taken together with $Y^3$ and $Y^4$ to form a bond (rendering the $Y^1$-containing ring a five-membered ring), provided that when $Y^2$ is O, then $Y^1$ is $CR^{7a}R^{7b}$ and $Y^3$ is $CR^{7e}R^{7f}$ or is taken together with $Y^4$ to form a bond;

$Y^3$ is O or $CR^{7e}R^{7f}$, or $Y^3$ is taken together with $Y^4$ to form a bond (rendering the $Y^1$-containing ring a six-membered ring), provided that when $Y^3$ is O, then $Y^2$ is $CR^{7c}R^{7d}$ and $Y^4$ is $CR^{7g}R^{7h}$ or a bond;

$Y^4$ is $CR^{7g}R^{7h}$, or $Y^4$ is a bond (rendering the $Y^1$-containing ring a seven-membered ring);

$R^6$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond;

each $R^{7c}$ and $R^{7d}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where applicable, are taken together to form a bond, or $R^{7c}$ and a vicinal $R^{5a}$, where applicable, are taken together to form a bond;

each $R^{7e}$ and $R^{7f}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In some variations, the compound is of the formula (VA2), or a salt or solvate thereof, where $R^4$ is H. In some variations, $R^4$ is unsubstituted alkyl (e.g., methyl). In some variations, $R^4$ is substituted alkyl. In some variations, the compound is of the formula (VA2), or a salt or solvate thereof, wherein each $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is independently H, hydroxyl, substituted or unsubstituted $C_1$-$C_8$ alkyl, substituted or unsubstituted aryl, substituted or unsubstituted heteroaryl, substituted or unsubstituted heterocyclyl, substituted or unsubstituted aralkyl, or acylamino, or $R^{5a}$ and $R^{5b}$ are taken together with the carbon to which they are attached to form a carbonyl moiety, or $R^{5a}$ and a vicinal $R^{7(a-h)}$, where applicable, are taken together to form a bond. In some of these variations, at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is a group containing a cyclic moiety, such as a substituted or unsubstituted aryl, a substituted or unsubstituted heteroaryl, a substituted or unsubstituted cycloalkyl, a substituted or unsubstituted heterocyclyl, a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl, or a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In some embodiments, the compound is of the formula (VA2), where $R^1$ is H or unsubstituted $C_1$-$C_8$ alkyl (e.g. methyl); $R^6$ is halo or unsubstituted $C_1$-$C_8$ alkyl (e.g. methyl); each $X^1$, $X^3$ and $X^4$ is independently CH or N; and:

(i) $Y^1$ is $CR^{7a}R^{7b}$, $Y^2$ is taken together with $Y^3$ and $Y^4$ to form a bond (rendering the $Y^1$-containing ring a five-membered ring), $R^{5a}$ and $R^{7a}$ are taken together to form a bond; $R^{5b}$ is H or unsubstituted $C_1$-$C_8$ alkyl (e.g. methyl); $R^{7b}$ is a substituted or unsubstituted aryl or a 5- or 6-membered substituted or unsubstituted heteroaryl;

(ii) $Y^1$ is O, $NR^8$ or $CR^{7a}R^{7b}$, $Y^2$ is $CR^{7c}R^{7d}$, $Y^3$ is taken together with $Y^4$ to form a bond (rendering the $Y^1$-containing ring a six-membered ring), $R^{5a}$ and $R^{7c}$ are taken together to form a bond; each $R^{5b}$, $R^{7a}$, $R^{7b}$ and $R^8$, where present, is independently H or unsubstituted $C_1$-$C_8$ alkyl (e.g. methyl); $R^{7d}$ is a substituted or unsubstituted aryl or a 5- or 6-membered substituted or unsubstituted heteroaryl; or (iii) $Y^1$ is O, $NR^8$ or $CR^{7a}R^{7b}$, $Y^2$ is O or $CR^{7c}R^{7d}$, $Y^3$ is $CR^{7e}R^{7f}$, $Y^4$ is a bond (rendering the $Y^1$-containing ring a seven-membered ring), $R^{5a}$ and $R^{7e}$ are taken together to form a bond; each $R^{5b}$, $R^{7a}$, $R^{7b}$, $R^{7c}$, $R^{7d}$ and $R^8$, where present, is independently H or unsubstituted $C_1$-$C_8$ alkyl (e.g. methyl); $R^{7f}$ is a substituted or unsubstituted aryl or a 5- or 6-membered substituted or unsubstituted heteroaryl.

In some embodiments, the compound is of the formula (VA2), where $R^1$ is H or unsubstituted $C_1$-$C_8$ alkyl (e.g. methyl); $R^6$ is halo or unsubstituted $C_1$-$C_8$ alkyl (e.g. methyl); each $X^1$, $X^3$ and $X^4$ is independently CH or N; $R^{5a}$ is a substituted or unsubstituted aryl or a 5- or 6-membered substituted or unsubstituted heteroaryl; and:

(i) $Y^1$ is O, $NR^8$ or $CR^{7a}R^{7b}$, $Y^2$ is taken together with $Y^3$ and $Y^4$ to form a bond (rendering the $Y^1$-containing ring a five-membered ring), each $R^{5b}$, $R^{7a}$, $R^{7b}$ and $R^8$, where present, is independently H or unsubstituted $C_1$-$C_8$ alkyl (e.g. methyl);

(ii) $Y^1$ is O, $NR^8$ or $CR^{7a}R^{7b}$, $Y^2$ is O or $CR^{7c}R^{7d}$, $Y^3$ is taken together with $Y^4$ to form a bond (rendering the $Y^1$-containing ring a six-membered ring), each $R^{5b}$, $R^{7a}$, $R^{7b}$, $R^{7c}$, $R^{7d}$ and $R^8$, where present, is independently H or unsubstituted $C_1$-$C_8$ alkyl (e.g. methyl); or (iii) $Y^1$ is O, $NR^8$ or $CR^{7a}R^{7b}$, $Y^2$ is O or $CR^{7c}R^{7d}$, $Y^3$ is O or $CR^{7e}R^{7f}$, $Y^4$ is a bond (rendering the $Y^1$-containing ring a seven-membered ring), each $R^{5b}$, $R^{7a}$, $R^{7b}$, $R^{7c}$, $R^{7d}$, $R^{7e}$, $R^{7f}$ and $R^8$, where present, is independently H or unsubstituted $C_1$-$C_8$ alkyl (e.g. methyl).

In one aspect, compounds of the formula (IA) are provided:

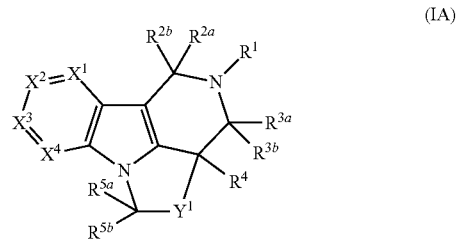

(IA)

or a salt or solvate thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7a}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{5a}$ are taken together to form a bond, or $R^{7a}$ and $R^4$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, provided is a compound of the formula (IA) where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In another aspect, compounds of the formula (IB) are provided:

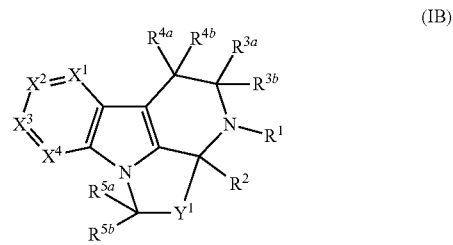

(IB)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2$—$CH_2$—) moiety or a propylene (—CH$_2$CH$_2$—CH$_2$—) moiety, or R$^{4a}$ and R$^2$ are taken together to form a methylene (—CH$_2$—) moiety or an ethylene (—CH$_2$CH$_2$—) moiety, or R$^{4a}$ and R$^{3a}$ are taken together to form a propylene (—CH$_2$CH$_2$CH$_2$—) moiety or a butylene (—CH$_2$CH$_2$CH$_2$CH$_2$—) moiety;

each R$^{5a}$ and R$^{5b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{5a}$ and R$^{5b}$ are taken together with the carbon to which they are attached to form a carbonyl moiety, or R$^{5a}$ and R$^{7a}$ are taken together to form a bond;

each X$^1$, X$^2$, X$^3$ and X$^4$ is independently N, CH or CR$^6$;
Y$^1$ is CR$^{7a}$R$^{7b}$, NR$^8$, O, S, S(O) or SO$_2$;
each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{7a}$ and R$^{7b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7a}$ and R$^{7b}$ are taken together with the carbon to which they are attached to form a carbonyl moiety, or R$^{7a}$ and R$^{5a}$ are taken together to form a bond, or R$^{7a}$ and R$^2$ are taken together to form a bond; and R$^8$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IB), provided that the compound is other than cis-4-ethyl-2,3,3a,4-tetrahydro-3-(phenylmethyl)benzo[b]pyrido[2,3,4-gh]pyrrolizin-5(1H)-one and 1,2,3,3a,4,5-hexahydro-8-methoxy-4,4-dimethylbenzo[b]pyrido[2,3,4-gh]pyrrolizine.

In another variation, the compound is of the formula (IB), provided that (i) when each X$^1$, X$^2$, X$^3$ and X$^4$ is CH, each R$^2$, R$^{3a}$, R$^{3b}$, R$^{4a}$ and R$^{4b}$ is H, R$^{5a}$ and R$^{5b}$ are taken together with the carbon to which they are attached to form a carbonyl moiety, and Y$^1$ is CR$^{7a}$R$^{7b}$ where one of R$^{7a}$ and R$^{7b}$ is ethyl and the other is hydrogen, R$^1$ is other than benzyl, and (ii) when each X$^1$, X$^2$ and X$^4$ is CH, X$^3$ is CR$^6$ where R$^6$ is methoxy, CH, each R$^2$, R$^{3a}$, R$^{3b}$, R$^{4a}$, R$^{4b}$, R$^{5a}$ and R$^{5b}$ is H, and Y$^1$ is CR$^{7a}$R$^{7b}$ where each R$^{7a}$ and R$^{7b}$ is methyl, R$^1$ is other than hydrogen.

In one variation, provided is a compound of the formula (IB) where at least one of X$^1$, X$^2$, X$^3$ and X$^4$ is N. In another variation, one of X$^1$, X$^2$, X$^3$ and X$^4$ is N. In one variation, X$^1$ is N and each X$^2$, X$^3$ and X$^4$ is independently CH or CR$^6$. In another variation, X$^2$ is N and each X$^1$, X$^3$ and X$^4$ is independently CH or CR$^6$. In yet another variation, X$^3$ is N and each X$^1$, X$^2$ and X$^4$ is independently CH or CR$^6$. In yet another variation, X$^4$ is N and each X$^1$, X$^2$ and X$^3$ is independently CH or CR$^6$. In another variation, two of X$^1$, X$^2$, X$^3$ and X$^4$ is N. In one variation, each X$^1$ and X$^3$ is N, and X$^2$ and X$^4$ is independently CH or CR$^6$. In another variation, each X$^2$ and X$^4$ is N, and X$^1$ and X$^3$ is independently CH or CR$^6$. In another variation, each X$^1$ and X$^4$ is N, and X$^2$ and X$^3$ is independently CH or CR$^6$.

In another aspect, compounds of the formula (IIA) are provided:

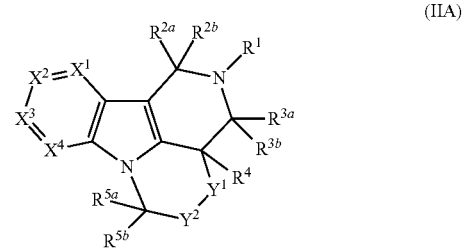

(IIA)

or a salt or solvate thereof;
wherein:

R$^1$ is H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or R$^1$ and R$^{2a}$ are taken together to form a propylene (—CH$_2$CH$_2$CH$_2$—) moiety or a butylene (—CH$_2$CH$_2$CH$_2$CH$_2$—) moiety, or R$^1$ and R$^{3a}$ are taken together to form a propylene (—CH$_2$CH$_2$CH$_2$—) moiety or a butylene (—CH$_2$CH$_2$CH$_2$CH$_2$—) moiety, or R$^1$ and R$^4$ are taken together to form an ethylene (—CH$_2$CH$_2$—) moiety or a propylene (—CH$_2$CH$_2$CH$_2$—) moiety;

each R$^{2a}$ and R$^{2b}$ is independently H, substituted or unsubstituted C$_1$-C$_8$ alkyl, halo, cyano, hydroxyl, alkoxy, nitro, substituted or unsubstituted amino, acyloxy, acylamino, aryl, heteroaryl, cycloalkyl, heterocyclyl, or R$^{2a}$ and R$^{2b}$ are taken together with the carbon to which they are attached to form a carbonyl moiety or a cycloalkyl moiety, or R$^{2a}$ and R$^1$ are taken together to form a propylene (—CH$_2$CH$_2$CH$_2$—) moiety or a butylene (—CH$_2$CH$_2$CH$_2$CH$_2$—) moiety, or R$^{2a}$ and R$^{3a}$ are taken together to form an ethylene (—CH$_2$—CH$_2$—) moiety or a propylene (—CH$_2$CH$_2$—CH$_2$—) moiety, or R$^{2a}$ and R$^4$ are taken together to form a methylene (—CH$_2$—) moiety or an ethylene (—CH$_2$CH$_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7c}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IIA), provided that the compound is other than 1,2,3,3a,5,6-hexahydro-4H-indolo[3,2,1-ij][1,6]naphthyridin-4-one.

In one variation, the compound is of the formula (IIA), provided that when each $X^1$, $X^2$, $X^3$ and $X^4$ is CH, each $R^{2a}$, $R^{2b}$, $R^{3a}$, $R^{3b}$, $R^4$, $R^{5a}$ and $R^{5b}$ is H, $Y^1$ is carbonyl and $Y^2$ is $CH_2$, $R^1$ is other than hydrogen.

In one variation, provided is a compound of the formula (IIA) where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In another aspect, compounds of the formula (IIB) are provided:

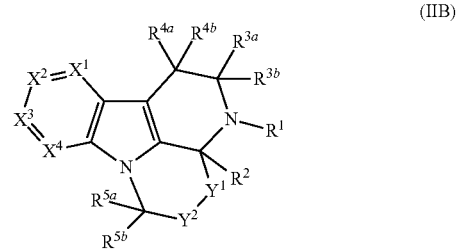

(IIB)

or a salt or solvate thereof;

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—$CH_2CH_2CH_2$—) moiety or a butylene (—$CH_2CH_2CH_2CH_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—$CH_2$—$CH_2$—) moiety or a propylene (—$CH_2CH_2$—$CH_2$—) moiety, or $R^{4a}$ and $R^2$ are taken together to form a methylene (—$CH_2$—) moiety or an ethylene (—$CH_2CH_2$—) moiety, or $R^{4a}$ and $R^{3a}$ are taken together to form a propylene (—$CH_2CH_2CH_2$—) moiety or a butylene (—$CH_2CH_2CH_2CH_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7c}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^2$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$ and $Y^2$ are as defined for formula (IIB), provided that at least one of $X^1$, $X^2$, $X^3$ and $X^4$ is N or $CR^6$.

In another variation, the compound is of the formula (IIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$ and $Y^2$ are as defined for formula (IIB), provided that at least one of $X^1$, $X^2$, $X^3$ and $X^4$ is N or $CR^6$, and when $Y^1$ is $CR^{7a}R^{7b}$ and $Y^2$ is $CR^{7c}R^{7d}$, at least one of $R^{5a}$, $R^{5b}$, $R^{7a}$, $R^{7b}$, $R^{7c}$ and $R^{7d}$ is a group containing a cyclic moiety. In one such variation, at least one of $R^{5a}$, $R^{5b}$, $R^{7a}$, $R^{7b}$, $R^{7c}$ and $R^{7d}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$ and $R^{7d}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ and $R^{7d}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In one variation, provided is a compound of the formula (IIB) where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In another aspect, compounds of the formula (IIIA) are provided:

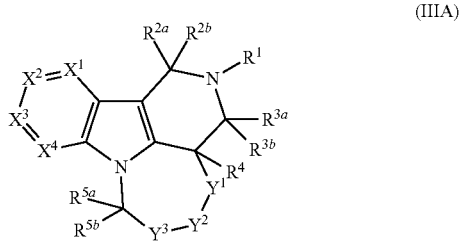

(IIIA)

or a salt or solvate thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{1a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7e}$ are taken together to form a bond;

each $X^1$, $X^2$, $X^3$ and $X^4$ is independently N, CH or $CR^6$;
$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;
$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$ is $CR^{7e}R^{7f}$;
$Y^3$ is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$;
each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, provided is a compound of the formula (IIIA) where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In another aspect, compounds of the formula (IIIB) are provided:

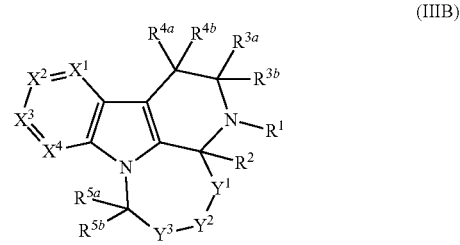

(IIIB)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—$CH_2CH_2CH_2$—) moiety or a butylene (—$CH_2CH_2CH_2CH_2$—) moiety, or $R^2$ and $R^{3a}$ are taken together to form an ethylene (—$CH_2CH_2$—) moiety or a propylene (—$CH_2CH_2CH_2$—) moiety, or $R^2$ and $R^{4a}$ are taken together to form a methylene (—$CH_2$—) moiety or an ethylene (—$CH_2CH_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^2$ are taken together to form an ethylene (—$CH_2CH_2$—) moiety or a propylene (—$CH_2CH_2CH_2$—) moiety, or $R^{3a}$ and $R^{4a}$ are taken together to form a propylene (—CH₂CH₂CH₂—) moiety or a butylene (—CH₂CH₂CH₂CH₂—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH₂—CH₂—) moiety or a propylene (—CH₂CH₂—CH₂—) moiety, or $R^{4a}$ and $R^2$ are taken together to form a methylene (—CH₂—) moiety or an ethylene (—CH₂CH₂—) moiety, or $R^{4a}$ and $R^{3a}$ are taken together to form a propylene (—CH₂CH₂CH₂—) moiety or a butylene (—CH₂CH₂CH₂CH₂—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7e}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^2$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IIIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$ and $Y^3$ are as defined for formula (IIB), provided that at least one of $X^1$, $X^2$, $X^3$ and $X^4$ is N or $CR^6$.

In another variation, the compound is of the formula (IIIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$ and $Y^3$ are as defined for formula (IIIB), provided that at least one of $X^1$, $X^2$, $X^3$ and $X^4$ is N or $CR^6$, and when $Y^1$ is $CR^{7a}R^{7b}$ and $Y^2$ is $CR^{7c}R^{7d}$, at least one of $R^{5a}$, $R^{5b}$, $R^{7a}$, $R^{7b}$, $R^{7c}$ and $R^{7d}$ is a group containing a cyclic moiety. In one such variation, at least one of $R^{5a}$, $R^{5b}$, $R^{7a}$, $R^{7b}$, $R^{7c}$ and $R^{7d}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$ and $R^{7d}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$ and $R^{7d}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another variation, the compound is of the formula (IIIB), wherein $R^1$, $R^2$, $R^{3a}$, $R^{3b}$, $R^{4a}$, $R^{4b}$, $R^{5a}$, $R^{5b}$, $X^1$, $X^2$, $X^3$, $X^4$, $Y^1$, $Y^2$ and $Y^3$ are as defined for formula (IIIB), provided that at least one of $X^1$, $X^2$, $X^3$ and $X^4$ is N or $CR^6$, and when $Y^1$ is $CR^{7a}R^{7b}$, $Y^2$ is $CR^{7c}R^{7d}$ and $Y^3$ is $CR^{7e}R^{7f}$ at least one of $R^{5a}$, $R^{5b}$, $R^{7a}$, $R^{7b}$, $R^{7c}$, $R^{7d}$, $R^{7e}$ and $R^{7f}$ is a group containing a cyclic moiety. In one such variation, at least one of $R^{5a}$, $R^{5b}$, $R^{7a}$, $R^{7b}$, $R^{7c}$, $R^{7d}$, $R^{7e}$ and $R^{7f}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of $R^{5a}$, $R^{5b}$, $R^{7a}$, $R^{7b}$, $R^{7c}$, $R^{7d}$, $R^{7e}$ and $R^{7f}$ is a $C_1$-$C_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of $R^{5a}$, $R^{5b}$, $R^{7a}$, $R^{7b}$, $R^{7c}$, $R^{7d}$, $R^{7e}$ and $R^{7f}$ is a $C_2$-$C_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In one variation, provided is a compound of the formula (IIIB) where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In another aspect, compounds of the formula (IVA) are provided:

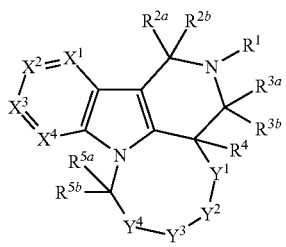

(IVA)

or a salt or solvate thereof;
wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$ is $CR^{7g}R^{7h}$;

$Y^4$ is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$ are taken together to form a bond;

each $R^{7g}$ and $R^{7h}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, provided is a compound of the formula (IVA) where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In another aspect, compounds of the formula (IVB) are provided:

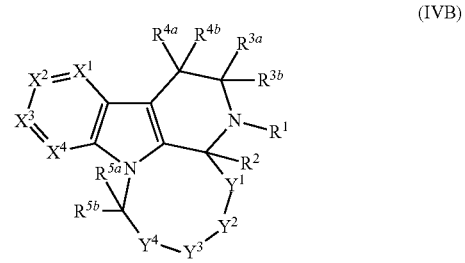

(IVB)

or a salt or solvate thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^2$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^{4a}$ are taken together to form an ethylene (—$CH_2CH_2$—) moiety or a propylene (—$CH_2CH_2CH_2$—) moiety;

$R^2$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^2$ and $R^1$ are taken together to form a propylene (—CH$_2$CH$_2$CH$_2$—) moiety or a butylene (—CH$_2$CH$_2$CH$_2$CH$_2$—) moiety, or $R^2$ and $R^{3a}$ are taken together to form an ethylene (—CH$_2$CH$_2$—) moiety or a propylene (—CH$_2$CH$_2$CH$_2$—) moiety, or $R^2$ and $R^{4a}$ are taken together to form a methylene (—CH$_2$—) moiety or an ethylene (—CH$_2$CH$_2$—) moiety, or $R^2$ and $R^{7a}$ are taken together to form a bond;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—CH$_2$CH$_2$CH$_2$—) moiety or a butylene (—CH$_2$CH$_2$CH$_2$CH$_2$—) moiety, or $R^{3a}$ and $R^2$ are taken together to form an ethylene (—CH$_2$CH$_2$—) moiety or a propylene (—CH$_2$CH$_2$CH$_2$—) moiety, or $R^{3a}$ and $R^{4a}$ are taken together to form a propylene (—CH$_2$CH$_2$CH$_2$—) moiety or a butylene (—CH$_2$CH$_2$CH$_2$CH$_2$—) moiety;

each $R^{4a}$ and $R^{4b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{4a}$ and $R^{4b}$ are taken together with the carbon to which they are attached to form a carbonyl moiety or a cycloalkyl moiety, or $R^{4a}$ and $R^1$ are taken together to form an ethylene (—CH$_2$—CH$_2$—) moiety or a propylene (—CH$_2$CH$_2$—CH$_2$—) moiety, or $R^{4a}$ and $R^2$ are taken together to form a methylene (—CH$_2$—) moiety or an ethylene (—CH$_2$CH$_2$—) moiety, or $R^{4a}$ and $R^{3a}$ are taken together to form a propylene (—CH$_2$CH$_2$CH$_2$—) moiety or a butylene (—CH$_2$CH$_2$CH$_2$CH$_2$—) moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or SO$_2$, provided that when $Y^1$ is $NR^8$, O, S, S(O) or SO$_2$, then $Y^2$ is $CR^{7c}R^{7d}$;

$Y^2$ is $CR^{7c}R^{7d}$, $NR^8$, O, S, S(O) or SO$_2$, provided that when $Y^2$ is $NR^8$, O, S, S(O) or SO$_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or SO$_2$, provided that when $Y^3$ is $NR^8$, O, S, S(O) or SO$_2$, then $Y^2$ is $CR^{7c}R^{7d}$ and $Y^4$ is $CR^{7g}R^{7h}$;

$Y^4$ is $CR^{7g}R^{7h}$, $NR^8$, O, S, S(O) or SO$_2$, provided that when $Y^4$ is $NR^8$, O, S, S(O) or SO$_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^2$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$ are taken together to form a bond;

each $R^{7g}$ and $R^{7h}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or R$^{7g}$ and R$^{7e}$ are taken together to form a bond, or R$^{7g}$ and R$^{5a}$ are taken together to form a bond; and each R$^8$ is independently H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

In one variation, the compound is of the formula (IVB), wherein R$^1$, R$^2$, R$^{3a}$, R$^{3b}$, R$^{4a}$, R$^{4b}$, R$^{5a}$, R$^{5b}$, X$^1$, X$^2$, X$^3$, X$^4$, Y$^1$, Y$^2$, Y$^3$ and Y$^4$ are as defined for formula (IVB), provided when Y$^1$ is CR$^{7a}$R$^{7b}$, Y$^2$ is CR$^{7c}$R$^{7d}$, Y$^3$ is CR$^{7e}$R$^{7f}$ and Y$^4$ is CR$^{7g}$R$^{7h}$ at least one of R$^{5a}$, R$^{5b}$, R$^{7a}$, R$^{7b}$, R$^{7c}$, R$^{7d}$, R$^{7e}$, R$^{7f}$, R$^{7g}$ and R$^{7h}$ is a group containing a cyclic moiety. In one such variation, at least one of R$^{5a}$, R$^{5b}$, R$^{7a}$, R$^{7b}$, R$^{7c}$, R$^{7d}$, R$^{7e}$, R$^{7f}$, R$^{7g}$ and R$^{7h}$ is selected from the group consisting of substituted or unsubstituted aryl, substituted or unsubstituted heteroaryl, substituted or unsubstituted cycloalkyl, and substituted or unsubstituted heterocyclyl. In another such variation, at least one of R$^{5a}$, R$^{5b}$, R$^{7a}$, R$^{7b}$, R$^{7c}$, R$^{7d}$, R$^{7e}$, R$^{7f}$, R$^{7g}$ and R$^{7h}$ is a C$_1$-C$_8$ alkyl substituted with a group selected from the group consisting of substituted or unsubstituted aryl, substituted or unsubstituted heteroaryl, substituted or unsubstituted cycloalkyl, and substituted or unsubstituted heterocyclyl. In yet another such variation, at least one of R$^{5a}$, R$^{5b}$, R$^{7a}$, R$^{7b}$, R$^{7c}$, R$^{7d}$, R$^{7e}$, R$^{7f}$, R$^{7g}$ and R$^{7h}$ is a C$_2$-C$_8$ alkenyl substituted with a group selected from the group consisting of substituted or unsubstituted aryl, substituted or unsubstituted heteroaryl, substituted or unsubstituted cycloalkyl, and substituted or unsubstituted heterocyclyl.

In another variation, the compound is of the formula (IVB), wherein R$^1$, R$^2$, R$^{3a}$, R$^{3b}$, R$^{4a}$, R$^{4b}$, R$^{5a}$, R$^{5b}$, X$^1$, X$^2$, X$^3$, X$^4$, Y$^1$, Y$^2$, Y$^3$ and Y$^4$ are as defined for formula (IVB), provided when Y$^1$ is CR$^{7a}$R$^{7b}$, Y$^2$ is CR$^{7c}$R$^{7d}$, Y$^3$ is CR$^{7e}$R$^{7f}$ and Y$^4$ is CR$^{7g}$R$^{7h}$ at least one of X$^1$, X$^2$, X$^3$ and X$^4$ is N or CR$^6$ and R$^{5a}$ and R$^{5b}$ are not taken together with the carbon to which they are attached to form a carbonyl moiety.

In one variation, provided is a compound of the formula (IVB) where at least one of X$^1$, X$^2$, X$^3$ and X$^4$ is N. In another variation, one of X$^1$, X$^2$, X$^3$ and X$^4$ is N. In one variation, X$^1$ is N and each X$^2$, X$^3$ and X$^4$ is independently CH or CR$^6$. In another variation, X$^2$ is N and each X$^1$, X$^3$ and X$^4$ is independently CH or CR$^6$. In yet another variation, X$^3$ is N and each X$^1$, X$^2$ and X$^4$ is independently CH or CR$^6$. In yet another variation, X$^4$ is N and each X$^1$, X$^2$ and X$^3$ is independently CH or CR$^6$. In another variation, two of X$^1$, X$^2$, X$^3$ and X$^4$ is N. In one variation, each X$^1$ and X$^3$ is N, and X$^2$ and X$^4$ is independently CH or CR$^6$. In another variation, each X$^2$ and X$^4$ is N, and X$^1$ and X$^3$ is independently CH or CR$^6$. In another variation, each X$^1$ and X$^4$ is N, and X$^2$ and X$^3$ is independently CH or CR$^6$.

In another aspect, the invention provides a method of treating a cognitive disorder, psychotic disorder, neurotransmitter-mediated disorder or a neuronal disorder in an individual comprising administering to an individual in need thereof an effective amount of any formulae detailed herein, such as a compound of formulae (IA)-(VA), (IB)-(VB), (IA1)-(IA6), (IIA1)-(IIA6), (IIIA1)-(IIIA6), (IVA1)-(IVA6), (VA1), (VA2), (A1)-(A4), (B1)-(B2), (C1)-(C8), (D1)-(D4), (E1)-(E4), (F1)-(F7), (G1)-(G10), (H1)-(H2), (J-1)-(J-4), (J-1a)-(J-4-a), (K-1)-(K-4), or (K-1a)-(K-4-a).

When at least one of R$^{5a}$, R$^{5b}$ and R$^{7a-h}$ is an unsubstituted or substituted heteroaryl, in one variation it is a heteroaryl containing an annular nitrogen atom. In one aspect, when at least one of R$^{5a}$, R$^{5b}$ and R$^{7a-h}$ is an unsubstituted or substituted heteroaryl the heteroaryl contains only nitrogen and carbon annular atoms. In a particular variation, at least one of R$^{5a}$, R$^{5b}$ and R$^{7a-h}$ is an unsubstituted pyridyl that may be bound to the respective R$^{5a}$, R$^{5b}$ or R$^{7a-h}$ at any available ring position. For example, in one variation of formulae (IA), (IB), (IIA), (IIB), (IIIA), (IIIB), (IVA), (IVA), (VA) or (VB), at least one of R$^{5a}$, R$^{5b}$ and R$^{7a-h}$ is 4-pyridyl, 3-pyridyl or 2-pyridyl. When at least one of R$^{5a}$, R$^{5b}$ and R$^{7a-h}$ is a substituted heteroaryl in one aspect it is a substituted pyridyl. When at least one of R$^{5a}$, R$^{5b}$ and R$^{7a-h}$ is a substituted pyridyl, the pyridyl may be substituted with one or more than one substituent and the substituted pyridyl may be bound to the parent structure at any available ring position. For example, in one variation of formulae (IA), (IB), (IIA), (IIB), (IIIA), (IIIB), (IVA), (IVA), (VA) or (VB), at least one of R$^{5a}$, R$^{5b}$ and R$^{7a-h}$ is a mono-substituted pyridyl where the substituent is a C$_1$-C$_8$ unsubstituted alkyl (e.g., methyl).

In another variation, the compound is of formulae (IA), (IB), (IIA), (IIB), (IIIA), (IIIB), (IVA), (IVA), (VA) or (VB) where at least one of R$^{5a}$, R$^{5b}$ and R$^{7a-h}$ is a di- or tri-substituted aryl, substituted heteroaryl, substituted or unsubstituted cycloalkyl, substituted or unsubstituted cycloalkenyl or substituted or unsubstituted heterocyclyl. In one aspect, the compound is of formulae (IA), (IB), (IIA), (IIB), (IIIA), (IIIB), (IVA), (IVA), (VA) or (VB) where at least one of R$^{5a}$, R$^{5b}$ and R$^{7a-h}$ is a di- or tri-substituted aryl. When at least one of R$^{5a}$, R$^{5b}$ and R$^{7a-h}$ is a di- or tri-substituted aryl, the substituents may be the same or different and may be located at any available position on the aryl ring. In one aspect, at least one of R$^{5a}$, R$^{5b}$ and R$^{7a-h}$ is a di- or tri-substituted phenyl (e.g., 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl and 2,4,6-trifluorophenyl). In another aspect, at least one of R$^{5a}$, R$^{5b}$ and R$^{7a-h}$ is a phenyl substituted with at least one chloro or methyl group (e.g., 4-chlorophenyl and 4-methylphenyl). In yet another aspect, the compound is of formulae (IA), (IB), (IIA), (IIB), (IIIA), (IIIB), (IVA), (IVA), (VA) or (VB) where at least one of R$^{5a}$, R$^{5b}$ and R$^{7a-h}$ is a substituted heteroaryl (e.g., where at least one of R$^{5a}$, R$^{5b}$ and R$^{7a-h}$ is 6-methyl-3-pyridyl, 6-trifluoromethyl-3-pyridyl, 5-trifluoromethyl-3-pyridyl or pyrimidinyl). In one aspect, at least one of R$^{5a}$, R$^{5b}$ and R$^{7a-h}$ is a substituted pyridyl such as 6-methyl-3-pyridyl, 6-trifluoromethyl-3-pyridyl and 5-trifluoromethyl-3-pyridyl.

In one variation, the compound is of formulae (IA), (IB), (IIA), (IIB), (IIIA), (IIIB), (IVA), (IVA), (VA) or (VB) where at least one of X$^1$-X$^4$ is CR$^6$ where R$^6$ is chloro. In such variation, X$^2$ is CR$^6$ where R$^6$ is chloro. In another variation, X$^2$ is CR$^6$, and X$^1$ and X$^3$ are each CH.

In specific variations, compounds of the formula (IA) have the structure:

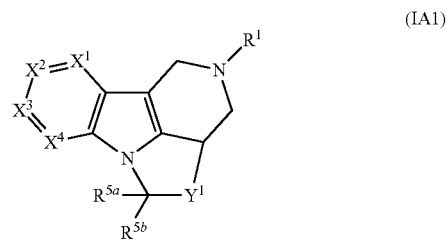

(IA1)

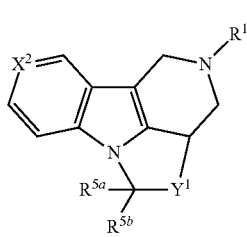

(IA2)

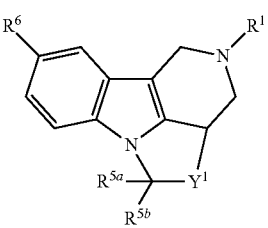

(IA3)

or a salt or solvate thereof; wherein $R^1$, $R^{5a}$, $R^{5b}$, $R^6$, $X^1$, $X^2$, $X^3$, $X^4$ and $Y^1$ are defined as for formula (IA) and, where applicable, any variation thereof detailed herein. That is, variations of formula (IA) detailed throughout, where applicable, apply to formulae (IA1)-(IA3) the same as if each and every variation were specifically and individually listed for formulae (IA1)-(IA3). Pharmaceutically acceptable salts of compounds of formulae (IA1)-(IA3) are also provided.

In some variations of formula (IA1), at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

In one variation of formula (IA2), $X^2$ is CH or $CR^6$ where $R^6$ is halo or substituted or unsubstituted $C_1$-$C_8$ alkyl. In a particular variation of formula (IA2), $X^2$ is $CR^6$ where $R^6$ is halo (e.g. chloro). In another particular variation of formula (IA2), $X^2$ is $CR^6$ where $R^6$ is unsubstituted $C_1$-$C_8$ alkyl (e.g. methyl). In a particular variation of formula (IA2), $X^2$ is CH. In further variations of formula (IA2), at least one of $R^{5a}$, $R^{5b}$ and $R^{7a-h}$ is a substituted or unsubstituted heteroaryl. In one variation, at least one of $R^{5a}$, $R^{5b}$ and $R^{7a-h}$ is an unsubstituted heteroaryl (e.g. 4-pyridyl or 4-pyrimidyl). In still further variations of formula (IA2), $X^2$ is CH or $CR^6$ where $R^6$ is halo or substituted or unsubstituted $C_1$-$C_8$ alkyl and at least one of $R^{5a}$, $R^{5b}$ and $R^{7a-h}$ is a substituted or unsubstituted heteroaryl. In one aspect of formula (IA2), $X^2$ is $CR^6$ where $R^6$ is a $C_1$-$C_8$ alkyl (e.g., methyl) and at least one of $R^{5a}$, $R^{5b}$ and $R^{7a-h}$ is a substituted or unsubstituted heteroaryl. In another aspect of formula (IA2), $X^2$ is $CR^6$ where $R^6$ is halo (e.g., chloro) and at least one of $R^{5a}$, $R^{5b}$ and $R^{7a-h}$ is a substituted or unsubstituted heteroaryl. In another aspect of formula (IA2), $X^2$ is CH and at least one of $R^{5a}$, $R^{5b}$ and $R^{7a-h}$ is a substituted or unsubstituted heteroaryl. In a further aspect of formula (IA2), $X^2$ is CH or $CR^6$ where $R^6$ is methyl or chloro and at least one of $R^{5a}$, $R^{5b}$ and $R^{7a-h}$ is 4-pyridyl.

In one variation, compounds of the formula (IA3) are provided, or a salt or solvate thereof, where $R^1$ is a substituted or unsubstituted $C_1$-$C_8$ alkyl; $R^6$ is halo, trifluoromethyl, a $C_1$-$C_8$ unsubstituted alkyl or a substituted amino; and at least one of $R^{5a}$, $R^{5b}$ and $R^{7a-h}$ is substituted aryl or a substituted or unsubstituted heteroaryl. In one variation of formula (IA3), $R^1$ is an unsubstituted $C_{1-8}$ alkyl or a $C_1$-$C_8$ alkyl substituted with a halo or hydroxyl group. In one such variation, $R^1$ is methyl, 2-haloethyl (e.g., 2-fluoroethyl), 2,2,2-trifluoroethyl, or a hydroxyl-substituted pentyl group. In a particular variation of formula (IA3), $R^1$ is —$CH_3$, —$CH_2CH_2F$, —$CH_2CF_3$, or —$CH_2CH_2C(CH_3)_2OH$. In another variation of formula (IA3), $R^6$ is halo, methyl, trifluoromethyl, or a substituted amino of the formula —N(H)($C_1$-$C_8$ unsubstituted alkyl). When $R^6$ is a halo (e.g., fluoro or chloro), in one aspect $R^6$ is chloro. In one variation of formula (IA3), $R^6$ is methyl or chloro. When $R^6$ is a substituted amino of the formula —N(H)($C_1$-$C_8$ unsubstituted alkyl), in one aspect $C_1$-$C_8$ unsubstituted alkyl is a linear $C_1$-$C_8$ unsubstituted alkyl such as methyl or ethyl. In a particular variation of formula (IA3), $R^6$ is —N(H)($CH_3$). It is understood that any $R^1$ for formula (IA3) may be combined with any $R^6$ of formula (IA3) the same as if each and every combination were specifically and individually listed. For example, compounds of the formula (IA3) are provided where $R^1$ is —$CH_3$, —$CH_2CH_2F$, —$CH_2CF_3$, or —$CH_2CH_2C(CH_3)_2OH$ and $R^6$ is chloro, fluoro, methyl, trifluoromethyl, or —N(H)($CH_3$). Likewise, compounds of the formula (IA3) are provided where $R^1$ is methyl and $R^6$ is halo, methyl or a substituted amino of the formula —N(H)($C_1$-$C_8$ unsubstituted alkyl). In one such aspect, compounds of the formula (IA3) are provided where $R^1$ is methyl and $R^6$ is halo or methyl. In one such aspect, compounds of the formula (IA3) are provided where $R^1$ is methyl and $R^6$ is halo (e.g., fluoro or chloro), trifluoromethyl, or methyl. When at least one of $R^{5a}$, $R^{5b}$ and $R^{7a-h}$ of formula (IA3) is a substituted aryl, in one aspect at least one of $R^{5a}$, $R^{5b}$ and $R^{7a-h}$ is a substituted phenyl. In one aspect, at least one of $R^{5a}$, $R^{5b}$ and $R^{7a-h}$ is a mono-substituted phenyl. In a particular aspect, at least one of $R^{5a}$, $R^{5b}$ and $R^{7a-h}$ of formula (IA3) is a halo-substituted phenyl, alkoxy-substituted phenyl or an acylamino-substituted phenyl. Thus, compounds of the formula (IA3) are provided where at least one of $R^{5a}$, $R^{5b}$ and $R^{7a-h}$ in one variation is a phenyl mono-substituted with a fluoro, $C_1$-$C_8$ alkoxy (e.g., methoxy), an acylamino moiety of the formula —C(O)NH($C_1$-$C_8$ unsubstituted alkyl) or an acylamino moiety of the formula —C(O)N($C_1$-$C_8$ unsubstituted alkyl)$_2$, such as 2-fluoro-phenyl, 4-fluoro-phenyl, 4-methoxy-phenyl, 4-(C(O)NH($CH_3$)) and 4-(C(O)N($CH_3$)$_2$)-phenyl. In one aspect, at least one of $R^{5a}$, $R^{5b}$ and $R^{7a-h}$ is a di-substituted phenyl. In one aspect, at least one of $R^{5a}$, $R^{5b}$ and $R^{7a-h}$ of formula (IA3) is a di-halo substituted phenyl group such as 3,4-difluoro-phenyl. In a particular aspect, at least one of $R^{5a}$, $R^{5b}$ and $R^{7a-h}$ of formula (IA3) is a phenyl group substituted with one halo group and one $C_1$-$C_8$ alkoxy group (e.g., methoxy). Thus, compounds of the formula (IA3) are provided where at least one of $R^{5a}$, $R^{5b}$ and $R^{7a-h}$ in one variation is a phenyl substituted with a fluoro and a $C_1$-$C_8$ alkoxy group, such as 3-fluoro-4-methoxy-phenyl. When at least one of $R^{5a}$, $R^{5b}$ and $R^{7a-h}$ of formula (IA3) is a substituted or unsubstituted heteroaryl, in one variation the substituted or unsubstituted heteroaryl is a pyridyl or pyrimidyl moiety. Thus, in one aspect of formula (IA3), at least one of $R^{5a}$, $R^{5b}$ and $R^{7a-h}$ is an unsubstituted pyridyl or pyrimidyl, such as 3-pyridyl, 4-pyridyl and 4-pyrimidyl. In another aspect of formula (IA3), at least one of $R^{5a}$, $R^{5b}$ and $R^{7a-h}$ is a substituted pyridyl, such as 6-methyl-3-pyridyl. It is understood that any $R^{5a}$, $R^{5b}$ or $R^{7a-h}$ for formula (IA3) may be combined with any $R^1$ and/or $R^6$ of formula (IA3) the same as if each and every combination were specifically and individually listed. For example, compounds of the formula (IA3) are provided where R[1] is —CH$_3$, —CH$_2$CH$_2$F, —CH$_2$CF$_3$, or —CH$_2$CH$_2$C(CH$_3$)$_2$OH; R[6] is chloro, fluoro, methyl, trifluoromethyl, or —N(H)(CH$_3$) and at least one of R[5a], R[5b] and R[7a-h] is 4-pyridyl, 3-pyridyl, 6-methyl-3-pyridyl, 6-pyrimidyl, 4-fluoro-phenyl, 4-methoxy-phenyl, 3-fluoro-4-methoxy-phenyl or 4-dimethylcarbamoyl-phenyl. Likewise, compounds of the formula (IA3) are provided where R[1] is methyl; R[6] is halo or methyl and at least one of R[5a], R[5b] and R[7a-h] is an unsubstituted pyridyl.

All variations referring to the formulae herein, such as formulae (IA), (IA1), (IA2), (IA3), where applicable, may apply equally to any of formulae (IB), (IIA), (IIB), (IIIA), (IIIB), (IVA), and (IVB), the same as if each and every variation were specifically and individually listed.

In specific variations, compounds of the formula (IA) have the structure:

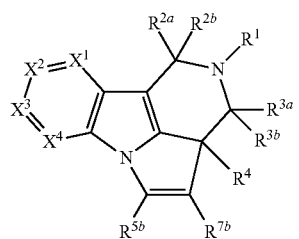

(IA4)

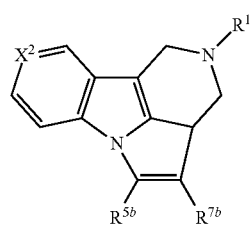

(IA5)

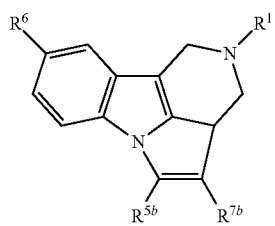

(IA6)

or a salt or solvate thereof; wherein R[1], R[2a], R[2b], R[3a], R[3b], R[4], R[5b], R[6], R[7b], X[1], X[2], X[3], and X[4], where applicable, are defined as for formula (IA). That is, variations of formula (IA) detailed throughout, where applicable, apply to formulae (IA4)-(IA6), the same as if each and every variation were specifically and individually listed for formulae (IA4)-(IA6). Pharmaceutically acceptable salts of compounds of formulae (IA4)-(IA6) are also provided.

In some variations of formula (IA4), at least one of X[1], X[2], X[3] and X[4] is N. In another variation, one of X[1], X[2], X[3] and X[4] is N. In one variation, X[1] is N and each X[2], X[3] and X[4] is independently CH or CR[6]. In another variation, X[2] is N and each X[1], X[3] and X[4] is independently CH or CR[6]. In yet another variation, X[3] is N and each X[1], X[2] and X[4] is independently CH or CR[6]. In yet another variation, X[4] is N and each X[1], X[2] and X[3] is independently CH or CR[6]. In another variation, two of X[1], X[2], X[3] and X[4] is N. In one variation, each X[1] and X[3] is N, and X[2] and X[4] is independently CH or CR[6]. In another variation, each X[2] and X[4] is N, and X[1] and X[3] is independently CH or CR[6]. In another variation, each X[1] and X[4] is N, and X[2] and X[3] is independently CH or CR[6].

All variations referring to the formulae herein, such as formulae (IA1)-(IA6), where applicable, may apply equally to any of formula (IB), the same as if each and every variation were specifically and individually listed.

In specific variations, compounds of the formula (IIA) have the structure:

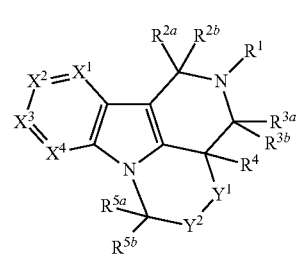

(IIA1)

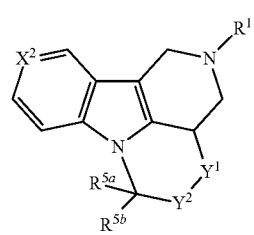

(IIA2)

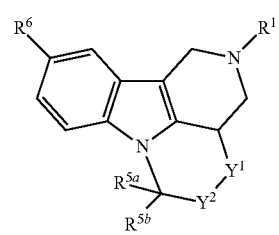

(IIA3)

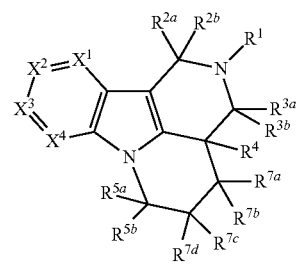

(IIA4)

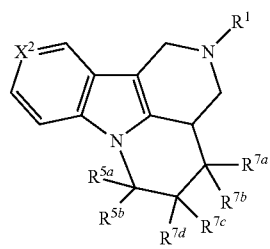

(IIA5)

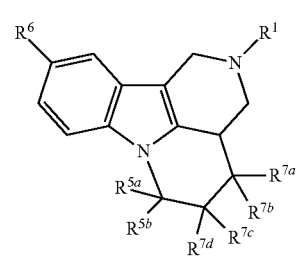

(IIA6)

or a salt or solvate thereof; wherein $R^1$, $R^{2a}$, $R^{2b}$, $R^{3a}$, $R^{3b}$, $R^4$, $R^{5a}$, $R^{5b}$, $R^6$, $R^{7a}$, $R^{7b}$, $R^{7c}$, $R^{7d}$, $X^1$, $X^2$, $X^3$, $X^4$, $Y^1$ and $Y^2$, where applicable, are defined as for formula (IIA). That is, variations of formula (IIA) detailed throughout, where applicable, apply to formulae (IIA1)-(IIA6), the same as if each and every variation were specifically and individually listed for formulae (IIA1)-(IIA6). In one aspect of this variation, $R^{7c}$ is taken together with either $R^{7a}$ or $R^{5a}$ to form a double bond. Pharmaceutically acceptable salts of compounds of the formula (IIA1)-(IIA6) are also provided.

In some variations of formula (IIA1) or (IIA4), at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

All variations referring to the formulae herein, such as formulae (IIA1)-(IIA6), where applicable, may apply equally to any of formulae (IIB), the same as if each and every variation were specifically and individually listed.

In specific variations, compounds of the formula (IIIA) have the structure:

(IIIA1)

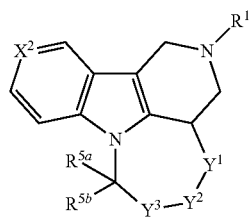

(IIIA2)

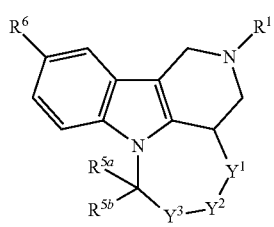

(IIIA3)

(IIIA4)

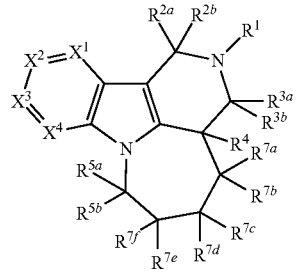

(IIIA5)

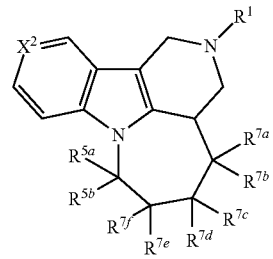

(IIIA6)

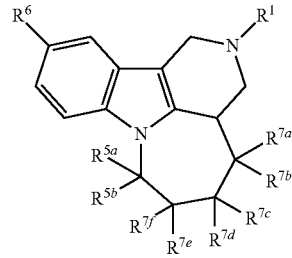

or a salt or solvate thereof; wherein $R^1$, $R^{2a}$, $R^{2b}$, $R^{3a}$, $R^{3b}$, $R^4$, $R^{5a}$, $R^{5b}$, $R^6$, $R^{7a}$, $R^{7b}$, $R^{7c}$, $R^{7d}$, $R^{7e}$, $R^{7f}$, $X^1$, $X^2$, $X^3$, $X^4$, $Y^1$, $Y^2$, and $Y^3$, where applicable, are defined as for formula (IIIA). That is, variations of formula (IIIA) detailed throughout, where applicable, apply to formulae (IIIA1)-(IIIA6), the same as if each and every variation were specifically and individually listed for formulae (IIIA1)-(IIIA6). In one aspect of this variation, $R^{7c}$ is taken together with either $R^{7a}$ or $R^{7e}$ to form a double bond. In another aspect, $R^{7e}$ is taken together with either $R^{7c}$ or $R^{5a}$ to form a double bond. In the aspects described above, more than one double bond may be present in the ring encompassed by the carbon atoms bearing $R^{7a-f}$ and $R^{5a-b}$, provided that no two double bonds are adjacent to each other. Pharmaceutically acceptable salts of compounds of formulae (IIIA1)-(IIIA6) are also provided.

In some variations of formula (IIIA1) or (IIIA4), at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

All variations referring to the formulae herein, such as formulae (IIIA1)-(IIIA6), where applicable, may apply equally to any of formulae (IIIB), the same as if each and every variation were specifically and individually listed.

In specific variations, compounds of the formula (IVA) have the structure:

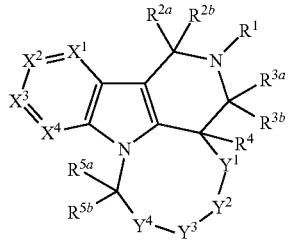
(IVA1)

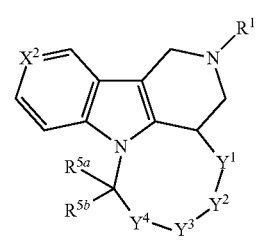
(IVA2)

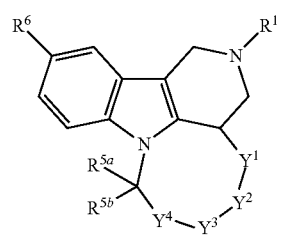
(IVA3)

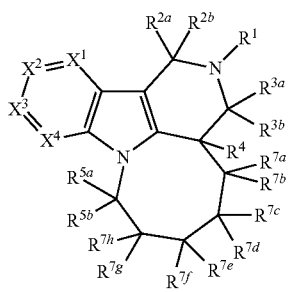
(IVA4)

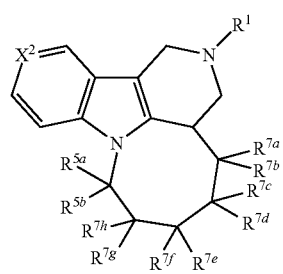
(IVA5)

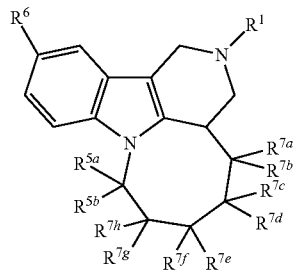
(IVA6)

or a salt or solvate thereof; wherein $R^1$, $R^{2a}$, $R^{2b}$, $R^{3a}$, $R^{3b}$, $R^4$, $R^{5a}$, $R^{5b}$, $R^6$, $R^{7a}$, $R^{7b}$, $R^{7c}$, $R^{7d}$, $R^{7e}$, $R^{7f}$, $R^{7g}$, $R^{7h}$, $X^1$, $X^2$, $X^3$, $X^4$, $Y^1$, $Y^2$, $Y^3$, and $Y^4$, where applicable, are defined as for formula (IVA). That is, variations of formula (IVA) detailed throughout, where applicable, apply to formulae (IVA1)-(IVA6), the same as if each and every variation were specifically and individually listed for formulae (IVA1)-(IVA6). In one aspect of this variation, $R^{7c}$ is taken together with either $R^{7a}$ or $R^{7e}$ to form a double bond. In another aspect, $R^{7e}$ is taken together with either $R^{7c}$ or $R^{7g}$ to form a double bond. In another aspect, $R^{7g}$ is taken together with either $R^{7e}$ or $R^{5a}$ to form a double bond. In the aspects described above, more than one double bond may be present in the ring encompassed by the carbon atoms bearing $R^{7a-h}$ and $R^{5a-b}$, provided that no two double bonds are adjacent to each other. Pharmaceutically acceptable salts of compounds of formulae (IVA1)-(IVA6) are also provided.

In some variations of formula (IVA1) or (IVA4), at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

All variations referring to the formulae herein, such as formulae (IVA1)-(IVA6), where applicable, may apply equally to any of formulae (IVB), the same as if each and every variation were specifically and individually listed.

In one variation, compounds of the formulae (IA)-(IVA) have the structure:

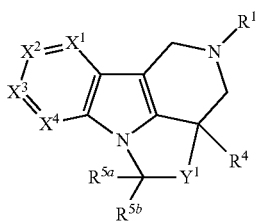
(A1)

-continued (A2)
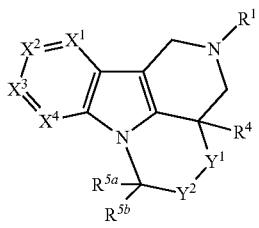

(A3)
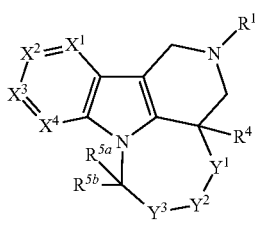

(A4)
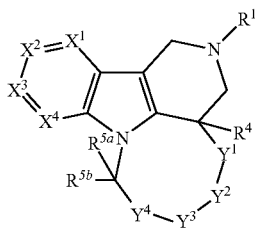

or a salt or solvate thereof; wherein $R^1$, $R^4$, $R^{5a}$, $R^{5b}$, $Y^1$, $Y^2$, $Y^3$ and $Y^4$, where present, are defined herein and, where applicable, any variation thereof detailed herein, and at least one of $X^1$, $X^2$, $X^3$ and $X^4$ is N. That is, variations of the formulae (IA)-(IVA) detailed throughout, where applicable, apply to formulae (A1)-(A4) the same as if each and every variation were specifically and individually listed for formulae (A1)-(A4). In one aspect of this variation, $X^4$ is N, and each of $X^1$, $X^2$ and $X^3$ is independently CH or $CR^6$, where $R^6$ is as defined herein. In another aspect of this variation, both $X^1$ and $X^3$ are N, and both $X^2$ and $X^4$ are $CR^6$, where $R^6$ is as defined herein. In another aspect of this variation, both $X^2$ and $X^4$ are N, and both $X^1$ and $X^3$ are $CR^6$, where $R^6$ is as defined herein. In another aspect of this variation, both $X^1$ and $X^4$ are N, and both $X^2$ and $X^3$ are $CR^6$, where $R^6$ is as defined herein. Pharmaceutically acceptable salts of compounds of formulae (A1)-(A4) are also provided.

All variations referring to the formulae (IA)-(IVA), such as formulae (A1)-(A4), where applicable, may apply equally to formulae (IB)-(IVB), the same as if each and every variation were specifically and individually listed.

In another variation, compounds of formulae (IA)-(IIA) have the structure:

(B1)
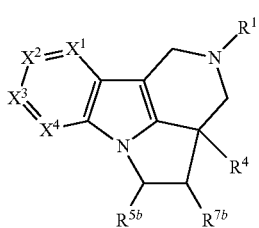

(B2)
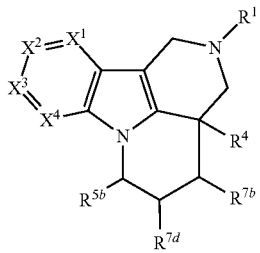

or a salt or solvate thereof; wherein $R^1$, $R^4$, $R^{5b}$, $R^{7b}$, $R^{7d}$, $X^1$, $X^2$, $X^3$ and $X^4$ are defined as for formulae (IA)-(IIA) and, where applicable, any variation thereof detailed herein. That is, variations of formulae (IA)-(IIA) detailed throughout, where applicable, apply to formulae (B1)-(B2) the same as if each and every variation were specifically and individually listed for formulae (B1)-(B2). In one aspect of this variation, $X^4$ is N, and each of $X^1$, $X^2$ and $X^3$ is independently CH or $CR^6$, where $R^6$ is as defined herein. In another aspect of this variation, both $X^1$ and $X^3$ are N, and each $X^2$ and $X^4$ is independently CH or $CR^6$, where $R^6$ is as defined herein. In another aspect of this variation, both $X^2$ and $X^4$ are N, and each $X^1$ and $X^3$ is independently CH or $CR^6$, where $R^6$ is as defined herein. In another aspect of this variation, both $X^1$ and $X^4$ are N, and each $X^2$ and $X^3$ is independently CH or $CR^6$, where $R^6$ is as defined herein. Pharmaceutically acceptable salts of compounds of formulae (B1)-(B2) are also provided.

In one variation, the compound is of formulae (B1)-(B2), where $R^4$ is H or a $C_1$-$C_8$ unsubstituted alkyl (e.g., methyl).

In another variation, the compound is of formula (B1), where $R^{5b}$ is a substituted or unsubstituted aryl, or substituted or unsubstituted heteroaryl, and $R^{7b}$ is H or acylamino. In another variation, the compound is of formula (B1), where $R^{5b}$ is H or acylamino, and $R^{7b}$ is a substituted or unsubstituted aryl, or substituted or unsubstituted heteroaryl.

In another variation, the compound is of formula (B2), where at least one of $R^{5b}$, $R^{7b}$ and $R^{7d}$ is a substituted or unsubstituted aryl, or substituted or unsubstituted heteroaryl. In another variation, the compound is of formula (B2), where one of $R^{5b}$, $R^{7b}$ and $R^{7d}$ is a substituted or unsubstituted aryl, or substituted or unsubstituted heteroaryl, and the other two of $R^{5b}$, $R^{7b}$ and $R^{7d}$ are independently H or acylamino. In another variation, the compound is of formula (B2), where two of $R^{5b}$, $R^{7b}$ and $R^{7d}$ are independently substituted or unsubstituted aryl, or substituted or unsubstituted heteroaryl, and the remaining $R^{5b}$, $R^{7b}$ and $R^{7d}$ is H or acylamino.

In another variation, the compound is of formulae (B1)-(B2), where at least one of $R^{5b}$, $R^{7b}$ and $R^{7d}$, where present, is a substituted or unsubstituted $C_1$-$C_8$ alkyl, substituted or unsubstituted aryl, or substituted or unsubstituted heteroaryl, substituted or unsubstituted cycloalkyl, substituted or unsubstituted heterocyclyl, substituted or unsubstituted aralkyl. The substituent $R^{5b}$, $R^{7b}$ or $R^{7d}$, may be linked to the parent structure at any position on the substituent, where chemically feasible. For example, an unsubstituted pyridyl may be attached at any position that is chemically feasible, e.g., to provide a 2-pyridyl, 3-pyridyl or 4-pyridyl moiety. Similarly, a substituted pyridyl may be substituted at any position that is chemically feasible and the moiety may be attached at any position that is chemically feasible. Taking a fluoropyridyl as an example, the fluoro group may be present on the pyridyl at any available position (e.g., to provide a 2-fluoropyridyl, 3-fluoropyridyl, 4-fluoropyridyl, 5-fluoropyridyl or 6-fluoropyridyl moiety) and the moiety may be attached to the parent structure at any available position (e.g., taking 2-fluoropyridyl as an example, to provide a 2-fluoro-3-pyryidyl or a 2-fluoro-4-pyridyl; taking 6-fluoropyridyl as an example, to provide 6-fluoro-2-pyridyl or a 6-fluoro-3-pyridyl). Examples of particular substituents include 4-fluorophenyl, 3-(N-methylacetamido)phenyl, pyridin-4-yl, 6-methylpyridin-3-yl, 6-trifluoromethylpyridin-3-yl, 2-carboxamidophenyl, 6-isopropylpyridin-3-yl, 3-sulfonamidophenyl, 2-methylsulfonylphenyl, 5-fluoropyridin-3-yl, 5-chloropyridin-3-yl, 5-methylthiophen-2-yl, 3-methylthiophen-2-yl, 4-methylthiophen-3-yl, furan-3-yl, thiazol-5-yl, (1H)-pyrazol-4-yl, 1-methyl-(1H)-pyrazol-4-yl, 1-methyl-(1H)-pyrazol-5-yl, 3,5-dimethylisoxazol-4-yl, 2-dimethylaminopyrimidin-5-yl, 4-acetamidophenyl, (1H)-indazol-4-yl, (1H)-benzimidazol-4-yl, naphthalen-1-yl, 1-methyl-(1H)-indol-6-yl, isoquinolin-5-yl, isoquinolin-3-yl, 1,2,3,4-tetrahydroquinolin-3-yl, 1,2,3,4-tetrahydroisoquinolin-7-yl, 1,2,3,4-tetrahydroisoquinolin-5-yl, benzo[b]thiophen-2-yl, 1-methyl-(1H)-pyrrol-2-yl, (piperidinamido)methyl, N-(pyridin-2-yl)aminomethyl, and N-(pyridin-3-yl)aminomethyl.

All variations referring to the formulae herein, such as formulae (B1)-(B2), where applicable, may apply equally to formula (IB)-(IIB), the same as if each and every variation were specifically and individually listed.

In another variation, compounds of formulae (IA)-(IVA) have the structure:

(C1)

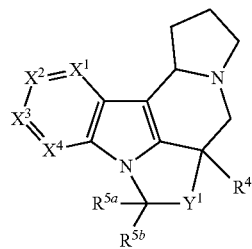

(C2)

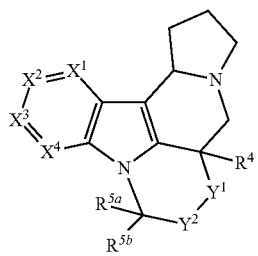

(C3)

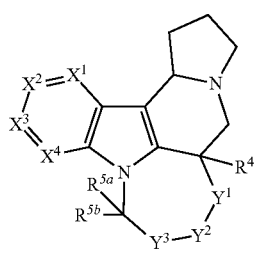

(C4)

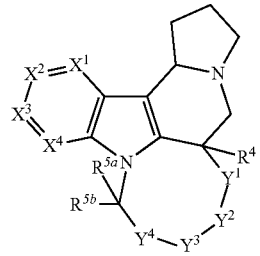

(C5)

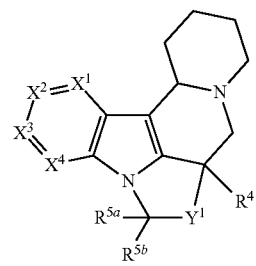

(C6)

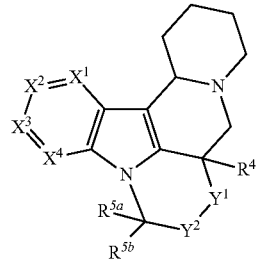

(C7)

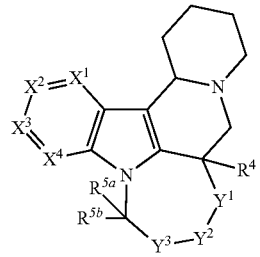

(C8)

or a salt or solvate thereof; wherein $R^4$, $R^{5a}$, $R^{5b}$, $X^1$, $X^2$, $X^3$, $X^4$, $Y^1$, $Y^2$, $Y^3$ and $Y^4$ are defined as for formulae (IA)-(IVA) and, where applicable, any variation thereof detailed herein. That is, variations of formulae (IA)-(IVA) detailed throughout, where applicable, apply to formulae (C1)-(C8) the same as if each and every variation were specifically and individually listed for formulae (C1)-(C8). In one aspect of this variation, $X^4$ is N, and each of $X^1$, $X^2$ and $X^3$ is independently CH or $CR^6$, where $R^6$ is as defined herein. In another aspect of this variation, both $X^1$ and $X^3$ are N, and each $X^2$ and $X^4$ is independently CH or $CR^6$, where $R^6$ is as defined herein. In another aspect of this variation, both $X^2$ and $X^4$ are N, and each $X^1$ and $X^3$ is independently CH or $CR^6$, where $R^6$ is as defined herein. In another aspect of this variation, both $X^1$ and $X^4$ are N, and each $X^2$ and $X^3$ is independently CH or $CR^6$, where $R^6$ is as defined herein. Pharmaceutically acceptable salts of compounds of formulae (C1)-(C8) are also provided.

All variations referring to the formulae (IA)-(IVA), such as formulae (C1)-(C8), where applicable, may apply equally to formulae (IB)-(IVB), the same as if each and every variation were specifically and individually listed.

In another variation, compounds of formulae (IA)-(IVA) have the structure:

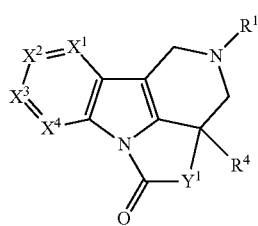

(D1)

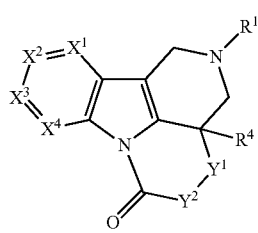

(D2)

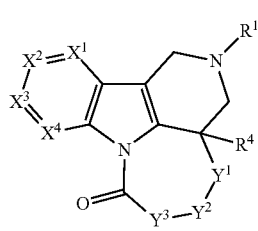

(D3)

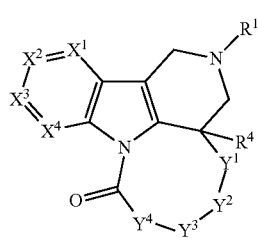

(D4)

or a salt or solvate thereof; wherein $R^4$, $X^1$, $X^2$, $X^3$, $X^4$, $Y^1$, $Y^2$, $Y^3$ and $Y^4$ are defined as for formulae (IA)-(IVA) and, where applicable, any variation thereof detailed herein. That is, variations of formulae (IA)-(IVA) detailed throughout, where applicable, apply to formulae (D1)-(D4) the same as if each and every variation were specifically and individually listed for formulae (D1)-(D4). In particular aspects of this variation, the substituents $Y^1$ of formula (D1), $Y^2$ of formula (D2), $Y^3$ of formula (D3) and $Y^4$ of formula (D4) above are each $NR^8$ wherein $R^8$ is substituted or unsubstituted aryl, or substituted or unsubstituted heteroaryl. In one aspect of this variation, $X^4$ is N, and each of $X^1$, $X^2$ and $X^3$ is independently CH or $CR^6$, where $R^6$ is as defined herein. In another aspect of this variation, both $X^1$ and $X^3$ are N, and each $X^2$ and $X^4$ is independently CH or $CR^6$, where $R^6$ is as defined herein. In another aspect of this variation, both $X^2$ and $X^4$ are N, and each $X^1$ and $X^3$ is independently CH or $CR^6$, where $R^6$ is as defined herein. In another aspect of this variation, both $X^1$ and $X^4$ are N, and each $X^2$ and $X^3$ is independently CH or $CR^6$, where $R^6$ is as defined herein. Pharmaceutically acceptable salts of compounds of formulae (D1)-(D4) are also provided.

In some variations, provided is a compound of any one of the formulae (A1)-(A4), (B1)-(B2), (C1)-(C8) and (D1)-(D4), where at least one of $X^1$, $X^2$, $X^3$ and $X^4$ is N. In another variation, one of $X^1$, $X^2$, $X^3$ and $X^4$ is N. In one variation, $X^1$ is N and each $X^2$, $X^3$ and $X^4$ is independently CH or $CR^6$. In another variation, $X^2$ is N and each $X^1$, $X^3$ and $X^4$ is independently CH or $CR^6$. In yet another variation, $X^3$ is N and each $X^1$, $X^2$ and $X^4$ is independently CH or $CR^6$. In yet another variation, $X^4$ is N and each $X^1$, $X^2$ and $X^3$ is independently CH or $CR^6$. In another variation, two of $X^1$, $X^2$, $X^3$ and $X^4$ is N. In one variation, each $X^1$ and $X^3$ is N, and $X^2$ and $X^4$ is independently CH or $CR^6$. In another variation, each $X^2$ and $X^4$ is N, and $X^1$ and $X^3$ is independently CH or $CR^6$. In another variation, each $X^1$ and $X^4$ is N, and $X^2$ and $X^3$ is independently CH or $CR^6$.

All variations referring to the formulae (IA)-(IVA), such as formulae (D1)-(D4), where applicable, may apply equally to formulae (IB)-(IVB), the same as if each and every variation were specifically and individually listed.

In a particular variation, compounds of formula (IA) have the structure:

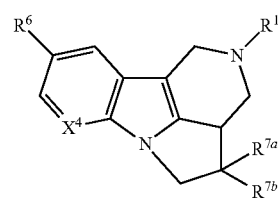

(E1)

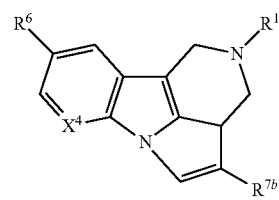

(E2)

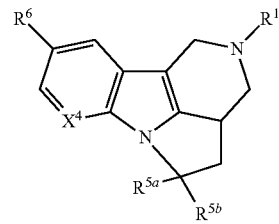

(E3)

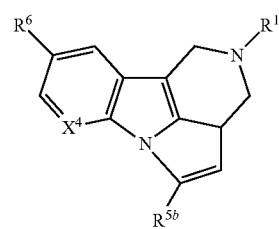

(E4)

or a salt or solvate thereof; wherein $R^1$, $R^{5a}$, $R^{5b}$, $R^6$, $R^{7a}$, $R^{7b}$ and $X^4$ are defined as for formula (IA) and, where applicable, any variation thereof detailed herein. That is, variations of formulae (IA) detailed throughout, where applicable, apply to formulae (E1)-(E4) the same as if each and every variation were specifically and individually listed for formulae (E1)-(E4). In particular aspects of this variation, the substituents $R^{7b}$ of formulae (E1)-(E2), and $R^{5b}$ of formulae (E3)-(E4) are each a substituted or unsubstituted aryl, or substituted or unsubstituted heteroaryl. In one particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In one particular aspect of this variation, $R^1$ and $R^6$ are methyl. Pharmaceutically acceptable salts of compounds of formulae (E1)-(E4) are also provided.

All variations referring to the formulae (IA), such as formulae (E1)-(E4), where applicable, may apply equally to formulae (IB), the same as if each and every variation were specifically and individually listed.

In a particular variation, compounds of formula (IIA) have the structure:

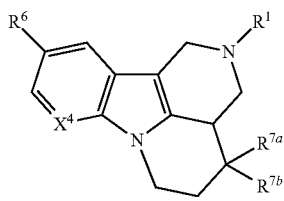

(F1)

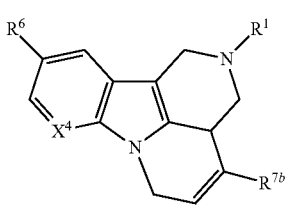

(F2)

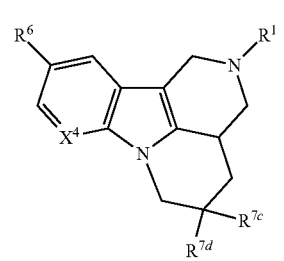

(F3)

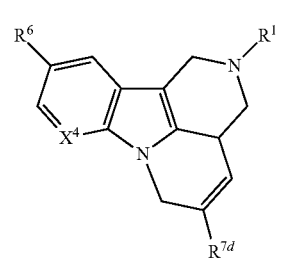

(F4)

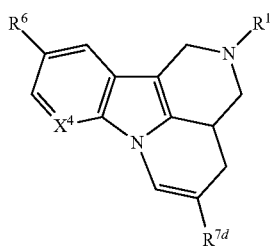

(F5)

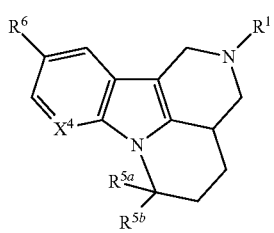

(F6)

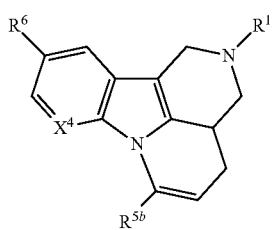

(F7)

or a salt or solvate thereof; wherein $R^1$, $R^{5a}$, $R^{5b}$, $R^6$, $R^{7a}$, $R^{7b}$, $R^{7c}$, $R^{7d}$ and $X^4$ are defined as for formula (IIA) and, where applicable, any variation thereof detailed herein. That is, variations of formulae (IIA) detailed throughout, where applicable, apply to formulae (F1)-(F7) the same as if each and every variation were specifically and individually listed for formulae (F1)-(F7). In particular aspects of this variation, the substituents $R^{7b}$ of formulae (F1)-(F2), $R^{7d}$ of formulae (F3)-(F5) and $R^{5b}$ of formulae (F6)-(F7) are each a substituted or unsubstituted aryl, or substituted or unsubstituted heteroaryl. In one particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In one particular aspect of this variation, $R^1$ and $R^6$ are methyl. Pharmaceutically acceptable salts of compounds of formulae (F1)-(F7) are also provided.

All variations referring to the formulae (IIA), such as formulae (F1)-(F7), where applicable, may apply equally to formulae (IIB), the same as if each and every variation were specifically and individually listed.

In a particular variation, compounds of formula (IIIA) have the structure:

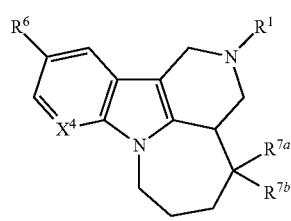

(G1)

(G2)
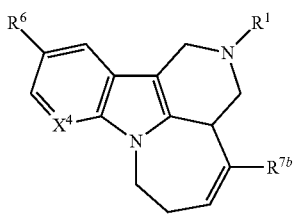

(G3)
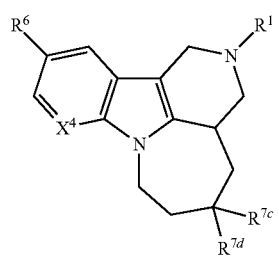

(G4)
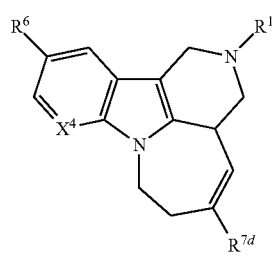

(G5)
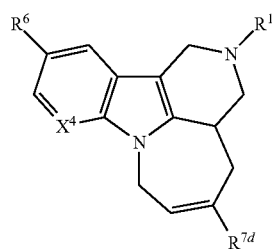

(G6)
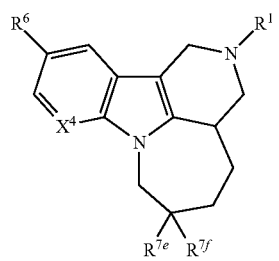

(G7)
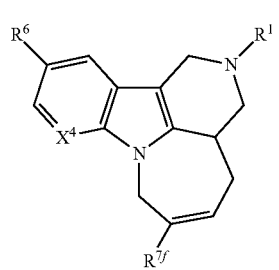

(G8)
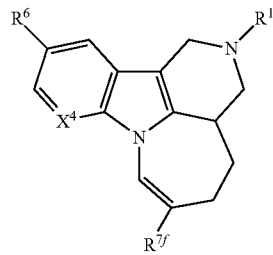

(G9)
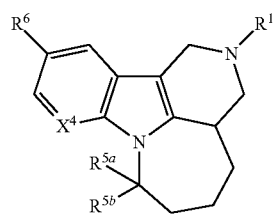

(G10)
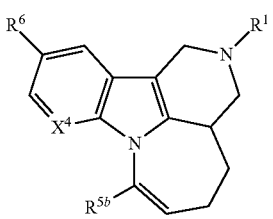

or a salt or solvate thereof; wherein $R^1$, $R^{5a}$, $R^{5b}$, $R^6$, $R^{7a}$, $R^{7b}$, $R^{7c}$, $R^{7d}$, $R^{7e}$, $R^{7f}$ and $X^4$ are defined as for formula (IIIA) and, where applicable, any variation thereof detailed herein. That is, variations of formulae (IIIA) detailed throughout, where applicable, apply to formulae (G1)-(G10) the same as if each and every variation were specifically and individually listed for formulae (G1)-(G10). In particular aspects of this variation, the substituents $R^{7b}$ of formulae (G1)-(G2), $R^{7d}$ of formulae (G3)-(G5), $R^{7f}$ of formulae (G6)-(G8), and $R^{5b}$ of formulae (G9)-(G10) are each a substituted or unsubstituted aryl, or substituted or unsubstituted heteroaryl. In one particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In one particular aspect of this variation, $R^1$ and $R^6$ are methyl. Pharmaceutically acceptable salts of compounds of formulae (G1)-(G10) are also provided.

All variations referring to the formulae (IIIA), such as formulae (G1)-(G10), where applicable, may apply equally to formulae (IIIB), the same as if each and every variation were specifically and individually listed.

In a particular variation, compounds of formula (IIA) have the structure:

(H1)
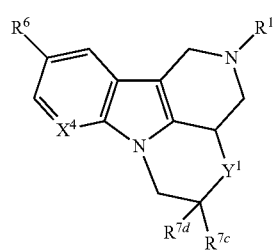

-continued (H2)

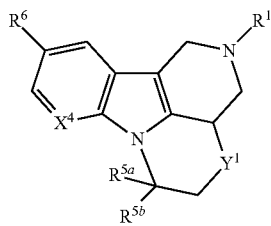

or a salt or solvate thereof; wherein $R^1$, $R^{5a}$, $R^{5b}$, $R^6$, $R^{7c}$, $R^{7d}$, $X^4$ and $Y^1$ are defined as for formula (IIA) and, where applicable, any variation thereof detailed herein. That is, variations of formulae (IIA) detailed throughout, where applicable, apply to formulae (H1)-(H2) the same as if each and every variation were specifically and individually listed for formulae (H1)-(H2). In particular aspects of this variation, $Y^1$ is $NR^8$, O, S, S(O) or $SO_2$, where $R^8$ is defined as for formula (IIA), and the substituents $R^{7d}$ of formula (H1) and $R^{5b}$ of formula (H2) are each a substituted or unsubstituted aryl, or substituted or unsubstituted heteroaryl. In one particular aspect of this variation, $X^4$ is N. In another particular aspect of this variation, $X^4$ is CH. In another aspect of this variation, $R^1$ and $R^6$ are each a substituted or unsubstituted $C_1$-$C_8$ alkyl. In one particular aspect of this variation, $R^1$ and $R^6$ are methyl. Pharmaceutically acceptable salts of compounds of formulae (H1)-(H2) are also provided.

All variations referring to the formulae (IIA), such as formulae (H1)-(H2), where applicable, may apply equally to formulae (IIB), the same as if each and every variation were specifically and individually listed.

The invention also embraces compounds of formulae (J-1) to (J-4):

(J-1)

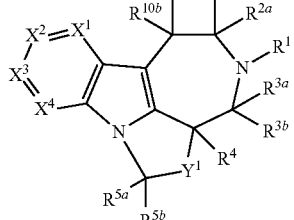

(J-2)

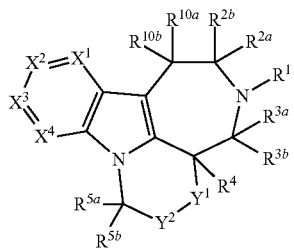

(J-3)

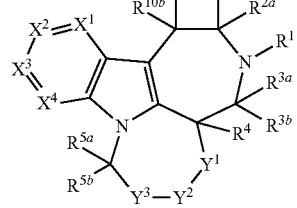

(J-4)

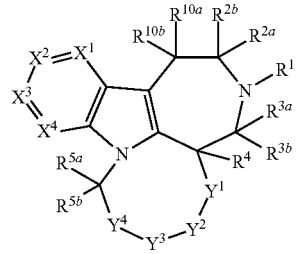

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{2a}$ and $R^{2b}$ are taken together with the carbon to which they are attached to form a carbonyl moiety or a cycloalkyl moiety;

each $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{3a}$ and $R^{3b}$ are taken together with the carbon to which they are attached to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;

each $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{10a}$ and $R^{10b}$ are taken together with the carbon to which they are attached to form a carbonyl moiety or a cycloalkyl moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or in formula (J-1) $R^{5a}$ and $R^{7a}$ are taken together to form a bond, or in formula (J-2) $R^{5a}$ and $R^{7c}$ are taken together to form a bond, or in formula (J-3) $R^{5a}$ and $R^{7e}$ are taken together to form a bond, or in formula (J-4) $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In a particular embodiment, compounds of formulae (J-1)-(J-4) are provided wherein the ring comprising $X^1$, $X^2$, $X^3$ and $X^4$ is a phenyl, pyridyl, pyrimidinyl or pyrazinyl ring, optionally substituted with 0-3 $R^6$ groups (i.e., $(R^6)_n$ where n is 0, 1, 2 or 3). In some such embodiments, n is 1, 2 or 3 and each $R^6$ is independently halo, methyl or $CF_3$.

In particular variation, compounds of formulae (J-1)-(J-4) have the structure:

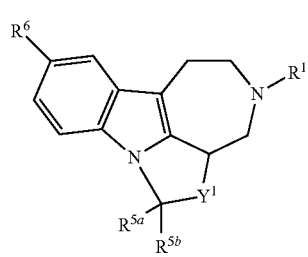
(J-1a)

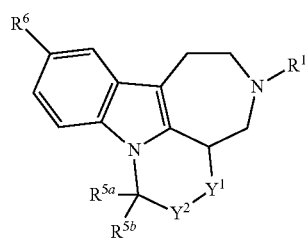
(J-2b)

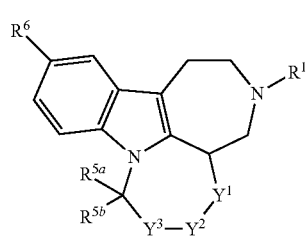
(J-3a)

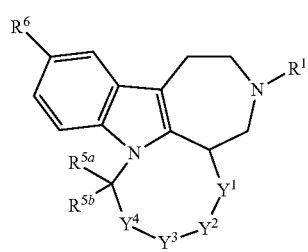
(J-4a)

or a salt or solvate thereof; wherein $R^1$, $R^{5a}$, $R^{5b}$, $R^6$, $Y^1$, $Y^2$, $Y^3$ and $Y^4$, where present, are defined as for formulae (J-1)-(J-4) and, where applicable, any variation thereof detailed herein. That is, variations of formulae (J-1)-(J-4) detailed throughout, where applicable, apply to formulae (J-1a)-(J-4a) the same as if each and every variation were specifically and individually listed for formulae (J-1a)-(J-4a). In one particular aspect of this variation, $R^{5b}$ is a substituted or unsubstituted aryl, or substituted or unsubstituted heteroaryl. In another particular aspect of this variation, $Y^1$ is $CR^{7a}R^{7b}$ wherein $R^{7b}$ is substituted or unsubstituted aryl, or substituted or unsubstituted heteroaryl. In another particular aspect of this variation, $Y^2$, where present, is $CR^{7c}R^{7d}$ wherein $R^{7d}$ is substituted or unsubstituted aryl, or substituted or unsubstituted heteroaryl. In another particular aspect of this variation, $Y^3$, where present, is $CR^{7e}R^{7f}$ wherein $R^{7f}$ is substituted or unsubstituted aryl, or substituted or unsubstituted heteroaryl. In another particular aspect of this variation, $Y^4$, where present, is $CR^{7g}R^{7h}$ wherein $R^{7h}$ is substituted or unsubstituted aryl, or substituted or unsubstituted heteroaryl. Pharmaceutically acceptable salts of compounds of formulae (J-1a)-(J-4a) are also provided.

The invention also embraces compounds of formulae (K-1) to (K-4):

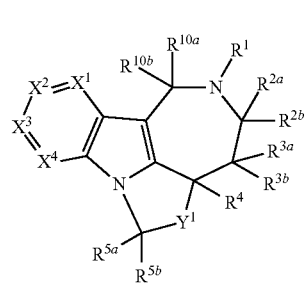
(K-1)

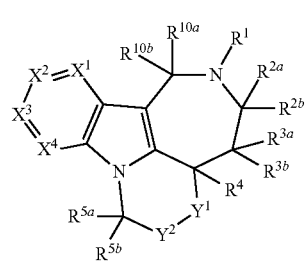
(K-2)

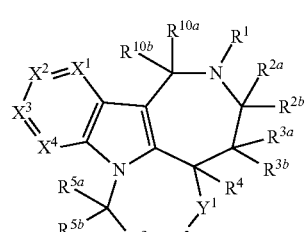
(K-3)

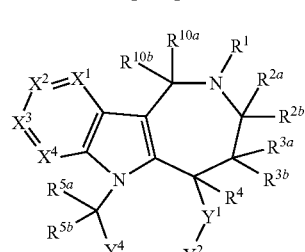
(K-4)

or a salt or solvate thereof, wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{2a}$ and $R^{2b}$ are taken together with the carbon to which they are attached to form a carbonyl moiety or a cycloalkyl moiety;

each $R^{3a}$ and $R^{3b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{3a}$ and $R^{3b}$ are taken together with the carbon to which they are attached to form a carbonyl moiety or a cycloalkyl moiety;

$R^4$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^4$ and $R^{7a}$ are taken together to form a bond;

each $R^{10a}$ and $R^{10b}$ is independently H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl, alkylsulfonylamino, or carbonylalkylenealkoxy, or $R^{10a}$ and $R^{10b}$ are taken together with the carbon to which they are attached to form a carbonyl moiety or a cycloalkyl moiety;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{5a}$ and $R^{5b}$ are taken together with the carbon to which they are attached to form a carbonyl moiety, or in formula (J-1) $R^{5a}$ and $R^{7a}$ are taken together to form a bond, or in formula (J-2) $R^{5a}$ and $R^{7c}$ are taken together to form a bond, or in formula (J-3) $R^{5a}$ and $R^{7e}$ are taken together to form a bond, or in formula (J-4) $R^{5a}$ and $R^{7g}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$, where present, is $CR^{7c}R^{7d}$;

$Y^2$, where present, is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$, where present, is $CR^{7e}R^{7f}$;

$Y^3$, where present, is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$ and $Y^4$, where present, is $CR^{7g}R^{7h}$;

$Y^4$, where present, is $CR^{7g}R^{7h}$, $NR^8$, O, S, S(O) or $SO_2$, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, —S(O)-alkyl, —S(O)-aryl, —S(O)-aralkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$, where present, are taken together to form a bond, or $R^{7a}$ and $R^4$ are taken together to form a bond;

each $R^{7c}$ and $R^{7d}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where present, are taken together to form a bond;

each $R^{7e}$ and $R^{7f}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7e}$ and $R^{7f}$, where present, are taken together with the carbon to which they are attached to form a carbonyl moiety, or $R^{7e}$ and $R^{7c}$ are taken together to form a bond, or $R^{7e}$ and $R^{7g}$, where present, are taken together to form a bond;

each $R^{7g}$ and $R^{7h}$, where present, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, —S(O)-alkyl, —S(O)-aryl, —S(O)-aralkyl, sulfonyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy.

In a particular embodiment, compounds of formulae (K-1)-(K-4) are provided wherein the ring comprising $X^1$, $X^2$, $X^3$ and $X^4$ is a phenyl, pyridyl, pyrimidinyl or pyrazinyl ring, optionally substituted with 0-3 $R^6$ groups (i.e., $(R^6)_n$ where n is 0, 1, 2 or 3). In some such embodiments, n is 1, 2 or 3 and each $R^6$ is independently halo, methyl or $CF_3$.

In particular variation, compounds of formulae (K-1)-(K-4) have the structure:

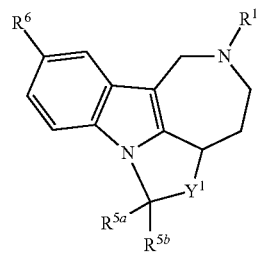

(K-1a)

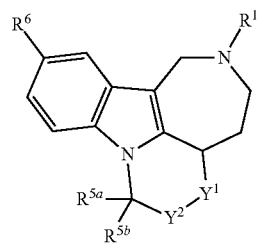

(K-2a)

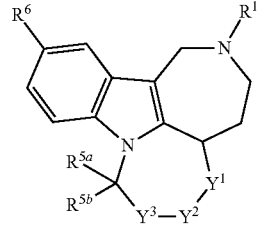

(K-3a)

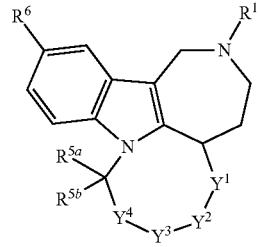

(K-4a)

or a salt or solvate thereof; wherein $R^1$, $R^{5a}$, $R^{5b}$, $R^6$, $Y^1$, $Y^2$, $Y^3$ and $Y^4$, where present, are defined as for formulae (K-1)-(K-4) and, where applicable, any variation thereof detailed herein. That is, variations of formulae (K-1)-(K-4) detailed throughout, where applicable, apply to formulae (K-1a)-(K-4a) the same as if each and every variation were specifically and individually listed for formulae (K-1a)-(K-4a). In a particular aspect of this variation, $R^{5b}$ is a substituted or unsubstituted aryl, or substituted or unsubstituted heteroaryl. In another particular aspect of this variation, $Y^1$ is $CR^{7a}R^{7b}$ wherein $R^{7b}$ is substituted or unsubstituted aryl, or substituted or unsubstituted heteroaryl. In another particular aspect of this variation, $Y^2$, where present, is $CR^{7c}R^{7d}$ wherein $R^{7d}$ is substituted or unsubstituted aryl, or substituted or unsubstituted heteroaryl. In another particular aspect of this variation, $Y^3$, where present, is $CR^{7e}R^{7f}$ wherein $R^{7f}$ is substituted or unsubstituted aryl, or substituted or unsubstituted heteroaryl. In another particular aspect of this variation, $Y^4$, where present, is $CR^{7g}R^{7h}$ wherein $R^{7h}$ is substituted or unsubstituted aryl, or substituted or unsubstituted heteroaryl. Pharmaceutically acceptable salts of compounds of formulae (K-1a)-(K-4a) are also provided.

In certain embodiments, compounds are provided wherein $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In specific embodiments, $R^1$ is a substituted or unsubstituted $C_1$-$C_8$ alkyl, acyl, acyloxy, carbonylalkoxy, substituted or unsubstituted heterocyclyl or substituted or unsubstituted aryl. In more specific embodiments, $R^1$ is an unsubstituted $C_1$-$C_8$ alkyl such as methyl and cyclopropyl.

In certain embodiments, compounds are provided wherein $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, substituted or unsubstituted amino, acylamino, aminoacyl, aminocarbonylamino, aminocarbonyloxy, aminosulfonyl, sulfonylamino, sulfonyl or carbonylalkylenealkoxy. In more specific embodiments, $R^1$ is a sulfonyl such as —$SO_2$-alkyl, —$SO_2$-aryl and —$SO_2$-aralkyl.

In certain embodiments, compounds are provided where $R^1$ is selected from the following moieties:

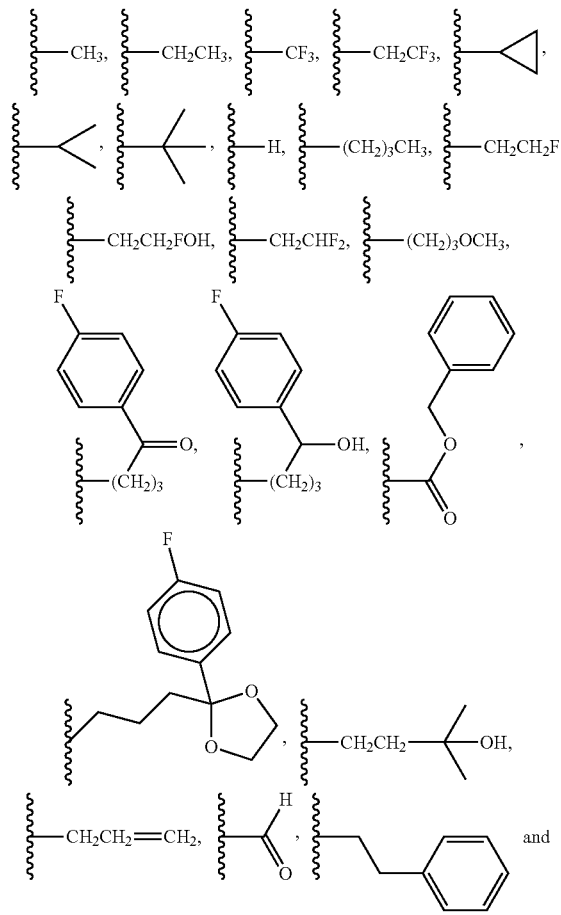

-continued

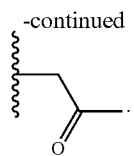

In certain compounds described herein, each $R^{3a}$ and $R^{3b}$ is independently H, substituted or unsubstituted $C_1$-$C_8$ alkyl, halo, cyano, hydroxyl, alkoxy, nitro or $R^{3a}$ and $R^{3b}$ are taken together to form a carbonyl moiety. In specific embodiments, each $R^{3a}$ and $R^{3b}$ is independently H, methyl, fluoro or $R^{3a}$ and $R^{3b}$ are taken together to form a carbonyl moiety. In a specific embodiment, $R^{3a}$ and $R^{3b}$ are both H.

In certain compounds of the formulae (IA)-(IVA) or variations thereof described herein, each $R^{2a}$ and $R^{2b}$ is independently H, substituted or unsubstituted $C_1$-$C_8$ alkyl, halo, cyano, hydroxyl, alkoxy, nitro or $R^{2a}$ and $R^{2b}$ are taken together to form a carbonyl moiety. In specific embodiments, each $R^{2a}$ and $R^{2b}$ is independently H or fluoro. In another specific embodiment, $R^{2a}$ and $R^{2b}$ are both H. In a further specific embodiment, $R^{2a}$ and $R^{2b}$ are both H and $R^{3a}$ and $R^{3b}$ are both H.

In certain compounds of the formulae (IA)-(IVA) or variations thereof described herein, $R^4$ is H, substituted or unsubstituted $C_1$-$C_8$ alkyl, halo, cyano, hydroxyl, alkoxy, or nitro. In specific embodiments, $R^4$ is H, halo, hydroxyl or methyl. In another specific embodiment, $R^4$ is H. In a further specific embodiment, $R^4$ is H and $R^{3a}$, $R^{3b}$, $R^{2a}$ and $R^{2b}$ are each H.

In certain compounds of the formulae (IB)-(IVB) or variations thereof described herein, each $R^{4a}$ and $R^{4b}$ is independently H, substituted or unsubstituted $C_1$-$C_8$ alkyl, halo, cyano, hydroxyl, alkoxy, nitro or $R^{4a}$ and $R^{4b}$ are taken together to form a carbonyl moiety. In specific embodiments, each $R^{4a}$ and $R^{4b}$ is independently H, halo, hydroxyl or methyl or $R^{4a}$ and $R^{4b}$ are taken together to form a carbonyl moiety. In another specific embodiment, $R^{4a}$ and $R^{4b}$ are both H. In a further specific embodiment, $R^{4a}$ and $R^{4b}$ are both H and $R^{3a}$ and $R^{3b}$ are both H.

In certain compounds of the formulae (IB)-(IVB) or variations thereof described herein, $R^2$ is H, substituted or unsubstituted $C_1$-$C_8$ alkyl, halo, cyano, hydroxyl, alkoxy, or nitro. In specific embodiments, $R^2$ is H, halo, hydroxyl or methyl. In another specific embodiment, $R^2$ is H. In a further specific embodiment, $R^2$ is H and $R^{3a}$, $R^{3b}$, $R^{4a}$ and $R^{4b}$ are each H.

In certain compounds described herein, each $X^1$, $X^2$ $X^3$, and $X^4$ is independently N, CH or $CR^6$. In certain embodiments, each $X^1$, $X^2$ $X^3$, and $X^4$ is CH or $CR^6$, such that the ring comprising $X^1$, $X^2$ $X^3$, and $X^4$ is an optionally substituted phenyl ring. In specific embodiments, $X^2$ is $CR^6$ where $R^6$ is halo or alkyl and $X^1$, $X^3$ and $X^4$ are each CH. In other embodiments, one of $X^1$, $X^2$, $X^3$ and $X^4$ is N, and the others are CH or $CR^6$, such that the ring comprising $X^1$, $X^2$ $X^3$, and $X^4$ is an optionally substituted pyridine ring. In further embodiments, two of $X^1$, $X^2$ $X^3$, and $X^4$ are N, and the other is CH or $CR^6$, such that the ring comprising $X^1$, $X^2$ $X^3$, and $X^4$ is an optionally substituted pyrimidine or pyrazine ring.

In certain compounds, each $R^6$, where present, is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl. In one variation, at least one of $X^1$-$X^4$ is $CR^6$ where $R^6$ is halo. In a particular variation, one of $X^1$-$X^4$ is $CR^6$ where $R^6$ is chloro and the others are CH. In a specific variation, $X^1$, $X^3$ and $X^4$ are each CH and $X^2$ is $CR^6$ where $R^6$ is chloro.

In certain embodiments, each $R^6$, where present, is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl. In further embodiments, each $R^6$, where present, is independently hydroxyl, halo, $C_1$-$C_4$ perhaloalkyl, substituted or unsubstituted $C_1$-$C_4$ alkyl, substituted or unsubstituted aryl, substituted or unsubstituted heteroaryl, or $C_1$-$C_4$ alkoxy; or in still a further variation, each $R^6$, where present, is independently halo, unsubstituted $C_1$-$C_4$ alkyl or $C_1$-$C_4$ perhaloalkyl.

In specific embodiments, the ring comprising $X^1$, $X^2$ $X^3$, and $X^4$ is a phenyl, pyridyl, pyrimidinyl or pyrazinyl ring, optionally substituted with 0-2 $R^6$ groups (i.e., $(R^6)_n$ where n is 0, 1 or 2). In some such embodiments, n is 1 or 2 and each $R^6$ is independently halo, methyl or $CF_3$.

In certain compounds, at least one of $R^{5a}$, $R^{5b}$ and $R^{7a-h}$ is a substituted or unsubstituted aryl, substituted or unsubstituted heteroaryl, substituted or unsubstituted cycloalkyl, substituted or unsubstituted cycloalkenyl, substituted or unsubstituted heterocyclyl, substituted or unsubstituted amino, alkoxy, aminoacyl, acyloxy, carbonylalkoxy, aminocarbonylalkoxy or acylamino. In one variation, compounds are provided where at least one of $R^{5a}$, $R^{5b}$ and $R^{7a-h}$ is a substituted or unsubstituted aryl, substituted or unsubstituted heteroaryl, substituted or unsubstituted $C_3$-$C_8$ cycloalkyl, substituted or unsubstituted $C_3$-$C_8$ cycloalkenyl or substituted or a unsubstituted heterocyclyl. In certain embodiments, at least one of $R^{5a}$, $R^{5b}$ and $R^{7a-h}$ is a substituted or unsubstituted 5- or 6-membered aryl or heteroaryl. In some such embodiments, at least one of $R^{5a}$, $R^{5b}$ and $R^{7a-h}$ is a substituted or unsubstituted phenyl, pyridyl or pyrimidinyl ring. When at least one of $R^{5a}$, $R^{5b}$ and $R^{7a-h}$ is substituted, it is frequently substituted with from 1-3 substituents selected from group consisting of halo, $C_1$-$C_4$ alkyl, $C_1$-$C_4$ perhaloalkyl, and $C_1$-$C_4$ alkoxy.

In a particular variation, at least one of $R^{5a}$, $R^{5b}$ and $R^{7a-h}$ is a substituted heteroaryl, a mono-substituted aryl group substituted with a chloro or alkyl group or a di- or tri-substituted aryl moiety. For instance, at least one of $R^{5a}$, $R^{5b}$ and $R^{7a-h}$ in one variation is selected from the group consisting of 4-methoxy-3-fluorophenyl, 3,4-di-fluorophenyl, 4-chloro-3-fluorophenyl, 3,4-dichlorophenyl, 3-chloro-4-fluorophenyl, 2,4-difluorophenyl, 2,4-dichlorophenyl, 2,4,6-trifluorophenyl, 4-chlorophenyl, 4-methylphenyl, 6-methyl-3-pyridyl, 6-trifluoromethyl-3-pyridyl, 5-trifluoromethyl-3-pyridyl and pyrimidinyl. In one aspect, at least one of $R^{5a}$, $R^{5b}$ and $R^{7a-h}$ is a substituted pyridyl such as 6-methyl-3-pyridyl, 6-trifluoromethyl-3-pyridyl and 5-trifluoromethyl-3-pyridyl.

In particular embodiments, each $X^1$, $X^2$ $X^3$, and $X^4$ is CH or $CR^6$. In other embodiments, at least one of $X^1$, $X^2$ $X^3$, and $X^4$ is N. Another variation provides a compound where at least two of $X^1$, $X^2$ $X^3$, and $X^4$ are N. A further variation provides a compound where two of $X^1$, $X^2$, $X^3$, and $X^4$ are N and one of $X^1$, $X^2$ $X^3$, and $X^4$ is CH or $CR^6$. Compounds where one of $X^1$, $X^2$ $X^3$, and $X^4$ is N and two of $X^1$, $X^2$ $X^3$, and $X^4$ are CH or $CR^6$ are also embraced by this invention.

In another variation, a compound is provided wherein the ring comprising $X^1$, $X^2$, $X^3$, and $X^4$ is an aromatic moiety selected from the following structures:

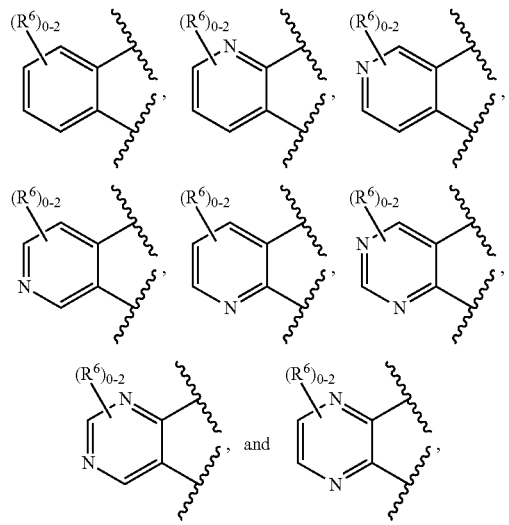

where each $R^6$ is as defined. In a particular variation, each $R^6$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl. In a further variation, each $R^6$ is independently halo, unsubstituted $C_1$-$C_4$ alkyl, $C_1$-$C_4$ perhaloalkyl, or $C_1$-$C_4$ alkoxy.

In still a further variation, a compound of the invention is provided, wherein the ring comprising $X^1$, $X^2$, $X^3$ and $X^4$ is an aromatic moiety selected from the following structures:

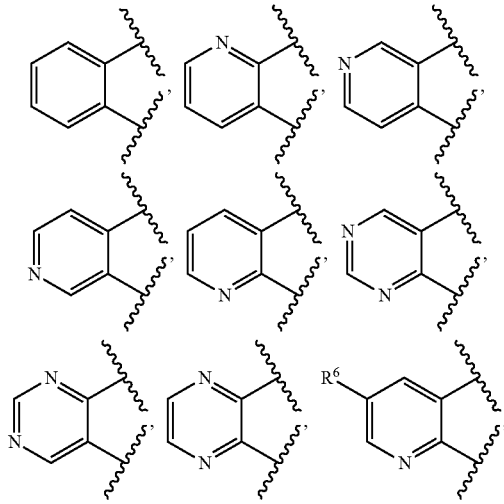

-continued

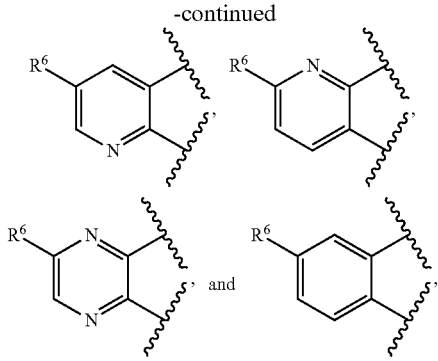

wherein $R^6$ is as defined herein; or in a particular variation, where $R^6$ is hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or amino, alkylsulfonylamino or acyl; or in still a further variation, where each $R^6$ is independently halo, unsubstituted $C_1$-$C_4$ alkyl, $C_1$-$C_4$ perhaloalkyl, or $C_1$-$C_4$ alkoxy.

In a further variation, a compound of the invention is provided, wherein the ring comprising $X^1$, $X^2$, $X^3$ and $X^4$ is an aromatic moiety selected from the following structures:

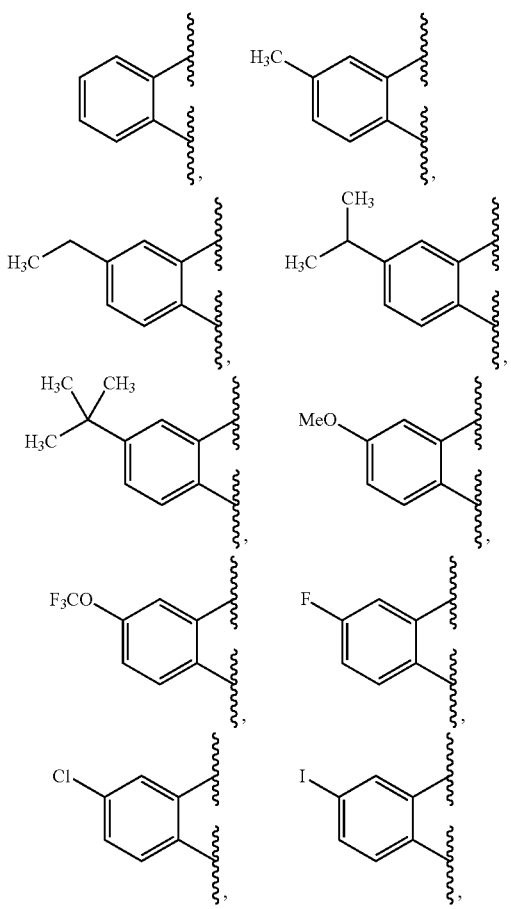

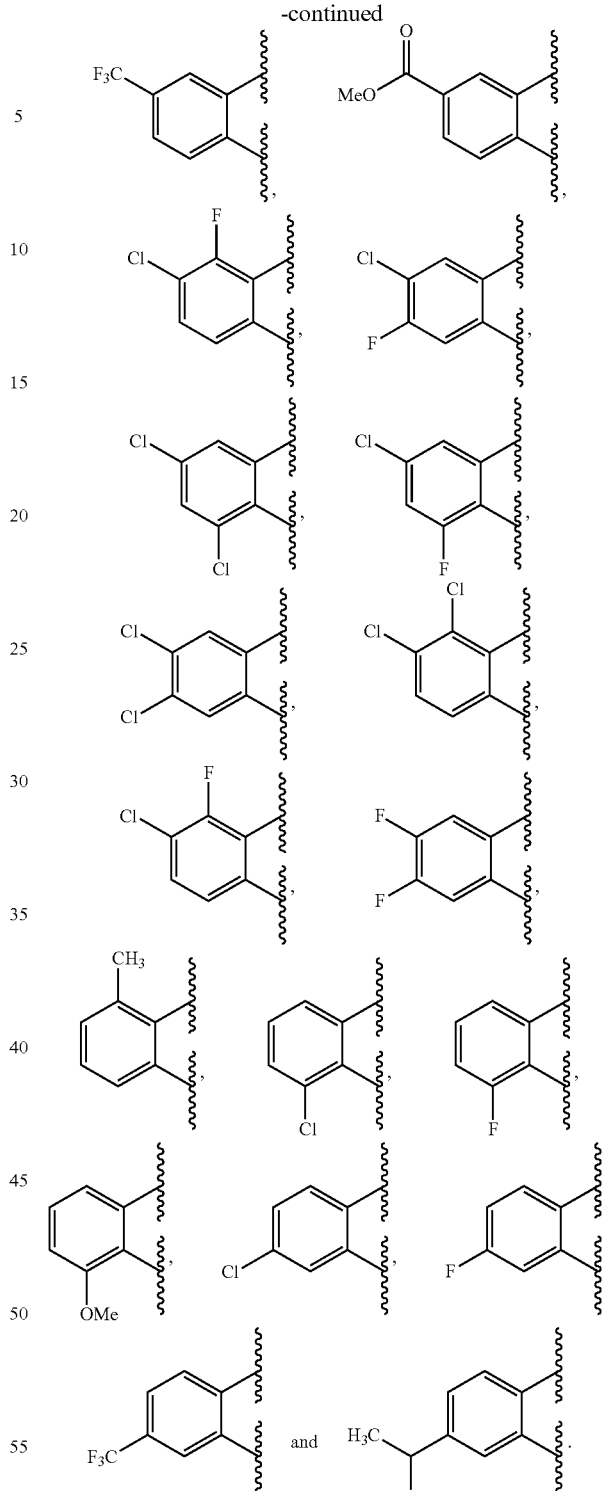

Any formula detailed herein, where applicable, may in one variation have $X^1$, $X^2$, $X^3$ and $X^4$ taken together to provide an aromatic moiety detailed herein above. It is understood that by "where applicable" it is intended that in one variation such $X^1$, $X^2$, $X^3$ and $X^4$ groups are taken together to provide a moiety hereinabove if the formula encompasses such a structure. For example, if a given formula does not encompass structures wherein $X^1$, $X^2$, $X^3$ and $X^4$ groups are taken together provide a pyridyl moiety, then a pyridyl moiety as detailed hereinabove is not applicable to that particular formula, but remains applicable to formulae that do encompass structures where $X^1$, $X^2$, $X^3$ and $X^4$ groups are taken together provide a pyridyl moiety.

In another embodiment, a compound of the invention is provided, wherein $X^1$-$X^4$ are as defined or as detailed in any variation herein, where R' is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is provided, wherein $X^1$-$X^4$ are as defined or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is provided, wherein $X^1$-$X^4$ are as defined or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

When any carbon of the preceding formulae is optically active, it may be in the (R)- or (S)-configuration and compositions comprising substantially pure (R) or (S) compound or mixtures thereof in any amount are embraced by this invention.

In one variation, a compound of the invention is provided wherein the ring comprising N, $R^1$, $R^{2a}$, $R^{2b}$, $R^{3a}$, $R^{3b}$ and $R^4$ is a moiety selected from the following structures:

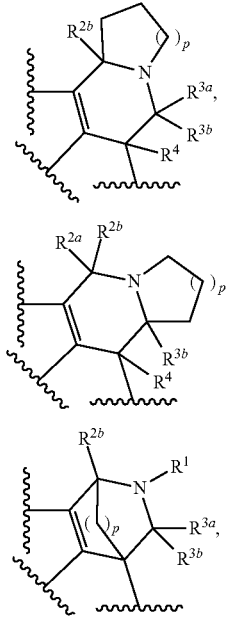

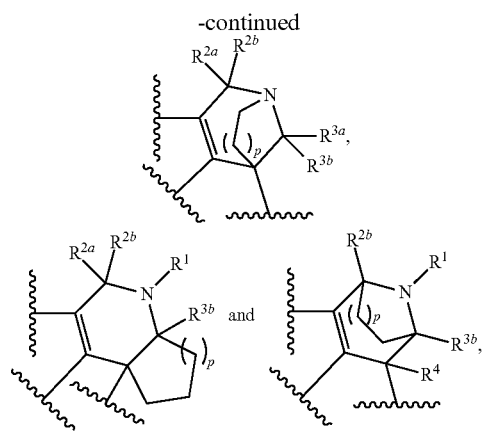

wherein $R^1$, $R^{2a}$, $R^{2b}$, $R^{3a}$, $R^{3b}$ and $R^4$ are as defined, and p is 1 or 2.

In another variation, a compound of the invention is provided wherein the ring comprising N, $R^1$, $R^2$, $R^{3a}$, $R^{3b}$, $R^{4a}$ and $R^{4b}$ is a moiety selected from the following structures:

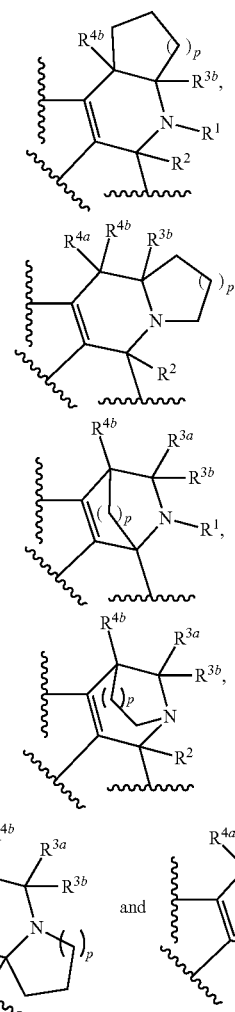

wherein $R^1$, $R^2$, $R^{3a}$, $R^{3b}$, $R^{4a}$ and $R^{4b}$ are as defined, and p is 1 or 2.

In another variation, a compound of the invention is provided wherein the ring comprising N, $R^1$, $R^{2a}$, $R^{2b}$, $R^{3a}$, $R^{3b}$ and $R^4$ is a moiety selected from the following structures:

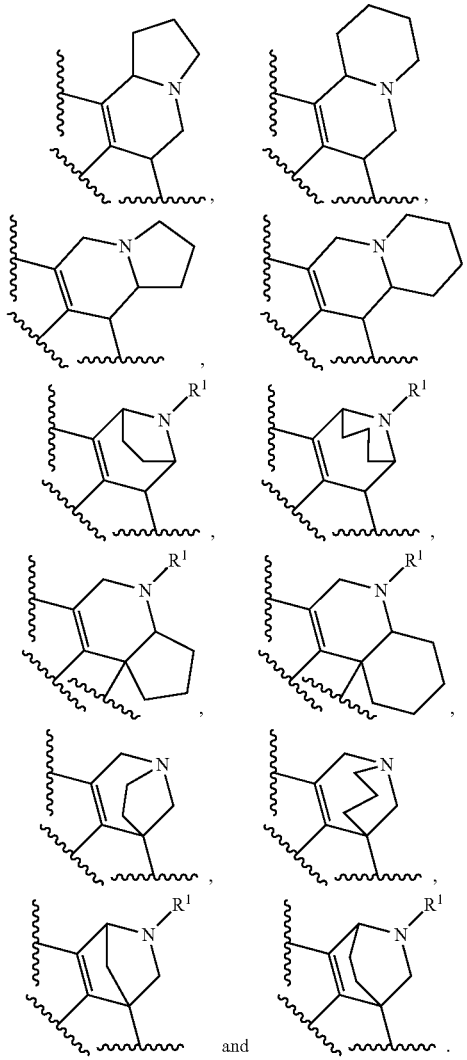

In another variation, a compound of the invention is provided wherein the ring comprising N, $R^1$, $R^2$, $R^{3a}$, $R^{3b}$, $R^{4a}$ and $R^{4b}$ is a moiety selected from the following structures:

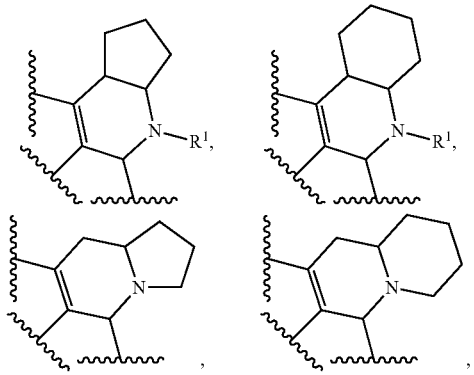

-continued

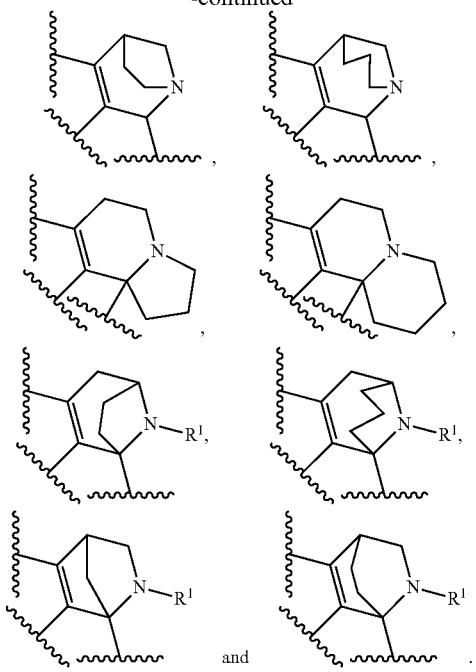

In any one of the variations of compounds of the formulae described herein, all stereoisomers are intended. For example, the ring can be either

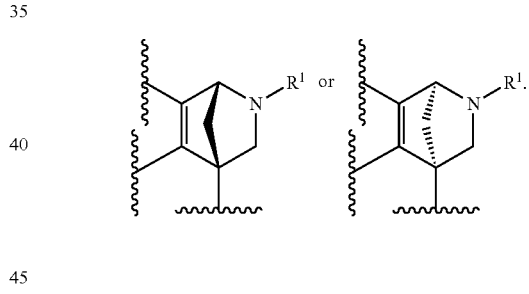

Compositions comprising a single stereoisomer or mixtures of more than one stereoisomer are also intended. Compositions comprising a mixture of stereoisomers in any ratio are embraced, including mixtures of two or more stereochemical forms of a compound of the invention in any ratio, such that racemic, non-racemic, enantioenriched and scalemic mixtures of a compound are embraced.

In some embodiments, the ring comprising N, $R^1$, $R^{2a}$, $R^{2b}$, $R^{3a}$, $R^{3b}$ and $R^4$ is a moiety selected from the following structures:

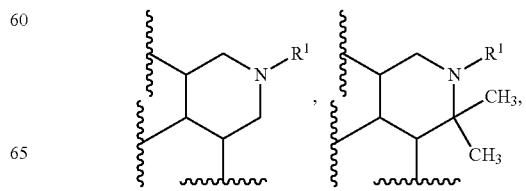

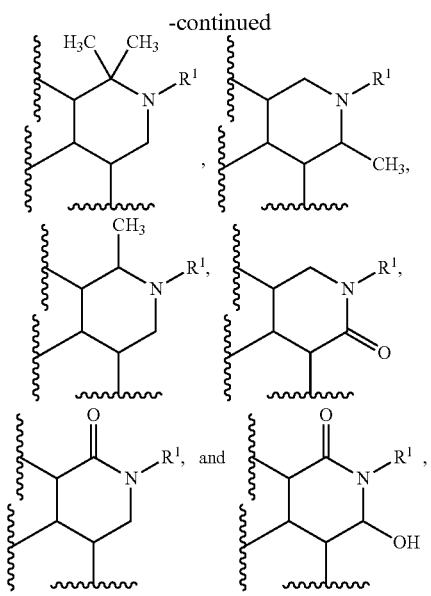

where $R^1$ in the structures above is as defined or any particular variation detailed herein. In some embodiments, the ring comprising N, $R^{2a}$, $R^{2b}$, $R^{3a}$, $R^{3b}$ and $R^4$ is a moiety selected from the following structures:

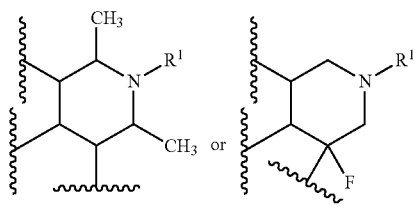

where $R^1$ is as defined or any particular variation detailed herein. Any formula detailed herein, where applicable, may in one variation have a ring according to the structures above.

In certain compounds where applicable in one variation, at least one of $R^{5a}$, $R^{5b}$ and $R^{7a-h}$ is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is provided, where at least one of $R^{5a}$, $R^{5b}$ and $R^{7a-h}$ is a substituted or unsubstituted phenyl or pyridyl group. In a particular variation, at least one of $R^{5a}$, $R^{5b}$ and $R^{7a-h}$ is a phenyl or pyridyl group substituted with at least one methyl, trifluoromethyl, methoxy or halo substituent. In another variation, a compound of the invention is provided, where at least one of $R^{5a}$, $R^{5b}$ and $R^{7a-h}$ is a pyridyl, phenyl, pyrimidinyl, pyrazinyl, imidazolyl, furanyl, pyrrolyl or thiophenyl group substituted with at least one substituted or unsubstituted $C_1$-$C_4$ alkyl, $C_1$-$C_4$ alkoxy, halo or $C_1$-$C_4$ perhaloalkyl moiety.

In still another variation, a compound of the invention is provided, where at least one of $R^{5a}$, $R^{5b}$ and $R^{7a-h}$ is a substituted or unsubstituted $C_3$-$C_8$ cycloalkyl or a substituted or unsubstituted heterocyclyl. In another variation, at least one of $R^{5a}$, $R^{5b}$ and $R^{7a-h}$ is a substituted or unsubstituted $C_3$-$C_8$ cycloalkyl or a substituted or unsubstituted heterocyclyl. In yet another variation, a compound of the invention is provided where at least one of $R^{5a}$, $R^{5b}$ and $R^{7a-h}$ is a substituted or unsubstituted pyridyl, phenyl, pyrazinyl, piperazinyl, pyrrolidinyl or thiomorpholinyl group. In a particular variation, at least one of $R^{5a}$, $R^{5b}$ and $R^{7a-h}$ is a pyridyl, phenyl, pyrazinyl, piperazinyl, pyrrolidinyl or thiomorpholinyl group substituted with at least one methyl, $CF_3$, methoxy or halo group.

In one variation, a compound of the invention is provided where at least one of $R^{5a}$, $R^{5b}$ and $R^{7a-h}$ is an unsubstituted cycloalkyl or an unsubstituted heterocyclyl. In another variation, at least one of $R^{5a}$, $R^{5b}$ and $R^{7a-h}$ is an unsubstituted $C_3$-$C_8$ cycloalkyl or an unsubstituted heterocyclyl. In another variation, a compound of the invention is of the formula (I) or any variation of the foregoing detailed herein, where at least one of $R^{5a}$, $R^{5b}$ and $R^{7a-h}$ is a substituted or unsubstituted cyclohexyl, morpholinyl, piperazinyl, thiomorpholinyl, cyclopentyl or pyrrolidinyl moiety. In yet another variation, a compound of the invention is provided where at least one of $R^{5a}$, $R^{5b}$ and $R^{7a-h}$ is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group. $R^{5a}$, $R^{5b}$ or $R^{7a-h}$ groups may be attached to the parent structure at any available position on the $R^{5a}$, $R^{5b}$ or $R^{7a-h}$ moiety. Thus, although specific attachment points for certain $R^{5a}$, $R^{5b}$ or $R^{7a-h}$ moieties are depicted herein, it is understood that such $R^{5a}$, $R^{5b}$ or $R^{7a-h}$ moieties, may also be connected to the parent structure at any available position. For example, if a mono-fluoro-phenyl is depicted herein, it is understood that each of the available mono-fluoro-phenyl moieties are intended, e.g., 2-fluoro-phenyl, 3-fluoro-phenyl and 4-fluoro-phenyl. It is also understood that any formula detailed herein, where applicable, may in one variation have a $R^{5a}$, $R^{5b}$ or $R^{7a-h}$ moiety as detailed herein and below.

In still another variation, a compound of the invention is provided where at least one of $R^{5a}$, $R^{5b}$ and $R^{7a-h}$ is a moiety selected from the structures:

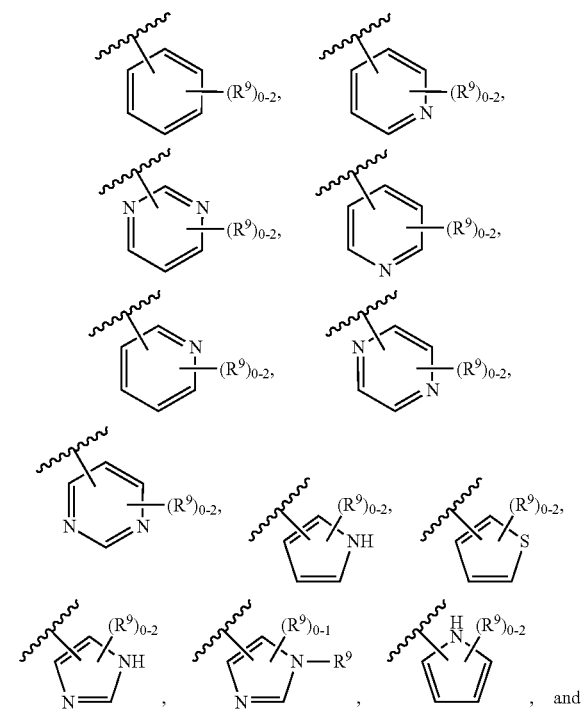

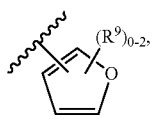

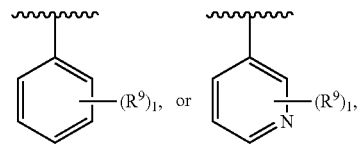

wherein each $R^9$ is independently a halo, cyano, nitro, perhaloalkyl ($C_1$-$C_8$), perhaloalkoxy ($C_1$-$C_8$), substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, the $R^{5a}$, $R^{5b}$ or $R^{7a\text{-}h}$ is substituted with no more than one $R^9$ group. In another variation, the $R^{5a}$, $R^{5b}$ or $R^{7a\text{-}h}$ is substituted with only one $R^9$ group. In one variation, the $R^{5a}$, $R^{5b}$ or $R^{7a\text{-}h}$ is substituted with two $R^9$ groups. In a further variation, at least one of $R^{5a}$, $R^{5b}$ and $R^{7a\text{-}h}$ is selected from the aromatic structures detailed where the residue has the moiety —$(R^9)_0$ such that the $R^{5a}$, $R^{5b}$ or $R^{7a\text{-}h}$ either contains no $R^9$ functionality or a moiety of the formula N—$R^9$. In one variation, at least one of $R^{5a}$, $R^{5b}$ and $R^{7a\text{-}h}$ is selected from the aromatic structures detailed where the $R^{5a}$, $R^{5b}$ or $R^{7a\text{-}h}$ is substituted with no more than one $R^9$ group. In another variation, the $R^{5a}$, $R^{5b}$ or $R^{7a\text{-}h}$ is substituted with only one $R^9$ group. In one variation, the $R^{5a}$, $R^{5b}$ or $R^{7a\text{-}h}$ is substituted with two $R^9$ groups. In a further variation, at least one of $R^{5a}$, $R^{5b}$ and $R^{7a\text{-}h}$ is selected from the aromatic structures detailed where the residue has the moiety $(R^9)_0$ such that the $R^{5a}$, $R^{5b}$ or $R^{7a\text{-}h}$ either contains no $R^9$ functionality or a moiety of the formula N—$R^9$.

In another variation, a compound of the invention is provided where at least one of $R^{5a}$, $R^{5b}$ and $R^{7a\text{-}h}$ is a moiety selected from the structures:

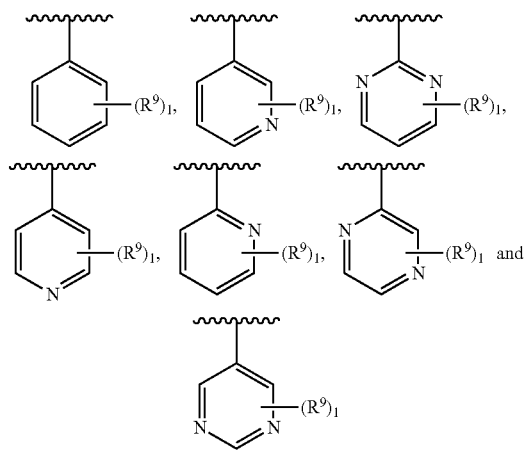

wherein $R^9$ is connected to the $R^{5a}$, $R^{5b}$ or $R^{7a\text{-}h}$ ortho or para to the position at which $R^{5a}$, $R^{5b}$ or $R^{7a\text{-}h}$ is connected to the carbon bearing the $R^{5a}$, $R^{5b}$ or $R^{7a\text{-}h}$. In a particular variation, at least one of $R^{5a}$, $R^{5b}$ and $R^{7a\text{-}h}$ is a structure of the formula and $R^9$ is connected to the $R^{5a}$, $R^{5b}$ or $R^{7a\text{-}h}$ para to the position at which the $R^{5a}$, $R^{5b}$ or $R^{7a\text{-}h}$ is connected to the carbon bearing the $R^{5a}$, $R^{5b}$ or $R^{7a\text{-}h}$. In another particular variation, at least one of $R^{5a}$, $R^{5b}$ and $R^{7a\text{-}h}$ is a structure of the formula

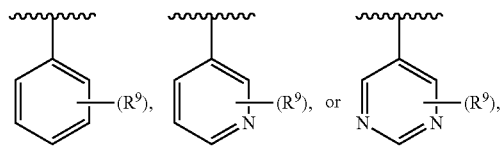

where each $R^9$ is independently alkyl, perhaloalkyl or halo.

In another variation, a compound of the invention is provided where at least one of $R^{5a}$, $R^{5b}$ and $R^{7a\text{-}h}$ is a moiety selected from the structures:

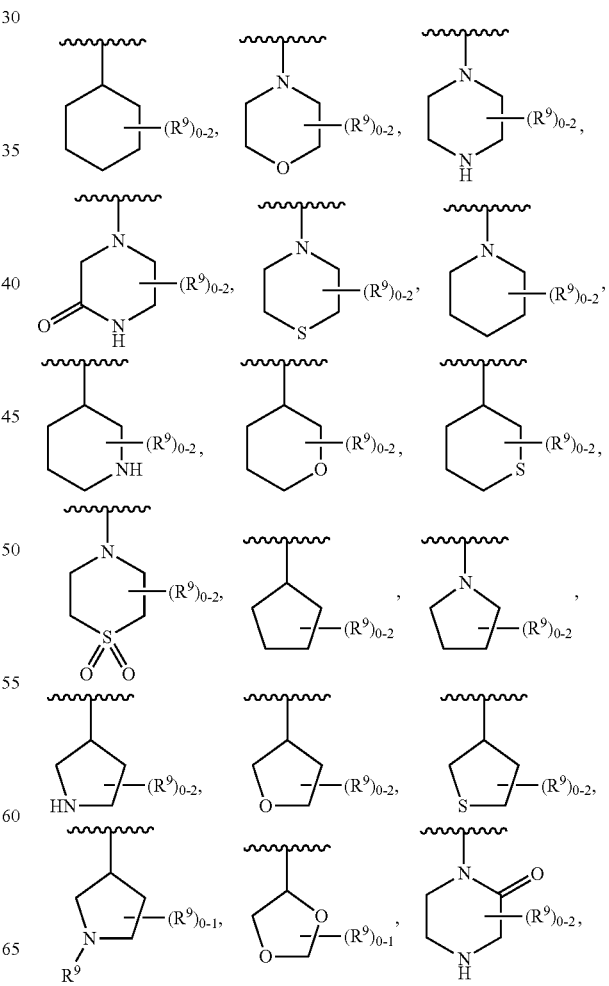

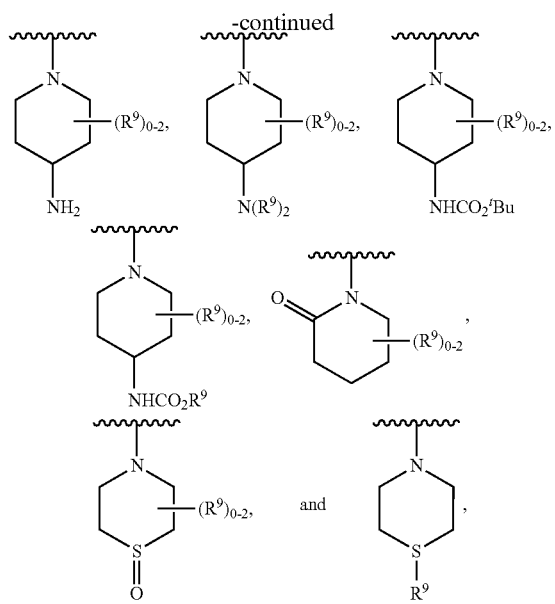

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, at least one of $R^{5a}$, $R^{5b}$ and $R^{7a-h}$ is substituted with no more than one $R^9$ group. In another variation, at least one of $R^{5a}$, $R^{5b}$ and $R^{7a-h}$ is substituted with only one $R^9$ group. In yet another variation, at least one of $R^{5a}$, $R^{5b}$ and $R^{7a-h}$ is substituted with two $R^9$ groups. In a particular variation, at least one of $R^{5a}$, $R^{5b}$ and $R^{7a-h}$ is selected from the carbocyclic and heterocyclic structures detailed where the residue has the moiety $(R^9)_0$ such that at least one of $R^{5a}$, $R^{5b}$ and $R^{7a-h}$ either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, a compound of the invention is provided where at least one of $R^{5a}$, $R^{5b}$ and $R^{7a-h}$ is a moiety selected from the structures:

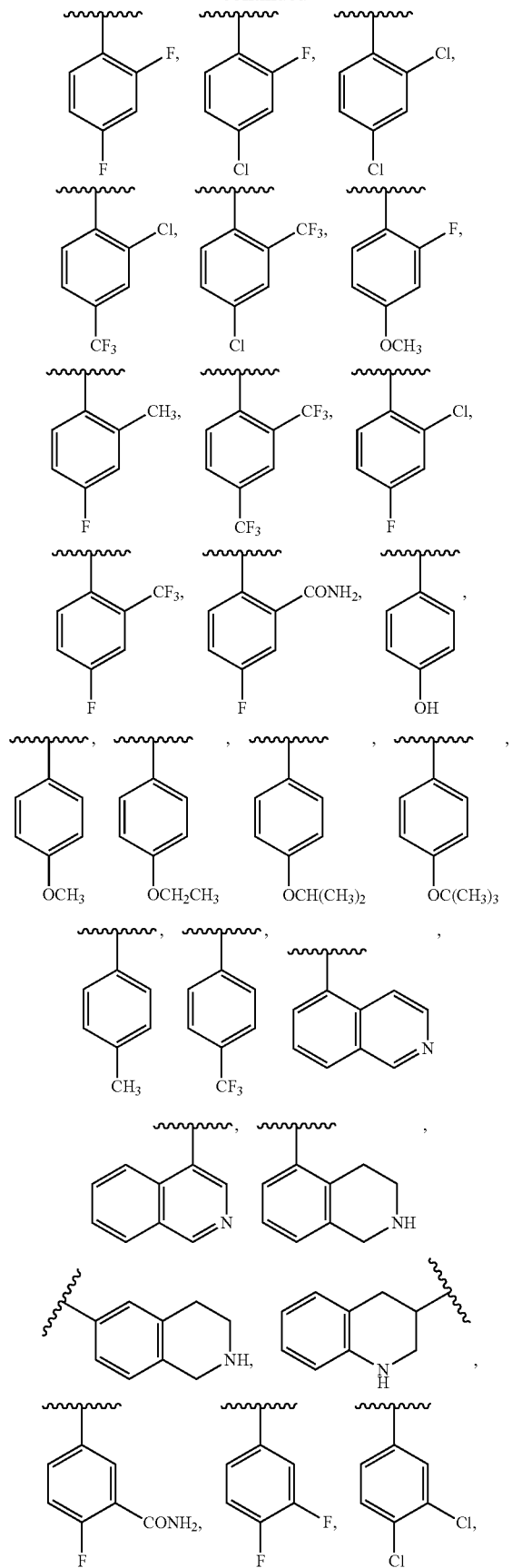

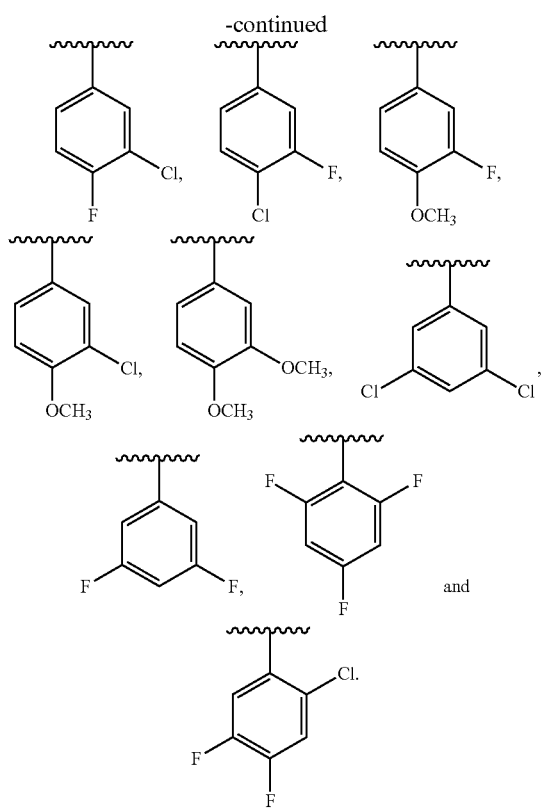
In another variation, a compound of the invention is provided where at least one of $R^{5a}$, $R^{5b}$ and $R^{7a-h}$ is a heteroaromatic moiety selected from the structures:
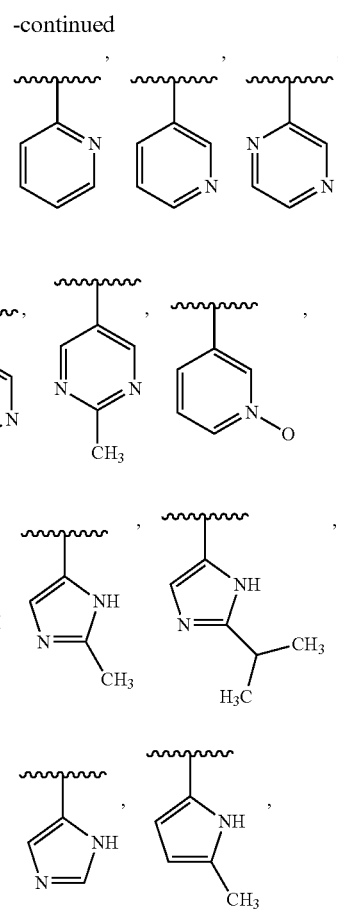
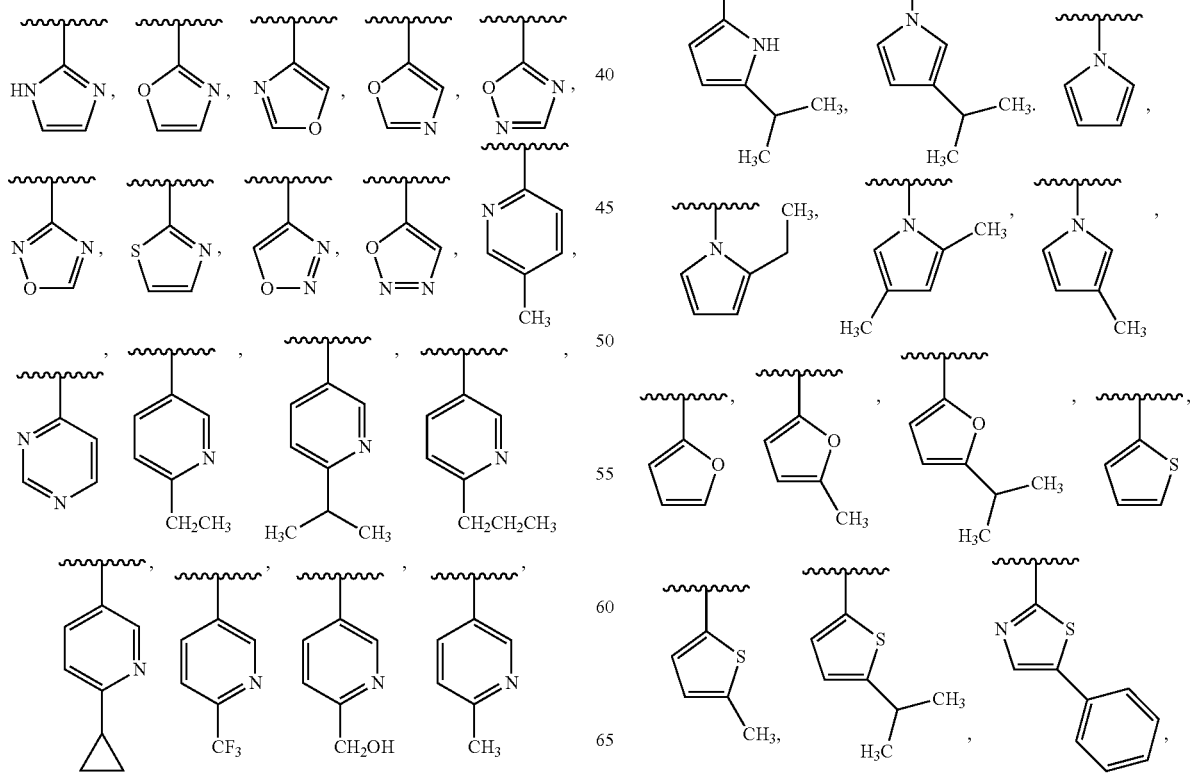

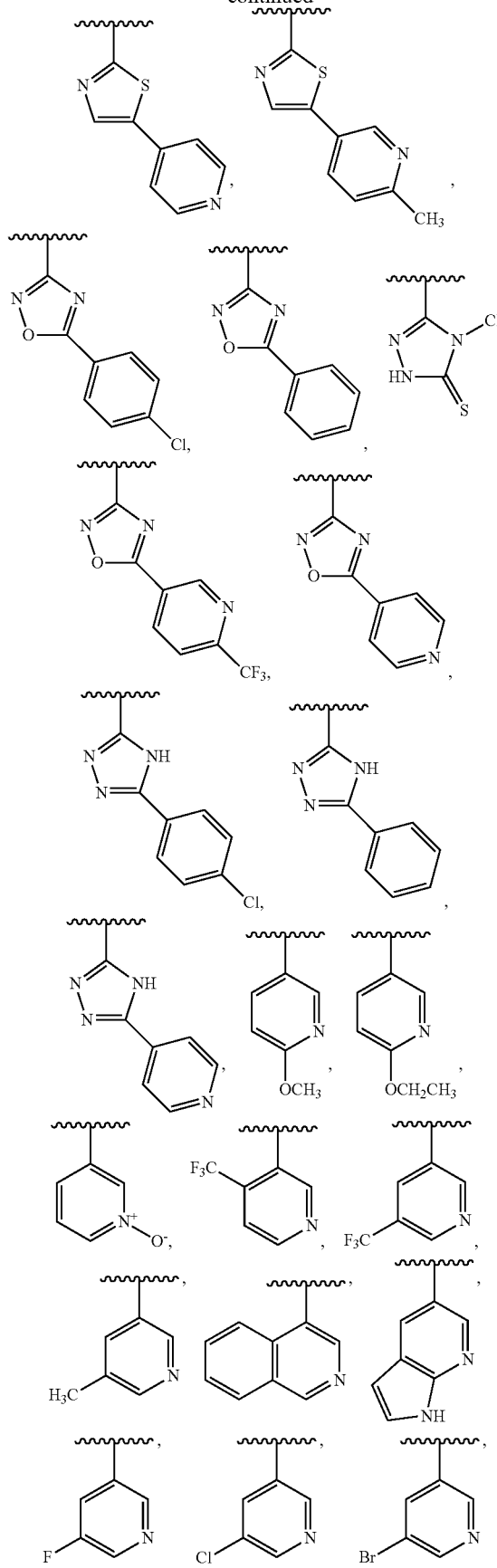
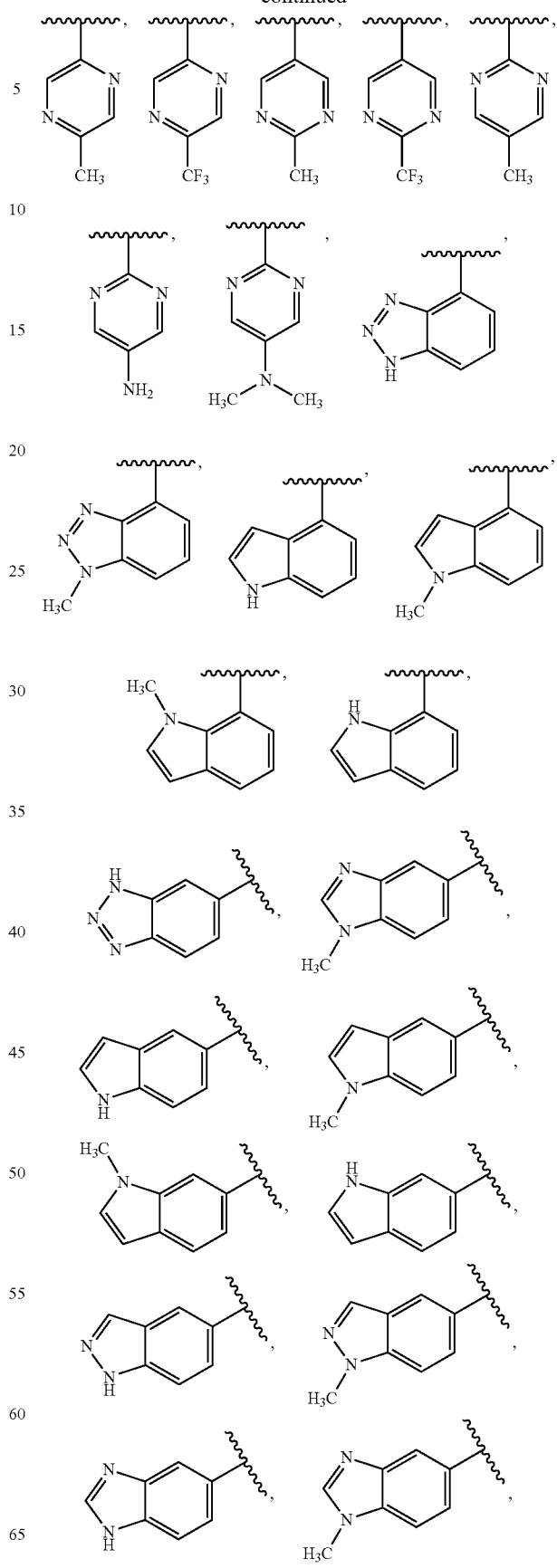

-continued

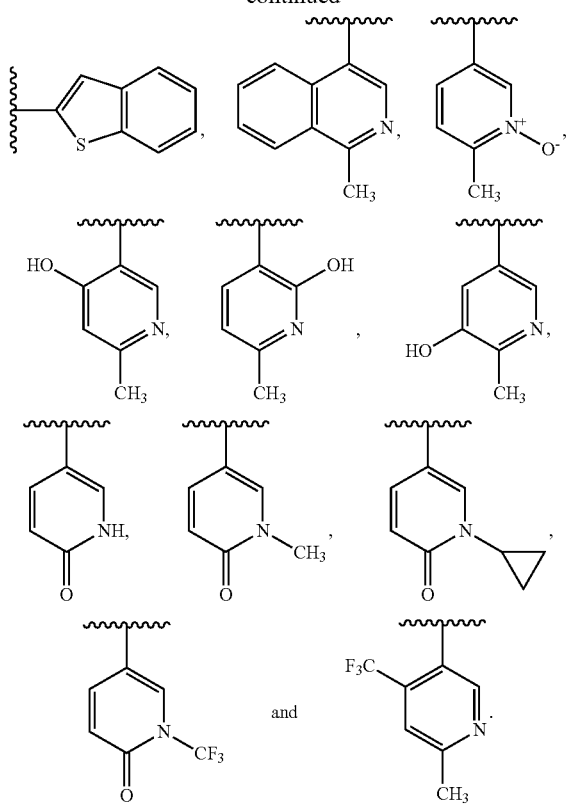

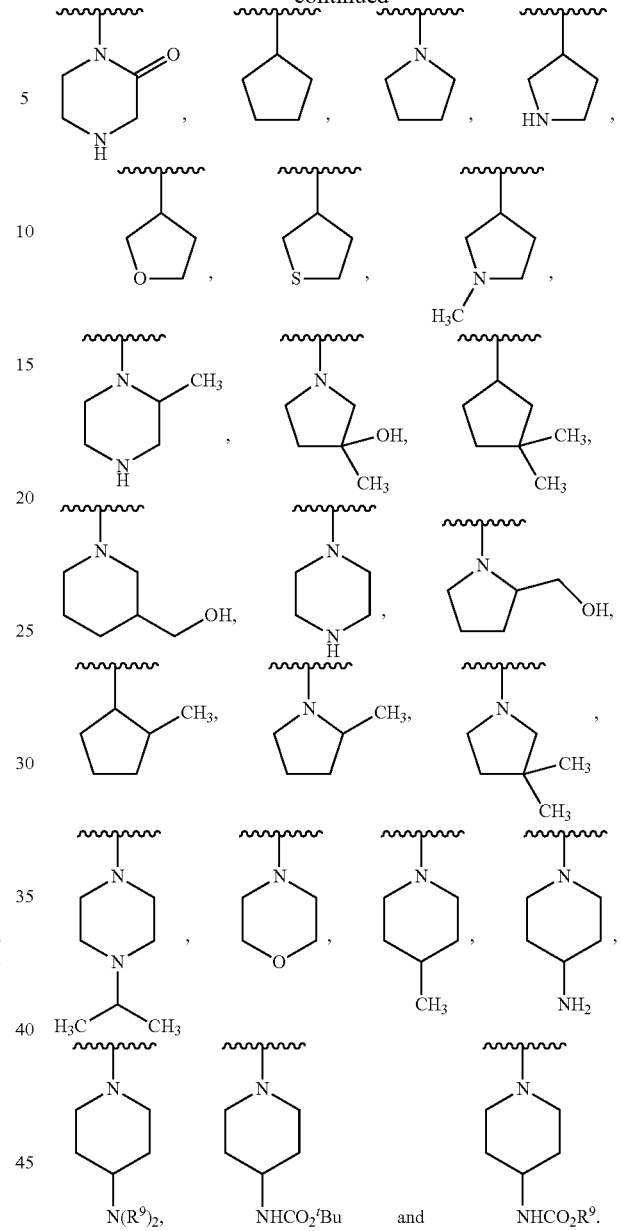

In yet another variation, a compound of the invention is provided where at least one of $R^{5a}$, $R^{5b}$ and $R^{7a-h}$ is a moiety selected from the structures:

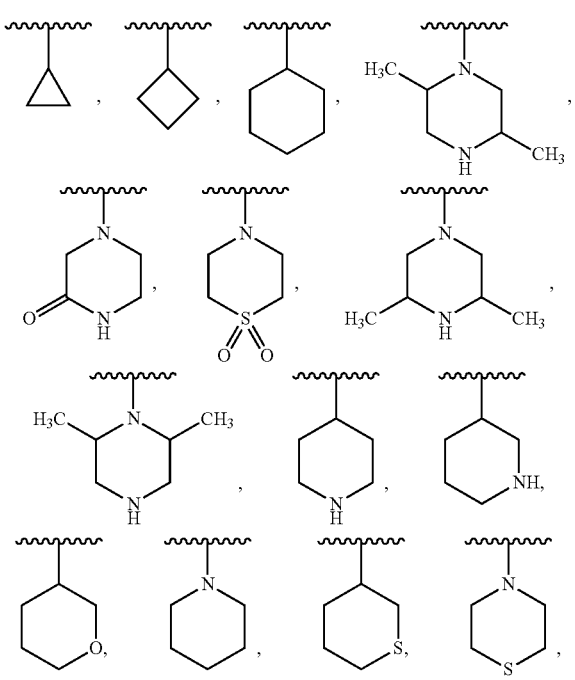

In any of the variations described herein for $R^{5a}$, $R^{5b}$, and $R^{7a-h}$, only one point of attachment of each moiety to the parent structure may be depicted, however it is understood that the moiety may be attached to the parent structure at any position, where chemically feasible.

In another variation, a compound of the invention is provided where at least one of $R^{5a}$, $R^{5b}$ and $R^{7a-h}$ is a moiety selected from the structures:

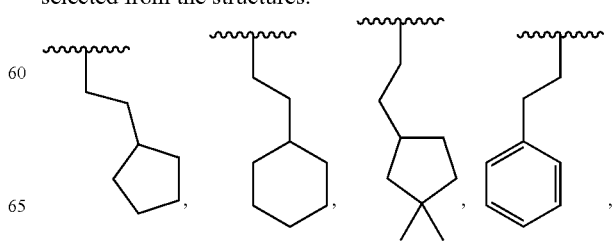

147
-continued
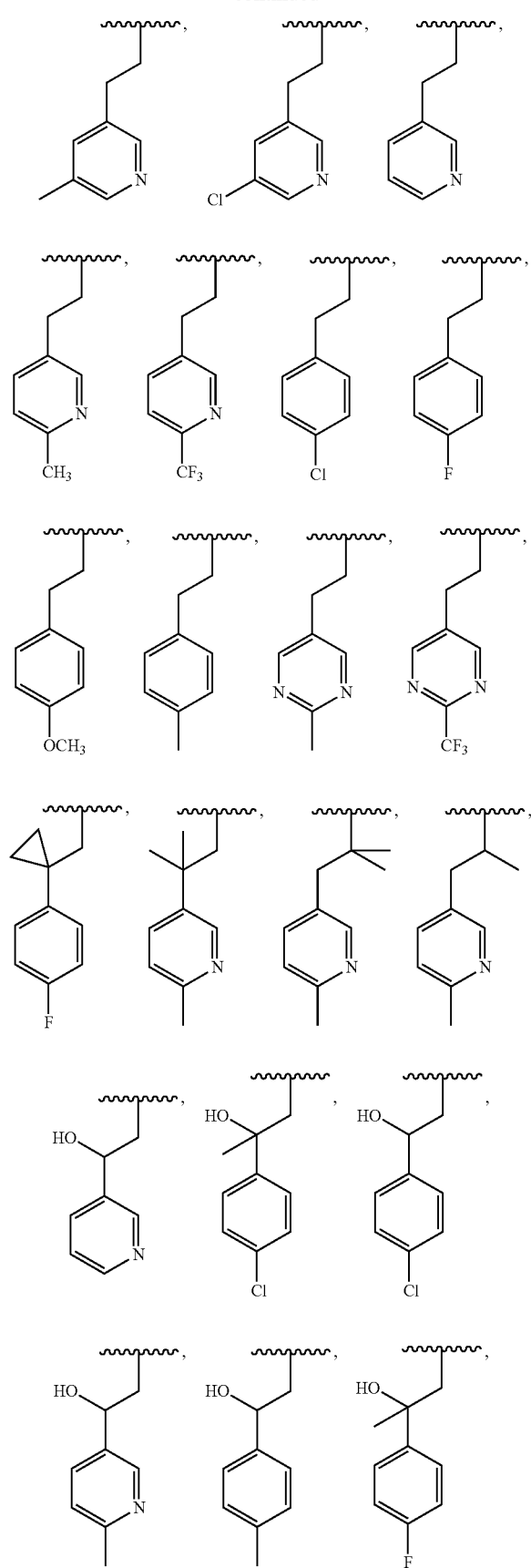
148
-continued
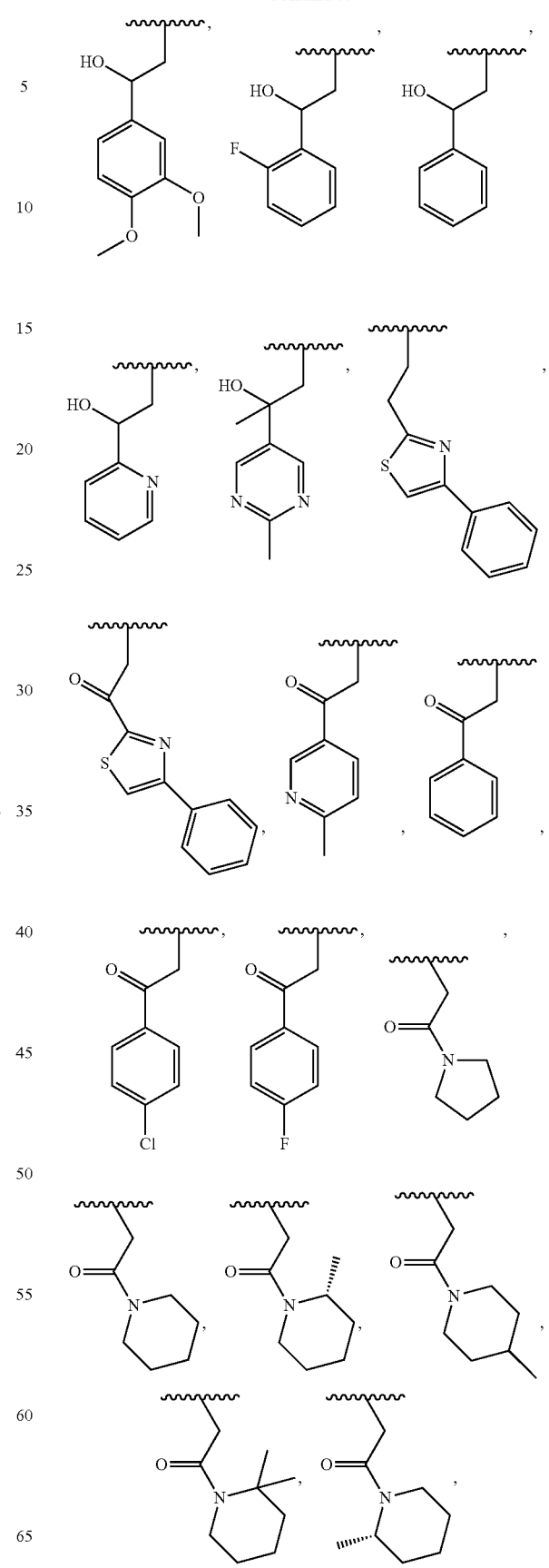

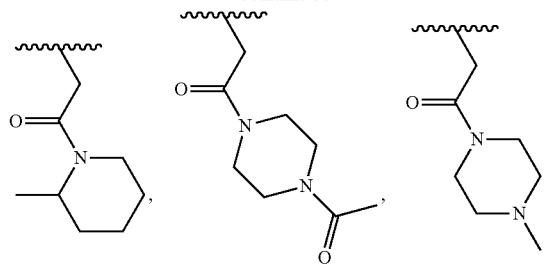
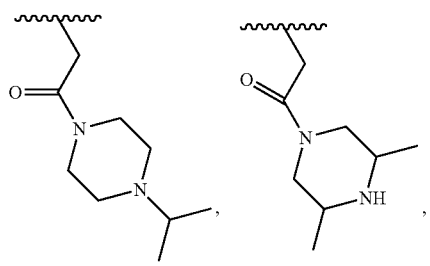
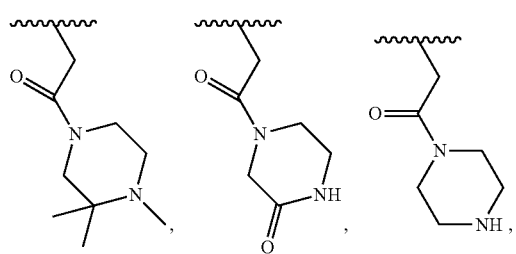
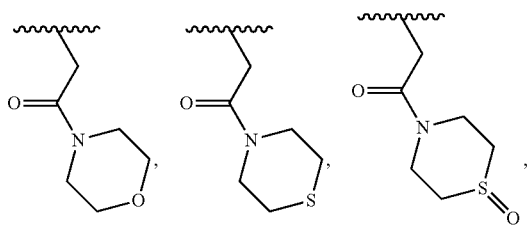
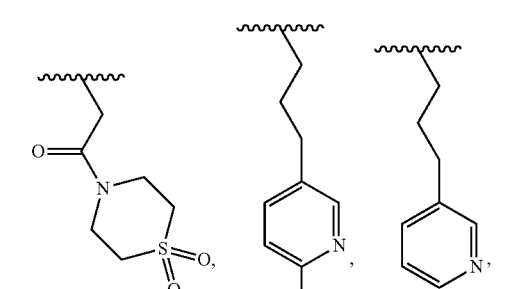
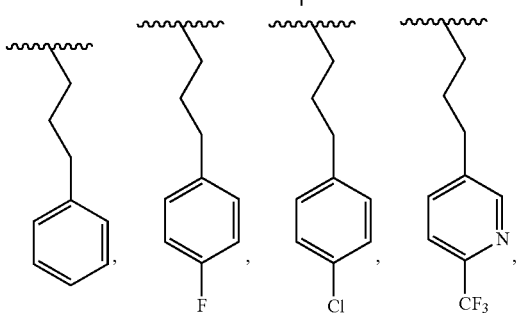
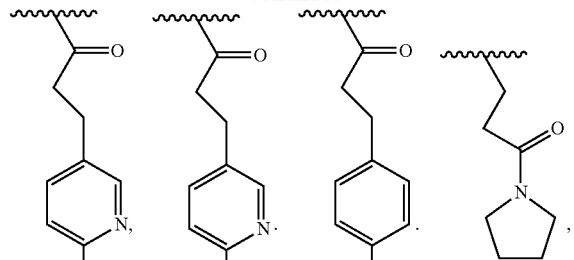
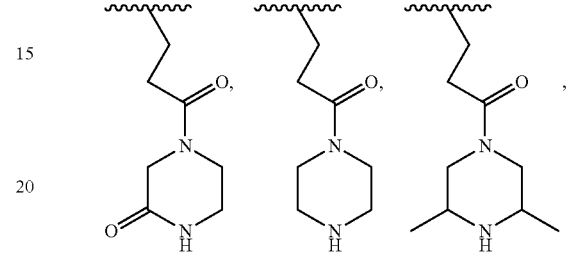
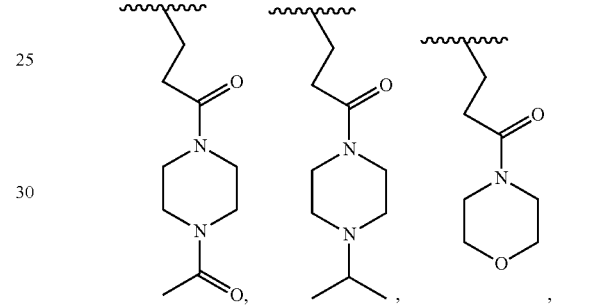
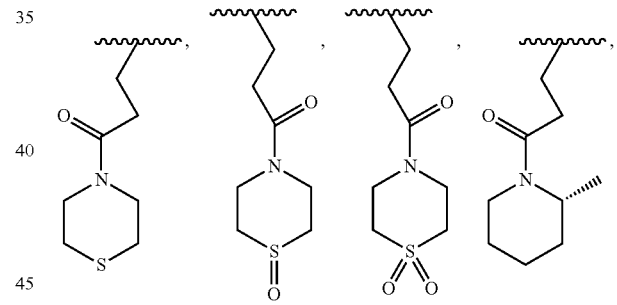
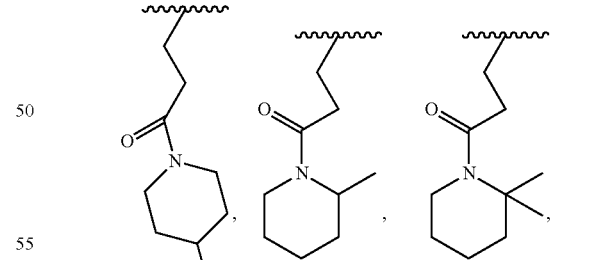
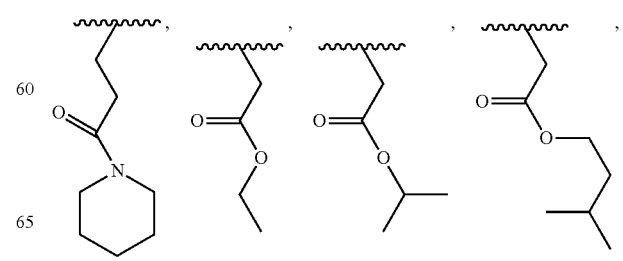

-continued

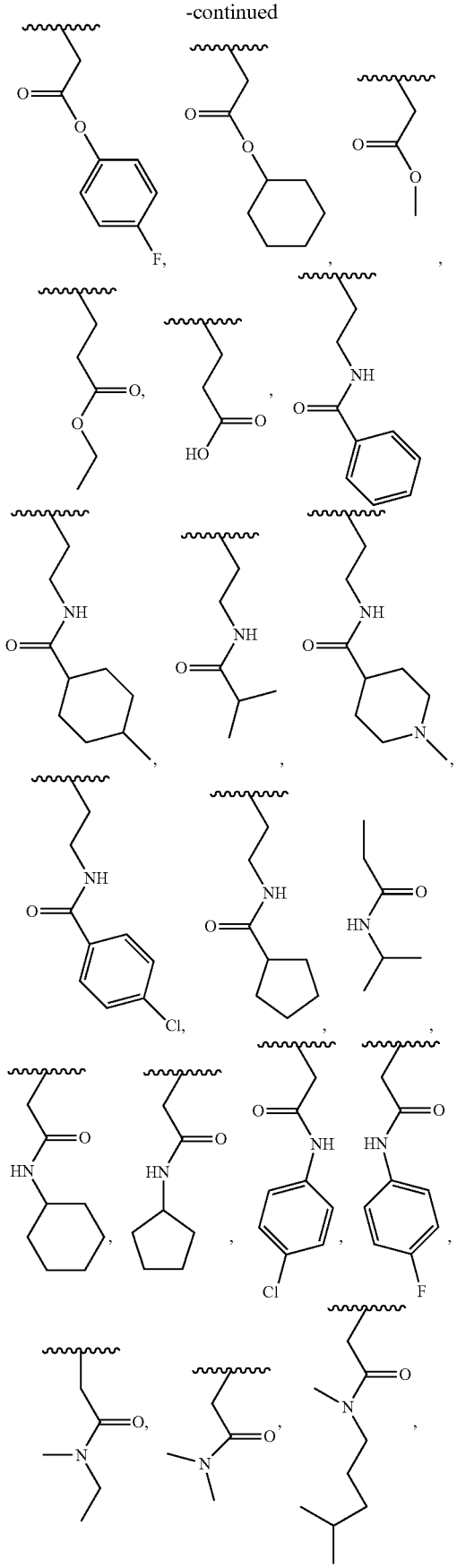

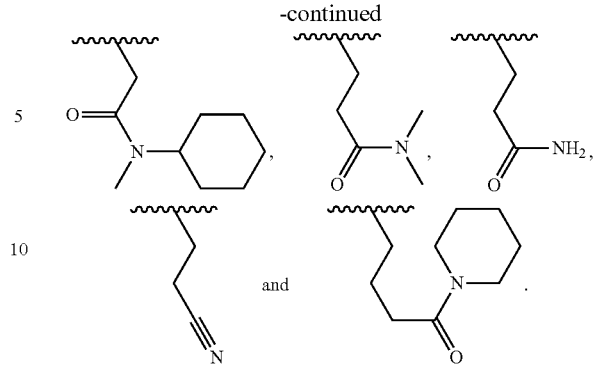

and

In another variation, a compound of the invention is provided where at least one of $R^{5a}$, $R^{5b}$ and $R^{7a-h}$ is a substituted or unsubstituted amino, alkoxy, aminoacyl, acyloxy, carbonylalkoxy, aminocarbonylalkoxy or acylamino moiety. In a particular variation, at least one of $R^{5a}$, $R^{5b}$ and $R^{7a-h}$ is an unsubstituted amino. In another variation, at least one of $R^{5a}$, $R^{5b}$ and $R^{7a-h}$ is a substituted amino of the formula —N($C_1$-$C_8$alkyl)$_2$ such as the moiety —N(Me)$_2$ or —N(CH$_3$)(CH$_2$CH$_3$). In another variation, at least one of $R^{5a}$, $R^{5b}$ and $R^{7a-h}$ is a substituted amino of the formula —N(H)(cycloalkyl or substituted cycloalkyl), such as a moiety of the formula:

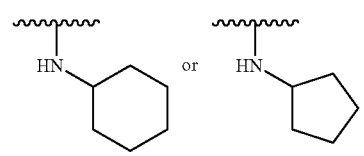

In another variation, each $R^2$ or $R^6$ is independently a substituted amino of the formula —N(H)(aryl or substituted aryl), such as a moiety of the formula:

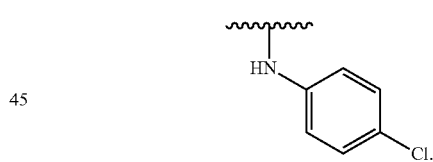

The invention also embraces compounds where at least one of $R^{5a}$, $R^{5b}$ and $R^{7a-h}$ is an aminoacyl moiety. In one variation, at least one of $R^{5a}$, $R^{5b}$ and $R^{7a-h}$ is an aminoacyl group where at least one of $R_a$ and $R_b$ is H, such as when at least one of $R^{5a}$, $R^{5b}$ and $R^{7a-h}$ is of the formula —NHC(O)$R_b$. In one variation, at least one of $R^{5a}$, $R^{5b}$ and $R^{7a-h}$ is an aminoacyl moiety selected from the group consisting of: —NHC(O)-heterocyclyl, —NHC(O)-substituted heterocyclyl, —NHC(O)-alkyl, —NHC(O)-cycloalkyl, —NHC(O)-aralkyl and —NHC(O)-substituted aryl. In another variation, at least one of $R^{5a}$, $R^{5b}$ and $R^{7a-h}$ is an aminoacyl moiety selected from the group consisting of: —NHC(O)—$C_5$-$C_7$ heterocyclyl, —NHC(O)—$C_1$-$C_6$ alkyl, —NHC(O)—$C_3$-$C_7$ cycloalkyl, —NHC(O)—$C_1$-$C_3$ aralkyl and —NHC(O)-substituted phenyl. In a particular variation, at least one of $R^{5a}$, $R^{5b}$ and $R^{7a-h}$ is a moiety of the formula:

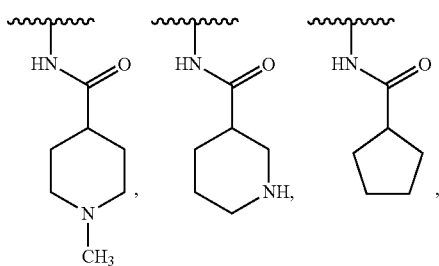

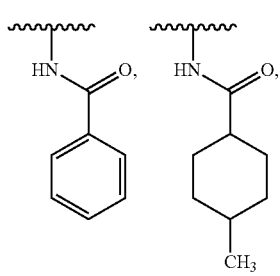

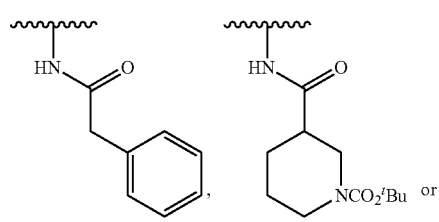

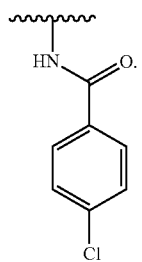

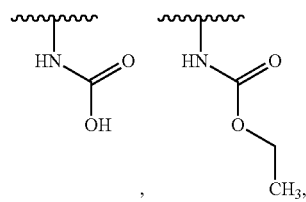

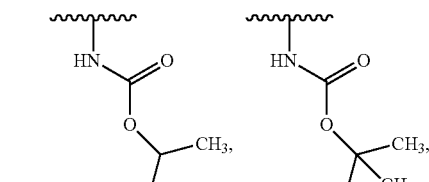

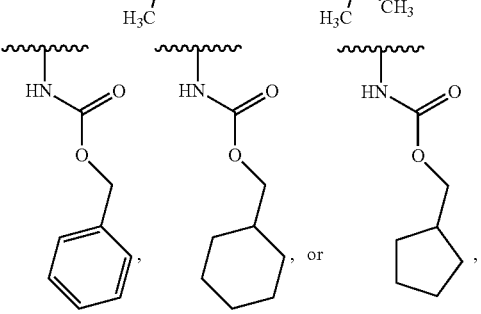

In one variation, a compound of the invention is provided where at least one of $R^{5a}$, $R^{5b}$ and $R^{7a-h}$ is acyloxy.

In one variation, a compound of the invention is provided where at least one of $R^{5a}$, $R^{5b}$ and $R^{7a-h}$ is a carbonylalkoxy moiety. In one variation, at least one of $R^{5a}$, $R^{5b}$ and $R^{7a-h}$ is a carbonylalkoxy moiety of the formula —C(O)—O—R where R is H, alkyl, substituted alkyl or alkaryl. In one variation, at least one of $R^{5a}$, $R^{5b}$ and $R^{7a-h}$ is a carbonylalkoxy moiety of the formula —C(O)—O—$C_1$-$C_6$ alkyl. In a particular variation, at least one of $R^{5a}$, $R^{5b}$ and $R^{7a-h}$ is a carbonylalkoxy moiety of the formula —C(O)—O—$C_2H_5$. In one variation, at least one of $R^{5a}$, $R^{5b}$ and $R^{7a-h}$ is a carbonylalkoxy moiety selected from the group consisting of: —C(O)—O—$C_1$-$C_{10}$alkyl, —C(O)—O—$C_1$-$C_3$alkaryl, —C(O)—O—$C_1$-$C_3$ substituted alkyl and —C(O)—OH. In another variation, $R^{5a}$, $R^{5b}$ or $R^{7a-h}$ is —C(O)—O—$C_1$-$C_6$alkyl. In a particular variation, at least one of $R^{5a}$, $R^{5b}$ and $R^{7a-h}$ is a moiety of the formula:

In another variation, a compound of the invention is provided where at least one of $R^{5a}$, $R^{5b}$ and $R^{7a-h}$ is an aminocarbonylalkoxy moiety. In one variation, at least one of $R^{5a}$, $R^{5b}$ and $R^{7a-h}$ is an aminocarbonylalkoxy moiety of the formula —NHC(O)—O—$R_b$. In another variation, at least one of $R^{5a}$, $R^{5b}$ and $R^{7a-h}$ is an aminocarbonylalkoxy moiety of the formula —NHC(O)—O—$R_b$ where $R_b$ is a substituted alkyl group. In a particular variation, at least one of $R^{5a}$, $R^{5b}$ and $R^{7a-h}$ is a moiety of the formula —NH—C(O)—O—$CH_2$—$CCl_3$.

The invention also embraces compounds where at least one of $R^{5a}$, $R^{5b}$ and $R^{7a-h}$ is an acylamino moiety. In one variation, at least one of $R^{5a}$, $R^{5b}$ and $R^{7a-h}$ is an acylamino group where at least one of $R_a$ and $R_b$ is H, such as when $R^{5a}$, $R^{5b}$ or $R^{7a-h}$ is of the formula —C(O)N(H)($R_b$). In another variation, at least one of $R^{5a}$, $R^{5b}$ and $R^{7a-h}$ is an acylamino group where both $R_a$ and $R_b$ are alkyl. In one variation, at least one of $R^{5a}$, $R^{5b}$ and $R^{7a-h}$ is an acylamino moiety selected from the group consisting of: —C(O)—N(H)(alkyl), —C(O)—N(alkyl)$_2$, —C(O)—N(H)(aralkyl) and —C(O)—N(H)(aryl). In another variation, at least one of $R^{5a}$, $R^{5b}$ and $R^{7a-h}$ is an acylamino moiety selected from the group consisting of: —C(O)—N(H)$_2$, —C(O)—N(H)($C_1$-$C_8$ alkyl), —C(O)—N($C_1$-$C_6$alkyl)$_2$ and —C(O)—N(H)($C_1$-$C_3$aralkyl). In a particular variation, at least one of $R^{5a}$, $R^{5b}$ and $R^{7a-h}$ is a moiety of the formula:

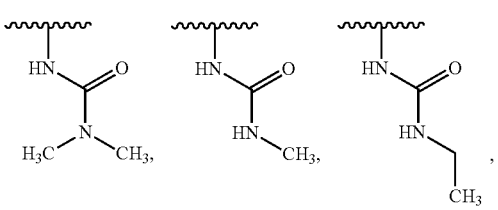

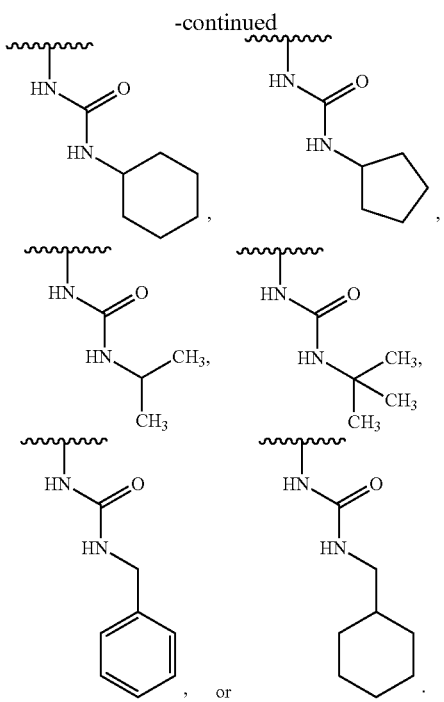

In a further variation, a compound of the invention is provided where $R^1$ is an unsubstituted alkyl, $R^{2a}$, $R^{2b}$, $R^{3a}$, $R^{3b}$ and $R^4$ are each H, each $X^1$, $X^2$, $X^3$ and $X^4$ is independently N or CH, and at least one of $R^{5a}$, $R^{5b}$ and $R^{7a-h}$ is a substituted or unsubstituted aryl, substituted or unsubstituted heteroaryl, including but not limited to a substituted or unsubstituted phenyl or pyridyl group. Where at least one of $R^{5a}$, $R^{5b}$ and $R^{7a-h}$ is a substituted phenyl or pyridyl group, in one variation it is substituted with at least one methyl or halo group.

In yet a further variation, a compound of the invention is provided where $R^1$ is a substituted or unsubstituted $C_1$-$C_8$ alkyl, acyl, acyloxy, carbonylalkoxy, substituted or unsubstituted heterocyclyl, substituted or unsubstituted aryl; each $R^{2a}$ and $R^{2b}$ is independently H, unsubstituted $C_1$-$C_8$ alkyl or halo; each $R^{3a}$ and $R^{3b}$ is independently H or halo; each $X^1$, $X^2$ and $X^3$ is CH or $CR^6$, where $R^6$ is as defined or as detailed in a particular variation, $R^6$ is halo, pyridyl, methyl or trifluoromethyl; $R^{4a}$ and $R^{4b}$ are both H, and at least one of $R^{5a}$, $R^{5b}$ and $R^{7a-h}$ is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, at least one of $R^{5a}$, $R^{5b}$ and $R^{7a-h}$ is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is provided where $R^1$ is a substituted or unsubstituted $C_1$-$C_8$ alkyl; each $R^{2a}$, $R^{2b}$, $R^{3a}$ and $R^{3b}$ is independently H or halo; each $R^6$ is independently halo, $C_1$-$C_8$ perhaloalkyl, substituted or a unsubstituted $C_1$-$C_8$ alkyl; and at least one of $R^{5a}$, $R^{5b}$ and $R^{7a-h}$ is a substituted or unsubstituted cyclohexyl, morpholinyl, piperazinyl, thiomorpholinyl, cyclopentyl or pyrrolidinyl moiety. The invention also embraces a compound where $R^1$ is a methyl; at least one of $X^1$ and $X^2$ is $CR^6$, and each $R^6$ is independently halo, methyl or trifluoromethyl. The invention embraces compounds where at least one of $R^{5a}$, $R^{5b}$ and $R^{7a-h}$ in any variation detailed is substituted with at least one carbonyl, hydroxymethyl, methyl or hydroxyl group, to the extent such substituent makes chemical sense.

In a particular variation, a compound is provided where $R^1$ is a substituted or unsubstituted $C_1$-$C_8$ alkyl; each $R^{2a}$ and $R^{2b}$ is independently H, a substituted or unsubstituted $C_1$-$C_8$ alkyl or $R^{2a}$ and $R^{2b}$ are taken together to form a carbonyl moiety; $R^{3a}$ and $R^{3b}$ are both H; each $R^6$ is independently halo or a substituted or unsubstituted $C_1$-$C_8$ alkyl; each $R^{4a}$ and $R^{4b}$ is independently H, halo, a substituted or unsubstituted $C_1$-$C_8$ alkyl, hydroxyl, alkoxy or $R^{4a}$ and $R^{4b}$ are taken together to form a carbonyl moiety, provided that at least one of $R^{4a}$ and $R^{4b}$ is other than H. In one aspect of this variation, at least one of $R^{5a}$, $R^{5b}$ and $R^{7a-h}$ may be a substituted or unsubstituted pyridyl, phenyl, pyrazinyl, piperazinyl, pyrrolidinyl or thiomorpholinyl group. In another aspect of this variation, at least one of $R^{5a}$, $R^{5b}$ and $R^{7a-h}$ is a pyridyl, phenyl, pyrazinyl, piperazinyl, pyrrolidinyl or thiomorpholinyl group substituted with at least one methyl or halo group. In yet another aspect of this variation, $X^1$, $X^2$, $X^3$ and $X^4$ are CH or $CR^6$ and each $R^6$ is independently halo or methyl.

The embodiments and variations described herein are suitable for compounds of any formulae detailed herein, where applicable. For instance, all variations referring to the formula (IA)-(VA) detailed herein, such as formulae (VA1), (VA2), (IA1)-(IA6), (IIA1)-(IIA6), (IIIA1)-(IIIA6), (IVA1)-(IVA6), (A1)-(A4), (B1)-(B2), (C1)-(C8), (D1)-(D4), (E1)-(E4), (F1-F7), (G1-G10), (H1)-(H2), where applicable, where applicable, may apply to formulae (IB)-(VB), (J-1)-(J-5) and (K-1)-(K-5) the same as if each and every variation were specifically and individually listed.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Kits comprising a compound of the invention, or a salt or solvate thereof, and suitable packaging are provided. In one embodiment, a kit further comprises instructions for use. In one aspect, a kit comprises a compound of the invention, or a salt or solvate thereof, and instructions for use of the compounds in the treatment of a cognitive disorder, psychotic disorder, neurotransmitter-mediated disorder or a neuronal disorder.

Articles of manufacture comprising a compound of the invention, or a salt or solvate thereof, in a suitable container are provided. The container may be a vial, jar, ampoule and the like.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha_{1D}$, $\alpha_{2A}$ and $\alpha_{2B}$), inhibition of binding of a ligand to a serotonin receptor (e.g., $5\text{-HT}_{2A}$, $5\text{-HT}_{2C}$, $5\text{-HT}_6$ and $5\text{-HT}_7$), inhibition of binding of a ligand to a dopamine receptor (e.g., $D_{2L}$), and inhibition of binding of a ligand to a histamine receptor (e.g., $H_1$, $H_2$ and $H_3$); agonist/antagonist activity to a serotonin receptor (e.g., $5\text{-HT}_{2A}$, $5\text{-HT}_6$); agonist/antagonist activity to a dopamine receptor (e.g., $D_{2L}$, $D_{2S}$); agonist/antagonist activity to a histamine receptor (e.g., $H_1$); activity in a neurite outgrowth assay; efficacy in a preclinical model of memory dysfunction associated with cholinergic dysfunction/hypofunction; efficacy in a preclinical model of attention impulsivity and executive function, and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85% and about 95% or between about 90% and about 100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha_{1D}$, $\alpha_{2A}$, $\alpha_{2B}$, $5\text{-HT}_{2A}$, $5\text{-HT}_{2C}$, $5\text{-HT}_6$, $5\text{-HT}_8$, $D_{2L}$, $H_1$, $H_2$, $H_3$). In one variation, a compound of the invention inhibits binding of a ligand to at least one receptor and as many as eleven as detailed herein (e.g. $\alpha_{1D}$, $\alpha_{2A}$, $\alpha_{2B}$, $5\text{-HT}_{2A}$, $5\text{-HT}_{2C}$, $5\text{-HT}_6$, $5\text{-HT}_7$, $D_2$, $H_1$, $H_2$, $H_3$). In one variation, a compound of the invention inhibits binding of a ligand to at least one and as many as eleven receptors detailed herein and further displays agonist or antagonist activity to one or more receptors detailed herein (e.g., serotonin receptor $5\text{-HT}_{2A}$, serotonin receptor $5\text{-HT}_6$, dopamine receptor $D_{2L}$, dopamine receptor $D_{2S}$ and histamine receptor $H_1$) as measured in the assays described herein. In one variation, agonist response of serotonin receptor $5\text{-HT}_{2A}$ is inhibited by compounds of the invention by at least about any one of 50%, 60%, 70%, 80%, 90%, 100%, 110%, 120%, 130%, 140%, 150% as determined in a suitable assay such as the assay described herein.

In one variation, a compound of the invention displays the above described neurotransmitter receptor binding profile e.g. inhibits binding of a ligand to at least one receptor and as many as eleven as detailed herein and further stimulates neurite outgrowth, e.g. as measured by the assays described herein. Certain compounds of the invention showed activity in neurite outgrowth assays using primary neurons in culture. Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neuronal disorders include ADHD. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, and in preclinical models of attention/impulsivity and executive function, e.g. shows pro-cognitive effects in a preclinical model of memory dysfunction. Compounds of the invention have been shown to be effective in a preclinical model of memory dysfunction associated with cholinergic hypofunction (see relevant Examples). As $H_1$ antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a 5-$HT_6$ antagonist may have cognition-enhancing effects as serotonin acting through this receptor may impair memory.

In another variation, a compound of the invention inhibits binding of a ligand to at least one and as many as eleven receptors as detailed herein, further shows efficacy in a preclinical model of memory dysfunction associated with cholinergic dysfunction/hypofunction e.g. shows pro-cognitive effects in a preclinical model of memory dysfunction, in preclinical models of attention/impulsivity and executive function, and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction e.g. shows pro-cognitive effects in a preclinical model of memory dysfunction, and in preclinical models of attention/impulsivity and executive function, and further stimulates neurite outgrowth.

In another variation, a compound of the invention inhibits at least one and as many as eleven receptors as detailed herein, further shows efficacy in a preclinical model of memory dysfunction associated with cholinergic dysfunction/hypofunction e.g. shows pro-cognitive effects in a preclinical model of memory dysfunction, in preclinical models of attention/impulsivity and executive function, further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, e.g., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, and in preclinical models of attention/impulsivity and executive function, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In a further variation, a compound of the invention inhibits binding of a ligand to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment, and in preclinical models of attention/impulsivity and executive function.

In one aspect, compounds of the invention inhibit binding of a ligand to adrenergic receptors $\alpha_{1D}$, $\alpha_{2A}$, $\alpha_{2B}$ and inhibit binding of a ligand to serotonin receptor 5-HT$_6$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$. In another variation, compounds of the invention inhibit binding of a ligand to adrenergic receptors $\alpha_{1D}$, $\alpha_{2A}$, $\alpha_{2B}$, to serotonin receptor 5-HT$_6$ and to any one or more of the following receptors: serotonin receptor 5-HT$_7$, 5-HT$_{2A}$ and 5-HT$_{2C}$ and further show weak inhibition of binding of a ligand to histamine receptor H$_1$ and/or H$_2$. In one variation, compounds of the invention that also display strong inhibition of binding of a ligand to the serotonin receptor 5-HT$_7$ are particularly desired. In another variation, compounds of the invention inhibit binding of a ligand to adrenergic receptors $\alpha_{1D}$, $\alpha_{2A}$, $\alpha_{2B}$, to serotonin receptor 5-HT$_6$ and further show weak inhibition of binding of a ligand to histamine receptor H$_1$ and/or H$_2$. Weak inhibition of binding of a ligand to the histamine H$_1$ receptor is permitted as agonists of this receptor have been implicated in stimulating memory as well as weight gain. In one variation, binding to histamine receptor H$_1$ is inhibited by less than about 80%. In another variation, binding of a ligand to histamine receptor H$_1$ is inhibited by less than about any of 75%, 70%, 65%, 60%, 55%, or 50% as determined by a suitable assay known in the art such as the assays described herein.

In another variation, compounds of the invention inhibit binding of a ligand to a dopamine receptor D$_2$. In another variation, compounds of the invention inhibit binding of a ligand to dopamine receptor D$_{2L}$. In another variation, compounds of the invention inhibit binding of a ligand to dopamine receptor D$_2$ and to serotonin receptor 5-HT$_{2A}$. In another variation, compounds of the invention inhibit binding of a ligand to dopamine receptor D$_{2L}$ and to serotonin receptor 5-HT$_{2A}$. In another variation, compounds of the invention inhibit binding of a ligand to histamine receptor H$_1$. In certain aspects, compounds of the invention further show one or more of the following properties: strong inhibition of binding of a ligand to the serotonin 5-HT$_7$ receptor, strong inhibition of binding of a ligand to the serotonin 5-HT$_{2A}$ receptor, strong inhibition of binding of a ligand to the serotonin 5-HT$_{2C}$ receptor, weak inhibition of binding of a ligand to the histamine H$_1$ receptor, weak inhibition of binding of ligands to the histamine H$_2$ receptor, and antagonist activity to serotonin receptor 5-HT$_{2A}$.

In one variation, compounds of the invention show any of the receptor binding aspects detailed herein and further display agonist/antagonist activity to one or more of the following receptors: serotonin receptor 5-HT$_{2A}$, serotonin receptor 5-HT$_6$, dopamine receptor D$_{2L}$, dopamine receptor D$_{2S}$ and histamine receptor H$_1$. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction, such as enhancement of memory retention and reduction of memory impairment and in preclinical models of attention/impulsivity and executive function. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT$_{2A}$, 5-HT$_6$, dopamine receptor D$_{2L}$, dopamine receptor D$_{2S}$ and histamine receptor H$_1$), neurite outgrowth, a preclinical model of memory dysfunction associated with cholinergic dysfunction/hypofunction and a preclinical model of schizophrenia.

In some aspects, compounds of the invention inhibit binding of a ligand to adrenergic receptors $\alpha_{1D}$, $\alpha_{2A}$, $\alpha_{2B}$, serotonin receptor 5-HT$_6$ and a dopamine receptor D$_2$ by at least about 80% as determined in a suitable assay known in the art such as the assays described herein. In one variation binding is inhibited by at least about 80% as measured in a suitable assay such as the assays described herein. In some aspects, compounds of the invention inhibit binding of a ligand to adrenergic receptors $\alpha_{1D}$, $\alpha_{2A}$, $\alpha_{2B}$, serotonin receptor 5-HT$_6$ and dopamine receptor D$_{2L}$ by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85% and about 95% or between about 90% and about 100% as determined in a suitable assay known in the art such as the assays described herein.

In some aspects, compounds of the invention display the above described neurotransmitter receptor binding profile and further show antipsychotic effects. It is recognized that compounds of the invention have binding profiles similar to compounds with antipsychotic activity and several compounds of the invention have been shown to be effective in a preclinical model of schizophrenia (see relevant Examples). In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction such as enhancement of memory retention and reduction of memory impairment. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In one variation, cognitive disorder as used herein includes and intends disorders that contain a cognitive component, such as psychotic disorders (e.g., schizophrenia) containing a cognitive component (e.g., CIAS). In one variation, cognitive disorder includes ADHD. In another aspect, the compounds described herein may be used to treat, prevent, delay the onset and/or delay the development of a psychotic disorder. In one variation, psychotic disorder as used herein includes and intends disorders that contain a psychotic component, for example cognitive disorders (e.g., Alzheimer's disease) that contain a psychotic component (e.g., psychosis of Alzheimer's Disease or dementia). In one variation, methods of improving at least one cognitive and/or psychotic symptom associated with schizophrenia are provided. In one aspect, methods of improving cognition in an individual who has or is suspected of having CIAS are provided. In a particular aspect, methods of treating schizophrenia are provided wherein the treatment provides for an improvement in one or more negative symptom and/or one or more positive symptom and/or one or more disorganized symptom of schizophrenia. In yet another aspect, the compounds described herein may be used to treat, prevent, delay the onset and/or delay the development of a neurotransmitter-mediated disorders disorder. In one aspect, a neurotransmitter-mediated disorder includes ADHD. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis, depression and ADHD. In one variation, depression as used herein includes and intends treatment-resistant depression, depression related to a psychotic disorder, or depression related to a bipolar disorder. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects. In a particular variation, a method of treating schizophrenia is provided, wherein the treatment provides an improvement in at least one cognitive function, such as an improvement in a cognitive function in an individual who has or is suspected of having CIAS. In a further variation, a method of treating schizophrenia is provided wherein the method reduces psychotic effects associated with schizophrenia. In one embodiment, a method of treating schizophrenia is provided wherein the method improves the negative symptoms of schizophrenia in an individual in need thereof. In one embodiment, a method of treating schizophrenia is provided wherein the method improves the positive symptoms of schizophrenia in an individual in need thereof. In a further variation, a method of treating schizophrenia is provided wherein the method both improves cognitive function and reduces psychotic effects in an individual in need thereof. A method of improving one or more negative, positive and disorganized symptoms of schizophrenia is also provided, where the method entails administering a compound as detailed herein, or a pharmaceutically acceptable salt thereof, to an individual in need of such improvement. In one variation, a method of improving at least one negative symptom of schizophrenia is provided, where the method entails administering a compound as detailed herein, or a pharmaceutically acceptable salt thereof, to an individual in need of such improvement. In another variation, a method of improving at least one negative and at least one positive symptom of schizophrenia is provided, where the method entails administering a compound as detailed herein, or a pharmaceutically acceptable salt thereof, to an individual in need of such improvement. In yet another variation, a method of improving at least one negative and at least one disorganized symptom of schizophrenia is also provided, where the method entails administering a compound as detailed herein, or a pharmaceutically acceptable salt thereof, to an individual in need of such improvement. In still another variation, a method of improving at least one positive and at least one disorganized symptom of schizophrenia is also provided, where the method entails administering a compound as detailed herein, or a pharmaceutically acceptable salt thereof, to an individual in need of such improvement. In still a further variation, a method of improving at least one negative, at least one positive and at least one disorganized symptom of schizophrenia is provided, where the method entails administering a compound as detailed herein, or a pharmaceutically acceptable salt thereof, to an individual in need of such improvement.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor $\alpha_{1D}$, $\alpha_{2A}$, $\alpha_{2B}$, serotonin receptor 5-$HT_{2A}$, 5-$HT_6$, 5-$HT_7$, histamine receptor $H_1$ and/or $H_2$ is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$ and a serotonin receptor 5-$HT_6$ receptor is expected to be or is beneficial for the cognitive disorders, psychotic disorders, neurotransmitter-mediated disorders and/or neuronal disorders. In some variations, modulation of adrenergic receptor $\alpha_{1D}$, $\alpha_{2A}$, $\alpha_{2B}$, and a serotonin receptor 5-$HT_6$ receptor and modulation of one or more of the following receptors serotonin 5-$HT_7$, 5-$HT_{2A}$, 5-$HT_{2C}$ and histamine $H_1$ and $H_2$ is expected to be or is beneficial for the cognitive disorders, psychotic disorders, neurotransmitter-mediated disorders and/or neuronal disorders. In some variations, modulation of a dopamine receptor $D_2$ is expected to be or is beneficial for the cognitive disorders, psychotic disorders, neurotransmitter-mediated disorders and/or neuronal disorders. In some variations, modulation of dopamine receptor $D_{2L}$ is expected to be or is beneficial for the cognitive disorders, psychotic disorders, neurotransmitter-mediated disorders and/or neuronal disorders. In some variations, modulation of a dopamine receptor $D_2$ is expected to be or is beneficial for the cognitive disorders, psychotic disorders, neurotransmitter-mediated disorders and/or neuronal disorders. In certain variations, modulation of a dopamine $D_{2L}$ receptor and serotonin receptor 5-$HT_{2A}$ is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor $\alpha_{1D}$, $\alpha_{2A}$, $\alpha_{2B}$, serotonin receptor 5-$HT_{2A}$, 5-$HT_6$, 5-$HT_7$, histamine receptor $H_1$ and/or $H_2$ is desirable or expected to be desirable to improve cognitive functions. In some variations modulation of $\alpha_{1D}$, $\alpha_{2A}$, $\alpha_{2B}$ adrenergic receptors and a serotonin 5-$HT_6$ receptor is desirable or expected to be desirable to improve cognitive functions. In some variations, modulation of $\alpha_m$, $\alpha_{2A}$, $\alpha_{2B}$ adrenergic receptors and serotonin receptor 5-$HT_6$ and modulation of one or more of the following receptors: serotonin receptor 5-$HT_7$, 5-$HT_{2A}$, 5-$HT_{2C}$ and histamine receptor $H_1$ and $H_2$, is desirable or expected to be desirable to improve cognitive functions. In another aspect, the invention encompasses methods to reduce psychotic effects by administering a compound of the invention to an individual in need thereof. In some embodiments, modulation of a dopamine $D_2$ receptor is expected to be or is desirable to reduce psychotic effects. In some embodiments, modulation of a dopamine $D_{2L}$ receptor is expected to be or is desirable to reduce psychotic effects. In some embodiments, modulation of a dopamine $D_2$ receptor and a serotonin 5-$HT_{2A}$ receptor is expected to be or is desirable to reduce psychotic effects. In some embodiments, modulation of a dopamine $D_{2L}$ receptor and a serotonin 5-$HT_{2A}$ receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a $\alpha_{1D}$, $\alpha_{2A}$, $\alpha_{2B}$ adrenergic receptor and a serotonin 5-$HT_6$ receptor. In some variations, the aminergic G protein-coupled receptor is a $\alpha_{1D}$, $\alpha_{2A}$, $\alpha_{2B}$ adrenergic receptor and a serotonin 5-$HT_6$ and 5-$HT_7$ receptor. In some variations, the aminergic G protein-coupled receptor is a $\alpha_{1D}$, $\alpha_{2A}$, $\alpha_{2B}$ adrenergic receptor, a serotonin 5-$HT_6$ and one or more of the following receptors: serotonin 5-$HT_7$, 5-$HT_{2A}$ and 5-$HT_{2C}$ and histamine $H_1$ and $H_2$ receptor. In some variations, the aminergic G protein-coupled receptor is a dopamine $D_2$ receptor. In some variations, the aminergic G protein-coupled receptor is a dopamine $D_{2L}$ receptor. In some variations, the aminergic G protein-coupled receptor is a dopamine $D_2$ receptor and a serotonin 5-$HT_{2A}$ receptor. In some variations, the aminergic G protein-coupled receptor is a dopamine $D_{2L}$ receptor and a serotonin 5-$HT_{2A}$ receptor. In some variations, the aminergic G protein-coupled receptor is a histamine $H_1$ receptor.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

General methods of preparing compounds according to the invention are depicted in the exemplified methods below. Other compounds of the invention may be prepared by similar methods. Synthetic methods to provide similar intermediates have also been described in, for example, PCT Patent Application Nos. PCT/US2008/081390, PCT/US2009/032065, PCT/US2009/038142, PCT/US2009/038138, PCT/US2010/050078, PCT/US2010/050079 and PCT/US2010/050081. Synthetic methods to provide azepino[4,5-b]indole intermediates have been described in PCT Application No. PCT/US2009/062872. The experimental details of each of these Applications are incorporated herein by reference.

General Method 1

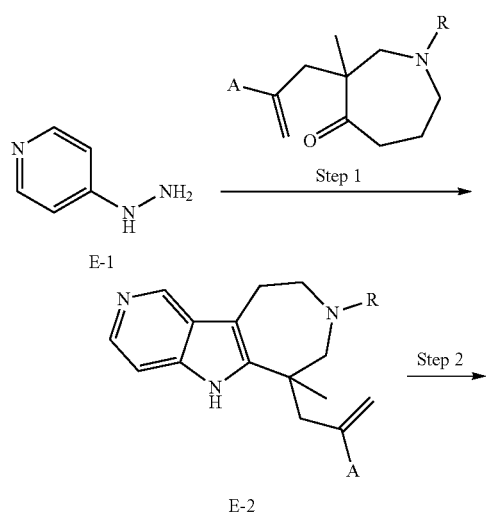

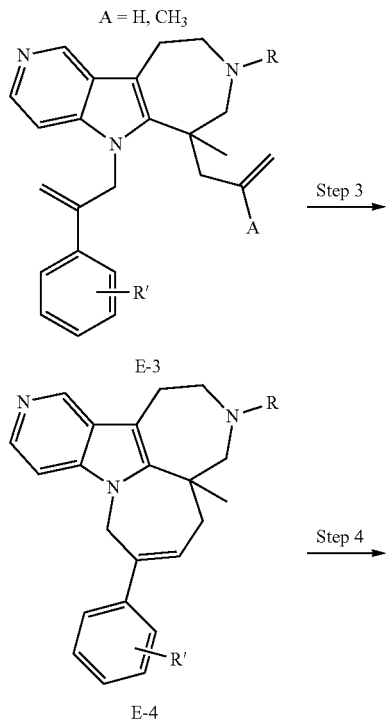

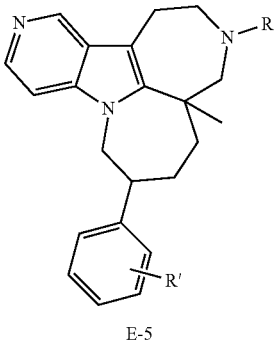

Condensation of appropriately functionalized 4-hydrazino pyridine E-1 with functionalized azepan-4-ones [(A) is, for example, H, Me] in step 1 yields the 9-aza-hexahydroazepino[5,4-b]indole intermediate E-2. Subjecting E-2 to alkene coupling conditions with appropriately functionalized alkenes in step 2 yields the adduct E-3 which, when treated under ring-closing metathesis reaction conditions of step 3 results in fused cyclic product E-4. Reduction of the double bond in the cycloalkene in step 4 affords the cycloalkyl derivative E-5. Although the Scheme depicts phenyl or pyridyl rings in the compounds, it is understood that a number of aromatic and heteroaromatic analogs are conceivable for such synthetic routes, including but not limited to pyrimidine, pyrazine, thiophene, furan, pyrrole, imidazole, thiazole, and the like. Similarly, the point of attachment of groups such as R' to the aromatic or heteroaromatic groups can be envisioned in a variety of chemically feasible locations. All possible attachment locations of functional groups on the aromatic ring(s) should be considered.

General Method 2

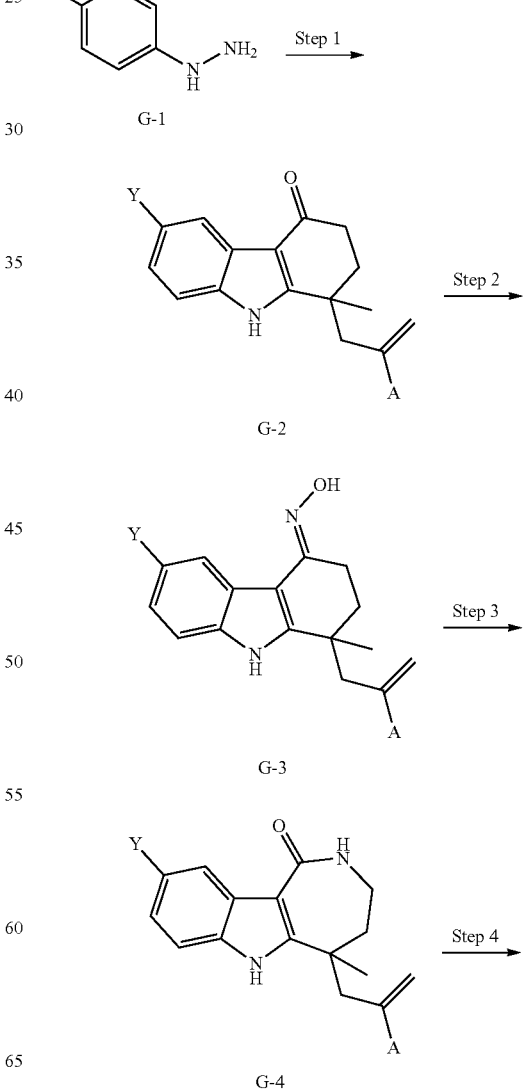

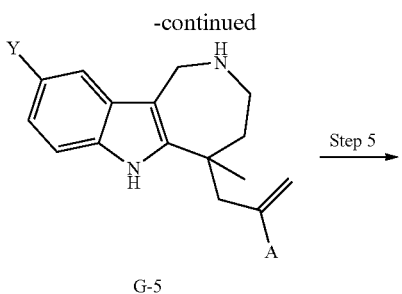

G-5

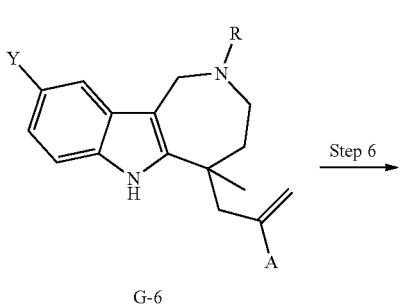

G-6

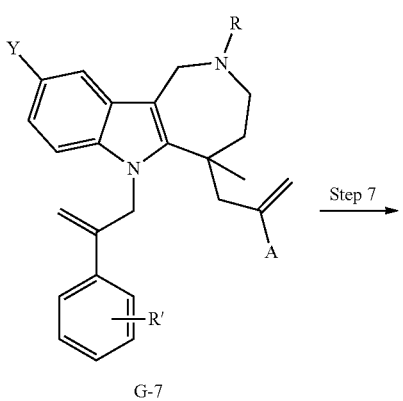

G-7

Y = CH₃, halo
A = H, CH³

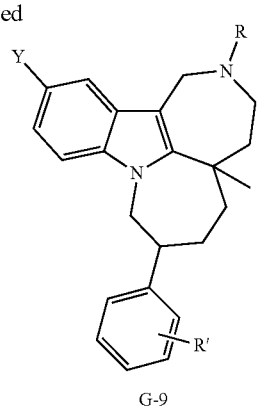

G-8

Step 5 → Step 6 → Step 7 → Step 8 →

G-9

Condensation of appropriately functionalized aryl hydrazine G-1 with appropriately functionalized cyclohexane-1,3-diones in step 1 yields the dihydrocarbazolone intermediate G-2. The keto group is then converted in step 2 using standard conditions to give oxime G-3 that can undergo a Beckmann rearrangement in step 3 to yield the tetrahydroazepinoindolone G-4. Reduction of the amide in step 4 provides hexahydroazepinoindole G-5, the secondary amino group of which can be functionalized in step 5 to provide functionalized tertiary amine G-6. Subjecting G-6 to alkene coupling conditions with appropriately functionalized alkenes in step 6 yields the adduct G-7 which, when treated under ring-closing metathesis reaction conditions of step 7 results in fused cyclic product G-8. Reduction of the double bond in the cycloalkene in step 8 affords the cycloalkyl derivative G-9. Although the Scheme depicts phenyl or pyridyl rings in the compounds, it is understood that a number of aromatic and heteroaromatic analogs are conceivable for such synthetic routes, including but not limited to pyrimidine, pyrazine, thiophene, furan, pyrrole, imidazole, thiazole, and the like. Similarly, the point of attachment of groups such as R' to the aromatic or heteroaromatic groups can be envisioned in a variety of chemically feasible locations. All possible attachment locations of functional groups on the aromatic ring(s) should be considered.

Representative compounds of the invention are shown in Table 1.

TABLE 1

Representative Compounds of the Invention

| Compound No. | Structure |
|---|---|
| 1 | (structure shown) |

TABLE 1-continued

Representative Compounds of the Invention

| Compound No. | Structure |
|---|---|
| 2 | *[structure]* |
| 3 | *[structure]* |
| 4 | *[structure]* |
| 5 | *[structure]* |
| 6 | *[structure]* |
| 7 | *[structure]* |
| 8 | *[structure]* |
| 9 | *[structure]* |

TABLE 1-continued

Representative Compounds of the Invention

| Compound No. | Structure |
|---|---|
| 10 | 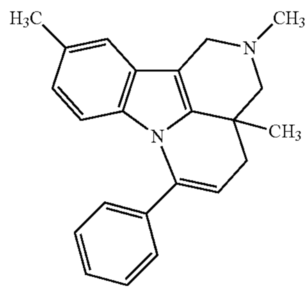 |
| 11 | 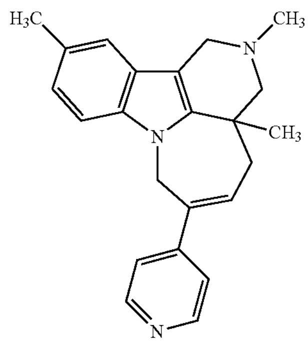 |
| 12 | 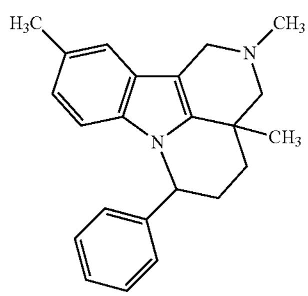 |
| 13 | 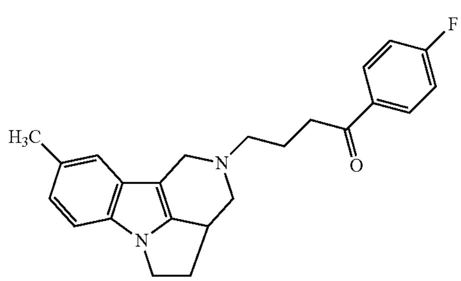 [SMILES: Cc1ccc2c(c1)c1c3n2CCC3CN(CCCC(=O)c2ccc(F)cc2)C1] |
| 14 | 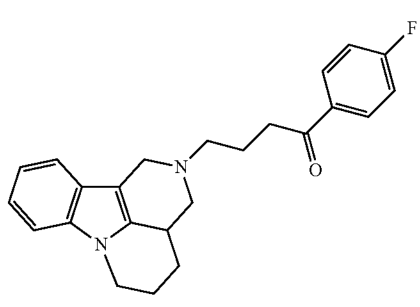 [SMILES: O=C(CCCN1Cc2c3n(c4ccccc24)CCCC3C1)c1ccc(F)cc1] |
| 15 | |
| 16 | |
| 17 | |
| 18 | |
| 19 | |

TABLE 1-continued

Representative Compounds of the Invention

| Compound No. | Structure |
|---|---|
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE 1-continued

Representative Compounds of the Invention

| Compound No. | Structure |
|---|---|
| 28 | 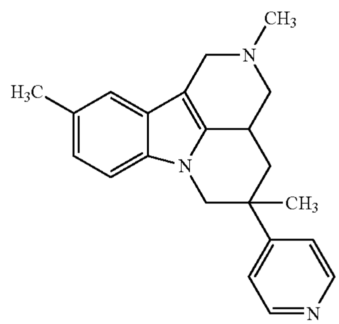 [SMILES: Cc1ccc2c(c1)c1c3n2CC(C)(c2ccncc2)CC3CN(C)C1] |
| 29 | 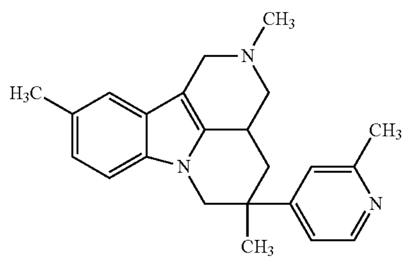 |
| 30 | 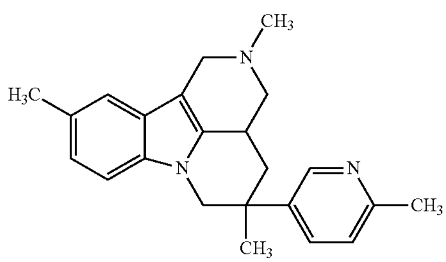 |
| 31 | 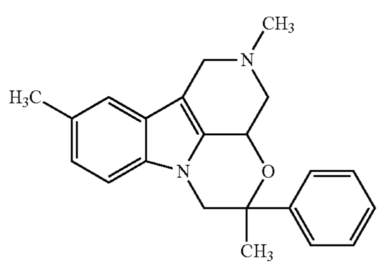 [SMILES: Cc1ccc2c(c1)c1c3n2CC(C)(c2ccccc2)OC3CN(C)C1] |
| 32 | 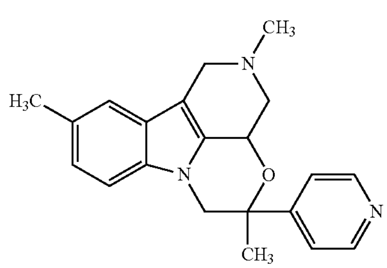 [SMILES: Cc1ccc2c(c1)c1c3n2CC(C)(c2ccncc2)OC3CN(C)C1] |
| 33 | |
| 34 | |
| 35 | |
| 36 | |
| 37 | |

TABLE 1-continued

Representative Compounds of the Invention

| Compound No. | Structure |
|---|---|
| 38 | (chemical structure) |
| 39 | (chemical structure) |
| 40 | (chemical structure) |
| 41 | (chemical structure) |
| 42 | (chemical structure) |
| 43 | (chemical structure) |
| 44 | (chemical structure) |
| 45 | (chemical structure) |

TABLE 1-continued

Representative Compounds of the Invention

| Compound No. | Structure |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |

TABLE 1-continued

Representative Compounds of the Invention

| Compound No. | Structure |
|---|---|
| 54 | 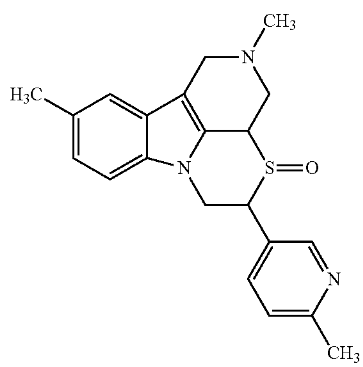 |
| 55 | 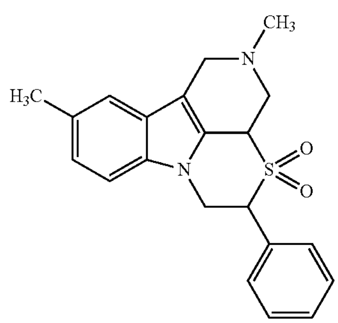 [SMILES: Cc1ccc2c(c1)c1c3n2CC(c2ccccc2)S(=O)(=O)C3CN(C)C1] |
| 56 | 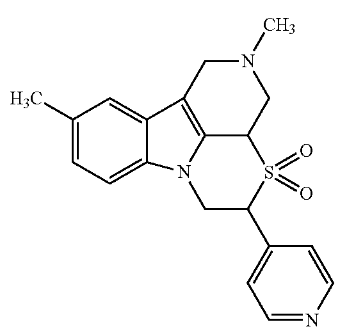 [SMILES: Cc1ccc2c(c1)c1c3n2CC(c2ccncc2)S(=O)(=O)C3CN(C)C1] |
| 57 | 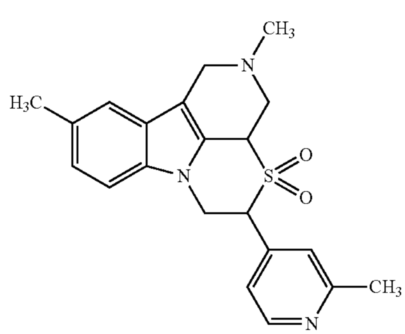 |
| 58 | |
| 59 | |
| 60 | |
| 61 | |

TABLE 1-continued

Representative Compounds of the Invention

| Compound No. | Structure |
|---|---|
| 62 | (structure) |
| 63 | (structure) |
| 64 | (structure) |
| 65 | (structure) |
| 66 | (structure) |
| 67 | (structure) |
| 68 | (structure) |
| 69 | (structure) |

TABLE 1-continued

Representative Compounds of the Invention

| Compound No. | Structure |
|---|---|
| 70 | (structure: chloro-substituted tetracyclic indole core with N-CH₃ and 4-(2-methylpyridin-4-yl) substituent) |
| 71 | (structure: chloro-substituted tetracyclic indole core with N-CH₃ and 3-(6-methylpyridin-3-yl) substituent) |
| 72 | (structure: chloro-substituted tetracyclic indole core with N-CH₃ and a CH₃, phenyl substituted carbon) |
| 73 | (structure: chloro-substituted tetracyclic indole core with N-CH₃, ketone (C=O), CH₃ and phenyl substituents) |
| 74 | (structure: chloro-substituted tetracyclic indole core with N-CH₃, CH₃ and pyridin-4-yl substituents) |
| 75 | (structure: chloro-substituted tetracyclic indole core with N-CH₃, 2-methylpyridin-4-yl and CH₃ substituents) |
| 76 | (structure: chloro-substituted tetracyclic indole core with N-CH₃, 6-methylpyridin-3-yl and CH₃ substituents) |
| 77 | (structure: chloro-substituted tricyclic indole core with N-CH₃, oxazine ring bearing phenyl and CH₃ substituents) |
| 78 | (structure: chloro-substituted tricyclic indole core with N-CH₃, oxazine ring bearing pyridin-4-yl and CH₃ substituents) |

TABLE 1-continued

Representative Compounds of the Invention

| Compound No. | Structure |
|---|---|
| 79 | 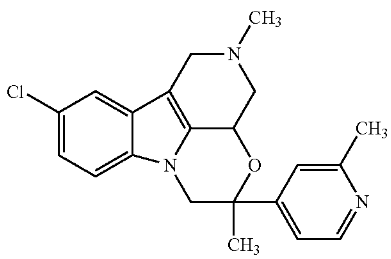 |
| 80 | 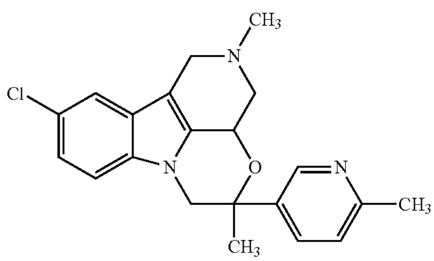 |
| 81 | 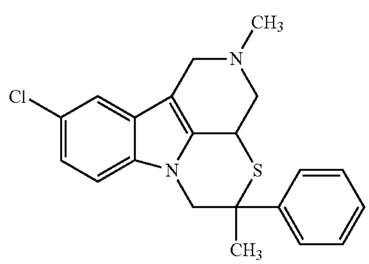 [SMILES: CN1Cc2c3n(c4ccc(Cl)cc24)CC(C)(c2ccccc2)OC3C1] |
| 82 | 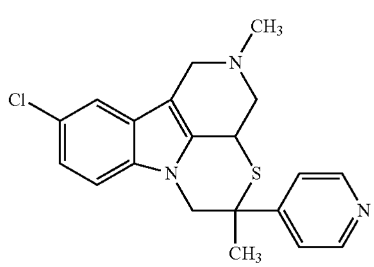 [SMILES: CN1Cc2c3n(c4ccc(Cl)cc24)CC(C)(c2ccncc2)SC3C1] |
| 83 | 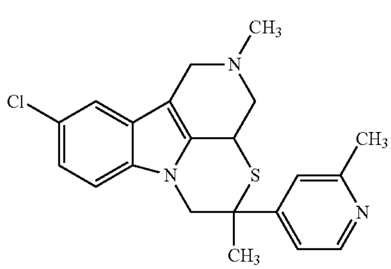 [SMILES: Cc1cc(C2(C)Cn3c4c(c5cc(Cl)ccc53)CN(C)CC4S2)ccn1] |
| 84 | 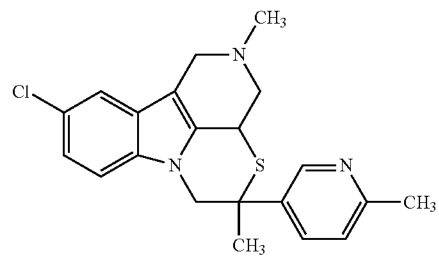 [SMILES: Cc1ccc(C2(C)Cn3c4c(c5cc(Cl)ccc53)CN(C)CC4S2)cn1] |
| 85 | 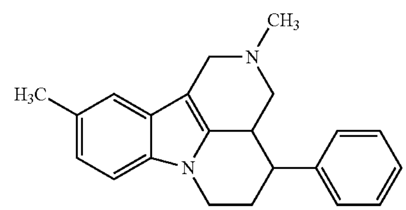 [SMILES: Cc1ccc2c(c1)c1c3n2CCC(c2ccccc2)C3CN(C)C1] |
| 86 | 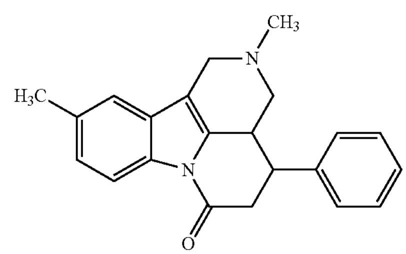 [SMILES: Cc1ccc2c(c1)c1c3n2C(=O)CC(c2ccccc2)C3CN(C)C1] |
| 87 | 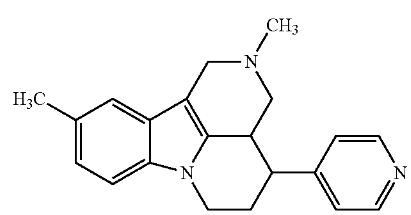 [SMILES: Cc1ccc2c(c1)c1c3n2CCC(c2ccncc2)C3CN(C)C1] |
| 88 | 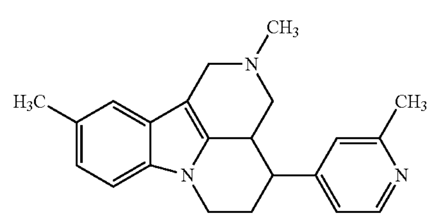 |
| 89 | 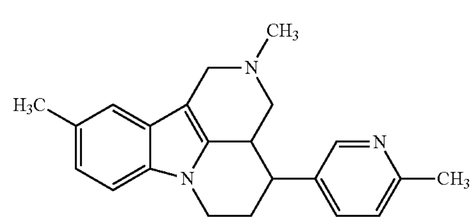 |

TABLE 1-continued

Representative Compounds of the Invention

| Compound No. | Structure |
|---|---|
| 90 | 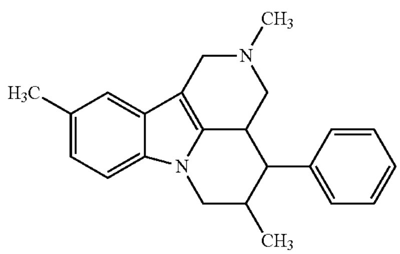 |
| 91 | 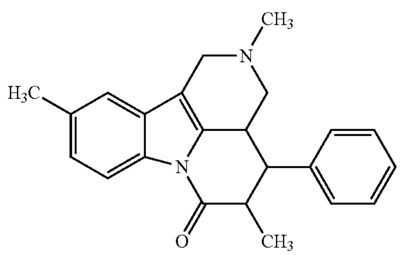 [SMILES: Cc1ccc2c(c1)c1c3n2C(=O)C(C)C(c2ccccc2)C3CN(C)C1] |
| 92 | 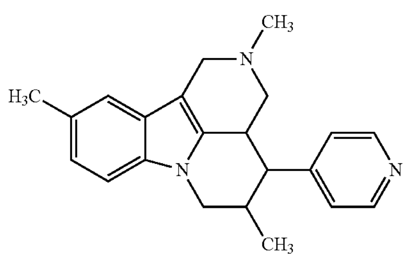 [SMILES: Cc1ccc2c(c1)c1c3n2CC(C)C(c2ccncc2)C3CN(C)C1] |
| 93 | 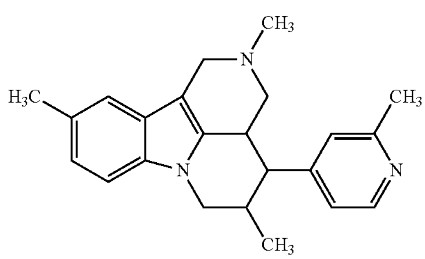 |
| 94 | 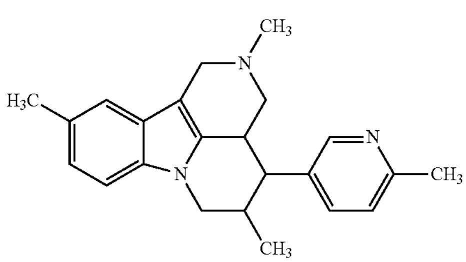 |
| 95 | |
| 96 | |
| 97 | |
| 98 | |
| 99 | |

TABLE 1-continued
Representative Compounds of the Invention
| Compound No. | Structure |
|---|---|
| 100 | 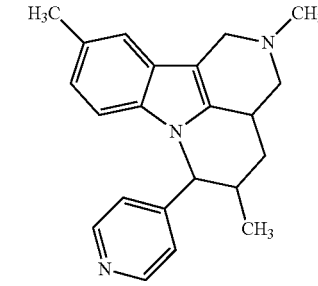 |
| 101 | 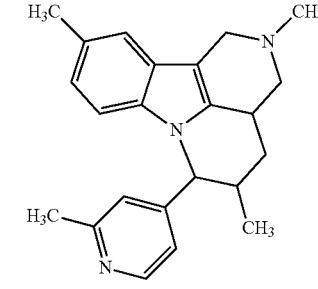 |
| 102 | 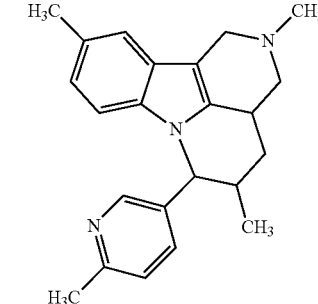 |
| 103 | 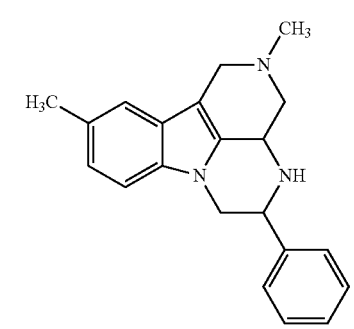 [SMILES: Cc1ccc2c(c1)c1c3n2CC(c2ccccc2)NC3CN(C)C1] |
| 104 | 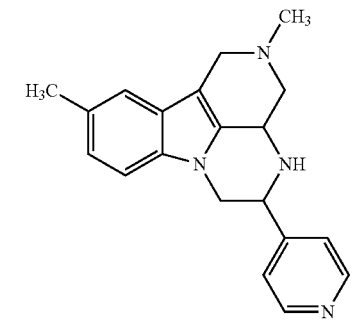 |
| 105 | 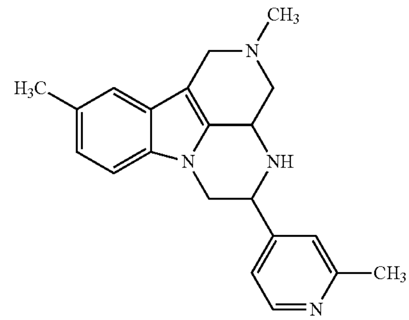 |
| 106 | 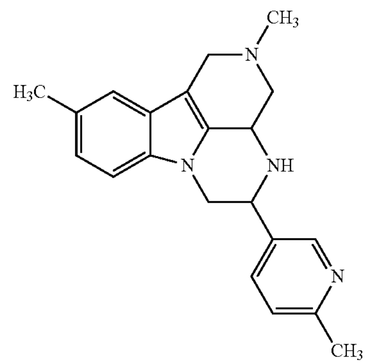 |
| 107 | 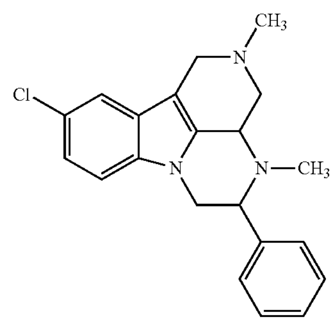 [SMILES: CN1Cc2c3n(c4ccc(Cl)cc24)CC(c2ccccc2)N(C)C3C1] |
| 108 | 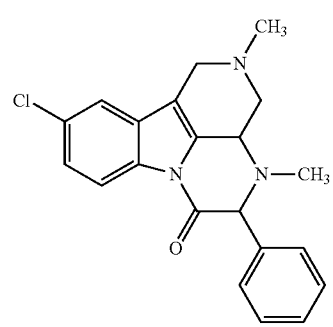 [SMILES: CN1Cc2c3n(c4ccc(Cl)cc24)C(=O)C(c2ccccc2)N(C)C3C1] |

TABLE 1-continued
Representative Compounds of the Invention
| Compound No. | Structure |
|---|---|
| 109 | 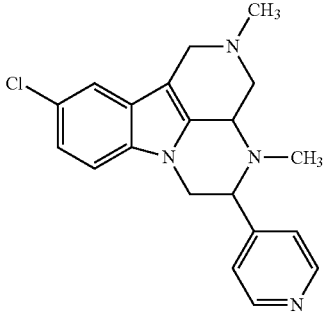 [SMILES: CN1Cc2c3n(c4ccc(Cl)cc24)CC(c2ccncc2)N(C)C3C1] |
| 110 | 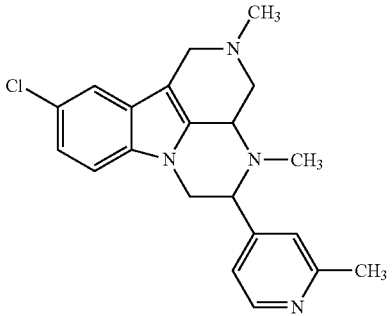 [SMILES: Cc1cc(C2Cn3c4c(c5cc(Cl)ccc53)CN(C)CC4N2C)ccn1] |
| 111 | 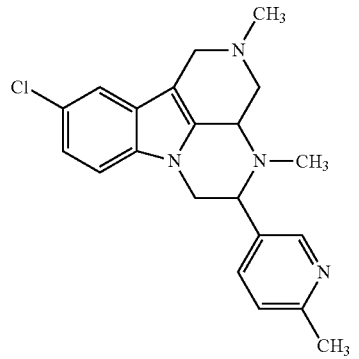 [SMILES: Cc1ccc(C2Cn3c4c(c5cc(Cl)ccc53)CN(C)CC4N2C)cn1] |
| 112 | 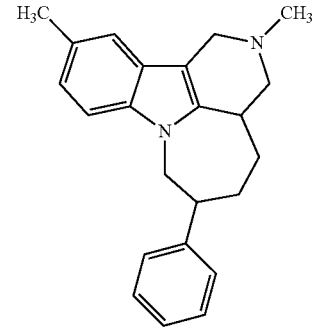 |
| 113 | 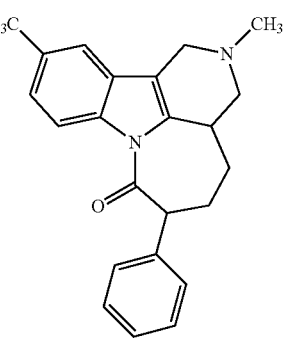 |
| 114 | 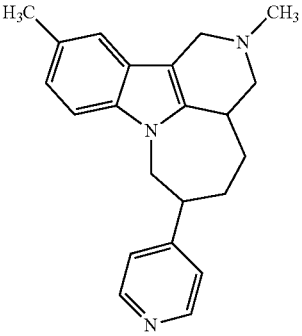 |
| 115 | 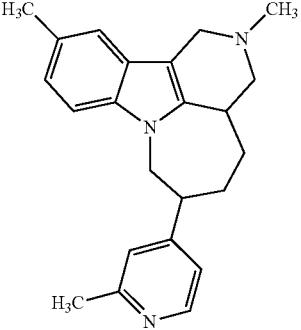 |
| 116 | 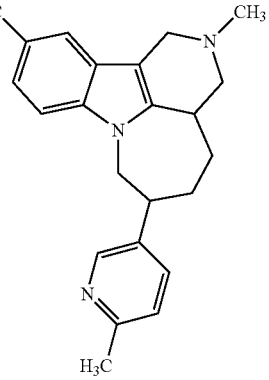 |

TABLE 1-continued

Representative Compounds of the Invention

| Compound No. | Structure |
|---|---|
| 117 | *structure* |
| 118 | *structure* |
| 119 | *structure* |
| 120 | *structure* |
| 121 | *structure* |
| 122 | *structure* |
| 123 | *structure* |
| 124 | *structure* |

TABLE 1-continued
Representative Compounds of the Invention
| Compound No. | Structure |
|---|---|
| 125 | 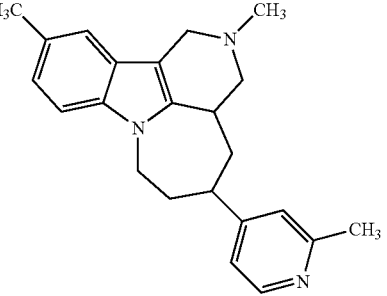 |
| 126 | 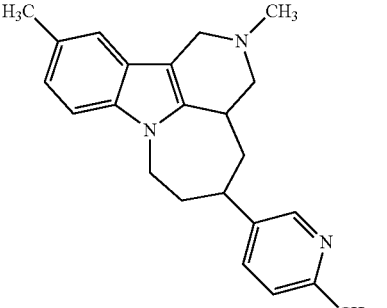 |
| 127 | 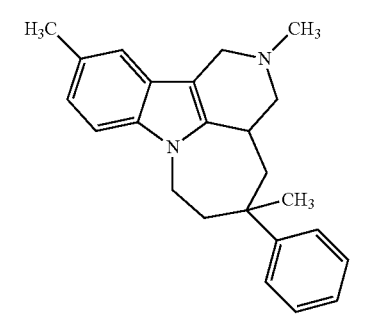 [SMILES: Cc1ccc2c(c1)c1c3n2CCC(C)(c2ccccc2)CC3CN(C)C1] |
| 128 | 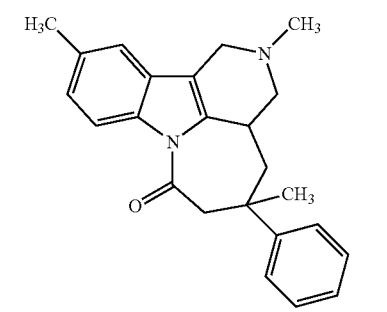 [SMILES: Cc1ccc2c(c1)c1c3n2C(=O)CC(C)(c2ccccc2)CC3CN(C)C1] |
| 129 | 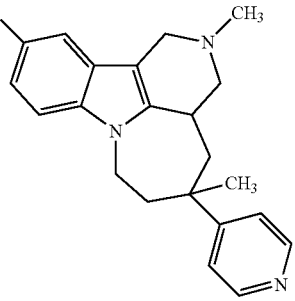 |
| 130 | 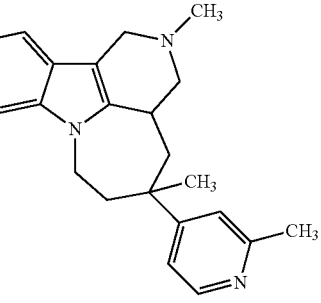 |
| 131 | 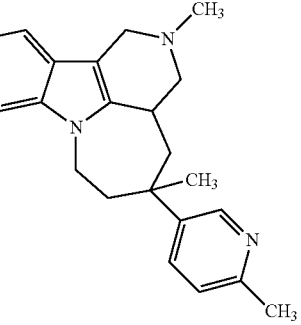 |
| 132 | 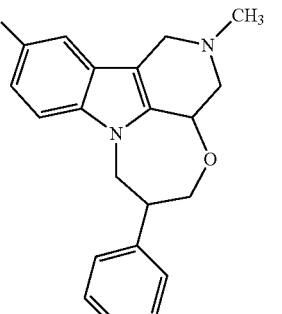 |

TABLE 1-continued
Representative Compounds of the Invention
| Compound No. | Structure |
|---|---|
| 133 | 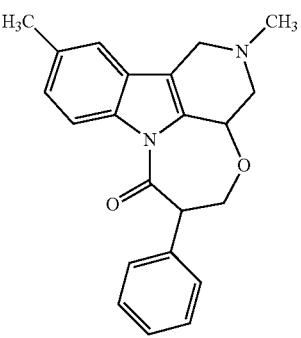 |
| 134 | 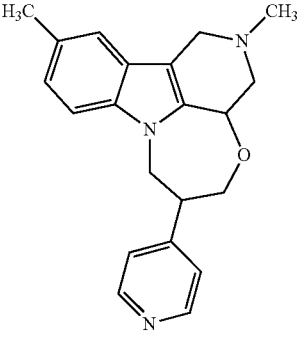 |
| 135 | 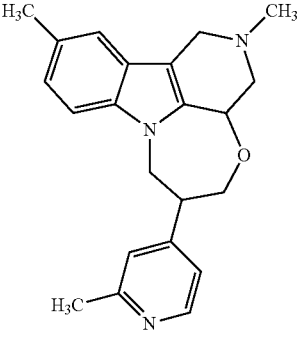 |
| 136 | 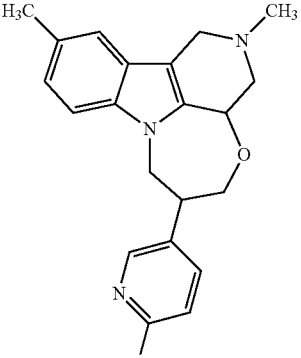 |
| 137 | 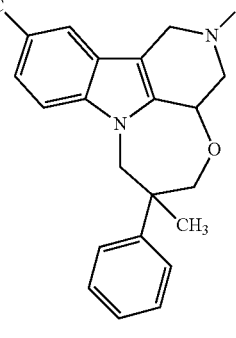 |
| 138 | 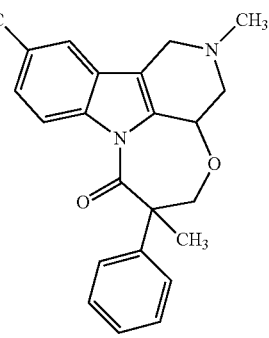 |
| 139 | 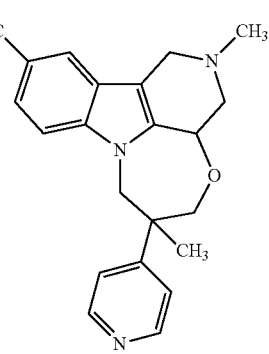 |
| 140 | 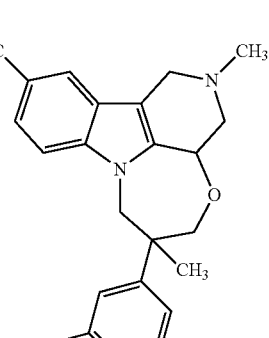 |

TABLE 1-continued

Representative Compounds of the Invention

| Compound No. | Structure |
|---|---|
| 141 | |
| 142 | |
| 143 | |
| 144 | |
| 145 | 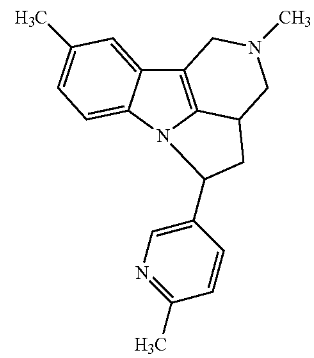 |
| 146 | 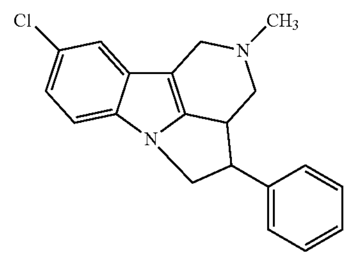 [SMILES: CN1Cc2c3n(c4ccc(Cl)cc24)CC(c2ccccc2)C3C1] |
| 147 | 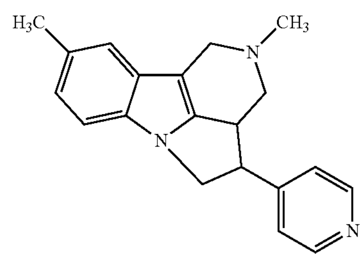 [SMILES: Cc1ccc2c(c1)c1c3n2CC(c2ccncc2)C3CN(C)C1] |
| 148 | 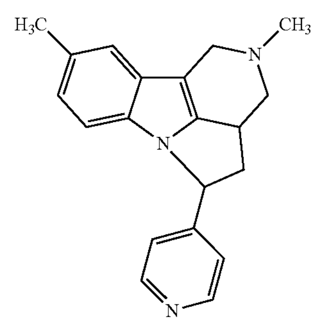 |
| 149 | 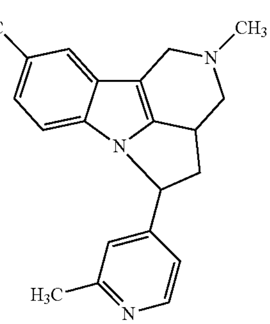 |

TABLE 1-continued

Representative Compounds of the Invention

| Compound No. | Structure |
|---|---|
| 150 | 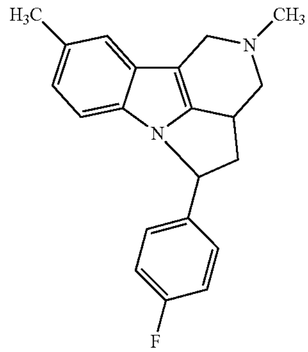 |
| 151 | 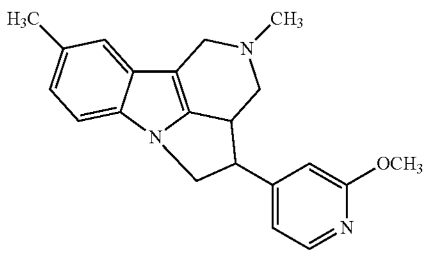 [SMILES: COc1cc(C2Cn3c4c(c5cc(C)ccc53)CN(C)CC42)ccn1] |
| 152 | 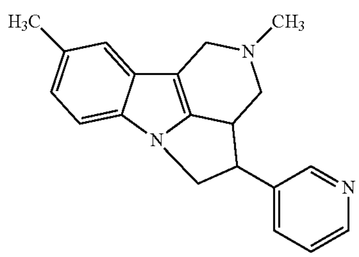 [SMILES: Cc1ccc2c(c1)c1c3n2CC(c2cccnc2)C3CN(C)C1] |
| 153 | 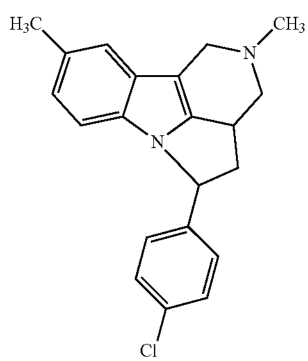 |
| 154 | 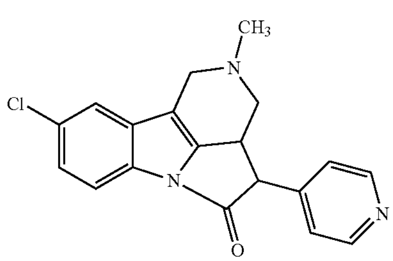 [SMILES: CN1Cc2c3n(c4ccc(Cl)cc24)C(=O)C(c2ccncc2)C3C1] |
| 155 | |
| 156 | |
| 157 | |
| 158 | |

TABLE 1-continued

Representative Compounds of the Invention

| Compound No. | Structure |
|---|---|
| 159 | 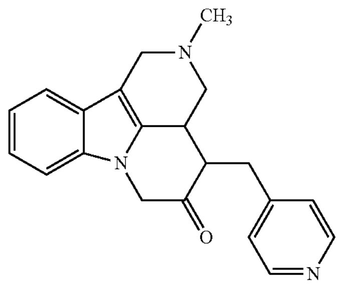 [SMILES: CN1Cc2c3n(c4ccccc24)CC(=O)C(Cc2ccncc2)C3C1] |
| 160 | 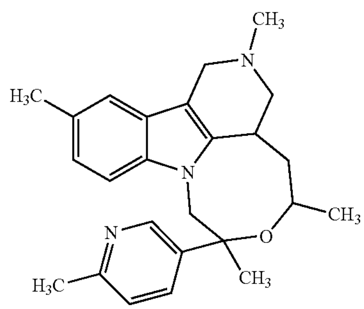 |
| 161 | 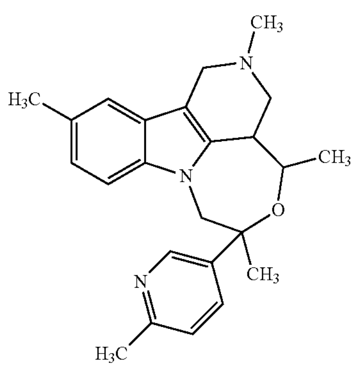 |
| 162 | 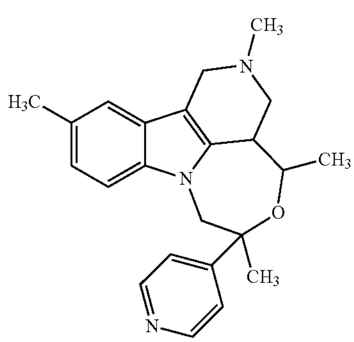 |
| 163 | 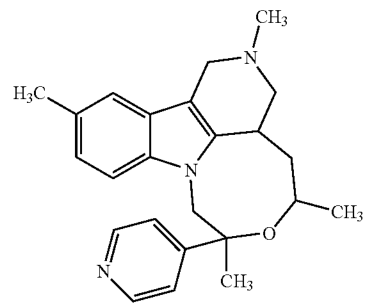 |
| 164 | 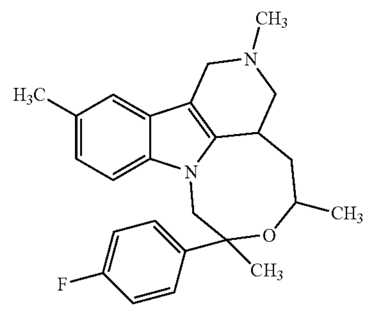 |
| 165 | 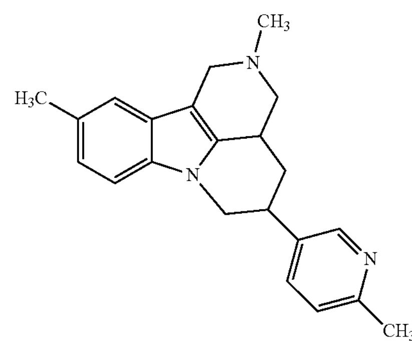 |
| 166 | 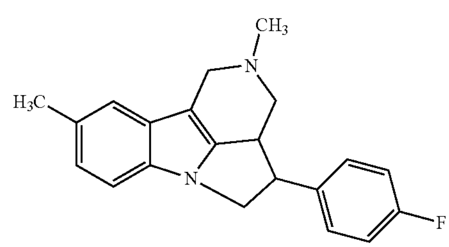 [SMILES: Cc1ccc2c(c1)c1c3n2CC(c2ccc(F)cc2)C3CN(C)C1] |
| 167 | 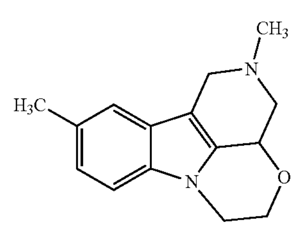 [SMILES: Cc1ccc2c(c1)c1c3n2CCOC3CN(C)C1] |

TABLE 1-continued

Representative Compounds of the Invention

| Compound No. | Structure |
|---|---|
| 168 | 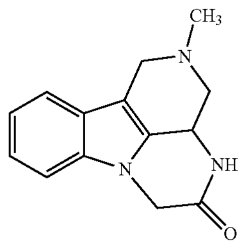 [SMILES: CN1Cc2c3n(c4ccccc24)CC(=O)NC3C1] |
| 169 | 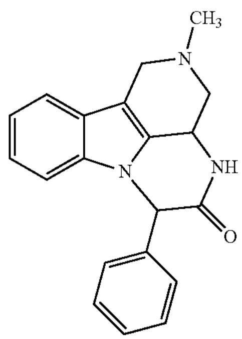 [SMILES: CN1Cc2c3n(c4ccccc24)C(c2ccccc2)C(=O)NC3C1] |
| 170 | 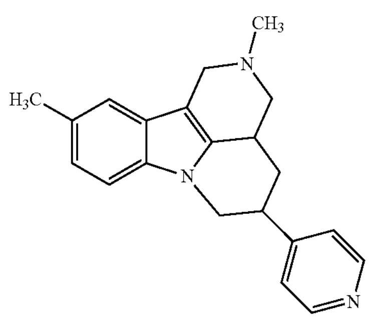 |
| 171 | 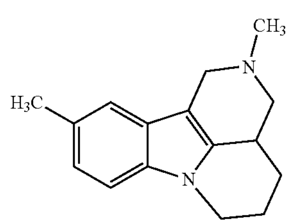 [SMILES: Cc1ccc2c(c1)c1c3n2CCCC3CN(C)C1] |
| 172 | 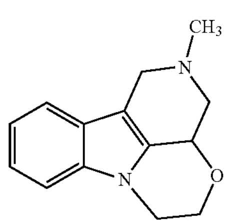 [SMILES: CN1Cc2c3n(c4ccccc24)CCOC3C1] |
| 173 | |
| 174 | |
| 175 | |
| 176 | |
| 177 | |

TABLE 1-continued
Representative Compounds of the Invention
| Compound No. | Structure |
|---|---|
| 178 | 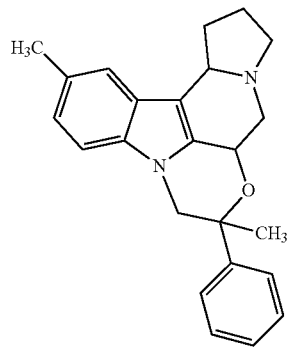 [SMILES: Cc1ccc2c(c1)c1c3n2CC(C)(c2ccccc2)OC3CN2CCCC12] |
| 179 | 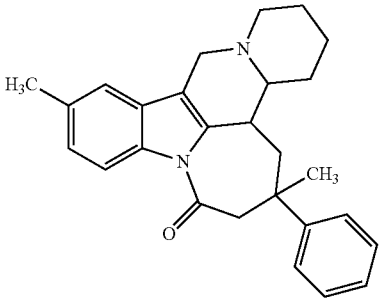 [SMILES: Cc1ccc2c(c1)c1c3n2C(=O)CC(C)(c2ccccc2)CC3C2CCCCN2C1] |
| 180 | 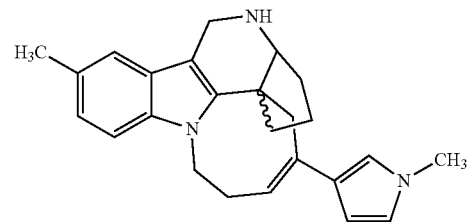 |
| 181 | 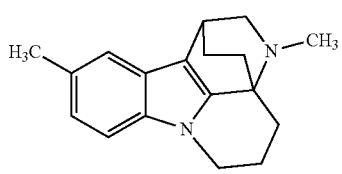 |
| 182 | 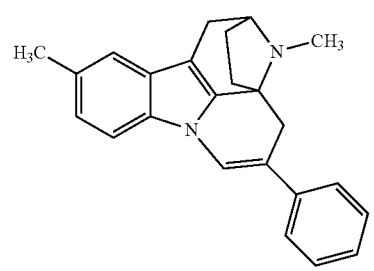 [SMILES: Cc1ccc2c(c1)c1c3n2C=C(c2ccccc2)CC32CCC(C1)N2C] |
| 183 | 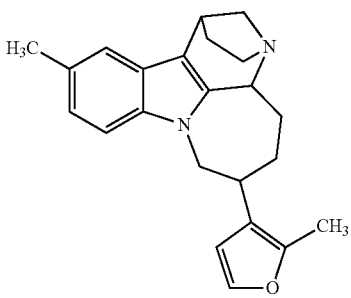 |
| 184 | 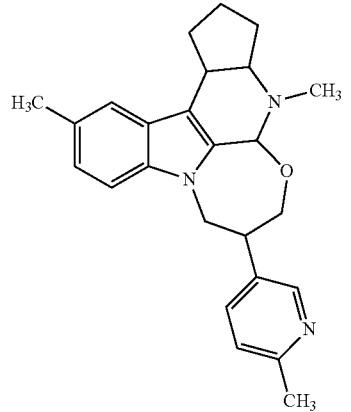 |
| 185 | 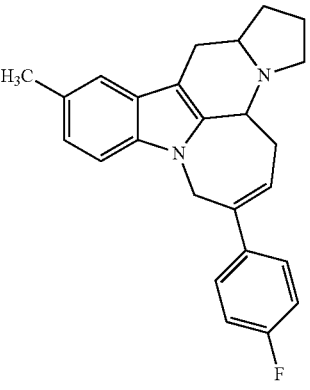 [SMILES: Cc1ccc2c(c1)c1c3n2CC(c2ccc(F)cc2)=CCC3N2CCCC2C1] |
| 186 | 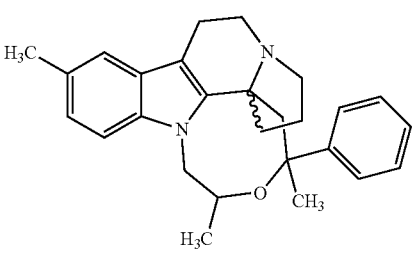 [SMILES: Cc1ccc2c(c1)c1c3n2CC(C)OC(C)(c2ccccc2)CC32CCCN2CC1] |

TABLE 1-continued
Representative Compounds of the Invention
| Compound No. | Structure |
|---|---|
| 187 | 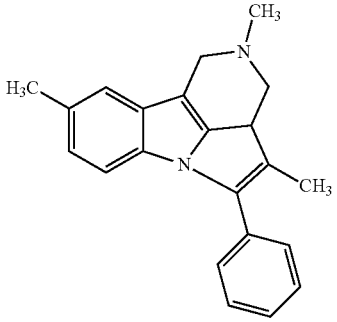 |
| 188 | 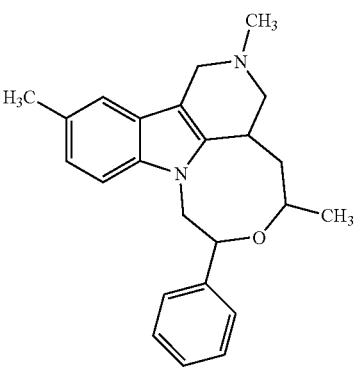 |
| 189 | 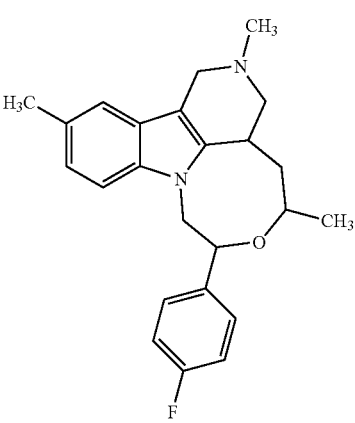 |
| 190 | 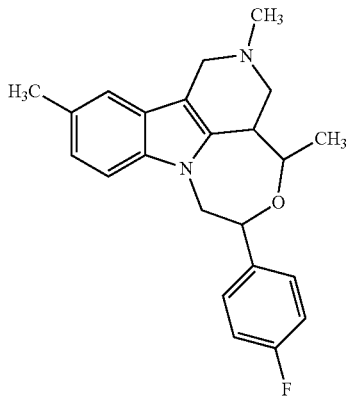 |
| 191 | 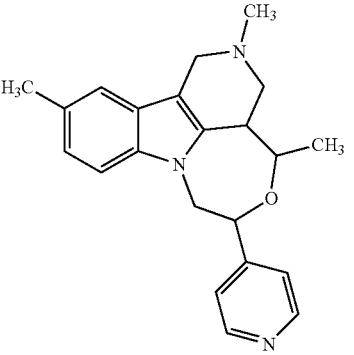 |
| 192 | 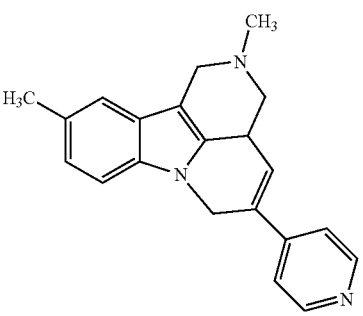 [SMILES: Cc1ccc2c(c1)c1c3n2CC(c2ccncc2)=CC3CN(C)C1] |
| 193 | 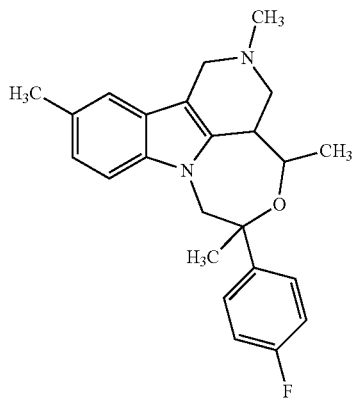 |
| 194 | 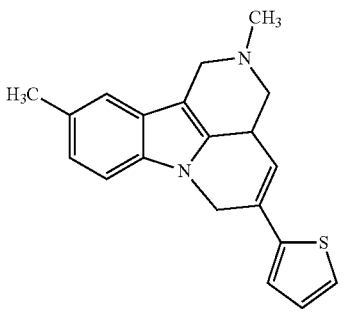 [SMILES: Cc1ccc2c(c1)c1c3n2CC(c2cccs2)=CC3CN(C)C1] |

TABLE 1-continued

Representative Compounds of the Invention

| Compound No. | Structure |
|---|---|
| 195 | 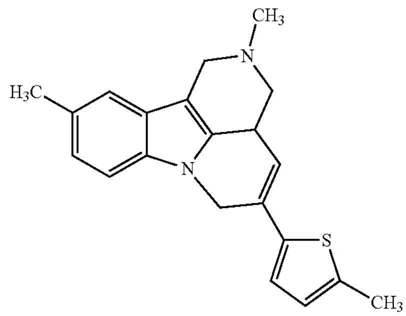 |
| 196 | 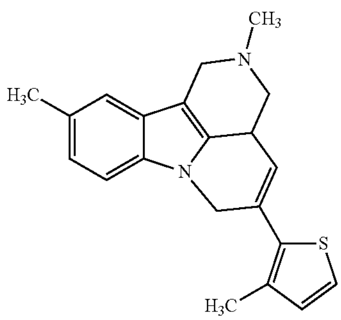 [SMILES: Cc1ccc2c(c1)c1c3n2CC(c2sccc2C)=CC3CN(C)C1] |
| 197 | 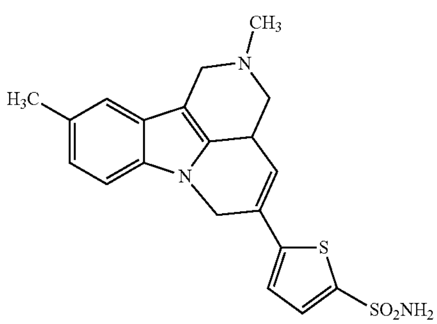 [SMILES: Cc1ccc2c(c1)c1c3n2CC(c2ccc(S(N)(=O)=O)s2)=CC3CN(C)C1] |
| 198 | 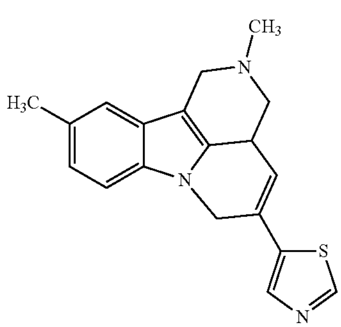 [SMILES: Cc1ccc2c(c1)c1c3n2CC(c2cncs2)=CC3CN(C)C1] |
| 199 | |
| 200 | |
| 201 | |
| 202 | |

TABLE 1-continued

Representative Compounds of the Invention

| Compound No. | Structure |
|---|---|
| 203 | 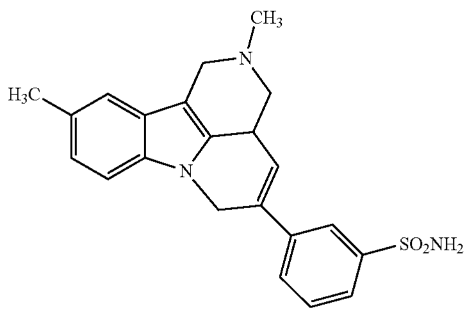 |
| 204 | 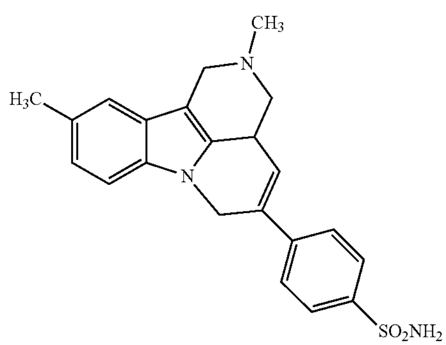 |
| 205 | 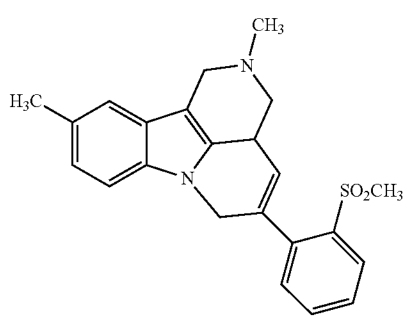 [SMILES: Cc1ccc2c(c1)c1c3n2CC(c2ccccc2S(N)(=O)=O)=CC3CN(C)C1] |
| 206 | 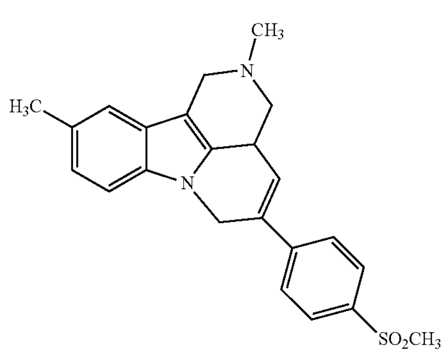 [SMILES: Cc1ccc2c(c1)c1c3n2CC(c2ccc(S(N)(=O)=O)cc2)=CC3CN(C)C1] |
| 207 | |
| 208 | |
| 209 | |
| 210 | |

TABLE 1-continued

Representative Compounds of the Invention

| Compound No. | Structure |
|---|---|
| 211 | (structure) |
| 212 | (structure) |
| 213 | (structure) |
| 214 | (structure) |
| 215 | (structure) |
| 216 | (structure) |
| 217 | (structure) |
| 218 | (structure) |

TABLE 1-continued

Representative Compounds of the Invention

| Compound No. | Structure |
|---|---|
| 219 | 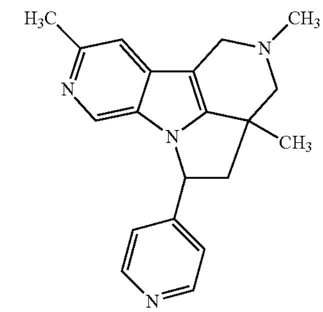 |
| 220 | 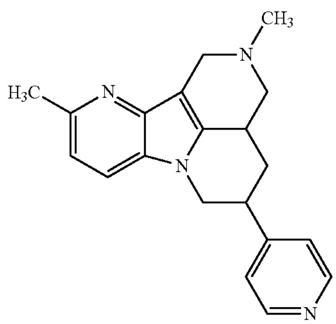 [SMILES: Cc1ccc2c(n1)c1c3n2CC(c2ccncc2)CC3CN(C)C1] |
| 221 | 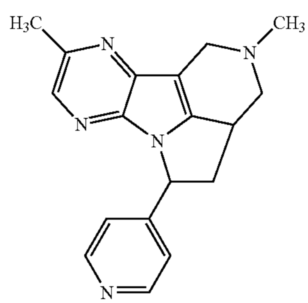 |
| 222 | 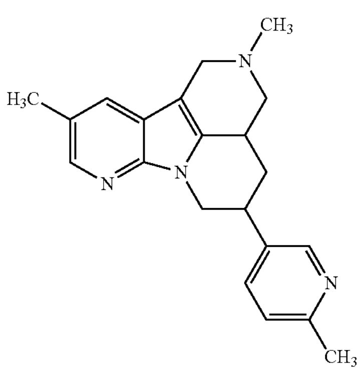 |
| 223 | |
| 224 | |
| 225 | |
| 226 | |

TABLE 1-continued

Representative Compounds of the Invention

| Compound No. | Structure |
|---|---|
| 227 | (structure) |
| 228 | (structure) |
| 229 | (structure) |
| 230 | (structure) |
| 231 | (structure) |
| 232 | (structure) |
| 233 | (structure) |
| 234 | (structure) |
| 235 | (structure) |

TABLE 1-continued

Representative Compounds of the Invention

| Compound No. | Structure |
|---|---|
| 236 | 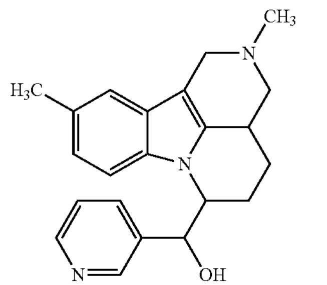 |
| 237 | 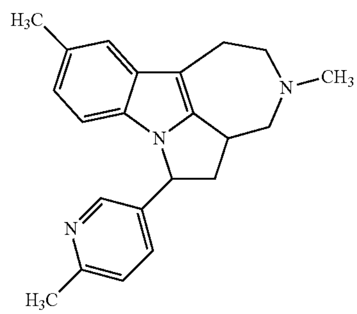 |
| 238 | 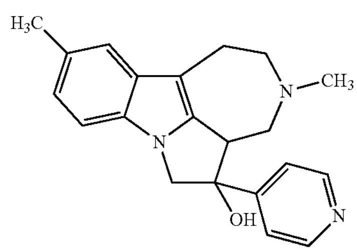 [SMILES: Cc1ccc2c(c1)c1c3n2CC(O)(c2ccncc2)C3CN(C)CC1] |
| 239 | 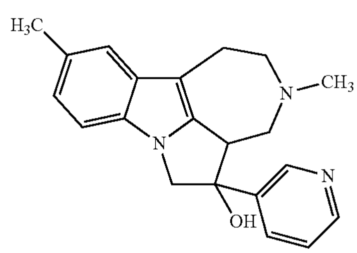 [SMILES: Cc1ccc2c(c1)c1c3n2CC(O)(c2cccnc2)C3CN(C)CC1] |
| 240 | 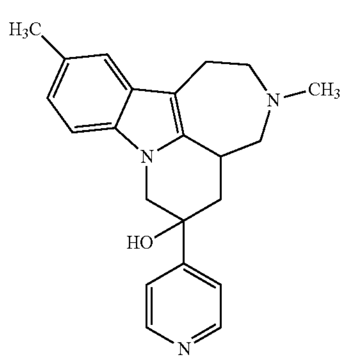 |
| 241 | |
| 242 | |
| 243 | |
| 244 | |

TABLE 1-continued

Representative Compounds of the Invention

| Compound No. | Structure |
|---|---|
| 245 | (structure) |
| 246 | (structure) |
| 247 | (structure) |
| 248 | (structure) |
| 249 | (structure) |
| 250 | (structure) |
| 251 | (structure) |
| 252 | (structure) |

TABLE 1-continued
Representative Compounds of the Invention
| Compound No. | Structure |
|---|---|
| 253 | 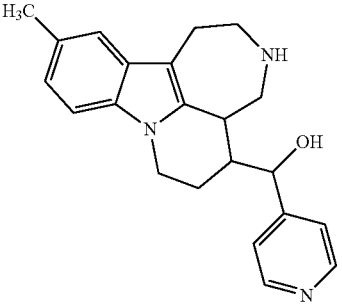 [SMILES: Cc1ccc2c(c1)c1c3n2CCC(C(O)c2ccncc2)C3CNCC1] |
| 254 | 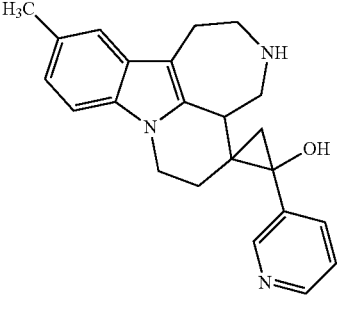 [SMILES: Cc1ccc2c(c1)c1c3n2CCC2(CC2(O)c2cccnc2)C3CNCC1] |
| 255 | 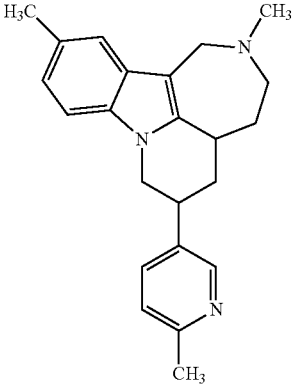 [SMILES: Cc1ccc2c(c1)c1c3n2CC(c2ccc(C)nc2)CC3CCN(C)C1] |
| 256 | 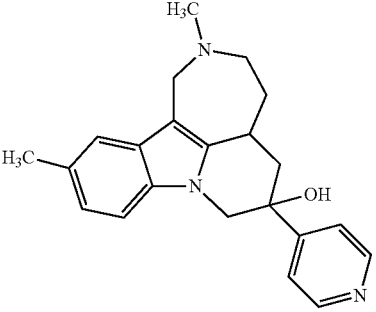 [SMILES: Cc1ccc2c(c1)c1c3n2CC(O)(c2ccncc2)CC3CCN(C)C1] |
| 257 | 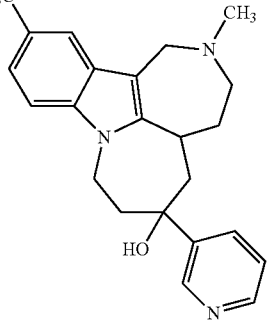 |
| 258 | 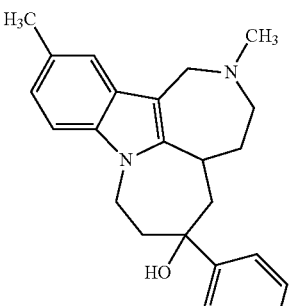 |
| 259 | 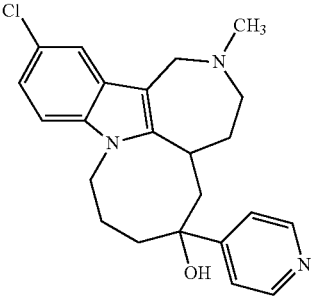 [SMILES: CN1CCC2CC(O)(c3ccncc3)CCCn3c2c(c2cc(Cl)ccc23)C1] |
| 260 | 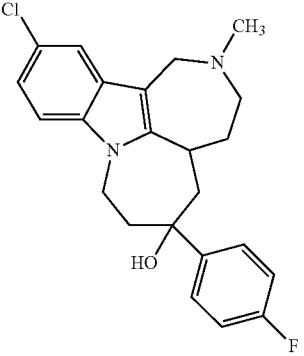 [SMILES: CN1CCC2CC(O)(c3ccc(F)cc3)CCn3c2c(c2cc(Cl)ccc23)C1] |

TABLE 1-continued

Representative Compounds of the Invention

| Compound No. | Structure |
|---|---|
| 261 | 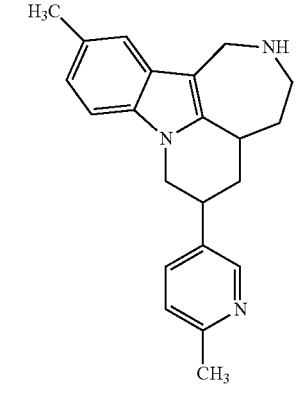 [SMILES: Cc1ccc2c(c1)c1c3n2CC(c2ccc(C)nc2)CC3CCNC1] |
| 262 | 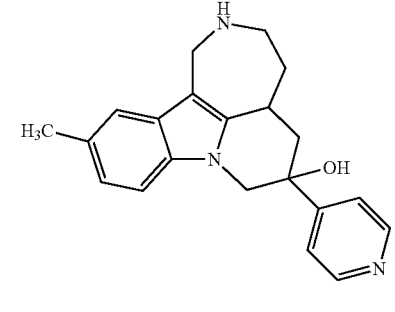 [SMILES: Cc1ccc2c(c1)c1c3n2CC(O)(c2ccncc2)CC3CCNC1] |
| 263 | 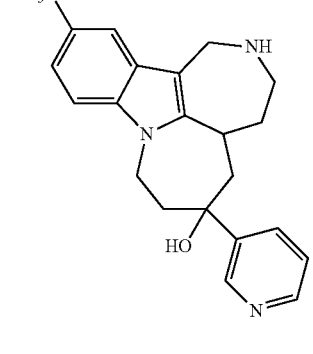 |
| 264 | 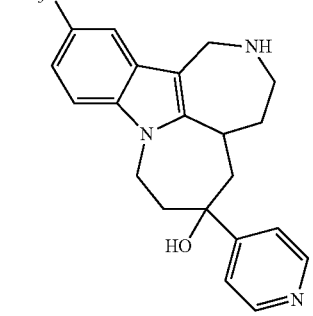 |

TABLE 1-continued

Representative Compounds of the Invention

| Compound No. | Structure |
|---|---|
| 265 | 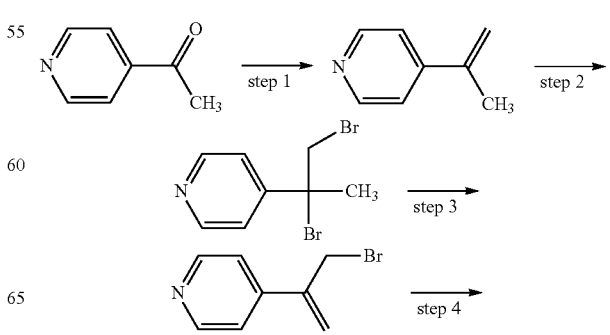 |
| 266 | 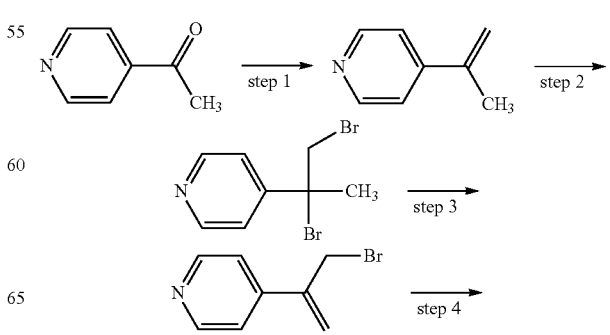 |

The methods detailed herein may be adapted as known by those of skill in the art to make compounds detailed herein. Compounds I-12 were prepared according to Examples 1-12, respectively.

The following Examples are provided to illustrate but not to limit the invention.

All references disclosed herein are incorporated by reference in their entireties.

EXAMPLES

Example 1

Preparation of Compound No. 4

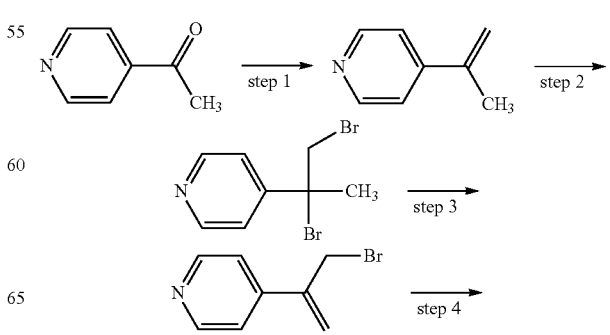

233

-continued

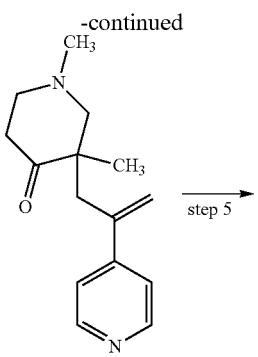

step 5 →

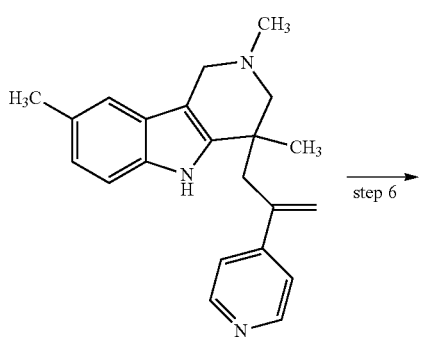

step 6 →

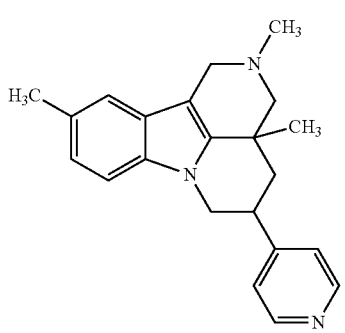

Compound No. 4

Step 1

Triphenylmethyl phosphonium bromide (22 g, 0.061 mol) was suspended in 200 mL dry THF and the suspension was cooled to 0° C. Potassium tert-butoxide (11.5 g, 0.102 mol) was added at 0° C. and stirring was continued for additional 10 min. 4-Acetyl pyridine (5 g, 0.041 mol) was dissolved in 20 mL THF and added to the reaction mixture dropwise at 0° C. The reaction mixture was warmed to and stirred at RT for 2 h. Solvent was evaporated under reduced pressure and the residue was purified by column chromatography 100-200 mesh silica gel) eluting with 0-25% hexane-ether.

Step 2

4-Isopropenyl-pyridine (12 g, 100 mmol) was dissolved in 120 mL carbon tetrachloride. Bromine (16.1 g, 100 mmol) was added dropwise at 0° C. for 15 min. The progress of the reaction was monitored by TLC. After consumption of starting material, the reaction mixture was concentrated under reduced pressure to obtain 27 g of 4-(1,2-dibromo-1-methyl-ethyl)-pyridine.

Step 3

4-(1,2-Dibromo-1-methyl-ethyl)-pyridine (27 g, 97.8 mmol) was dissolved in 120 mL tert-butanol. Potassium tert-butoxide (27.3 g, 244 mmol) was added portionwise and the reaction mixture was heated at 90° C. for 15 min. The reaction mixture was evaporated under reduced pressure and residue was diluted with water (200 mL) and extracted with EtOAc (3×250 mL). The combined organic layer was washed with water (2×150 mL) and dried over sodium sulfate and concentrated to obtain 12.6 g of product.

Step 4

1,3-Dimethyl-piperidin-4-one (1.0 g, 7.8 mmol) was dissolved in DMF (3 mL) and sodium hydride (468 mg, 11.7 mmol) was added. The reaction mixture was cooled to 0° C. and 4-(1-bromomethyl-vinyl)-pyridine (3.1 g, 15.6 mmol) diluted in DMF was added dropwise. The reaction mixture was further stirred for 60 min at 0° C. The reaction mixture was quenched with ice water and extracted with EtOAc (3×100 mL). The combined organic layer was washed with ice water (4×100 mL), dried over anhydrous sodium sulfate and concentrated. The residue was purified by column chromatography (neutral alumina, eluent 40% EtOAc in Hexane) to obtain 350 mg of title compound.

Step 5

P-Tolylhydrazinehydrochloride (150 mg, 0.94 mmol) and 1,3-dimethyl-3-(2-pyridin-4-yl-allyl)-piperidin-4-one (347 mg, 1.4 mmol) were dissolved in 1,4-dioxane (5 mL). Trifluoroacetic acid (0.3 mL) was added and the reaction mixture was heated to 100° C. for 16 h. The reaction mixture was concentrated under reduced pressure and residue was basified with saturated aqueous sodium bicarbonate. The product was extracted with EtOAc (3×30 mL), organic layer was washed with water (2×20 mL), dried over sodium sulfate and concentrated. The residue was purified by reverse phase chromatography to obtain 15 mg of 2,4,8-trimethyl-4-(2-pyridin-4-yl-allyl)-2,3,4,5-tetrahydro-1H-pyrido[4,3-b]indole.

Step 6

2,4,8-Trimethyl-4-(2-pyridin-4-yl-allyl)-2,3,4,5-tetrahydro-1H-pyrido[4,3-b]indole (15 mg, 0.04 mmol) was dissolved in DMF (0.5 mL) and sodium hydride (2 mg, 0.0675 mmol) was added. The reaction mixture was heated at 90° C. for 2 h, then cooled to RT and quenched with ice water. The product was extracted with EtOAc (2×10 mL). The organic layer was washed with water (3×10 mL), dried over sodium sulfate and concentrated. The residue was purified by reverse phase chromatography to obtain the title compound. $^1$H NMR (TFA salt, $CD_3OD$) δ (ppm): 8.78 (d, 2H), 7.90 (d, 2H), 7.50 (s, 1H), 7.30 (d, 1H), 7.05 (d, 1H), 4.70-4.50 (m, 2H), 4.30 (m, 2H), 4.08 (m, 1H), 3.58-3.40 (m, 2H), 3.16 (s, 3H), 2.40 (s, 3H), 2.30 (m, 2H), 1.90-1.80 (m, 2H), 1.70 (s, 3H).

Example 2

Preparation of Compound Nos. 3 and 5

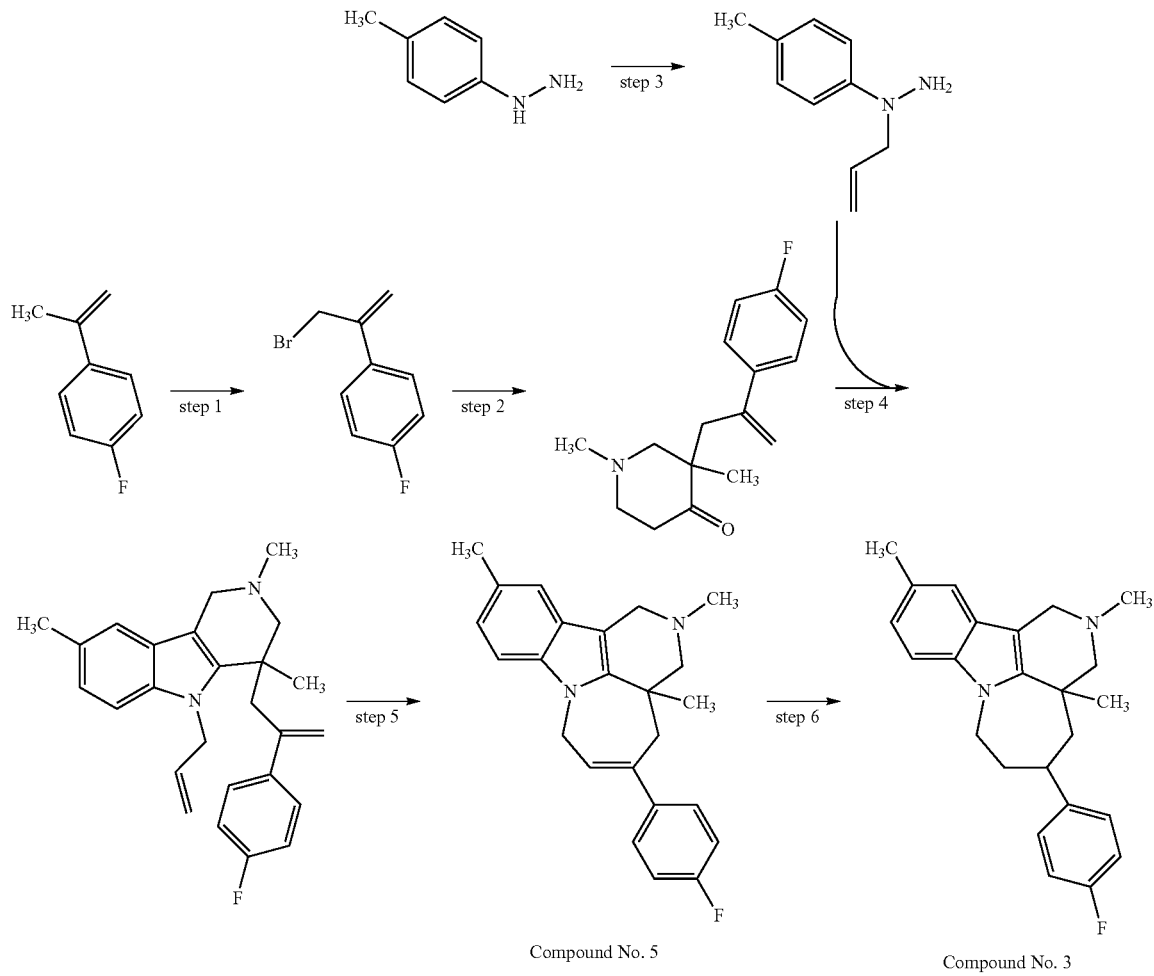

Step 1

To a solution of N-bromo succinimide (8.6 g, 48.48 mmol) in chloroform (60 mL) was added 1-fluoro-4-isopropenyl-benzene (6 g, 44.11 mmol) at RT. The reaction mixture was stirred at 60° C. for 15 h. The progress of reaction was monitored by TLC. The reaction mixture was cooled to RT and filtered. The residue was rinsed with DCM (50 mL). The combined filtrate was concentrated under reduced pressure to obtain crude product that was purified by column chromatography using silica (100:200) and pure hexane to yield 4.2 g of 1-(1-bromomethyl-vinyl)-4-fluoro-benzene.

Step 2

To a stirred solution of 1,3-dimethylpiperidin-4-one (2.8 g, 22.04 mmol) in DMF (10 mL) was added sodium hydride (970 mg, 24.25 mmol) at 0° C. After stiffing for 5 min, 1-(1-bromomethyl-vinyl)-4-fluoro-benzene (4.74 g, 22.04 mmol) was added dropwise and stirring was continued for 30 min. The reaction was quenched with ice water and extracted with EtOAc (2×100 mL). The combined organic layer was washed with water (4×100 mL), dried over anhydrous sodium sulfate and concentrated under reduced pressure. The residue was purified by column chromatography using silica (100:200) and 10% EtOAc-Hex as eluent to yield 3 g of 3-[2-(4-fluoro-phenyl)-allyl]-1,3-dimethyl-piperidin-4-one.

Step 3

P-Tolyl hydrazine hydrochloride (10 g, 63.29 mmol), allyl bromide (5.4 mL, 63.29 mmol) and triethylamine (26.66 mL, 190 mmol) were mixed and heated to 100° C. for 2 h. The reaction mixture was cooled to RT and diluted with water (200 mL). The product was extracted with EtOAc (2×150 mL) and the organic layer was washed with 100 mL water, dried over sodium sulfate, and concentrated under reduced pressure. The residue was purified by column chromatography over silica gel (100-200 mesh) to obtain 5.2 g of N-allyl-N-p-tolyl-hydrazine.

Step 4

N-Allyl-N-p-tolyl-hydrazine (600 mg, 3.70 mmol) and 3-[2-(4-fluoro-phenyl)-allyl]-1,3-dimethyl-piperidin-4-one (970 mg, 3.71 mmol) were dissolved in 1,4-dioxane (4 mL). Trifluoroacetic acid (1 mL) was added and the reaction mixture was heated to 100° C. for 3 h. 1,4-Dioxane was removed under reduced pressure, the residue was basified with aqueous sodium bicarbonate, and extracted with EtOAc (2×30 mL). The organic layer was dried over sodium sulfate and concentrated under reduced pressure. The residue was purified by column chromatography over silica gel (100-200 mesh, eluent as 5% EtOAc in hexane) to obtain 290 mg of 5-allyl-4-[2-(4-fluoro-phenyl)-allyl]-2,4,8-trimethyl-2,3,4,5-tetrahydro-1H-pyrido[4,3-b]indole.

Step 5

5-Allyl-4-[2-(4-fluoro-phenyl)-allyl]-2,4,8-trimethyl-2,3,4,5-tetrahydro-1H-pyrido[4,3-b]indole (100 mg, 0.25 mmol) was dissolved in DCM (15 mL) and purged with nitrogen. Hoveyda-Grubbs 2nd generation catalyst (10 mg, 0.015 mmol) was added and the reaction mixture was re-purged with nitrogen. The reaction mixture was heated at 80° C. for 6 h, cooled to RT, concentrated under reduced pressure and the residue purified by column chromatography using silica (100-200 mesh) eluting with 1% MeOH in DCM to obtain 87 mg of 5-(4-fluoro-phenyl)-2,3a,10-trimethyl-1,2,3,3a,4,7-hexahydro-2,7a-diaza-cyclohepta[jk]fluorene. $^1$H NMR (Oxalate salt, CD$_3$OD) δ (ppm): 7.40 (m, 2H), 7.30 (d, 1H), 7.26 (s, 1H), 7.05 (m, 3H), 6.06 (d, 1H), 5.22 (m, 1H), 4.76 (m, 1H), 4.60-4.40 (m, 2H), 3.60 (m, 2H), 3.18 (s, 3H), 3.05 (m, 1H), 2.70 (m, 1H), 2.40 (s, 3H), 1.66 (s, 3H).

Step 6

5-(4-Fluoro-phenyl)-2,3a,10-trimethyl-1,2,3,3a,4,7-hexahydro-2,7a-diaza-cyclohepta[jk]fluorene (30 mg, 0.083 mmol) was dissolved in MeOH (4 mL) and the solution was purged with nitrogen. Palladium chloride (15 mg) was added and hydrogen gas was bubbled through the reaction mixture for 2 h. The reaction mixture was filtered through Celite bed and the Celite bed was rinsed with MeOH. The filtrate was concentrated under reduced pressure to obtain 5-(4-fluoro-phenyl)-2,3a,10-trimethyl-1,2,3,3a,4,5,6,7-octahydro-2,7a-diaza-cyclohepta[jk]fluorene. $^1$H NMR, (HCl, salt, CD$_3$OD) δ (ppm): 7.30 (m, 3H), 7.18 (m, 1H), 7.05-6.95 (m, 3H), 4.70 (m, 2H), 4.30 (m, 2H), 4.10 (m, 1H), 3.58-3.40 (m, 2H), 3.15 (s, 3H), 2.42 (s, 3H), 2.30 (m, 2H), 1.90-1.80 (m, 2JH), 1.70 (s, 3H).

Example 3

Preparation of Compound Nos. 2 and 6

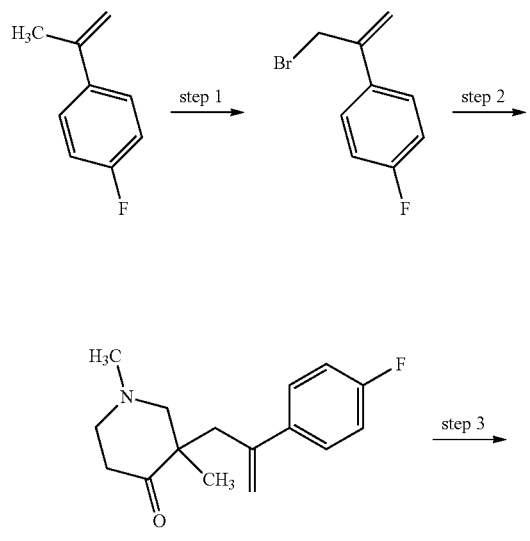

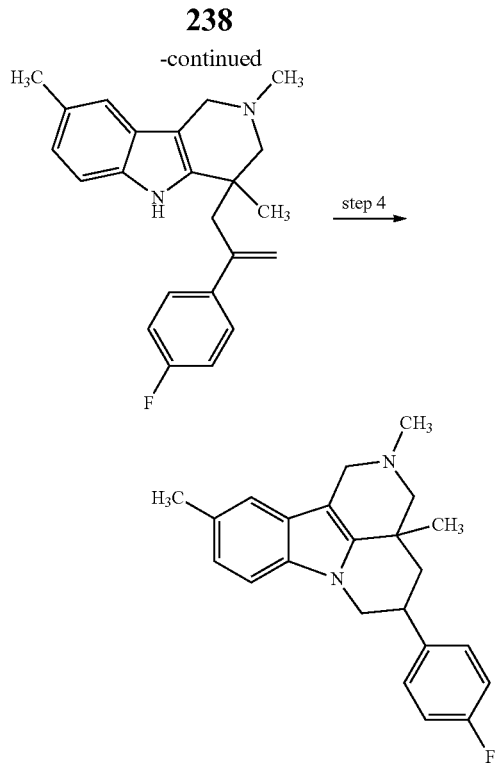

Compound No. 2: Diastereomer 1
Compound No. 6: Diastereomer 2

Step 1

To a solution of N-bromo succinimide (8.6 g, 48.48 mmol) in chloroform (60 mL) was added 1-fluoro-4-isopropenyl-benzene (6 g, 44.11 mmol) at RT. The reaction mixture was stirred at 60° C. for 15 h. The progress of reaction was monitored by TLC. The reaction mixture was cooled to RT and filtered. The residue was rinsed with DCM (50 mL). The combined filtrate was concentrated under reduced pressure to obtain crude product that was purified by column chromatography using silica (100:200) and pure hexane to yield 4.2 g of 1-(1-bromomethyl-vinyl)-4-fluoro-benzene.

Step 2

To a stirred solution of 1,3-dimethylpiperidin-4-one (2.8 g, 22.04 mmol) in DMF (10 mL) was added sodium hydride (970 mg, 24.25 mmol) at 0° C. After stiffing for 5 min, 1-(1-bromomethyl-vinyl)-4-fluoro-benzene (4.74 g, 22.04 mmol) was added dropwise and stirring was continued for 30 min. The reaction mass was quenched with ice water and extracted with EtOAc (2×100 mL). The combined organic layer was washed with water (4×100 mL), dried over anhydrous sodium sulfate and concentrated under reduced pressure. The residue was purified by column chromatography using silica (100:200) and 10% EtOAc-Hex as eluent to yield 3 g of 3-[2-(4-fluoro-phenyl)-allyl]-1,3-dimethyl-piperidin-4-one.

Step 3

P-Tolylhydrazinehydrochloride (150 mg, 0.94 mmol) and 34244-fluorophenyl)allyl)-1,3-dimethylpiperidin-4-one (365 mg, 1.4 mmol) were dissolved in 5 mL 1,4-dioxane. Trifluoroacetic acid (0.3 mL) was added and the reaction mixture was heated to 100° C. for 16 h. Solvent was removed under reduced pressure and residue was basified with saturated sodium bicarbonate, and extracted with EtOAc (3×30 mL). The organic layer was washed with water (2×20 mL), dried over sodium sulfate, concentrated, and the residue purified by reverse phase chromatography to obtain title compound.

Step 4

4-[2-(4-Fluoro-phenyl)-allyl]-2,4,8-trimethyl-2,3,4,5-tetrahydro-1H-pyrido[4,3-b]indole (300 mg, 0.86 mmol) was dissolved in DMF (3 mL) and sodium hydride (51 mg, 1.29 mmol) was added. The reaction mixture was heated at 100° C. for 3 h. The reaction mixture was cooled to RT, quenched with ice water and extracted with EtOAc (2×50 mL). The organic layer was washed with water (3×50 mL), dried over sodium sulfate and concentrated under reduced pressure. The residue (250 mg) was purified by reverse phase chromatography to obtain title compound as two diastereomers. Compound No. 2: $^1$H NMR (TFA salt) δ (ppm): 7.40 (m, 2H), 7.30 (m, 2H), 7.16-7.02 (m, 3H), 4.76 (m, 2H), 4.36 (m, 2H), 4.18 (m, 1H), 3.70 (m, 1H), 3.50 (m, 1H), 3.20 (s, 3H), 2.86 (m, 2H), 2.42 (s, 3H), 1.70 (s, 3H). Compound No. 6: 1H NMR (TFA salt, CD$_3$OD) δ (ppm): 7.42 (m, 2H), 7.26 (m, 2H), 7.16-7.0 (m, 3H), 4.80 (m, 1H), 4.52 (m, 1H), 4.36 (d, 1H), 3.95 (m, 1H), 3.70 (m, 1H), 3.50 (m, 2H), 3.20 (s, 3H), 2.40 (s, 3H), 2.05 (m, 1H), 1.92 (m, 1H), 1.72 (s, 3H).

Example 4

Preparation of Compound Nos. 1 and 7

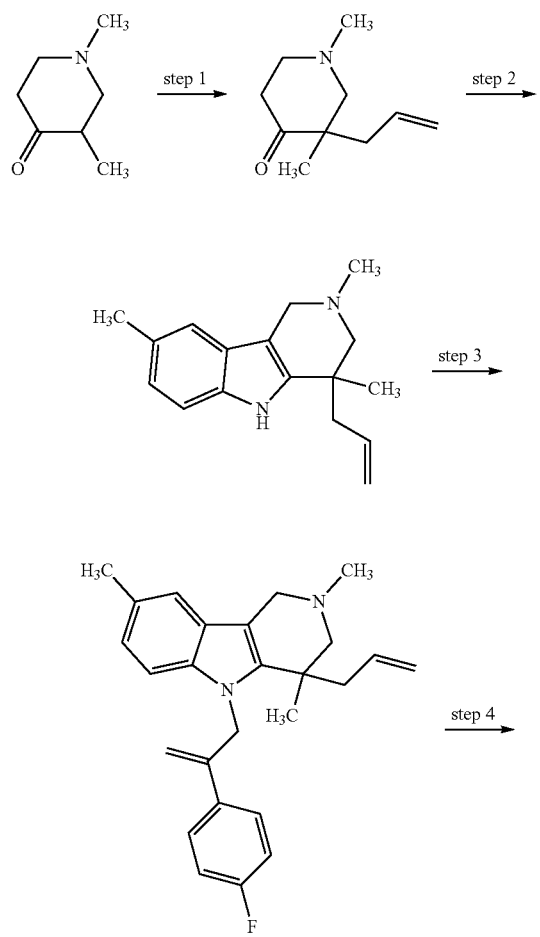

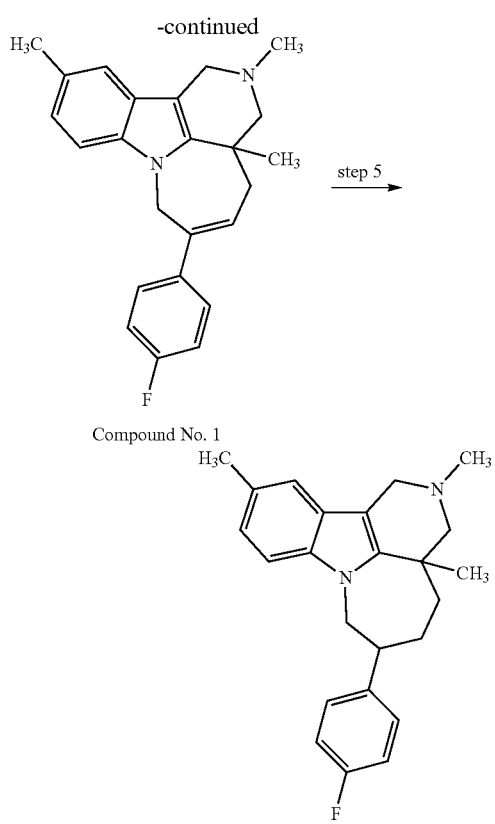

Compound No. 1

Compound No. 7

Step 1

1,3-Dimethyl-piperidin-4-one (6 g, 47.24 mmol) was dissolved in 20 mL DMF and sodium hydride (2.07 g, 51.95 mmol) was added portionwise at 0° C. under nitrogen atmosphere. This was followed by dropwise addition of allyl bromide (5.71 g, 47.19 mmol) in 4 mL DMF at 0° C. under nitrogen atmosphere. The reaction mixture was stirred at RT for 15 min, quenched with ice-water and extracted with EtOAc (3×100 mL), The organic layer was washed with water (3×100 mL), dried over sodium sulfate and concentrated under reduced pressure. The residue was purified by column chromatography (silica gel, 100-200 mesh) eluting with 7% EtOAc in hexane to obtain 3.2 g of 3-allyl-1,3-dimethyl-piperidin-4-one.

Step 2

To a stirred solution of p-tolylhydrazine. HCl (1.2 g, 7.56 mmol) and 3-allyl-1,3-dimethyl-piperidin-4-one (1.5 g, 9.077 mmol) in 1,4-dioxane (12 mL) at 25° C. was added conc. H$_2$SO$_4$ (1 mL). The reaction mixture was heated at 100° C. for 30 min after which the dioxane layer was decanted and residue was basified with saturated aqueous NaHCO$_3$ solution. The product was extracted with EtOAc (3×50 mL), organic layer dried over anhydrous sodium sulfate and concentrated under reduced pressure to obtain 1.7 g of 4-allyl-2,4,8-trimethyl-2,3,4,5-tetrahydro-1H-pyrido[4,3-b]indole as a solid.

Step 3

To a stirred suspension of sodium hydride (0.236 g, 5.9 mmol) in dry DMF (5 mL) at 0° C. was added 4-allyl-2,4,8-trimethyl-2,3,4,5-tetrahydro-1H-pyrido[4,3-b]indole (1 g, 3.937 mol, in dry DMF 2 mL). After addition was complete, reaction mixture was stirred at 0° C. for an additional 10 min. 1-(1-Bromomethyl-vinyl)-4-fluoro-benzene (1.09 g, 5.118 mmol) in dry DMF (3 mL) was added dropwise at 0° C. The reaction mixture was stirred at 25° C. for 16 h. The reaction mixture was diluted with ice-water and extracted with EtOAc (2×50 mL). The organic layer was repeatedly washed with water, dried over anhydrous sodium sulfate, concentrated under reduced pressure and the residue purified by chromatography on neutral aluminum oxide (eluting with EtOAc: Hexanes, 1:99) to obtain 700 mg of 4-allyl-5-[2-(4-fluorophenyl)-allyl]-2,4,8-trimethyl-2,3,4,5-tetrahydro-1H-pyrido[4,3-b]indole.

Step 4

To a solution of the 4-allyl-5-[2-(4-fluoro-phenyl)-allyl]-2,4,8-trimethyl-2,3,4,5-tetrahydro-1H-pyrido[4,3-b]indole (250 mg, 0.64 mmol) in degassed DCM (7 mL) was added dropwise a solution of Grubbs' 2nd generation catalyst (27.61 mg, 0.0325 mmol, 5 mol %) in degassed DCM (3 mL) under an nitrogen atmosphere. The resultant solution was heated at 115° C. for 1 h in a microwave. The solvent was evaporated in vacuo and the residue was purified by reverse HPLC to obtain 6-(4-fluoro-phenyl)-2,3a,10-trimethyl-1,2,3,3a,4,7-hexahydro-2,7a-diaza-cyclohepta[jk]fluorene as an off white solid (50 mg). $^1$H NMR (Freebase, CDCl$_3$) δ (ppm): 7.40 (m, 2H), 7.30 (d, 1H), 7.10 (d, 1H), 7.04-6.98 (m, 2H), 5.99 (d, 1H), 4.96 (d, 1H), 3.99 (d, 1H), 3.96 (s, 2H), 2.70 (d, 2H), 2.55 (s, 3H), 2.42 (s, 3H), 2.30 (d, 1H), 2.21 (m, 1H), 1.50 (s, 3H).

Step 5

To a stirred solution of 4-allyl-5-[2-(4-fluoro-phenyl)-allyl]-2,4,8-trimethyl-2,3,4,5-tetrahydro-1H-pyrido[4,3-b]indole (50 mg, 0.138 mmol) in MeOH (3 mL) was added PdCl$_2$ (25 mg, 0.14 mmol). Hydrogen gas was purged through the solution for 1 h. The reaction mixture was filtered through Celite bed and the Celite bed was rinsed with MeOH. The filtrate was concentrated under reduced pressure and the residue was purified by reverse HPLC to obtain 6-(4-fluorophenyl)-2,3a,10-trimethyl-1,2,3,3a,4,5,6,7-octahydro-2,7a-diaza-cyclohepta[jk]fluorene. $^1$H NMR (Freebase, CDCl$_3$) δ (ppm): 6.18-7.21 (m, 2H), 6.9-7.1 (m, 4H), 6.8 (m, 1H), 5.0 (d, 2H), 3.96 (d, 2H), 3.1 (d, 2H), 2.62 (m, 1H), 2.56 (s, 3H), 2.38 (s, 3H), 2.3 (m, 2H), 1.65 (m, 2H), 1.42 (s, 3H).

Example 5

Preparation of Compound No. 8

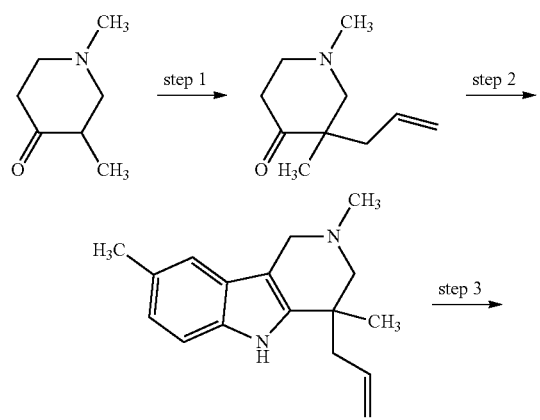

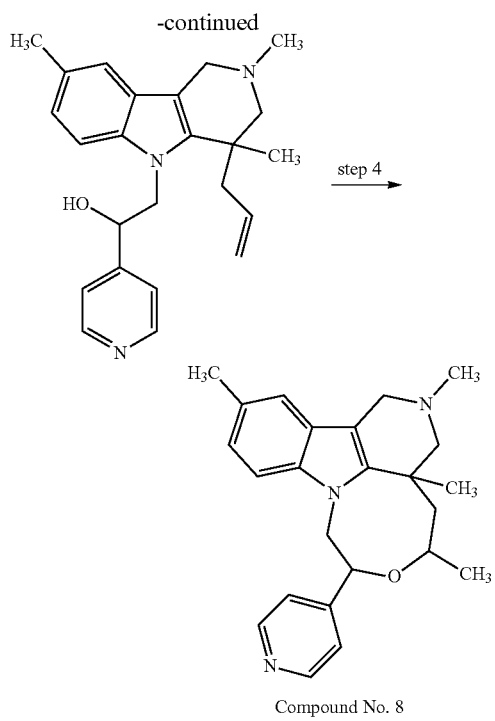

Compound No. 8

Step 1

1,3-Dimethyl-piperidin-4-one (6 g, 47.24 mmol) was dissolved in 20 mL DMF and sodium hydride (2.07 g, 51.95 mmol) was added portionwise at 0° C. under nitrogen atmosphere. This was followed by dropwise addition of allyl bromide (5.71 g, 47.19 mmol) in 4 mL DMF at 0° C. under nitrogen atmosphere. The reaction mixture was stirred at RT for 15 min, quenched with ice-water and extracted with EtOAc (3×100 mL). The organic layer was washed with water (3×100 mL), dried over sodium sulfate and concentrated under reduced pressure. The residue was purified by column chromatography (silica gel, 100-200 mesh) eluting with 7% EtOAc in hexane to obtain 3.2 g of 3-allyl-1,3-dimethyl-piperidin-4-one.

Step 2

To a stirred solution of p-tolylhydrazine.HCl (1.2 g, 7.56 mmol) and 3-allyl-1,3-dimethyl-piperidin-4-one (1.5 g, 9.077 mmol) in 1,4-dioxane (12 mL) at 25° C. was added conc. H$_2$SO$_4$ (1 mL). The reaction mixture was heated at 100° C. for 30 min after which the dioxane layer was decanted and residue was basified with saturated aqueous NaHCO$_3$ solution. The product was extracted with EtOAc (3×50 mL), organic layer dried over anhydrous sodium sulfate and concentrated under reduced pressure to obtain 1.7 g of 4-allyl-2,4,8-trimethyl-2,3,4,5-tetrahydro-1H-pyrido[4,3-b]indole as a solid.

Step 3

4-Allyl-2,4,8-trimethyl-2,3,4,5-tetrahydro-1H-pyrido[4,3-b]indole (2.5 g, 9.8 mmol) was dissolved in 18 mL of DMF and stirred for 10 min at RT. Sodium hydride (1.17 g, 29.2 mmol) was added portionwise and stiffing was continued for additional 10 min. This was followed by dropwise addition of 4-oxiranyl-pyridine (2.38 g, 19.6 mmol) as a solution in DMF. The reaction mixture was stirred at RT for 16 h, quenched with ice water and extracted with EtOAc (3×120 mL). The organic layer was washed with water, dried over sodium sulfate and concentrated under reduced pressure. The residue was recrystallized in ether to obtain 1 g of 2-(4-allyl-2,4,8-trimethyl-1,2,3,4-tetrahydro-pyrido[4,3-b]indol-5-yl)-1-pyridin-4-yl-ethanol.

Step 4

2-(4-Allyl-2,4,8-trimethyl-1,2,3,4-tetrahydro-pyrido[4,3-b]indol-5-yl)-1-pyridin-4-yl-ethanol (275 mg, 0.732 mmol) was dissolved in 6 mL of 6N HCl, and heated at 100° C. for 8 h. The reaction mixture was cooled to RT, basified with saturated aqueous sodium bicarbonate and extracted with EtOAc (3×25 mL). The organic layer was dried over sodium sulfate and concentrated. The residue was purified by column chromatography over silica gel (100-200 mesh) eluting with 2% MeOH in DCM to obtain 65 mg of product. $^1$H NMR (Di-HCl salt, CD$_3$OD) δ (ppm): 8.95 (m, 2H), 8.35 (m, 2H), 7.59 (d, 1H), 7.35 (s, 1H), 7.20 (d, 1H), 5.20 (d, 1H), 4.6-4.50 (m, 2H), 4.39 (d, 1H), 3.6-3.45 (m, 4H), 3.20 (s, 3H), 2.45 (s, 3H), 2.25 (d, 1H), 2.1 (t, 1H), 1.82 (s, 3H), 1.2 (d, 3H).

Example 6

Preparation of Compound No. 9

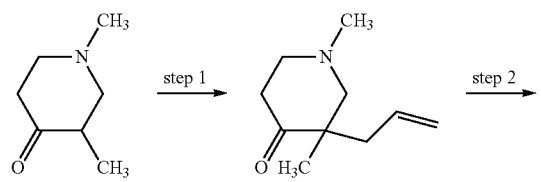

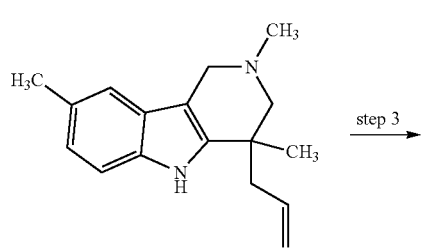

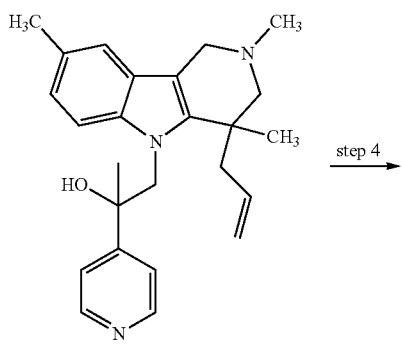

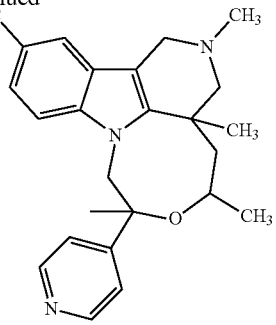

Compound No. 9

Step 1

1,3-Dimethyl-piperidin-4-one (6 g, 47.24 mmol) was dissolved in DMF (20 mL) and sodium hydride (2.07 g, 51.95 mmol) was added portionwise at 0° C. under nitrogen atmosphere. This was followed by dropwise addition of allyl bromide (5.71 g, 47.19 mmol) in DMF (4 mL) at 0° C. under nitrogen atmosphere. The reaction mixture was stirred at RT for 15 min, quenched with ice-water and extracted with EtOAc (3×100 mL). The organic layer was washed with water (3×100 mL), dried over sodium sulfate and concentrated under reduced pressure. The residue was purified by column chromatography (silica gel, 100-200 mesh) eluting with 7% EtOAc in hexane to obtain 3.2 g of 3-allyl-1,3-dimethyl-piperidin-4-one.

Step 2

To a stirred solution of p-tolylhydrazine.HCl (1.2 g, 7.56 mmol) and 3-allyl-1,3-dimethyl-piperidin-4-one (1.5 g, 9.077 mmol) in 1,4-dioxane (12 mL) at 25° C. was added conc. H$_2$SO$_4$ (1 mL). The reaction mixture was heated at 100° C. for 30 min after which the dioxane layer was decanted and residue was basified with saturated aqueous NaHCO$_3$ solution. The product was extracted with EtOAc (3×50 mL), organic layer dried over anhydrous sodium sulfate and concentrated under reduced pressure to obtain 1.7 g of 4-allyl-2,4,8-trimethyl-2,3,4,5-tetrahydro-1H-pyrido[4,3-b]indole as a solid.

Step 3

4-Allyl-2,4,8-trimethyl-2,3,4,5-tetrahydro-1H-pyrido[4,3-b]indole (1 g, 3.9 mmol) was dissolved in DMF (10 mL) and stirred for 10 min at RT. Sodium hydride (475 mg, 11.7 mmol) was added portionwise and stirring was continued for 15 min at RT. 4-(2-Methyl-oxiranyl)-pyridine (690 mg, 5.1 mmol) diluted in DMF was added dropwise at RT and the reaction mixture was further stirred for 16 h after which it was quenched with ice water and extracted with EtOAc (3×70 mL). The combined organic layer was washed with water, dried over sodium sulfate and concentrated under reduced pressure. The residue was recrystallized in ether to obtain 700 mg of 1-(4-allyl-2,4,8-trimethyl-1,2,3,4-tetrahydro-pyrido[4,3-b]indol-5-yl)-2-pyridin-4-yl-propan-2-ol.

Step 4

1-(4-Allyl-2,4,8-trimethyl-1,2,3,4-tetrahydro-pyrido[4,3-b]indol-5-yl)-2-pyridin-4-yl-propan-2-ol (100 mg, 0.257 mmol) was dissolved in 4 mL of 6N HCl, and heated at 100° C. for 8 h. The reaction mixture was cooled to RT, basified with sodium bicarbonate and extracted with EtOAc (3×20 mL). The organic layer was dried over sodium sulfate and concentrated under reduced pressure. The residue was purified by column chromatography over silica gel (100-200 mesh) eluting with 2% MeOH in DCM to obtain 22 mg of product. $^1$H NMR (HCl salt, CD$_3$OD) δ (ppm): 8.98 (d, 2H), 8.6 (d, 2H), 7.63 (d, 1H), 7.38 (s, 1H), 7.21 (d, 1H), 4.8 (m, 2H), 4.53 (d, 1H), 4.38 (d, 1H), 3.8 (m, 1H), 3.58 (m, 2H), 3.2 (s, 3H), 2.41 (s, 3H), 2.0 (m, 2H), 1.7 (s, 3H), 1.6 (s, 3H), 1.2 (d, 3H).

Example 7

Preparation of Compound No. 11

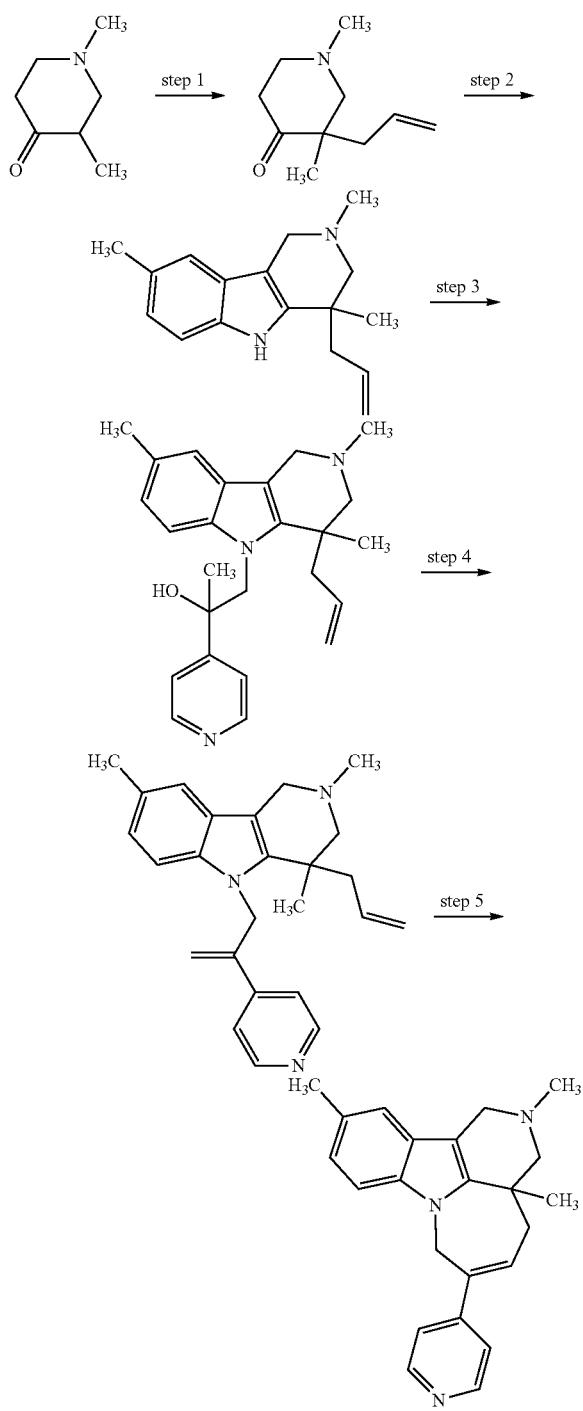

Compound No. 11

Step 1

1,3-Dimethyl-piperidin-4-one (6 g, 47.24 mmol) was dissolved in 20 mL DMF and sodium hydride (2.07 g, 51.95 mmol) was added portionwise at 0° C. under nitrogen atmosphere. This was followed by dropwise addition of allyl bromide (5.71 g, 47.19 mmol) in 4 mL DMF at 0° C. under nitrogen atmosphere. The reaction mixture was stirred at RT for 15 min, quenched with ice-water and extracted with EtOAc (3×100 mL). The organic layer was washed with water (3×100 mL), dried over sodium sulfate and concentrated under reduced pressure. The residue was purified by column chromatography (silica gel, 100-200 mesh) eluting with 7% EtOAc in hexane to obtain 3.2 g of 3-allyl-1,3-dimethyl-piperidin-4-one.

Step 2

To a stirred solution of p-tolylhydrazine.HCl (1.2 g, 7.56 mmol) and 3-allyl-1,3-dimethyl-piperidin-4-one (1.5 g, 9.077 mmol) in 1,4-dioxane (12 mL) at 25° C. was added conc. $H_2SO_4$ (1 mL). The reaction mixture was heated at 100° C. for 30 min after which the dioxane layer was decanted and residue was basified with saturated aqueous $NaHCO_3$ solution. The product was extracted with EtOAc (3×50 mL), organic layer dried over anhydrous sodium sulfate and concentrated under reduced pressure to obtain 1.7 g of 4-allyl-2, 4,8-trimethyl-2,3,4,5-tetrahydro-1H-pyrido[4,3-b]indole as a solid.

Step 3

4-Allyl-2,4,8-trimethyl-2,3,4,5-tetrahydro-1H-pyrido[4, 3-b]indole (1 g, 3.9 mmol) was dissolved in DMF (10 mL) and stirred for 10 min at RT. Sodium hydride (475 mg, 11.7 mmol) was added portionwise and stirring was continued for 15 min at RT. 4-(2-Methyl-oxiranyl)-pyridine (690 mg, 5.1 mmol) diluted in DMF was added dropwise at RT and the reaction mixture was further stirred for 16 h after which it was quenched with ice water and extracted with EtOAc (3×70 mL). The combined organic layer was washed with water, dried over sodium sulfate and concentrated under reduced pressure. The residue was recrystallized in ether to obtain 700 mg of 1-(4-Allyl-2,4,8-trimethyl-1,2,3,4-tetrahydro-pyrido [4,3-b]indol-5-yl)-2-pyridin-4-yl-propan-2-ol.

Step 4

1-(4-Allyl-2,4,8-trimethyl-1,2,3,4-tetrahydro-pyrido[4,3-b]indol-5-yl)-2-pyridin-4-yl-propan-2-ol (50 mg, 0.128 mmol) was dissolved in 0.5 mL of thionyl chloride and stirred for 15 min at RT. Excess thionyl chloride was removed under reduced pressure and the residue was basified with 1N NaOH. The product was extracted with EtOAc (2×10 mL), the organic layer was dried over sodium sulfate and concentrated under reduced pressure to obtain title compound.

Step 5

4-Allyl-2,4,8-trimethyl-5-(2-pyridin-4-yl-allyl)-2,3,4,5-tetrahydro-1H-pyrido[4,3-b]indole (300 mg, 0.808 mmol) was dissolved in DCM and the solution was purged with nitrogen for 5 min. Hoveyda-Grubbs 2nd generation catalyst (40 mg, 8 mol %) was added, the solution was re-purged with nitrogen and heated at 100° C. for 16 h. The reaction mixture was cooled to RT, filtered through Celite and the filtrate was concentrated under reduced pressure. The residue was purified by reverse phase chromatography to obtain 4 mg of 2,3a,10-trimethyl-6-pyridin-4-yl-1,2,3,3a,4,7-hexahydro-2, 7a-diaza-cyclohepta[jk]fluorene. $^1H$ NMR (Freebase, $CDCl_3$) δ (ppm): 8.61 (d, 2H), 7.37 (m, 2H), 7.21 (s, 1H), 7.19

(d, 1H), 7.0 (d, 1H), 6.21 (m, 1H), 5.18 (d, 1H), 5.0 (d, 1H), 3.80 (d, 2H), 3.56 (d, 2H), 2.59 (s, 2H), 2.41 (s, 3H), 2.12 (s, 3H), 1.58 (s, 3H).

Example 8

Preparation of Compound Nos. 10 and 12

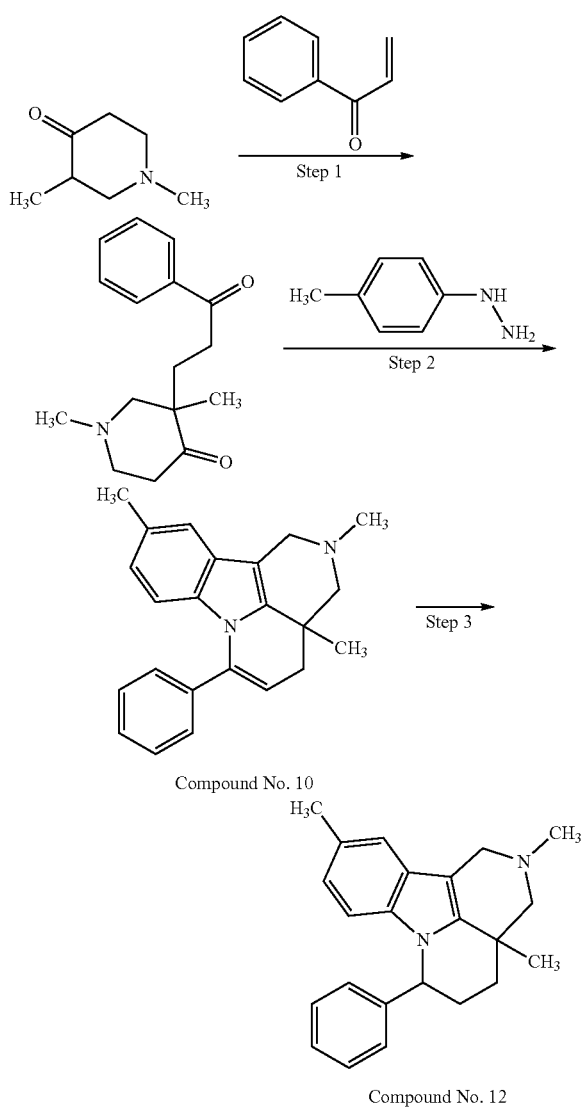

Compound No. 10

Compound No. 12

Step 1

To a stirred solution of 1,3-dimethyl-piperidin-4-one (0.1 g, 0.787 mmol) in mixture of 1,4 dioxane (2 mL) and water (0.1 mL) was added crushed KOH (44 mg, 0.787 mmol). The reaction mixture was stirred at 25° C. for 10 min. To this was added 1-phenylprop-2-en-1-one (103 mg, 0.787 mmol) dropwise. The reaction mixture was stirred at 25° C. for 2 h. The reaction mixture was concentrated under reduced pressure and the residue was diluted with water (10 mL) and EtOAc (20 mL), the organic layer was separated, dried over anhydrous sodium sulfate and concentrated under reduced pressure. The resulting crude product was purified by column chromatography on neutral alumina (eluted with EtOAc: Hexanes, 1:99) to afford 1,3-dimethyl-3-(3-oxo-3-phenyl-propyl)-piperidin-4-one as an oil (22 mg).

Step 2

A solution of p-tolylhydrazine.HCl (13 mg, 0.084 mmol) and 1,3-dimethyl-3-(3-oxo-3-phenyl-propyl)-piperidin-4-one (22 mg, 0.084 mmol) in ethanolic-HCl (5 mL) was stirred at 84° C. for 12 h. The reaction mixture was concentrated under reduced pressure and the residue was basified with saturated aqueous NaHCO₃ solution. The product was extracted with EtOAc (3×15 mL), organic layer dried over anhydrous sodium sulfate and concentrated under reduced pressure. The residue was purified by reverse phase HPLC to obtain 2,3a,10-trimethyl-6-phenyl-2,3,3a,4-tetrahydro-1H-indolo[3,2,1-ij][1,6]naphthyridine.

Step 3

To a solution of 2,3a,10-trimethyl-6-phenyl-2,3,3a,4-tetrahydro-1H-indolo[3,2,1-ij][1,6]naphthyridine (100 mg, 0.304 mmol) in MeOH (5 mL) was added 10% Pd—C (100 mg) and ammonium formate (96 mg, 1.524 mmol). The reaction mixture was stirred at 80° C. for 4 h under N₂. The reaction mixture was filtered on a Celite bed and washed with MeOH. The filtrate was concentrated under reduced pressure to obtain crude product which was purified by reverse phase HPLC to yield 2,3a,10-trimethyl-6-phenyl-2,3,3a,4,5,6-hexahydro-1H-indolo[3,2,1-ij][1,6]naphthyridine as an off-white solid.

To a solution of 4-allyl-5-[2-(4-fluoro-phenyl)-allyl]-2,4,8-trimethyl-2,3,4,5-tetrahydro-1H-pyrido[4,3-b]indole (250 mg, 0.64 mmol) in degassed DCM (7 mL) was added dropwise a solution of 2nd generation Grubbs' catalyst (27.61 mg, 0.0325 mmol, 5 mol %) in degassed DCM (3 mL) under nitrogen atmosphere. The resultant solution was heated at 115° C. for 1 h in a microwave. The solvent was evaporated in-vacuo and the residue was purified by reverse phase HPLC to obtain 50 mg of the title compound as an off white solid. ¹H NMR (CDCl₃, freebase) δ (ppm): 7.40 (m, 2H), 7.30 (d, 1H), 7.10 (d, 1H), 7.04-6.98 (m, 2H), 5.99 (d, 1H), 4.96 (d, 1H), 3.99 (d, 1H), 3.96 (s, 2H), 2.70 (d, 2H), 2.55 (s, 3H), 2.42 (s, 3H), 2.30 (d, 1H), 2.21 (m, 1H), 1.50 (s, 3H).

Example 9

Preparation of N-Methyl and N-Ethyl 9-Chloro-1,2,3,4,5,6-hexhydroazepino[4,3-b]indole

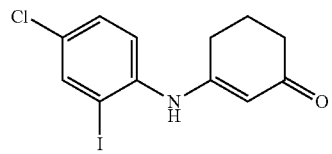 [SMILES: O=C1C=C(Nc2ccc(Cl)cc2I)CCC1]

A mixture of 4-chloro-2-iodoaniline (0.5 g, 1.97 mmol), 1,3-cyclohexanedione (0.22 g, 1.96 mmol) and p-toluenesulfonic acid monohydrate (catalytic) in toluene (6 mL) were heated to reflux for 2 h. The reaction was cooled and EtOAc (50 mL) was added and the organic phase was washed with water (20 mL) and brine (20 mL), dried over sodium sulfate, filtered and evaporated to give a brown solid, which was purified by column chromatography [Silica, eluent: EtOAc: hexane to give 3-(4-chloro-2-iodophenylamino)cyclohex-2-enone as a yellow solid (0.55 g, 80%).

A mixture of 3-(4-chloro-2-iodo-phenylamino)-cyclohex-2-enone (0.5 g, 1.44 mmol), cuprous iodide (27.4 mg, 0.14 mmol), L-proline (33.12 mg, 0.29 mmol) and potassium hydroxide (0.32 g, 5.70 mmol) in DMSO (6 mL) were heated to 90° C. for 24 h. The reaction was cooled and poured into water. The aqueous phase was extracted with EtOAc (3×50 mL). The combined organic phase was washed with brine (25 mL), dried over magnesium sulfate, filtered and the solvent removed under reduced pressure to give a dark brown solid. This was recrystallized using acetonitrile water to give a brown solid (0.17 g, 54%). mp 281-282° C.

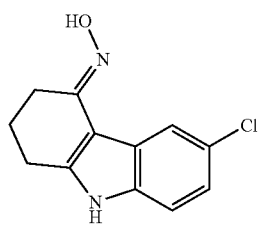 [SMILES: O/N=C1\CCCc2[nH]c3ccc(Cl)cc3c21]

A solution of 6-chloro-2,3-dihydro-1H-carbazol-4(9H)-one (500 mg, 2.27 mmol), hydroxylamine hydrochloride (238 mg, 3.41 mmol) and NaOAc (280 mg, 3.41 mmol) in EtOH:water (4.5:2 mL) was heated to reflux (125° C.) for 5 h. The reaction mixture was concentrated to dryness. Water was added to the residue and the solid filtered, dried under vacuum to yield the title compound.

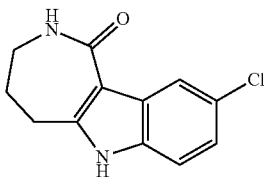 [SMILES: O=C1NCCCc2[nH]c3ccc(Cl)cc3c21]

6-Chloro-2,3-dihydro-1H-carbazol-4(9H)-one oxime (4.39 g, 18.71 mMol) and polyphosphoric acid (119 g) was heated together at 120° C. for 20 min. After cooling to RT, ice-water mixture was added to hydrolyze the mixture and stirred for 2 h. The mixture was filtered and washed with NH$_4$OH (40 ml) followed by water. The resultant solid was dissolved in MeOH and filtered. The methanolic solution was concentrated to yield 4.7 g of crude as a brown solid. The crude product was purified by flash column chromatography over silica-gel (230-400 mesh) using EtOAc/Hexane followed by MeOH/EtOAc, the product eluting at 2-10% MeOH/EA. Yield: 2.1 g (47.8%).

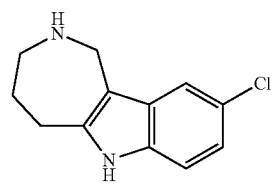 [SMILES: Clc1ccc2[nH]c3c(c2c1)CNCCC3]

To an ice-cooled stirred suspension of lithium aluminum hydride (486 mg, 12.8 mmol) in dry THF (29 mL) was added dropwise a solution of 9-chloro-2,3,4,5-tetrahydroazepino[4,3-b]indol-1(6H)-one (380 mg, 1.62 mmol) in dry THF (20 mL), and the reaction mixture heated to reflux for 15 h (89° C.). The reaction mixture was cooled to RT, quenched with water (3 mL), and 15% NaOH solution (6 mL) and water (9 mL), and then diluted with THF. The reaction mixture was filtered through Celite and the filtrate concentrated under reduced pressure to yield the title compound.

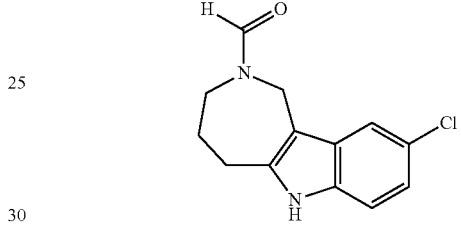

A solution of 9-chloro-1,2,3,4,5,6-hexahydroazepino[4,3-b]indole (360 mg, 1.6 mmol) in THF (1 mL) was added dropwise to ethyl formate (1 mL). The reaction mixture was stirred at RT for 30 min, followed by heating to reflux for 14 h. The solvent was removed under reduced pressure to yield the title compound.

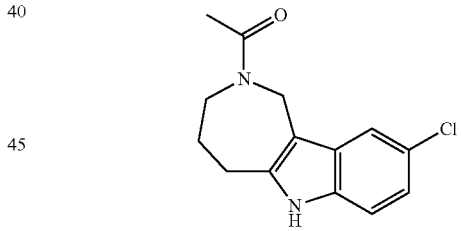

A solution of 9-chloro-1,2,3,4,5,6-hexahydroazepino[4,3-b]indole (360 mg, 1.6 mmol) was stirred in acetic anhydride for 12 h. The solvent was removed under reduced pressure to yield the title compound.

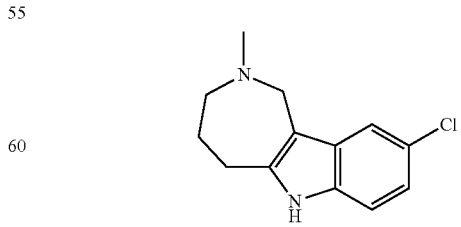

A solution of 9-chloro-1,2,3,4,5,6-hexahydroazepino[4,3-b]indole (12.3 g, 55.9 mmol) in ethyl formate (369 mL) was stirred at 55° C. for 2 h. The progress of reaction was monitored by TLC. The reaction mixture was concentrated under reduced pressure and the crude product (13.5 g) was used for the next step without purification. To a stirred suspension of lithium aluminum hydride (4.13 g, 108.8 mmol) in dry THF (405 mL) was added portionwise 9-chloro-3,4,5,6-tetrahydroazepino[4,3-b]indole-2(1H)-carbaldehyde (13.5 g) and the mixture heated to reflux for 2 h. The progress of reaction was monitored by TLC. The reaction was quenched with saturated aqueous sodium sulfate solution at 0° C., and the mixture filtered. The filtrate was dried over anhydrous sodium sulfate and evaporated to dryness. The residue was washed with diethyl ether to yield the title compound (9.7 g). $^1$H NMR (DMSO) δ (ppm): 11.02 (s, 1H, D$_2$O exchangeable), 7.45 (s, 1H), 7.25-7.22 (d, 1H), 6.98-6.95 (d, 1H), 3.72 (s, 2H), 2.90-2.80 (m, 4H), 2.30 (s, 3H), 1.82-1.77 (m, 2H).

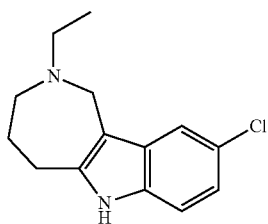 [SMILES: CCN1CCCc2[nH]c3ccc(Cl)cc3c2C1]

To an ice-cooled stirred suspension of lithium aluminum hydride (390 mg, 10.09 mmol) in 1,4-dioxane (15 mL) was added portionwise 1-(9-chloro-4,5-dihydroazepino[4,3-b]indol-2(1H,3H,6H)-yl)ethanone (300 mg, 1.14 mmol), and the reaction mixture heated to reflux for 6 h. The reaction mixture was quenched with water (1 mL), 15% aq. NaOH solution (3 mL) and water (3 mL), and extracted with warm EtOAc (3×50 mL). The combined organic extract was concentrated and the residue purified by silica gel (230-400 mesh) flash column chromatography (100% EtOAc) to yield the title compound (115 mg).

Example 10

Preparation of 2,9-dimethyl-1,2,3,4,5,6-hexahydroazepino[4,3-b]indole

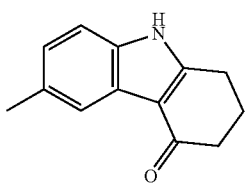

To a solution of p-tolylhydrazine hydrochloride (7.5 g, 47.2 mmol) in 1,4-dioxane:conc. H$_2$SO$_4$ (225:16.5 mL) was added cyclohexane-1,3-dione (4.42 g, 39.4 mmol), and the mixture heated to reflux for 16 h (85-90° C.). The reaction mixture was cooled to RT, basified with 15% aqueous KOH (pH 10) and extracted with EtOAc. The organic layer was washed twice with brine, dried over anhydrous sodium sulfate and concentrated under reduced pressure to yield the title compound (7.7 g, crude).

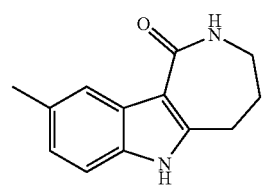 [SMILES: Cc1ccc2[nH]c3c(c2c1)C(=O)NCCC3]

A solution of 2,3-dihydro-6-methyl-1H-carbazol-4(9H)-one (5.8 g, 19.1 mmol), hydroxylamine hydrochloride (3.0 g, 43.6 mmol) and NaOAc (3.58 g, 43.6 mmol) in EtOH:water (58:25.3 mL) was heated to reflux (125° C.) for 5 h. The reaction mixture was concentrated to dryness. Water was added to the residue and the solid filtered, dried under vacuum to yield title compound.

To a preheated (105° C.) solution of polyphosphoric acid (225 g) was added powdered 6-methyl-2,3-dihydro-1H-carbazol-4(9H)-one oxime (10 g) under nitrogen and heating continued for 15 min. The reaction mixture was cooled and to it was added crushed ice water. The crystallized solid obtained was collected by filtration. The solid was washed with water and then by dilute ammonium hydroxide, then dried under vacuum to obtain the desired product (8 g, crude product).

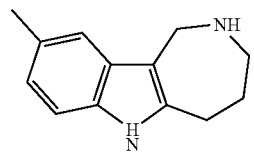

Lithium aluminum hydride (3 g, 78.95 mmol) was placed in 1,4-dioxane (100 mL) under inert atmosphere and 9-methyl-2,3,4,5-tetrahydroazepino[4,3-b]indol-1(6H)-one (3 g, 14.018 mmol) was added, and the mixture heated to reflux for 15 h. The reaction was monitored by TLC. The reaction was quenched with saturated aqueous sodium sulfate at 0° C., and the reaction mixture filtered. The filtrate was dried over anhydrous sodium sulfate and evaporated to dryness to afford solid, which was washed with water followed by EtOAc, and dried to afford 1.25 g of the title compound.

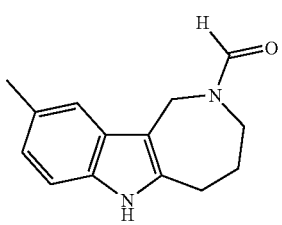 [SMILES: Cc1ccc2[nH]c3c(c2c1)CN(C=O)CCC3]

9-Methyl-1,2,3,4,5,6-hexahydroazepino[4,3-b]indole (0.25 g, 1.25 mmol) was taken in ethyl formate (18 mL, 227 mmol) and stirred at 55° C. for 3 h. The reaction was monitored by TLC. The reaction mixture was evaporated under reduced pressure and used for the next step without purification (0.2 g).

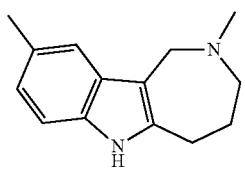 [SMILES: Cc1ccc2[nH]c3c(c2c1)CN(C)CCC3]

To a stirred suspension of lithium aluminum hydride (2 g, 52.63 mmol) in dry THF (150 mL) was added portionwise 9-methyl-3,4,5,6-tetrahydroazepino[4,3-b]indole-2(1H)-carbaldehyde (5.9 g, 25.87 mmol) and the reaction mixture stirred at 55° C. for 2 h. The progress of reaction was monitored by TLC. The reaction mixture was quenched with saturated sodium aqueous sulfate solution at 0° C. and then filtered. The filtrate was dried over anhydrous sodium sulfate and evaporated to dryness to afford the title compound (5.2 g).
$^1$H NMR (DMSO) δ (ppm): 7.12-7.05 (m, 2H), 6.80-6.6.76 (d, 1H), 3.65 (s, 2H), 2.90-2.80 (m, 4H), 2.34 (s, 3H), 2.26 (s, 3H), 1.80-1.72 (m, 2H).

Example B1

Determination of the Ability of Compounds of the Invention to Bind a Histamine Receptor Histamine $H_1$ To evaluate in radioligand binding assays the activity of compounds of the invention, human recombinant histamine $H_1$ receptor expressed in Chinese hamster ovary (CHO) K1 cells (De Backer, M. et al, Biochem. Biophys. Res. Comm. 197(3):1601, 1993) in a modified Tris-HCl buffer (50 mM Tris-HCl, pH 7.4, 2 mM $MgCl_2$, 100 mM NaCl, 250 mM Sucrose) was used. Compounds of the invention were incubated with 1.2 nM [$^3$H]Pyrilamine for 180 min at 25° C. Non-specific binding was estimated in the presence of 1 μM Pyrilamine. Receptor proteins were filtered and washed, the filters were then counted to determine [$^3$H]Pyrilamine specifically bound. Compounds were screened at 1 μM or lower, using 1% DMSO as vehicle. Biochemical assay results are presented as the percent inhibition of specific binding in Table 2.

Histamine $H_2$

To evaluate in radioligand binding assays the activity of compounds of the invention, human recombinant histamine $H_2$ receptor expressed in Chinese hamster ovary (CHO) K1 cells (Ruat, M., Proc. Natl. Acad. Sci. USA. 87(5):1658, 1990) in a 50 mM Phosphate buffer, pH 7.4 is used. Compounds of the invention are incubated with 0.1 nM [$^{125}$I] Aminopotentidine for 120 min at 25° C. Non-specific binding is estimated in the presence of 3 μM Tiotidine. Receptor proteins are filtered and washed, the filters are then counted to determine [$^{125}$I]Aminopotentidine specifically bound. Compounds are screened at 1 μM or lower, using 1% DMSO as vehicle. Compounds of the invention are tested in this biochemical assay and percent inhibition of specific binding is determined.

Histamine $H_3$

To evaluate in radioligand binding assays the activity of compounds of the invention, human recombinant histamine $H_3$ receptor expressed in Chinese hamster ovary (CHO) K1 cells (Krueger, K. et al. J. Pharmacol. Exp. Ther. 314(1):271, 2005); Yanai, K. et al, Jpn. J. Pharmacol. 65(2):107, 1994; Zhu, Y. et al, Mol. Pharmacol. 59(3):434, 2001) in a modified Tris-HCl buffer (50 mM Tris-HCl, pH 7.4, 5 mM $MgCl_2$, 0.1% BSA) is used. Compounds of invention are incubated with 0.4 nM [$^3$H]Nα-Methylhistamine for 12 min at 25° C. Non-specific binding is estimated in the presence of 1 μM R(−)-α-Methylhistamine. Receptor proteins are filtered and washed, the filters are then counted to determine [$^3$H] R(−)-α-Methylhistamine specifically bound. Compounds are screened at 1 μM or lower, using 1% DMSO as vehicle. Compounds of the invention are tested in this biochemical assay and percent inhibition of specific binding is determined.

TABLE 2

| | Binding data (Percentage inhibition) | |
|---|---|---|
| Compound No. | Histamine $H_1$ Binding (1 μM) | Histamine $H_1$ Binding (0.1 μM) |
| 1 | 11 | — |
| 2 | 63 | — |
| 3 | 78 | — |
| 4 | 12 | — |
| 5 | 94 | — |
| 6 | 51 | — |
| 7 | 19 | — |
| 8 | 6 | — |
| 9 | 6 | — |
| 10 | — | 3 |
| 11 | — | 2 |
| 12 | — | 20 |

Example B2

Determination of the Ability of Compounds of the Invention to Bind an Imidazoline $I_2$ Receptor Central Imidazoline $I_2$ To evaluate in radioligand binding assays the activity of compounds of the invention, rat central imidazoline $I_2$ receptor obtained from Wistar Rat cerebral cortex (Brown, C. et al, Br. J. Pharmacol. 99:803, 1990) in a modified Tris-HCl buffer (50 mM Tris-HCl buffer, pH 7.4, 0.5 mM EDTA) is used. Compounds of the invention are incubated with 2 nM [$^3$H] Idazoxan for 30 min at 25° C. Non-specific binding is estimated in the presence of 1 μM Idazoxan. Receptor proteins are filtered and washed, the filters are then counted to determine [$^3$H]Idazoxan specifically bound. Compounds are screened at 1 μM or lower, using 1% DMSO as vehicle.

Compounds of the invention are tested in this biochemical assay and percent inhibition of specific binding is determined.

Example B3

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. et al, Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds of the invention were screened at 1 µM or lower, using 1% DMSO as vehicle. Biochemical assay results are presented as the percent inhibition of specific binding in Table 3.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. et al, Biochem. Biophys. Res. Commun. 186:760, 1992; Michel, A. et al, Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds were screened at 1 µM or lower, using 1% DMSO as vehicle. Biochemical assay results are presented as the percent inhibition of specific binding in Table 3.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. et al, Br. J. Pharmacol. 115(6):981, 1995) in a 50 mM Tris-HCl buffer, pH 7.4, was used. Compounds of invention were incubated with 0.6 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds were screened at 1 µM or lower, using 1% DMSO as vehicle. Biochemical assay results are presented as the percent inhibition of specific binding in Table 3.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min at 25° C. MK912 is (2S-trans)-1,3,4,5',6,6',7,12b-octahydro-1',3'-dimethyl-spiro[2H-benzofuro[2,3-a]quinolizine-2,4'(1'H)-pyrimidin]-2' (3'H)-one hydrochloride Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 3.

Adrenergic $\alpha_{1D}$

To evaluate in radioligand binding assays the activity of compounds of the invention, human recombinant adrenergic $\alpha_{2B}$ receptor expressed in Chinese hamster ovary (CHO) K1 cells (Uhlen, S. et al, Eur. J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [$^3$H]Rauwolscine for 60 min at 25° C. Non-specific binding was estimated in the presence of 10 µM Prazosin. Receptor proteins were filtered and washed, the filters were then counted to determine [$^3$H]Rauwolscine specifically bound. Compounds were screened at 1 µM or lower, using 1% DMSO as vehicle. Biochemical assay results are presented as the percent inhibition of specific binding in Table 3.

Adrenergic $\alpha_{2C}$

To evaluate in radioligand binding assays the activity of compounds of the invention, human recombinant adrenergic $\alpha_{2C}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds of the invention were incubated with 1 nM [$^3$H]MK-912 for 60 min at 25° C. Non-specific binding was estimated in the presence of 10 µM WB-4101. Receptor proteins were filtered and washed, the filters were then counted to determine [$^3$H]MK-912 specifically bound. Compounds were screened at 1 µM or lower, using 1% DMSO as vehicle. Biochemical assay results are presented as the percent inhibition of specific binding in Table 3.

Example B4

Determination of the Ability of Compounds of the Invention to Bind a Dopamine Receptor Dopamine $D_{2L}$ To evaluate in radioligand binding assays the activity of compounds of the invention, human recombinant dopamine $D_{2L}$ receptor expressed in Chinese hamster ovary (CHO) cells (Grandy, D. et al, Proc. Natl. Acad. Sci. USA. 86:9762, 1989; Hayes, G. et al, Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H]Spiperone for 120 min at 25° C. Non-specific binding was estimated in the presence of 10 µM Haloperidol. Receptor proteins were filtered and washed, the filters were then counted to determine [$^3$H]Spiperone specifically bound. Compounds were screened at 1 µM or lower, using 1% DMSO as vehicle. Biochemical assay results are presented as the percent inhibition of specific binding in Table 3.

TABLE 3

Percentage inhibition of ligand binding to aminergic G protein-coupled receptors by compounds of the invention:

| Compound No. | Adrenergic (0.1 µM) | | | | | | Dopamine |
| | $\alpha_{1A}$ | $\alpha_{1B}$ | $\alpha_{1D}$ | $\alpha_{2A}$ | $\alpha_{2B}$ | $\alpha_{2C}$ | $D_{2L}$ (1 µM) |
|---|---|---|---|---|---|---|---|
| 1 | — | — | — | — | — | — | 12 |
| 2 | — | — | — | — | — | — | 13 |
| 3 | — | — | — | — | — | — | 22 |
| 4 | — | — | — | — | — | — | 14 |

TABLE 3-continued

Percentage inhibition of ligand binding to aminergic G protein-coupled receptors by compounds of the invention:

| Compound No. | Adrenergic (0.1 μM) | | | | | | Dopamine |
|---|---|---|---|---|---|---|---|
| | $\alpha_{1A}$ | $\alpha_{1B}$ | $\alpha_{1D}$ | $\alpha_{2A}$ | $\alpha_{2B}$ | $\alpha_{2C}$ | $D_{2L}$ (1 μM) |
| 5 | — | — | — | — | — | — | 60 |
| 6 | — | — | — | — | — | — | 6 |
| 7 | — | — | — | — | — | — | 0 |
| 8 | — | — | — | — | — | — | 13 |
| 9 | — | — | — | — | — | — | 2 |
| 10 | −4 | −3 | −6 | −1 | −6 | 2 | 9 |
| 11 | 25 | 16 | −5 | 8 | 30 | 1 | 3 |
| 12 | 12 | 10 | −3 | 5 | −7 | −3 | 5 |

Example B5

Determination of the Ability of Compounds of the Invention to Bind a Serotonin Receptor Serotonin (5-Hydroxytryptamine) 5-HT$_{1A}$ To evaluate in radioligand binding assays the activity of compounds of the invention, human recombinant serotonin (5-Hydroxytryptamine) 5-HT$_{1A}$ receptor expressed in Chinese hamster ovary (CHO) K1 cells (Martin, G. et al, Neuropharmacol. 33:261, 1994; May J. et al, J. Pharmacol. Exp. Ther. 306(1):301, 2003) in a modified Tris-HCl buffer (50 mM Tris-HCl, pH 7.4, 0.1% Ascorbic Acid, 0.5 mM EDTA, 10 mM MgSO$_4$) is used. Compounds of invention are incubated with 1.5 nM [$^3$H]8-OH-DPAT for 60 min at 25° C. Non-specific binding is estimated in the presence of 10 μM Metergoline. Receptor proteins are filtered and washed, the filters are then counted to determine [$^3$H] 8-OH-DPAT specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{1B}$

To evaluate in radioligand binding assays the activity of compounds of the invention, serotonin (5-Hydroxytryptamine) 5-HT$_{1B}$ receptor from Wistar Rat cerebral cortex (Hoyer et al, Eur. J. Pharmacol. 118:1, 1985; Pazos et al, Eur. J. Pharmacol. 106:531, 1985) in a modified Tris-HCl buffer (50 mM Tris-HCl, pH 7.4, 154 mM NaCl, 10 μM Pargyline, 30 μM Isoprenaline) is used. Compounds of invention are incubated with 10 pM [$^{125}$I]Cyanopindolol for 90 min at 37° C. Non-specific binding is estimated in the presence of 10 μM Serotonin (5-HT). Receptor proteins are filtered and washed, the filters are counted to determine [$^{125}$I]Cyanopindolol specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{2A}$

To evaluate in radioligand binding assays the activity of compounds of the invention, human recombinant serotonin (5-Hydroxytryptamine) 5-HT$_{2A}$ receptor expressed in Chinese hamster ovary (CHO) K1 cells (Bonhaus, D. et al, Br. J. Pharmacol. 115:622, 1995; Saucier, C. et al, J. Neurochem. 68:1998, 1997) in a 50 mM Tris-HCl buffer, pH 7.4, was used. Compounds of the invention were incubated with 0.5 nM [$^3$H]Ketanserin for 60 min at 25° C. Non-specific binding was estimated in the presence of 1 μM Mianserin. Receptor proteins were filtered and washed, the filters were then counted to determine [$^3$H]Ketanserin specifically bound. Compounds were screened at 1 μM or lower, using 1% DMSO as vehicle. Biochemical assay results are presented as the percent inhibition of specific binding in Table 4.

Serotonin (5-Hydroxytryptamine) 5-HT$_{2B}$

To evaluate in radioligand binding assays the activity of compounds of the invention, human recombinant serotonin (5-Hydroxytryptamine) 5-HT$_{2B}$ receptor expressed in Chinese hamster ovary (CHO) K1 cells (Bonhaus, D. et al, Br. J. Pharmacol. 115:622, 1995) in a modified Tris-HCl buffer (50 mM Tris-HCl, pH 7.4, 4 mM CaCl$_2$, 0.1% Ascorbic Acid) was used. Compounds of invention were incubated with 1.2 nM [$^3$H]Lysergic acid diethylamide (LSD) for 60 min. at 37° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Compounds of the invention are tested in this biochemical assay and percent inhibition of specific binding is determined.

Serotonin (5-Hydroxytryptamine) 5-HT$_{2C}$

To evaluate in radioligand binding assays the activity of compounds of the invention, human recombinant serotonin (5-Hydroxytryptamine) 5-HT$_{2C}$ receptor expressed in Chinese hamster ovary (CHO) K1 cells (Wolf, W. et al, J. Neurochem. 69:1449, 1997) in a modified Tris-HCl buffer (50 mM Tris-HCl, pH 7.4, 0.1% Ascorbic Acid, 10 μM Pargyline) was used. Compounds of the invention were incubated with 1 nM [$^3$H]Mesulergine for 60 min at 25° C. Non-specific binding was estimated in the presence of 1 μM Mianserin. Receptor proteins were filtered and washed, the filters were then counted to determine [$^3$H]Mesulergine specifically bound. Compounds were screened at 1 μM or lower, using 1% DMSO as vehicle. Biochemical assay results are presented as the percent inhibition of specific binding in Table 4.

Serotonin (5-Hydroxytryptamine) 5-HT$_3$

To evaluate in radioligand binding assays the activity of compounds of the invention, human recombinant serotonin (5-Hydroxytryptamine) 5-HT$_3$ receptor expressed in human embryonic kidney (HEK-293) cells (Miller, K. et al, Synapse 11:58, 1992; Boess, F. et al, Neuropharmacology 36:637, 1997) in a modified Tris-HCl buffer (50 mM Tris-HCl, pH 7.4, 1 mM EDTA, 5 mM MgCl$_2$) is used. Compounds of invention are incubated with 0.69 nM [$^3$H]GR-65630 for 60 min at 25° C. Non-specific binding is estimated in the presence of 10 μM MDL-72222. Receptor proteins are filtered and washed, the filters are then counted to determine [$^3$H]GR-65630 specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_4$

To evaluate in radioligand binding assays the activity of compounds of the invention, serotonin (5-Hydroxytryptamine) 5-HT$_4$ receptor from Duncan Hartley derived Guinea pig striatum (Grossman, C. et al, Br. J. Pharmacol. 109:618, 1993) in a 50 mM Tris-HCl, pH 7.4, is used. Compounds of invention are incubated with 0.7 nM [$^3$H]GR-113808 for 30 min at 25° C. Non-specific binding is estimated in the presence of 30 μM Serotonin (5-HT). Receptor proteins are filtered and washed, the filters are counted to determine [$^3$H]GR-113808 specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT$_{5A}$

To evaluate in radioligand binding assays the activity of compounds of the invention, human recombinant serotonin (5-Hydroxytryptamine) 5-HT$_{5A}$ receptor expressed in Chinese hamster ovary (CHO) K1 cells (Rees, S. et al, FEBS Lett. 355:242, 1994) in a modified Tris-HCl buffer (50 mM Tris-HCl, pH 7.4, 10 mM MgCl$_2$, 0.5 mM EDTA) was used. Compounds of the invention were incubated with 1.7 nM [$^3$H]Lysergic acid diethylamide (LSD) for 60 min at 37° C. Non-specific binding was estimated in the presence of 100 µM Serotonin (5-HT). Receptor proteins were filtered and washed, the filters were counted to determine [$^3$H]LSD specifically bound. Compounds were screened at 1 µM or lower, using 1% DMSO as vehicle. Biochemical assay results are presented as the percent inhibition of specific binding in Table 4.

Serotonin (5-Hydroxytryptamine) 5-HT$_6$

To evaluate in radioligand binding assays the activity of compounds of the invention, human recombinant serotonin (5-Hydroxytryptamine) 5-HT$_6$ receptor expressed in human HeLa cells (Monsma, F. Jr. et al, Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 min at 37° C. Non-specific binding was estimated in the presence of 5 µM Serotonin (5-HT). Receptor proteins were filtered and washed, the filters were then counted to determine [3H]LSD specifically bound. Compounds were screened at 1 µM or lower, using 1% DMSO as vehicle. Biochemical assay results are presented as the percent inhibition of specific binding in Table 4.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. et al, J. Pharmacol. Exp. Ther. 268:1403, 1994; Shen, Y. et al, J. Biol. Chem. 268: 18200, 1993) in a modified Tris-HCl buffer (50 mM Tris-HCl, pH 7.4, 10 mM MgCl$_2$, 0.5 mM EDTA) was used. Compounds of invention were incubated with 5.5 nM [$^3$H] Lysergic acid diethylamide (LSD) for 2 h at 25° C. Non-specific binding was estimated in the presence of 10 µM Serotonin (5-HT). Receptor proteins were filtered and washed, the filters were then counted to determine [$^3$H]LSD specifically bound. Compounds were screened at 1 µM or lower, using 1% DMSO as vehicle. Biochemical assay results are presented as the percent inhibition of specific binding in Table 4.

TABLE 4

Percentage inhibition of ligand binding to aminergic G protein-coupled receptors by compounds of the invention:

| Compound No. | Serotonin (0.1 µM) | | | | |
|---|---|---|---|---|---|
| | 5-HT$_{2A}$ | 5-HT$_{2C}$ | 5-HT$_{5A}$ | 5-HT$_6$ | 5-HT$_7$ |
| 1 | 56 | 45 | — | 8 | 26 |
| 2 | 49 | 36 | — | 12 | 34 |
| 3 | 45 | 39 | — | 10 | 46 |
| 4 | 47 | 35 | — | 6 | 38 |
| 5 | 54 | 32 | — | 39 | 35 |
| 6 | 54 | 38 | — | 35 | 39 |
| 7 | 57 | 41 | — | 6 | 54 |
| 8 | 68 | 54 | — | 4 | 55 |
| 9 | 87 | 73 | — | 21 | 57 |
| 10 | 13 | 17 | −8 | 7 | 12 |
| 11 | 10 | 7 | 9 | 5 | −8 |
| 12 | 12 | 11 | −21 | 21 | −17 |

Example B6

Determination of Serotonin (5-Hydroxytryptamine) 5-HT$_{2A}$ or 5-HT$_7$ Agonist/Antagonist Activity of Compounds of the Invention To determine for agonist or antagonist activity of compounds of the invention in functional assays, human recombinant serotonin 5-HT$_{2A}$ receptor expressed in human embryonic kidney (HEK-293) cells (Jerman et al., Eur. J. Pharmacol. 414:23-30, 2001) or human recombinant serotonin 5-HT$_7$ receptor expressed in CHO cells (Adham et al, J. Pharmacol. Exp. Ther. 287:508-514, 1998) is used. Cells are suspended in DMEM buffer, and distributed in microplates. For the 5-HT$_{2A}$ assay, a cytoplasmic calcium fluorescent indicator which varies proportionally to the free cytosolic Ca$^{2+}$ ion concentration is mixed with probenecid in HBSS buffer complemented with 20 mM HEPES (pH 7.4), added into each well and equilibrated with the cells for 30 min at 37° C. followed by 30 min at 22° C. For the 5-HT$_7$ assay, the reaction product is cAMP, detected by HTRF.

To measure 5-HT$_{2A}$ agonist effects, compounds of the invention, reference agonist or HBSS buffer (basal control) is added to the cells and changes in fluorescence intensity are measured using a microplate reader. For stimulated control measurements, 5-HT at 100 nM is added in separate assay wells. The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the compounds of the invention, reference antagonist or HBSS buffer is followed by the addition of 3 nM 5-HT (5-HT$_{2A}$), 100 nM 5-HT (5-HT$_7$) or HBSS buffer (basal control) prior the fluorescence measurements. The results are expressed as a percent inhibition of the control response to 3 nM 5-HT. The standard reference antagonist is ketanserin (5-HT$_{2A}$) or mesulergine (5-HT$_7$), which is tested in each experiment at several concentrations to generate a concentration-response curve from which its IC$_{50}$ value is calculated. Compounds are screened at 3 µM or lower, using DMSO as vehicle.

Example B7

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R. et al, J. Neurochem. 66:47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 µM IBMX, and then distributed in microplates and incubated for 45 min at 37° C. in the absence (control) or presence of compounds of the invention or the reference agonist or antagonist.

For agonist determinations, stimulated control measurement, separate assay wells contain 10 µM 5-HT. Following incubation, the cells are lysed and the fluorescence acceptor (D2-labeled cAMP) and fluorescence donor (anti-cAMP antibody labeled with europium cryptate) are added. After 60 min. at RT, the fluorescence transfer is measured at λex=337 nm and lem=620 and 665 nm using a microplate reader. The cAMP concentration is determined by dividing the signal measured at 665 nm by that measured at 620 nm (ratio).

The results are expressed as a percent of the control response to 10 μM 5-HT. The standard reference agonist is 5-HT, which is tested in each experiment at several concentrations to generate a concentration-response curve from which its $EC_{50}$ value is calculated.

For antagonist determinations, the reference agonist 5-HT is added at a final concentration of 100 nM. For basal control measurements, separate assay wells do not contain 5-HT. Following 45 min. incubation at 37° C., the cells are lysed and the fluorescence acceptor ($D_2$-labeled cAMP) and fluorescence donor (anti-cAMP antibody labeled with europium cryptate) are added.

After 60 min. at RT, the fluorescence transfer is measured as mentioned above. The results are expressed as a percent inhibition of the control response to 100 nM 5-HT. The standard reference antagonist is methiothepin.

Example B8

Determination of Dopamine $D_{2L}$ Antagonist Activity of Compounds

To determine for agonist or antagonist activity of compounds of the invention in functional assays, human recombinant dopamine $D_{2L}$ receptor stably expressed in Chinese hamster ovary (CHO) cells (Senogles, S. et al, J. Biol. Chem. 265(8):4507, 1990) is used. Compounds of the invention are pre-incubated with the membranes (0.1 mg/mL) and 10 mM GDP in modified HEPES buffer (20 mM HEPES, pH 7.4, 100 mM NaCl, 10 mM $MgCl_2$, 1 mM DTT, 1 mM EDTA) for 20 min. and Scintillation Proximity Assay (SPA) beads are added for another 60 min. at 30° C. The reaction is initiated by 0.3 nM [$^{35}$S]GTPγS for an additional 15 min. incubation period. Increase of [$^{35}$S]GTPγS binding by 50% or more (≥50%) relative to the 1 mM dopamine response by compounds of the invention indicates possible dopamine $D_{2L}$ receptor agonist's activity. Inhibition of a 10 μM dopamine-induced increase of [$^{35}$S]GTPγS binding response by 50% or more (≥50%) by compounds of the invention indicates receptor antagonist activity. Compounds are screened at 3 μM or lower, using 0.4% DMSO as vehicle. Assay results are presented as the percent response of specific binding.

Example B9

Determination of Dopamine $D_{2S}$ Antagonist Activity of Compounds of the Invention To determine for agonist or antagonist activity of compounds of the invention in functional assays, human recombinant dopamine $D_{2S}$ receptor stably expressed in Chinese hamster ovary (CHO) cells (Gilliland, S. et al, Naunyn-Schmiedeberg's Archives of Pharmacology 361:498, 2000) is used. Compounds of the invention are pre-incubated with the membranes (0.05 mg/mL) and 3 μM GDP in modified HEPES buffer (20 mM HEPES, pH 7.4, 100 mM NaCl, 10 mM $MgCl_2$, 1 mM DTT, 1 mM EDTA) for 20 min. and Scintillation Proximity Assay (SPA) beads are then added for another 60 min. at 30° C. The reaction is initiated by 0.3 nM [$^{35}$S]GTPγS for an additional 30 min incubation period. Increase of [$^{35}$S]GTPγS binding by 50 percent or more (≥50%) relative to the 100 μM dopamine response by compounds of the invention indicates possible dopamine $D_{2S}$ receptor agonist's activity. Inhibition of a 3 μM dopamine-induced increase of [$^{35}$S]GTPγS binding response by 50 percent or more (≥50%) by compounds of the invention indicates receptor antagonist activity. Compounds are screened at 3 μM or lower, using 0.4% DMSO as vehicle. Assay results are presented as the percent response of specific binding.

Example B10

Determination for Agonist or Antagonist Activity of Compounds of the Invention in a Histamine $H_1$ Functional Assay To determine for agonist or antagonist activity of compounds of the invention in functional assays, human recombinant Histamine $H_1$ receptor expressed in human embryonic kidney (HEK-293) cells (Miller, T. et al, J. Biomol. Screen. 4: 249-258, 1999) is used. Cells are suspended in DMEM buffer, and then distributed in microplates. A cytoplasmic calcium fluorescent indicator—which varies proportionally to the free cytosolic $Ca^{2+}$ ion concentration is mixed with probenecid in HBSS buffer complemented with 20 mM HEPES (pH 7.4) and is then added into each well and equilibrated with the cells for 30 min. at 37° C. and then for another 30 min. at 22° C. To measure agonist effects, compounds of the invention, reference agonist or HBSS buffer (basal control) are added to the cells and changes in fluorescence intensity are measured using a microplate reader. For stimulated control measurements, histamine at 10 μM is added in separate assay wells.

The results are expressed as a percent of the control response to 10 μM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 μM or lower, using DMSO as vehicle.

Example B11

Determination of Binding Activity of Compounds of the Invention at the 5-$HT_{1B}$ Receptor with a Radioligand Binding Competition Assay To determine the binding activity at the human recombinant serotonin 5-$HT_{1B}$ receptor of compounds of the invention, CHO-K1 cell line expressing the human 5-$HT_{1B}$ recombinant receptor is amplified to prepare membranes used for the radioligand binding assay throughout the study. Radioligand binding competition on 5-$HT_{1B}$ is performed by adding successively in the wells of a 96 well plate (Master Block, Greiner, 786201) 50 μL of test compounds or reference ligand (5-HT, Sigma, H-9523) at increasing concentrations (diluted in binding buffer: 50 mM Tris pH 7.4, 12.5 mM $MgCl_2$, 0.1% Ascorbic Acid, 1 mM EDTA, pH 7.4), 25 μL [$^3$H]5-CT (Amersham, TRK1038, diluted in assay buffer for a final concentration of 0.6 nM) and 25 μL 5-HT1B membrane extracts (7 μg/well). Non specific binding is determined by co-incubation with 200-fold excess of 5-HT. The plate is incubated 60 min at 25° C. in a water bath and then filtered over GF/B filters (Perkin Elmer, 6005177, presoaked in 0.5% PEI for 2 h at RT)

with a Filtration unit (Perkin Elmer). The filters are washed 3× with 0.5 mL of ice-cold washing buffer (50 mM Tris pH 7.4), 50 µL Microscint 20 (Packard) is added and the plate is incubated 15 min. on an orbital shaker and then counted with a TopCount™ for 1 min/well.

On each day of experimentation and prior to the testing of compounds, the reference compound is tested at several concentrations in duplicate (n=2) to obtain a dose-response curve and an estimated $IC_{50}$ value. The reference value thus obtained for the test is compared to a historical value obtained from the same receptor and used to validate the experimental session. A session is considered as valid only if the reference value is found to be within a 0.5 logs interval from the historical value. For replicate determinations, the maximum variability tolerated in the test is of +/−20% around the average of the replicates.

Compounds are tested for binding activity in the radioligand binding competition assay on human $5\text{-}HT_{1B}$ receptor, at one concentration 5 µM, in duplicate. Dose-response data from test compounds are analyzed with XLfit (IDBS) software using nonlinear regression applied to a sigmoidal dose-response model.

Example B12

Functional Activity on Recombinant Dopamine $D_{2L}$ and Serotonin $5\text{-}HT_{2A}$ Receptors Using Aequorin, cAMP and GTPγS Functional Assays To study the functional activity of compounds of the invention on the human recombinant dopamine $D_{2L}$ with Aequorin, GTPγS and cAMP functional assays and on the human recombinant serotonin $5\text{-}HT_{2A}$ receptor with Aequorin, CHO-K1 cell lines expressing $D_{2L}$ or $5\text{-}HT_{2A}$ recombinant receptor, mitochondrial apoaequorin and Gα16 are used for the Aequorin assay. CHO-K1 cell line expressing the recombinant $D_{2L}$ receptor is used for the cAMP assay and is amplified to prepare membranes used for the GTPγS assay.

Aequorin Assay Procedure: Aequorin dopamine $D_{2L}$ (FAST-0101A) or serotonin $5\text{-}HT_{2A}$ (FAST-0505A) cells, grown 18 h prior to the test in media without antibiotics, are detached by gentle flushing with PBS-EDTA (5 mM EDTA), recovered by centrifugation and resuspended in "assay buffer" (DMEM/HAM's F12 with HEPES, without phenol red+0.1% BSA protease free). Cells are incubated at RT for at least 4 h with Coelenterazine h (Molecular Probes). Dose response curves with reference compounds are performed before testing the compounds of the invention. $D_{2L}$ reference agonist and antagonist are quinpirol (Tocris, 1061) and haloperidol (Tocris, 0931), respectively. $5\text{-}HT_{2A}$ reference agonist and antagonist are α-methyl-5-HT (Sigma, M-110) and ketanserin (Tocris, 908), respectively. For agonist testing, 50 µL of cell suspension are injected on 50 µL of test compound or reference agonist plated in a 96-well plate. The resulting emission of light is recorded using the Hamamatsu Functional Drug Screening System 6000 (FDSS 6000). Following an incubation of 15 min. after the first injection, 100 µL of reference agonist at a concentration corresponding to its $EC_{80}$ is injected on the 100 µL of the mixture of cell suspension and test compound, for antagonist testing. The resulting emission of light is recorded using the same luminometer as for agonist testing. To standardize the emission of recorded light (determination of the "100% signal") across plates and across different experiments, some of the wells contain 100 µM digitonin or a saturating concentration of ATP (20 µM). Plates also contain the reference agonist at a concentration equivalent to the $EC_{100}$ and $EC_{80}$ obtained during the test validation.

Compounds are tested for agonist & antagonist activity at the human dopamine $D_{2L}$ receptor (FAST-0101A) and serotonin $5\text{-}HT_{2A}$ receptor (FAST-0505A) at the following nanomolar concentrations, in duplicate: Agonist (nM): 10, 30, 100, 300, 1000, 3000, 10000, 30000; Antagonist (nM): 5, 15, 50, 150, 500, 1500, 5000, 15000.

cAMP Assay Procedure: $D_{2L}$ CHO-K1 cells (FAST-0101C), grown to mid-log phase in culture media without antibiotics, are detached with PBS-EDTA (5 mM EDTA), centrifuged and resuspended in assay buffer (KRH, 1 mM IBMX) at a concentration of $2.1 \times 10^5$ cells/mL. The test is performed in 96 well plates. For agonist testing, 12 µL of cells (2,500 cells/well) are mixed with 6 µL of increasing concentrations of test compound or reference agonist and 6 µL of Forskolin 10 µM final concentration (Calbiochem, cat n° 344270). For antagonist testing, 12 µL of cells (2,500 cells/well) are mixed with 6 µL of test compound or reference antagonist at increasing concentrations. After incubation of 10 min. at RT, 6 µL of a mix of Forskolin 10 µM final concentration and the reference agonist at a final concentration corresponding to the $EC_{80}$ are added. The plates are then incubated for 30 min. at RT. During the incubation, the anti-cAMP cryptate antibody (K) and the cAMP-D2 (D2) are prepared according to the manufacturer specifications (HTRF kit from Cis-Bio International (cat n° 62AM2PEB). 12 µL of cAMP-$D_2$ solution followed by 12 µL of K solution are added to each well. The plate is then covered by a top-seal and incubated for at least 1 h at RT. The plate is then read on the Rubystar and data are analyzed by non-linear regression using a single site model. Compounds are tested for antagonist activity at the human dopamine $D_{2L}$ receptor (FAST-0101C) at the following nanomolar concentrations, in duplicate: Antagonist (nM): 5, 15, 50, 150, 500, 1500, 5000, 15000.

GTPγS Assay Procedure: Assay buffer [20 mM HEPES pH 7.4; 100 mM NaCl, 10 µg/mL saponin, 30 mM $MgCl_2$]; Membranes [Recombinant CHO-K1-$D_{2L}$ membrane extracts thawed on ice and diluted in assay buffer to give 1 mg/mL (10 µg/10 µL) and kept on ice]; GDP [diluted in assay buffer to give 3 µM final concentration]; Beads [PVT-WGA (Amersham, RPNQ0001), diluted in assay buffer at 25 mg/mL (0.25 mg/10 µL)]; GTPγ$^{35}$S [(PerkinElmer NEG030X), diluted in assay buffer to give 0.1 nM final concentration]; Ligand [Quinpirol (Tocris, 1061) as reference agonist and haloperidol (Tocris, 0931) as reference antagonist, diluted in assay buffer]. Membranes are mixed with GDP (volume:volume) and incubated for at least 15 min. on ice. In parallel, GTPγ[$^{35}$S] is mixed with the beads (volume:volume) just before starting the reaction. For agonist testing, the following reagents are successively added in the wells of an Optiplate (Perkin Elmer): 50 µL of test or reference ligand, 20 µL of the membranes:GDP mix, 10 µL of assay buffer and 20 µL of the GTPγ[$^{35}$S]:beads mix. For antagonist testing, the following reagents are successively added in the wells of an Optiplate (Perkin Elmer): 50 µL of test or reference ligand, 20 µL of the membranes:GDP mix, and then after an incubation of 15 min at RT, 10 µL of reference agonist at historical $EC_{80}$ concentration and 20 µL of the GTPγ[$^{35}$S]:beads mix. The plates are covered with a top seal, mixed on an orbital shaker for 2 min, and then incubated for 1 h at RT. Then the plates are centrifuged for 10 min. at 2000 rpm, incubated at RT 1 h and counted for 1 min/well with a Perkin Elmer TopCount reader. Compounds are tested for antagonist activity at the human dopamine $D_{2L}$ receptor (FAST-0101G) at the following nanomolar concentrations, in duplicate: Antagonist (nM): 5, 15, 50, 150, 500, 1500, 5000, 15000.

Example B13

Increase of Neurite Outgrowth of Neurons that are Cultured with Compounds of the Invention Neurite Outgrowth in Cortical Neurons Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation is prepared in Leibovitz's medium (L15; Gibco). The cortex is dissected out, and the meninges are removed. Trypsin (Gibco) is used to dissociate cortical C with DNAse I. The cells are triturated for 30 min. with a pipette in Dulbecco's Modified Eagle Media ("DMEM"; Gibco) with 10% Fetal Bovine Serum ("FBS") (Gibco) and centrifuged at 350×g for 10 min. at RT. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue is cut to small pieces. The cells are separated by 15-min. incubation with DNase and papain. The cells are collected by centrifugation (1500 rpm, 5 min). The tissue is triturated with a pipette and the cells are plated using the micro-islet protocol (20,000 cells in 25 µL medium) on poly-L-lysine coated 48 wells, in MEM supplemented with 2 mM glutamine, 0.1 µg/mL gentamicin, 10% heat-inactivated fetal bovine serum (FBS-HI) and 10% heat-inactivated horse serum (HS-HI). After the cells attach to the well, 250 µL medium is added to the wells. 4 h after plating, the medium is changed to fresh medium (MEM with supplements and 5% HS-HI) containing test compound at 0.5, 5 and 50 nM concentrations. As positive controls BDNF (50, 100 and/or 150 ng/mL), and/or NGF (50 ng/mL and/or 100 ng/mL) are used. After 2 days in vitro, the cell's conditioned media are collected from plates before fixing the cells. The media samples are centrifuged 13,000 rpm 3 min to get rid of cell debris. The samples are stored at −20° C. for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min and washed once with PBS. The fixed cells are first permeabilized and non-specific binding is blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software. The number of wells per compound concentration used is 6 (n=6). All data are presented as mean±standard deviation (SD) or standard error of mean (SEM), and differences are considered to be statistically significant at the p<0.05 level. Statistical analysis is performed using StatsDirect statistical software. Differences between group means are analyzed by using 1-way-ANOVA followed by Dunnet's test (comparison to the vehicle treated group).

Example B14

Use of an In Vivo Model to Evaluate the Ability of Compounds to Enhance Cognition, Learning and Memory in Scopolamine Treated Rats The two-trial object recognition paradigm developed by Ennaceur and Delacour in the rat is used as a model of episodic short term memory. Ennaceur, A., and Delacour, J. (1988), Behav. Brain Res. 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C. et al, Neurosci. Letts. 70:117-120, 1994; and Bartolini, L. et al, Biochem. Behav. 53:277-283, 1996.

Male Sprague-Dawley rats between six and seven weeks old, weighing between 220-300 grams are obtained from Centre d'Elevage (Rue Janvier, B. P. 55, Le Genest-Saint-Isle 53940, France). The animals are housed in groups of 2 to 4 in polypropylene cages (with a floor area of 1032 $cm^2$) under standard conditions: at RT (22±2° C.), under a 12 h light/12 h dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for 3 min. in the presence of two objects (habituation). Animals to be tested are placed in the experimental room at least 30 min before testing.

Novel object recognition test is comprised of two trials separated by an interval of 120 min. or 24 h. When agents that disrupt memory such as the cholinergic antagonist scopolamine are used an inter-trial interval of 120 min. is preferred. Alternatively a 24 h inter-trial interval is used when studying effect of natural forgetting on novel object recognition task. During the first, or acquisition, trial ($T_1$), rats are placed in the arena, where two identical objects have been previously placed. The time required for each animal to complete 15 sec of object exploration is determined, with a cut-off time of 4 min. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for 3 min, and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 sec of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel} - T_{Familiar}$) is evaluated. The % of animals in each group with $T_{Novel} - T_{Familiar}$ greater than or equal to 5 sec is also derived; described as % of good learners.

Animals not meeting a minimal level of object exploration are excluded from the study as having naturally low levels of spontaneous exploration. Thus, only rats exploring the objects for at least five sec ($T_{Novel} + T_{Familiar} > 5$ sec) are included in the study.

Animals are randomly assigned to groups of 14. Compounds of the invention and controls are administered to animals the groups as follows: Solutions of compounds are prepared freshly each day at a concentration of 0.25 mg/mL using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil is administered (e.g., intraperitoneally) 40 minutes before the acquisition trial (T1). Scopolamine is administered (e.g., intraperitoneally) 30 minutes before the acquisition trial (T1). Vehicle (purified water) or test compound is administered (e.g., by gavage) 25 minutes before the acquisition trial (T1), 5 min after scopolamine challenge. The volume of administration is 5 mL/kg body weight for compounds administered intraperitoneally, and 10 mL/kg for compounds administered orally.

Recognition scores and % of good learners for compounds of the invention are determined.

Example B15

Use of an In Vivo Model to Determine the Ability of Compounds to Treat, Prevent and/or Delay the Onset and/or the Development of Schizophrenia (Hyperactivity in PCP Treated Animals)

In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al, Science 277:953-955, 1997; and Piercey et al, Life Sci. 43(4):375-385, 1988. Standard experimental protocols may be employed in this or in other animal models. One protocol involves PCP-induced hyperactivity.

Male C57-B1/6J mice from Jackson Laboratories (Bar Harbor, Me.) are used. Mice are received at 6-weeks of age. Upon receipt, mice are assigned unique identification numbers (tail marked) and are group housed with 4 mice/cage in OPTIMICE ventilated cages. All animals remain housed in groups of 4 during the remainder of the study. All mice are acclimated to the colony room for at least 2 weeks prior to testing and are subsequently tested at an average age of 8 weeks of age. During the period of acclimation, mice are examined on a regular basis, handled, and weighed to assure adequate health and suitability. Animals are maintained on a 12 h/12 h light/dark cycle. The RT is maintained between 20 and 23° C. with a relative humidity maintained between 30% and 70%. Food and water are provided ad libitum for the duration of the study. In each test, animals are randomly assigned across treatment groups.

The following compounds are used for this study: 1) Compound of the invention (0.03, 0.1, 0.3, 1, 3, 10 & 30 mg/kg) is dissolved in 5% PEG-200 in sterile water and administered p.o. 30 min prior to PCP injection; 2) Clozapine (1.0 mg/kg) is dissolved in 10% DMSO and administered i.p. 30 min prior to phencyclidine (PCP) injection; 3) PCP (5.0 mg/kg) is dissolved in sterile water and administered i.p. immediately before the 60 min test. All compounds are administered at a dose volume of 10 mL/kg.

The open filed (OF) test assesses locomotor behavior to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone such that the infrared photobeams allow measurement of activity in the center and periphery of the field. Distance traveled is measured from horizontal beam breaks as the mouse moves whereas rearing activity is measured from vertical beam breaks. Mice (10 to 12 animals per treatment group) are brought to the activity experimental room for at least 1 h acclimation to the experimental room conditions prior to testing. Eight animals are tested in each run. Mice are administered vehicle (e.g., 10% DMSO or 5% PEG200 and 1% Tween 80), Compound of the invention, clozapine (positive control, 1 mg/kg i.p.) and placed in the OF chambers for 30 min following which they are injected with either water or PCP and placed back in the OF chambers for a 60-min session. At the end of each OF test session the OF chambers are thoroughly cleaned.

Data are analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fall above or below 2 standard deviations from the mean are removed from the final analyses. An effect is considered significant if $p < 0.05$.

Example B16

Use of an In Vivo Model to Determine the Ability of Compounds to Treat, Prevent and/or Delay the Onset and/or the Development of Schizophrenia (Hyperactivity in Amphetamine Treated Animals)

Male mice (various strains e.g., C57B1/6J) from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12 h/12 h light/dark cycle. The RT is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglass square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 h acclimation prior to start of treatment. Animals are administered with vehicle, haloperidol (positive control, 0.1 mg/kg i.p.) or compound of the invention and placed in the OF. The time of administration of test compound to each animal is recorded. Baseline activity is recorded for 30 min following which mice receive amphetamine (4 mg/kg) or water and are placed back in the OF chambers for a 60-min session. At the end of each open field test session the OF chambers are thoroughly cleaned.

Typically ten to twelve mice are tested in each group. Test compound doses typically range from 0.01 mg/kg to 60 mg/kg.

Data are analyzed by analysis of variance (ANOVA) followed by post-hoc comparisons with Fisher Tests when appropriate. Baseline activity is measured during the first 30 min of the test prior to amphetamine injection. Amphetamine-induced activity is measured during the 60 min following amphetamine injection. Statistical outliers that fall above or below 2 standard deviations from the mean are removed from the final analyses. An effect is considered significant if $p<0.05$. Total distance traveled and total rearing following amphetamine administration are compared between groups treated with compound and groups treated with vehicle and positive control haloperidol.

Example B17

Use of the In Vivo Conditioned Avoidance Response (CAR) Model to Determine the Ability of Compounds to Treat, Prevent and/or Delay the Onset and/or the Development of Schizophrenia All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds.

The effects of compounds of the invention, at concentrations including 0.1, 0.3, 1, 3, and 20 mg/kg, p.o., in the conditioned avoidance response model are assessed in the male Wistar rat. Risperidone (0.3 mg/kg, s.c.) is used in the present study as a positive reference compound.

For each testing session, animals are first placed for a 4-min habituation period in a shuttlebox with an electrified grid floor. Then, rats are submitted to 30 trials spaced by intertrial intervals varying at random between 20 and 30 sec. Each trial consists of a 10-sec light stimulus (conditioned stimulus, CS) followed by a 10-sec electric foot shock (unconditioned stimulus, US) in presence of the light presented in the compartment where the rat is located. If the animal moves to the other compartment during the initial 10-sec of the trial, the light is terminated (no shock is delivered) and the response is recorded as an avoidance response. If the rat changes compartment during the foot shock, the light and the shock are terminated and the response is recorded as an unconditioned response. If the rat does not change compartment during the 10-sec light period (CS) and during the 10-sec shock+light period (US+CS), an escape failure is recorded. If a response is made during an intertrial interval, the response is recorded as an intertrial crossing. Training is performed 5 days per week with one session of 30 trials per day, until rats reach the performance criterion of 80% of avoidance response on at least two consecutive daily sessions. Once the performance criterion is reached, each animal is sequentially administered with vehicle (15% HPBCD, p.o.), compound of the invention (0.1, 0.3, 1, 3, 10 and 20 mg/kg, p.o.) and risperidone (0.3 mg/kg, s.c.). A minimal wash-out period of 48 h is allowed between 2 treatments. During the wash-out period, animals are trained until they recover an avoidance performance of at least 80%.

Statistical analysis is performed using a Friedman two-way ANOVA by ranks followed by the Wilcoxon matched-pairs signed-ranks test to test each dose of the test compound administered versus vehicle control treated rats.

Example B18

An Animal Model of the Negative Symptoms of Schizophrenia: Subchronic PCP-Induced Social Interaction Deficits Phencyclidine (PCP) administered to humans as well to experimental animals induces full-spectrum of schizophrenia symptoms, including negative symptoms and cognitive deficits. A major symptom of schizophrenia is considered to be social isolation/withdrawal as part of the cluster of negative symptoms. Subchronic treatment with PCP in rats leads to the development of clear signs of social withdrawal as measured by deficits in the interaction time with a cage intruder rat.

Male Sprague Dawley rats (~150 g on arrival) from Harlan (Indiana) are used in this study. Upon receipt, rats are group housed in OPTI rats ventilated cages. Rats are housed in groups of 2-3/cage for the remainder of the study. During the period of acclimation, rats are examined on a regular basis, handled, and weighed to assure adequate health and suitability. Rats are maintained on a 12 h/12 h light/dark cycle with the light on at 7:00 a.m. The RT is maintained between 20 and 23° C. with a relative humidity maintained between 30% and 70%. Chow and water are provided ad libitum for the duration of the study. Animals are randomly assigned across treatment groups and balanced by age. Animals are not disturbed between test days.

The following compounds are used. 1) Compound of the invention (0.3, 1 and 3 mg/kg; p.o.) is dissolved in 3% Tween and PBS and administered 30 min prior to test; 2) PCP (2 mg/kg; s.c.) is dissolved in saline and administered twice daily for 5 days prior to test day; 3) Clozapine (2.5 mg/kg; i.p.) is dissolved in 5% PEG:5% Tween 80 in saline and administered 30 min prior to test. All compounds are administered at a dose volume of 1 mL/kg.

For 5 days prior to test, rats are injected twice daily with either PCP (2 mg/kg; s.c) or saline (s.c). On day 6 and following a 30 min pretreatment with vehicle, clozapine or compound of the invention, a pair of rats, unfamiliar to each other, receiving the same treatment are placed in a white plexiglass open field arena (24"×17"×8") and allowed to interact with each other for 6 min. Social interactions ('SI') include: sniffing the other rat; grooming the other rat; climbing over or under or around the other rat; following the other rat; or exploring the ano-genital area of the other rat. Passive contact and aggressive contact are not considered a measure of social interaction. The time the rats spend interacting with each other during the 6 min test is recorded by a trained observer. The social interaction chambers are thoroughly cleaned between the different rats.

Data are analyzed by analysis of variance (ANOVA) followed by post-hoc analysis (e.g., Fischer, Dunnett) when appropriate. An effect is considered significant if $p<0.05$.

Example B19

An Animal Model of Extrapyramidal Syndrome (EPS): Measurement of Catalepsy in the Mouse Bar Test Antipsychotic drugs are known to induce extrapyramidal syndrome (EPS) in animals and in humans. An animal model considered to be predictive of EPS is the mouse bar test, which measures cataleptic responses to pharmacological agents.

Male C57B1I6J mice from Jackson Laboratories (Bar Harbor, Me.) are used. Mice are received at 6-weeks of age. Upon receipt, mice are assigned unique identification numbers (tail marked) and are group housed with 4 mice/cage in OptiMICE ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12 h/12 h light/dark cycle. The RT is maintained between 20 and 23° C. with a relative humidity maintained between 30% and 70%. Chow and water are provided ad libitum for the duration of the study. In each test, animals are randomly assigned across treatment groups.

The following compounds are used for this study. 1) Compound of the invention (0.03, 0.1, 0.3, 1, 3, 10, 30 mg/kg) is dissolved in 3% Tween in PBS and administered orally at a dose volume of 10 mL/kg; 2) Haloperidol (2 mg/kg) is dissolved in 10% DMSO and administered i.p. at a dose volume of 10 mL/kg.

The front paws of a mouse are placed on a horizontal metal bar raised 2" above a Plexiglas platform and time is recorded for up to 30 sec per trial. The test ends when the animal's front paws return to the platform or after 30 sec. The test is repeated three times and the average of the three trials is reported as the intensity index of catalepsy. Antipsychotic agents such as haloperidol cause rigidity as a side effect. Animals treated with haloperidol will hold on to the bar without moving for several min. Mice are brought to the activity experimental room for at least 1 h acclimation to the experimental room conditions prior to testing. Following injection of either vehicle, Compound of the invention, or haloperidol, catalepsy is assessed at 3 time points: 30 min, 1 h and 3 h. At the end of each trial, the apparatus is thoroughly cleaned with 70% ethanol.

Data are analyzed by analysis of variance (ANOVA) followed by post-hoc comparisons with Fisher Tests when appropriate. An effect is considered significant if $p<0.05$.

Example B20

Use of the 5-Choice Serial Reaction Task to Determine the Ability of Compounds to Enhance Attention/Vigilance and Reduce Impulsivity Attention and impulsivity are characteristic of several disease states. The continuous performance test (CPT), used in humans, is capable of detecting attention deficits in a number of disorders, including attention deficit hyperactivity disorder, schizophrenia and mild cognitive impairment. The preclinical analogue of the CPT is the 5-choice serial reaction time task (5CSRTT). In this operant-based test, rats are required to be attentive and withhold responding while they monitor 5 apertures for the appearance of a brief stimulus light in one of the apertures. The brief illumination of the stimulus light in the 5CSRTT is analogous to the appearance of the "correct" letters in the CPT in humans. Upon observing the stimulus light, the rat must nose-poke in the corresponding aperture to receive a food reward. The 5CSRTT allows the measurement of similar behavioral responses as the CPT, including accuracy, speed of responding, impulsive and compulsive responding. In this study, drug tests are performed under altered test parameters which result in increased premature responding. This premature responding is hypothesized to indicate impulsivity, e.g., a failure to withhold an inappropriate response, and has been shown to be sensitive to atomoxetine.

Thirteen male Long-Evans rats (275-300 g) are obtained from Harlan Laboratories, Indianapolis, Ind. At the time of testing for the current study, the rats are approximately 16-18 months old. Upon arrival, the rats are assigned unique identification numbers (tail marked). Rats are single-housed in OptiRAT cages and acclimated for 7 days prior to commencing a food-restriction regimen: rats are held at 85% of age-matched free-feeding control bodyweights, receiving approximately 10-20 g of rat chow daily. Water is provided ad libitum, except during testing. Animals are maintained in a 12 h/12 h light/dark cycle (lights on at 0700 EST) with RT maintained at 22±2° C. and the relative humidity maintained at approximately 50%. All animals are examined, handled and weighed prior to initiation of the study to assure adequate health and suitability and to minimize non-specific stress associated with testing. The 5CSRTT sessions are performed during the animal's light cycle phase. All experiments and procedures are approved by the Institutional Animal Care and Use Committee of PsychoGenics, Inc.

The apparatus consists of 10 aluminum and Plexiglas chambers with grid floors (width 31.5 cm, depth 25.0 cm, height 33.0 cm), housed in sound-attenuating cabinets. Each cabinet is fitted with a low-level noise extractor fan which also helped to mask external noise. The left wall of each chamber is concavely curved with 5 apertures evenly spaced, located approximately 2.5 cm from the floor. Each aperture contains a standard 3 W LED to serve as stimulus lights. The opposite wall contains a food magazine, located approximately 3.0 cm from the floor. Each chamber is illuminated with a 3 W house-light located in the center of the ceiling panel. After each test session the apparatus is cleaned with 70% ethanol.

The following compounds are used for this study. 1) Compound of the invention is dissolved in saline, and administered p.o. at 0.1, 0.3 and 1.0 mg/kg, 30 min prior to testing at 1 mL/kg body weight; 2) The reference compound atomoxetine (1.0 mg/kg) is dissolved in saline and administered i.p. 30 min prior to testing at 1 mL/kg body weight.

Training:

Animals are trained to monitor the five apertures for stimulus light illumination. Each session is initiated by the illumination of the house light, and the delivery of a food reward into the magazine. The first trial begins when the rat opens the magazine to obtain the food pellet. After the inter-trial interval (ITI) one of the stimulus lights is illuminated for 500 msec. The rat must nose-poke in the illuminated aperture either during or within 5 sec of stimulus light illumination. Such a response is defined as a correct response, and is rewarded with delivery of a food pellet. Collection of the pellet initiates the next trial. A nose-poke response in a non-illuminated aperture (incorrect response) or a nose-poke after the 5 sec limited hold (missed trial) results in termination of the trial with extinction of the house-light and imposition of a time-out period.

Testing:

After acquisition of the 5CSRTT with a high level of accuracy (at least 75% correct, at least 50 trials completed per session), drug testing begins. Animals are treated with test compound (various doses, appropriate vehicle), vehicle and positive control (atomoxetine 1 mg/kg i.p.). During drug test sessions, the ITI is varied between 10, 7, 5 or 4 sec in duration, presented in groups of 4 trials (each of which contains 1 trial at each ITI duration in a randomized order). The session ends when 60 min have elapsed. All rats receive all drug treatments, according to a randomized-order within-subjects design. Drug tests are performed on Wednesdays and Fridays of each week, only when rats perform at least 75% correct trials for a minimum of 50 trials in the previous test session.

Measures obtained during the test sessions are: (1) percent correct, defined as the number of correct trials $X^{100}$, divided by the total number of correct and incorrect trials, (2) missed trials, defined as responding beyond the 5 sec limited hold or failing to respond, (3) correct latency, defined as the time taken to make a correct response after the illumination of the stimulus, (4) magazine latency, defined as the time taken to enter the magazine to collect the food pellet after making a correct response, (5) premature responding, defined as the total number of nose-poke responses made during the ITI, and (6) perseverative responding, defined as the total number of additional responses emitted after the initial nose-poke.

Example B21

An Animal Model to Test the Anxiolytic Effects of Compounds Using the Elevated Plus Maze (EPM) Test This study may be used to test the anxiolytic properties of compounds of the invention using the elevated plus maze (EPM) test in C57B1/6J mice.

Male C57B1/6J mice from Jackson Laboratories (Bar Harbor, Me.) are used for the open field study. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for approximately 2 week prior to testing and are subsequently tested at an average age of 8 weeks. During the period of acclimation, mice and rats are examined on a regular basis, handled, and weighed to assure adequate health and suitability. Animals are maintained on a 12 h/12 h light/dark cycle. The RT is maintained between 20 and 23° C. with a relative humidity maintained between 30% and 70%. Chow and water are provided ad libitum for the duration of the study. In each test, animals are randomly assigned across treatment groups. All animals are euthanized after the completion of the study.

The following compounds are used for this study: 1) Compound of the invention (0.03, 0.1 and 1 mg/kg) is dissolved in 5% PEG200/$H_2O$ and administered orally at a dose volume of 10 mL/kg 30 min prior to test; 2) Diazepam (2.5 mg/kg) is dissolved in 45% hydroxypropyl-β-cyclodextrin and administered orally at a dose volume of 10 mL/kg 30 min prior to test.

The elevated plus maze test assesses anxiety. The maze (Hamilton Kinder) consists of two closed arms (14.5 h×5 w×35 l cm) and two open arms (6 w×35 l cm) forming a cross, with a square center platform (6×6 cm). All visible surfaces are made of black acrylic. Each arm of the maze is placed on a support column 56 cm above the floor. Antistatic black vinyl curtains (7' tall) surround the EPM to make a 5'×5" enclosure. Animals are brought to acclimate to the experimental room at least 1 h before the test. Mice are placed in the center of the elevated plus maze facing the closed arm for a 5-min run. All animals are tested once. The time spent, distance traveled and entries in each arm are automatically recorded by the computer. The EPM is thoroughly cleaned after each mouse.

Data are analyzed using analysis of variance (ANOVA) followed by Fisher's LSD post hoc analysis when appropriate. An effect is considered significant if $p<0.05$.

Example B22

Cell Culture and Cell Viability Assay

SH-SY5Y cells cultured in DMEM/F12 media supplemented with 10% FBS were seeded in 96-well microplates at 150,000 cells/$cm^2$. After 24 h, cells were depleted from FBS and kept in culture for 24 h before the experiment. A stock solution was prepared by dissolving the calcium ionophore 4-Br-A23187 (Calbiochem Cat.N° 100107) in DMSO at 25 mM. Cells were then treated with 4-Br-A23187 (2 μM), hydrogen peroxide (300 μM) or the mitochondrial toxin rotenone (25 μM) in the presence of vehicle or Compound of the Invention for 24 h. Cell death was determined by measurements of LDH release according to the Cytotoxicity Detection KitPlus (Roche, Mannheim, Germany). Cell viability was determined by measuring the capacity of cells to metabolize MTS tetrazolium (MTS) according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA). Compounds were screened at 10 nM, using DMSO as vehicle. Assay results for the experiments with Br-A23187 are presented as the MTS reduction capacity (cell viability) of untreated cells (control), 4-Br-A23187-treated cells (vehicle), and co-incubation of Br-A23187 with Compounds of the Invention treated cells and using p-trifluoromethoxyphenylhydrazone (FCCP) at 10 μM for 30 min as a control. This assay assesses the ability of the test compounds to protect against cell death that is mediated by mitochondrial dysfunction. In the assay, the calcium ionophore 4-Br-A23187 is used to challenge the cells, causing calcium levels to rise in mitochondria, which leads to depolarization and cell death. Test compounds are assessed for their ability to prevent cell death in response to challenge with 4-Br-A23187.

TABLE 5

Relative Cytoprotection efficiency of compounds of the invention

| Compound No. | Mean | Standard Error | p value |
|---|---|---|---|
| Vehicle | 0 | 0 | ns |
| Control | 100 | 1.47E–06 | ns |
| 2 | 38.36419 | 24.02967 | ns |
| 5 | 72.11077 | 1.524916 | 4.00E–04 |
| 7 | 72.05842 | 8.628121 | 0.014 |
| 8 | 73.11748 | 10.89231 | 0.0215 |
| 9 | 81.05257 | 2.423629 | 9.00E–04 |
| 11 | 30.32596 | 2.105927 | 0.0048 |
| 12 | 32.51647 | 14.49203 | ns |

Example B23

Cell Culture and Cell Viability Assay

Cell Culture

SH-SY5Y cells stably transfected with a doxycyline-inducible wild-type α-synuclein (α-syn) gene along with control SH-SY5Y cells over-expressing the β-galactosidase (β-gal) gene (a gift from L. Stefanis, Division of Basic Neurosciences, Biomedical Research Foundation of the Academy of Athens, Athens, Greece) are cultured as described by Vekrellis et al. (Vekrellis K, Xilouri M, Emmanouilidou E, Stefanis L. (2009). Inducible over-expression of α-syn in human neuronal cells leads to caspase-dependent non-apoptotic death. J Neurochem 109, 1348-1362). In accordance with this method, cells are cultured and maintained in RPMI 1640, 10% fetal bovine serum supplemented with 250 µg/mL G418 and 50 µg/mL Hygromycin B. Expression of α-syn is switched off in stock cultures with doxycycline (2 µg/mL). For experimental procedures, cells are plated at $(4-8 \times 10^4$ cells/cm$^2$) and differentiated in absence of doxycycline and in the presence of 20 µM all-trans retinoic acid (RA) (Sigma, St Louis, Mo., USA).

Viability Assay

Cells are cultured in 96-well plates. After 24 h, cells are treated with RA and Compounds of Invention at 0.1 and 10 nM in the absence of doxycyline. Culture medium with RA and drugs is fully replaced after 7 days. Cell viability is measured by the release of lactate dehydrogenase (LDH) from necrotic cells into the culture medium and by measuring the capacity of cells to metabolize MTS tetrazolium (MTS) after 14 days in culture. LDH leakage is assessed according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA).

Immunoblotting of α-Synuclein and α-Synuclein Aggregates

Cells stably expressing α-synuclein are cultured in 6-well plates at a density of $4 \times 10^4$ cells/cm$^2$ cells per well. Cells are differentiated and treated with Compound of the Invention at 10 nM in absence of dox after 24 h of plating. Drug treatments are repeated after 7 days in freshly prepared medium containing RA. After 14 days, cells are washed twice with cold PBS and lysed in lysys buffer containing 1% Triton X-100, 20 mM HEPES, 150 mM NaCl, 10% glycerol, 1 mM EGTA, 1.5 mM MgCl$_2$, 1 mM PMSF pH 7.4, and 1× protease inhibitor mixture (Roche, Mannheim, Germany). Lysates are homogenized and subjected to four successive freeze-thaw cycles to disrupt membranes. Triton soluble fractions and triton insoluble pellets are obtained by ultracentrifugation at 100,000×g for 30 min at 4° C. The concentration of protein in each fraction is determined by BCA assay (Thermo Scientific).

Samples from total, soluble and triton insoluble fractions, are boiled in 1× sample buffer (20 mM Tris, 1% glycerol, 180 mM β-mercaptoethanol, 0.003% bromophenol blue, and 2% SDS, pH 6.8), loaded on 12% SDS-PAGE gels, and transferred to polyvinylidene difluoride (PVDF) membranes (0.2 µM-pore immobilon Biorad). Membranes are blocked in 1×TBS-Tween (20 mM Tris, pH 7.4, 150 mM NaCl, and 0.2% Tween 20) containing 5% milk for 1 h and incubated overnight at 4° C. with the following primary antibodies in blocking solution at the indicated dilutions: monoclonal anti-α-synuclein α-syn-1 (1:1000; BD Transduction Laboratories). (Perrin, R. J., Payton, J. E., Barnett, D. H., Wraight, C. L., Woods, W. S., Ye, L., and George, J. M. (2003). Epitope mapping and specificity of the anti-α-synuclein monoclonal antibody Syn-1 in mouse brain and cultured cell lines. Neurosci Lett 349, 133-135), and monoclonal vimentin (1:1000; BD PharMingen). Primary antibodies are detected with secondary anti-mouse antibodies conjugated to HRP (1:5000).

Isolation of RNA and RT-Quantitative PCR (RT-qPCR)

SH-SY5Y cells stably over-expressing α-syn are treated with Compound of the Invention (10 nM). Total RNA from these cells as well as control cells not treated with Compound is extracted using the E.Z.N.A RNA extraction Kit (OMEGAbiotek, Norcross, Ga.). 1 µg of RNA is reverse transcribed to cDNA using the M-Mulv reverse transcriptase enzyme (Promega Corporation, Madison, Wis., USA). RT-qPCR of cDNA templates is carried out using TAQMAN probes for human α-synuclein (Hs00240906_M1) and TAQMAN masterMix (Applied Biosystems) and a Mx3005P real-time PCR system (Agilent Technologies Inc., Santa Clara, Calif.). Levels of alpha-tubulin mRNA are used to normalize the amounts of total RNA between samples. Fold changes are calculated as described by (Pfaffl, M. W. (2001). A new mathematical model for relative quantification in real-time RT-PCR. Nucleic Acids Res 29, e45).

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of the formula (VA):

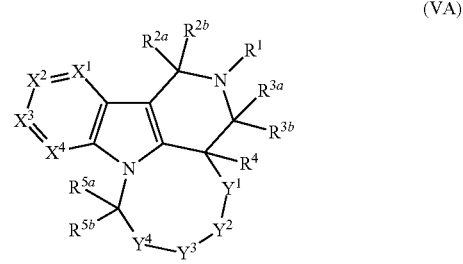

(VA)

or a salt thereof; wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and a vicinal $R^{7(a-h)}$, where applicable, are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$ or is taken together with $Y^3$ and $Y^4$ to form a bond, $Y^2$ is $CR^{7c}R^{7d}$, $NR^8$, O, S, S(O) or $SO_2$, or $Y^2$ is taken together with $Y^3$ and $Y^4$ to form a bond, provided that when $Y^2$ is $NR^8$, O, S, S(O) or $SO_2$, then $Y^1$ is $CR^{7a}R^{7b}$ and $Y^3$ is $CR^{7e}R^{7f}$ or is taken together with $Y^4$ to form a bond;

$Y^3$ is $CR^{7e}R^{7f}$, $NR^8$, O, S, S(O) or $SO_2$, or $Y^3$ is taken together with $Y^4$ to form a bond, provided that when $Y^3$ is $NR^8$, O, S, S(O) or $SO_2$, then $Y^2$ is $CR^{7c}R^{7d}$ and $Y^4$ is $CR^{7g}R^{7h}$ or a bond;

$Y^4$ is $CR^{7g}R^{7h}$, $NR^8$, O, S, S(O) or $SO_2$, or $Y^4$ is a bond, provided that when $Y^4$ is $NR^8$, O, S, S(O) or $SO_2$, then $Y^3$ is $CR^{7e}R^{7f}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond;

each $R^{7c}$ and $R^{7d}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$, where applicable, are taken together to form a bond, or $R^{7c}$ and a vicinal $R^{5a}$, where applicable, are taken together to form a bond;

each $R^{7e}$ and $R^{7f}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{7g}$, where applicable, are taken together to form a bond, or $R^{7e}$ and a vicinal $R^{5a}$, where applicable, are taken together to form a bond;

each $R^{7g}$ and $R^{7h}$, where applicable, is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7g}$ and $R^{7h}$ are taken together with the carbon to which they are attached to form a carbonyl moiety, or $R^{7g}$ and $R^{7e}$ are taken together to form a bond, or $R^{7g}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

provided that (1) at least one of $X^1$, $X^2$, $X^3$ and $X^4$ is CH or $CR^6$; and (2) at least one of $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$ is a group containing a cyclic moiety.

2. The compound of claim 1, or a salt thereof, wherein the compound is of the formula (VA1):

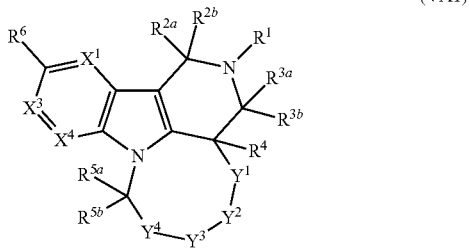

(VA1)

wherein:
each $X^1$, $X^3$ and $X^4$ is independently N or CH; and
each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond.

3. The compound of claim 1, or a salt thereof, wherein the compound is of the formula (VA2):

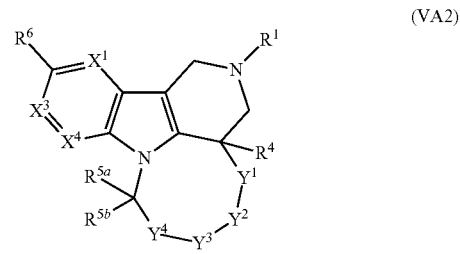

(VA2)

wherein:
$R^1$ is H or substituted or unsubstituted $C_1$-$C_8$ alkyl;
$R^4$ is H, substituted or unsubstituted $C_1$-$C_8$ alkyl, or is taken together with $R^{7a}$ to form a bond;
each $X^1$, $X^3$ and $X^4$ is independently N or CH;
$Y^2$ is O or $CR^{7c}R^{7d}$, or $Y^2$ is taken together with $Y^3$ and $Y^4$ to form a bond, provided that when $Y^2$ is O, then $Y^1$ is $CR^{7a}R^{7b}$ and $Y^3$ is $CR^{7e}R^{7f}$ or is taken together with $Y^4$ to form a bond;
$Y^3$ is O or $CR^{7e}R^{7f}$, or $Y^3$ is taken together with $Y^4$ to form a bond, provided that when $Y^3$ is O, then $Y^2$ is $CR^{7c}R^{7d}$ and $Y^4$ is $CR^{7g}R^{7b}$ or a bond;
$Y^4$ is $CR^{7g}R^{7b}$, or $Y^4$ is a bond; and
each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^4$ are taken together to form a bond, or $R^{7a}$ and $R^{7c}$, where applicable, are taken together to form a bond, or $R^{7a}$ and a vicinal $R^{5a}$, where applicable, are taken together to form a bond.

4. The compound of claim 3, or a salt thereof, wherein $R^4$ is H or methyl.

5. The compound of claim 3, or a salt thereof, wherein each $R^{5a}$, $R^{5b}$, $R^{7a}$, $R^{7b}$, $R^{7c}$, $R^{7d}$, $R^{7e}$, $R^{7f}$, $R^{7g}$ and $R^{7h}$, where applicable, is independently H, hydroxyl, substituted or unsubstituted $C_1$-$C_8$ alkyl, substituted or unsubstituted aryl, substituted or unsubstituted heteroaryl, substituted or unsubstituted heterocyclyl, substituted or unsubstituted aralkyl, or acylamino, or $R^{5a}$ and a vicinal $R^{7(a-h)}$, where applicable, are taken together to form a bond.

6. The compound of claim 1, or a salt thereof, wherein the group containing a cyclic moiety is selected from the group consisting of substituted or unsubstituted aryl, substituted or unsubstituted heteroaryl, substituted or unsubstituted cycloalkyl, and substituted or unsubstituted heterocyclyl.

7. The compound of claim 1, or a salt thereof, wherein the group containing a cyclic moiety is a $C_1$-$C_8$ alkyl, or a $C_2$-$C_8$ alkenyl, substituted with a group selected from the group consisting of substituted or unsubstituted aryl, substituted or unsubstituted heteroaryl, substituted or unsubstituted cycloalkyl, and substituted or unsubstituted heterocyclyl.

8. The compound of claim 1, wherein the compound is of the formula (IA):

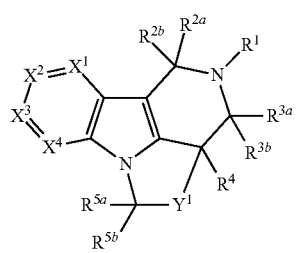

(IA)

or a salt thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2CH_2$—) moiety or a propylene (—$CH_2CH_2CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{7a}$ are taken together to form a bond;

each $X^1$, $X^2$, $X^3$ and $X^4$ is independently N, CH or $CR^6$;
$Y^1$ is $CR^{7a}R^{7b}$, $NR^8$, O, S, S(O) or $SO_2$;
each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{5a}$ are taken together to form a bond, or $R^{7a}$ and $R^4$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

9. The compound of claim 1, wherein the compound is of the formula (IIA):

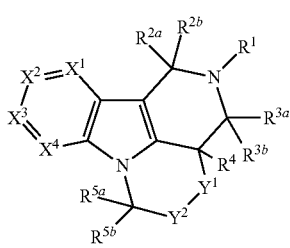

(IIA)

or a salt thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{7c}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{5a}$ are taken together to form a bond; and $R^8$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

provided that when each $X^1$, $X^2$, $X^3$ and $X^4$ is CH, each $R^{2a}$, $R^{2b}$, $R^{3a}$, $R^{3b}$, $R^4$, $R^{5a}$ and $R^{5b}$ is H, $Y^1$ is carbonyl and $Y^2$ is $CH_2$, $R^1$ is other than hydrogen.

10. The compound of claim 1, wherein the compound is of the formula (IIIA):

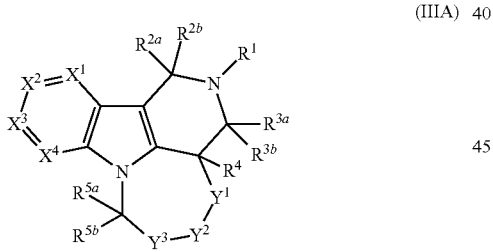

(IIIA)

or a salt thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—$CH_2CH_2CH_2$—) moiety or a butylene (—$CH_2CH_2CH_2CH_2$—) moiety;

$R^4$ is H, substituted or unsubstituted $C_1$-$C_8$ alkyl, halo, cyano, nitro, substituted or unsubstituted amino, hydroxyl, alkoxy, acyloxy, acylamino, aryl, heteroaryl, cycloalkyl, heterocyclyl, or $R^4$ and $R^1$ are taken together to form an ethylene (—$CH_2CH_2$—) moiety or a propylene (—$CH_2CH_2CH_2$—) moiety, or $R^4$ and $R^{2a}$ are taken together to form a methylene (—$CH_2$—) moiety or an ethylene (—$CH_2CH_2$—) moiety, or $R^4$ and $R^{3a}$ are taken together to form a propylene (—$CH_2CH_2CH_2$—) moiety or a butylene (—$CH_2CH_2CH_2CH_2$—) moiety, or $R^4$ and $R^{7a}$ are taken together to form a bond;

each $R^{5a}$ and $R^{5b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{5a}$ and $R^{7e}$ are taken together to form a bond;

each $X^1$, $X^2$, $X^3$ and $X^4$ is independently N, CH or $CR^6$;

$Y^1$ is $CR^{7a}R^{7b}$, $NR^8$, O, S, S(O) or $SO_2$, provided that when $Y^1$ is $NR^8$, O, S, S(O) or $SO_2$, then $Y^2$ is $CR^{7c}R^{7d}$;

$Y^2$ is $CR^{7c}R^{7d}$, $NR^8$, O, S, S(O) or $SO_2$, provided that when $Y^2$ is $NR^8$, O, S, S(O) or $SO_2$, then $Y^1$ is $CR^{7a}R^{7b}$ and $Y^3$ is $CR^{7e}R^{7f}$;

$Y^3$ is $CR^{7e}R^{7f}$, $NR^8$, O, S, S(O) or $SO_2$, provided that when $Y^3$ is $NR^8$, O, S, S(O) or $SO_2$, then $Y^2$ is $CR^{7c}R^{7d}$;

each $R^6$ is independently hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, substituted or unsubstituted $C_1$-$C_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{7a}$ and $R^{7b}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7a}$ and $R^{7b}$ are taken together with the carbon to which they are attached to form a carbonyl moiety, or $R^{7a}$ and $R^{7c}$ are taken together to form a bond, or $R^{7a}$ and $R^4$ are taken together to form a bond;

each $R^{7c}$ and $R^{7d}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7c}$ and $R^{7d}$ are taken together with the carbon to which they are attached to form a carbonyl moiety, or $R^{7c}$ and $R^{7a}$ are taken together to form a bond, or $R^{7c}$ and $R^{7e}$ are taken together to form a bond;

each $R^{7e}$ and $R^{7f}$ is independently H, hydroxyl, halo, nitro, cyano, substituted or unsubstituted $C_1$-$C_8$ alkyl, substituted or unsubstituted $C_1$-$C_8$ alkoxy, $C_1$-$C_8$ perhaloalkyl, $C_1$-$C_8$ perhaloalkoxy, substituted or unsubstituted $C_2$-$C_8$ alkenyl, substituted or unsubstituted $C_2$-$C_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or $R^{7e}$ and $R^{7f}$ are taken together with the carbon to which they are attached to form a carbonyl moiety, or $R^{7e}$ and $R^{7c}$ are taken together to form a bond, or $R^{7e}$ and $R^{5a}$ are taken together to form a bond; and each $R^8$ is independently H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

11. The compound of claim 1, wherein the compound is of the formula (IVA):

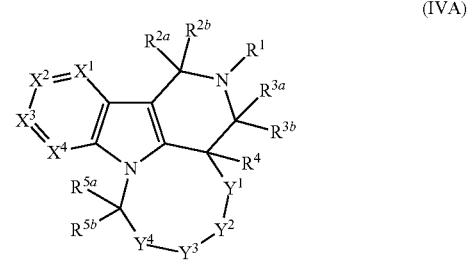

(IVA)

or a salt thereof;
wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy, or $R^1$ and $R^{2a}$ are taken together to form a propylene (—$CH_2CH_2CH_2$—) moiety or a butylene (—$CH_2CH_2CH_2CH_2$—) moiety, or $R^1$ and $R^{3a}$ are taken together to form a propylene (—$CH_2CH_2CH_2$—) moiety or a butylene (—$CH_2CH_2CH_2CH_2$—) moiety, or $R^1$ and $R^4$ are taken together to form an ethylene (—$CH_2CH_2$—) moiety or a propylene (—$CH_2CH_2CH_2$—) moiety;

each $R^{2a}$ and $R^{2b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{2a}$ and $R^{2b}$ are taken together with the carbon to which they are attached to form a carbonyl moiety or a cycloalkyl moiety, or $R^{2a}$ and $R^1$ are taken together to form a propylene (—$CH_2CH_2CH_2$—) moiety or a butylene (—$CH_2CH_2CH_2CH_2$—) moiety, or $R^{2a}$ and $R^{3a}$ are taken together to form an ethylene (—$CH_2$—$CH_2$—) moiety or a propylene (—$CH_2CH_2$—$CH_2$—) moiety, or $R^{2a}$ and $R^4$ are taken together to form a methylene (—$CH_2$—) moiety or an ethylene (—$CH_2CH_2$—) moiety;

each $R^{3a}$ and $R^{3b}$ is independently H, substituted or unsubstituted $C_1$-$C_8$ alkyl, halo, cyano, hydroxyl, alkoxy, nitro, substituted or unsubstituted amino, acyloxy, acylamino, aryl, heteroaryl, cycloalkyl, heterocyclyl, or $R^{3a}$ and $R^{3b}$ are taken together with the carbon to which they are attached to form a carbonyl moiety or a cycloalkyl moiety, or $R^{3a}$ and $R^1$ are taken together to form a propylene (—$CH_2CH_2CH_2$—) moiety or a butylene (—$CH_2CH_2CH_2CH_2$—) moiety, or $R^{3a}$ and $R^{2a}$ are taken together to form an ethylene (—$CH_2CH_2$—) moiety or a propylene (—$CH_2CH_2CH_2$—) moiety, or $R^{3a}$ and $R^4$ are taken together to form a propylene (—CH$_2$CH$_2$CH$_2$—) moiety or a butylene (—CH$_2$CH$_2$CH$_2$CH$_2$—) moiety;

R$^4$ is H, substituted or unsubstituted C$_1$-C$_8$ alkyl, halo, cyano, nitro, substituted or unsubstituted amino, hydroxyl, alkoxy, acyloxy, acylamino, aryl, heteroaryl, cycloalkyl, heterocyclyl, or R$^4$ and R$^1$ are taken together to form an ethylene (—CH$_2$CH$_2$—) moiety or a propylene (—CH$_2$CH$_2$CH$_2$—) moiety, or R$^4$ and R$^{2a}$ are taken together to form a methylene (—CH$_2$—) moiety or an ethylene (—CH$_2$CH$_2$—) moiety, or R$^4$ and R$^{3a}$ are taken together to form a propylene (—CH$_2$CH$_2$CH$_2$—) moiety or a butylene (—CH$_2$CH$_2$CH$_2$CH$_2$—) moiety, or R$^4$ and R$^{7a}$ are taken together to form a bond;

each R$^{5a}$ and R$^{5b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{5a}$ and R$^{7g}$ are taken together to form a bond;

each X$^1$, X$^2$, X$^3$ and X$^4$ is independently N, CH or CR$^6$;

Y$^1$ is CR$^{7a}$R$^{7b}$, NR$^8$, O, S, S(O) or SO$_2$, provided that when Y$^1$ is NR$^8$, O, S, S(O) or SO$_2$, then Y$^2$ is CR$^{7c}$R$^{7d}$;

Y$^2$ is CR$^{7c}$R$^{7d}$, NR$^8$, O, S, S(O) or SO$_2$, provided that when Y$^2$ is NR$^8$, O, S, S(O) or SO$_2$, then Y$^1$ is CR$^{7a}$R$^{7b}$ and Y$^3$ is CR$^{7e}$R$^{7f}$;

Y$^3$ is CR$^{7e}$R$^{7f}$, NR$^8$, O, S, S(O) or SO$_2$, provided that when Y$^3$ is NR$^8$, O, S, S(O) or SO$_2$, then Y$^2$ is CR$^{7c}$R$^{7d}$ and Y$^4$ is CR$^{7g}$R$^{7h}$;

Y$^4$ is CR$^{7g}$R$^{7h}$, NR$^8$, O, S, S(O) or SO$_2$, provided that when Y$^4$ is NR$^8$, O, S, S(O) or SO$_2$, then Y$^3$ is CR$^{7e}$R$^{7f}$;

each R$^6$ is independently hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, substituted or unsubstituted C$_1$-C$_8$ alkoxy, substituted or unsubstituted aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{7a}$ and R$^{7b}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7a}$ and R$^{7b}$ are taken together with the carbon to which they are attached to form a carbonyl moiety, or R$^{7a}$ and R$^{7c}$ are taken together to form a bond, or R$^{7a}$ and R$^4$ are taken together to form a bond;

each R$^{7c}$ and R$^{7d}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7c}$ and R$^{7d}$ are taken together with the carbon to which they are attached to form a carbonyl moiety, or R$^{7c}$ and R$^{7a}$ are taken together to form a bond, or R$^{7c}$ and R$^{7e}$ are taken together to form a bond;

each R$^{7e}$ and R$^{7f}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7e}$ and R$^{7f}$ are taken together with the carbon to which they are attached to form a carbonyl moiety, or R$^{7e}$ and R$^{7c}$ are taken together to form a bond, or R$^{7e}$ and R$^{7g}$ are taken together to form a bond;

each R$^{7g}$ and R$^{7h}$ is independently H, hydroxyl, halo, nitro, cyano, substituted or unsubstituted C$_1$-C$_8$ alkyl, substituted or unsubstituted C$_1$-C$_8$ alkoxy, C$_1$-C$_8$ perhaloalkyl, C$_1$-C$_8$ perhaloalkoxy, substituted or unsubstituted C$_2$-C$_8$ alkenyl, substituted or unsubstituted C$_2$-C$_8$ alkynyl, substituted or unsubstituted aryl, substituted or unsubstituted aryloxy, substituted or unsubstituted heteroaryl, substituted or unsubstituted cycloalkyl, substituted or unsubstituted heterocyclyl, substituted or unsubstituted aralkyl, substituted or unsubstituted amino, aminoacyl, acyl, acylamino, acyloxy, carbonylalkoxy, carboxyl, thiol, thioalkyl, aminocarbonylamino, aminocarbonylalkoxy, aminosulfonyl, or sulfonylamino, or R$^{7g}$ and R$^{7h}$ are taken together with the carbon to which they are attached to form a carbonyl moiety, or R$^{7g}$ and R$^{7e}$ are taken together to form a bond, or R$^{7g}$ and R$^{5a}$ are taken together to form a bond; and each R$^8$ is independently H, hydroxyl, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy.

12. A compound selected from the group consisting of compounds 1-12, 15-16, 18-21, 23-26, 28-62, 64-67, 69-72, 74-85, 87-90, 92-107, 109-112, 114-117, 119-122, 124-127, 129-132, 134-137, 139-142, 144-153, 155-166, 169-170, 173, 175, 177-178, 180, and 187-236, or a pharmaceutically acceptable salt thereof.

13. A pharmaceutical composition comprising (a) a compound of claim 1 or a pharmaceutically acceptable salt thereof and (b) a pharmaceutically acceptable carrier.

14. A method of treating a cognitive disorder, psychotic disorder, neurotransmitter-mediated disorder or a neuronal disorder in an individual comprising administering to an individual in need thereof an effective amount of a compound of claim 1 or a pharmaceutically acceptable salt thereof.

15. A method of treating a cognitive disorder, psychotic disorder, neurotransmitter-mediated disorder or a neuronal disorder in an individual comprising administering to an individual in need thereof an effective amount of a compound or a pharmaceutically acceptable salt thereof, wherein the compound is selected from the group consisting of compounds 15-16, 18-21, 23-26, 28-62, 64-67, 69-72, 74-85, 1-12, 87-90, 92-107, 109-112, 114-117, 119-122, 124-127, 129-132, 134-137, 139-142, 144-153, 155-166, 169-170, 173, 175, 177-178, 180, and 187-236.

16. A kit comprising a compound according to claim 1 or a pharmaceutically acceptable salt thereof and instructions for use in the treatment of a cognitive disorder, psychotic disorder, neurotransmitter-mediated disorder or a neuronal disorder.

\* \* \* \* \*